US009150577B2

(12) United States Patent
Boyer et al.

(10) Patent No.: US 9,150,577 B2
(45) Date of Patent: Oct. 6, 2015

(54) HETEROCYCLIC COMPOUNDS CONTAINING AN INDOLE CORE

(75) Inventors: Stephen J. Boyer, Bethany, CT (US); Donghong Amy Gao, Hopewell Junction, NY (US); Xin Guo, Danbury, CT (US); Thomas Martin Kirrane, Jr., Middlebury, CT (US); Christopher Ronald Sarko, New Milford, CT (US); Roger John Snow, Danbury, CT (US); Fariba Soleymanzadeh, Danbury, CT (US); Yunlong Zhang, North Haven, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 406 days.

(21) Appl. No.: 13/513,954

(22) PCT Filed: Nov. 30, 2010

(86) PCT No.: PCT/US2010/058271

§ 371 (c)(1),
(2), (4) Date: Aug. 8, 2012

(87) PCT Pub. No.: WO2011/071716

PCT Pub. Date: Jun. 16, 2011

(65) Prior Publication Data

US 2013/0109679 A1 May 2, 2013

Related U.S. Application Data

(60) Provisional application No. 61/267,175, filed on Dec. 7, 2009.

(51) Int. Cl.
*C07D 487/04* (2006.01)
*C07D 487/20* (2006.01)
*C07D 491/20* (2006.01)

(52) U.S. Cl.
CPC ........... *C07D 487/04* (2013.01); *C07D 487/20* (2013.01); *C07D 491/20* (2013.01)

(58) Field of Classification Search
None
See application file for complete search history.

(56) References Cited

U.S. PATENT DOCUMENTS

2006/0276453 A1* 12/2006 Goldberg et al.

OTHER PUBLICATIONS

Goldberg, D.R. et al. "Pyrazinoindolone inhibitors of MAPKAP-K2" Bioorganic & Medicinal Chemistry Letters 18 (2008) pp. 938-941.
International Search Report for PCT/US2010/058271 mailed Feb. 25, 2011.
Xiong, Zhaoming et al. "Synthesis and SAR studies of indole-based MK2 inhibitors" Bioorganic & Medicinal Chemistry Letters 18 (2008) pp. 1994-1999.

* cited by examiner

*Primary Examiner* — Savitha Rao
*Assistant Examiner* — Gregg Polansky
(74) *Attorney, Agent, or Firm* — Michael P. Morris; Usha R. Patel

(57) ABSTRACT

Disclosed are novel compounds which inhibit RSK, methods of making such compounds and pharmaceutical compositions comprising such compounds. Also disclosed are methods of treating RSK2 regulated disorders using compounds of the invention.

3 Claims, No Drawings

HETEROCYCLIC COMPOUNDS CONTAINING AN INDOLE CORE

This application is the national phase entry under 35 U.S.C. §371 of International Application No. PCT/US2010/058271, filed Nov. 30, 2010, which claims priority to U.S. Provisional Application No. 61/267,175, filed Dec. 7, 2009, which are hereby incorporated by reference in their entireties.

TECHNICAL FIELD

The present invention relates to novel compounds which inhibit RSK, methods of making such compounds and their use as medicaments.

BACKGROUND

The p90 ribosomal s6 kinases (RSKs) are a group of serine/threonine kinases that are constituents of the AGC subfamily in the human kinome. Each of the 4 RSK isoforms are products of separate genes and are characterized by 75%-80% sequence identity. While the RSK isoforms are widely distributed among human tissues, their variable tissue expression patterns indicate that they may have distinct physiologic/pathologic roles. The RSK isoforms are activated by growth factors, cytokines, peptide hormones and neurotransmitters that stimulate the Ras-ERK pathway.

RSK regulates numerous biological processes through its phosphorylation of cellular substrates. One important cardiovascular target of RSK is the $Na^+/H^+$ exchanger isoform 1 (NHE1). RSK-mediated phosphorylation of NHE1 at S703 is responsible for increased NHE1 activity following Ang II stimulation, oxidative stress, and myocardial injury. NHE1 is a highly validated target for its role in both ischemia reperfusion (I/R) injury and congestive heart failure. Increased NHE1 activity correlates to the extent of myocardial damage following I/R, while NHE1 inhibitors administered in a prophylactic manner are capable of preserving cardiac function after I/R. Additionally, increased NHE1 activity is observed in isolated myocytes from failing human hearts and in animal models of hypertrophy suggesting chronic activation of this exchanger in cardiovascular pathologies. Despite robust preclinical data linking NHE1 activity to cardiovascular dysfunction, there are currently no approved NHE1 inhibitors on the market. Adverse events, such as headache, eye pain, and paresthesia, were reported in clinical trials, and it is hypothesized that these events are due to direct and complete NHE1 inhibition which impairs its physiological function of maintaining intracellular pH. Based on this safety concern, alternate approaches that do not inhibit basal NHE1 activity but regulate activity during periods of cardiovascular stress may offer an additional safety margin.

In cardiomyocytes RSK has been recognized as a predominant kinase that phosphorylates the c-terminal regulatory region of NHE1 and is required for NHE1 activation in response to I/R, oxidative stress, and receptor activation by Ang II and phenylephrine. Recent studies by Maekawa et al. (Naoya Maekawa, Jun-ichi Abe, Tetsuro Shishido, Seigo Itoh, Bo Ding, Virendra K. Sharma, Shey-Shing Sheu, Burns C. Blaxall and Bradford C. Berk *Circulation* 113:2516-2523, 2006) demonstrated that that RSK was rapidly activated in the heart tissue exposed to I/R. Furthermore, cardiomyocyte specific expression of dominant negative RSK prevented cardiomyocyte apoptosis and improved post MI remodeling and left ventricular function. Importantly, inhibition of RSK activity by means of overexpressing a dominant negative RSK protein decreased agonist-activated NHE1 function without affecting basal, homeostatic NHE1 function. Similarly, the RSK inhibitor, fmk, has been shown to inhibit phosphorylation of NHE1 and phenylephrine-induced enhanced NHE1 activity without affecting basal activity (Friederike Cuello, Andrew K. Snabaitis, Michael S. Cohen, Jack Taunton, and Metin Avkiran, *Mol Pharmacol* 71:799-806, 2007). These findings suggest that inhibition of RSK activity may be an alternative therapeutic strategy by which NHE1 activity can be differentially regulated, effectively preserving basal function and increasing the safety window.

SUMMARY OF THE INVENTION

In one embodiment, the invention relates to a compound selected from those identified as Examples 1 to 239 in Table 1 below, and any combination thereof, and pharmaceutically acceptable salts thereof.

TABLE 1

| Example | Structure | Name |
|---|---|---|
| 1 | 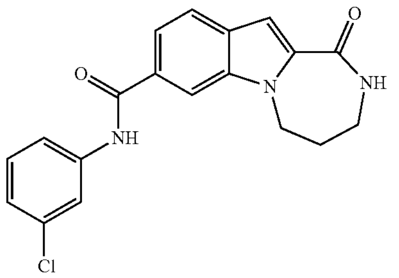 [SMILES: O=C(Nc1cccc(Cl)c1)c1ccc2cc3n(c2c1)CCCNC3=O] | N-(3-chlorophenyl)-1-oxo-2,3,4,5-tetrahydro-1H-[1,4]diazepino[1,2-a]indole-8-carboxamide |
| 2 | 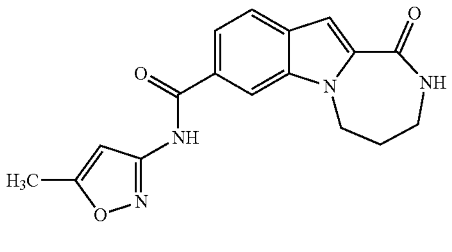 [SMILES: Cc1cc(NC(=O)c2ccc3cc4n(c3c2)CCCNC4=O)no1] | N-(5-methyl-1,2-oxazol-3-yl)-1-oxo-2,3,4,5-tetrahydro-1H-[1,4]diazepino[1,2-a]indole-8-carboxamide |

TABLE 1-continued

| Example | Structure | Name |
| --- | --- | --- |
| 3 | 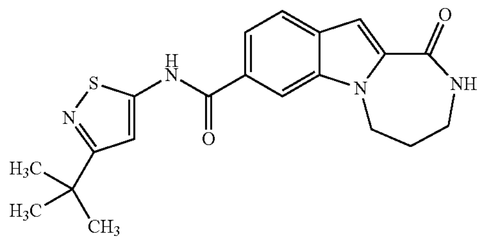 [SMILES: CC(C)(C)c1cc(NC(=O)c2ccc3cc4n(c3c2)CCCNC4=O)sn1] | N-(3-tert-butyl-1,2-thiazol-5-yl)-1-oxo-2,3,4,5-tetrahydro-1H-[1,4]diazepino[1,2-a]indole-8-carboxamide |
| 4 | 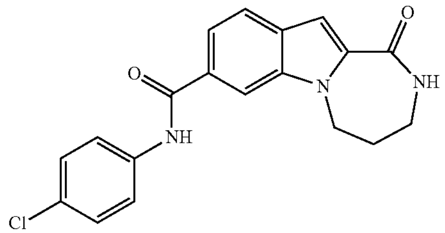 [SMILES: O=C(Nc1ccc(Cl)cc1)c1ccc2cc3n(c2c1)CCCNC3=O] | N-(4-chlorophenyl)-1-oxo-2,3,4,5-tetrahydro-1H-[1,4]diazepino[1,2-a]indole-8-carboxamide |
| 5 | 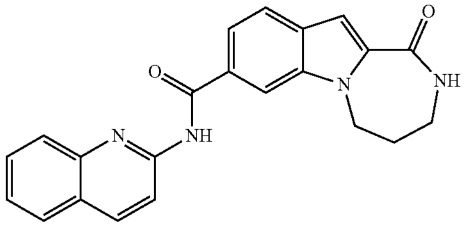 [SMILES: O=C(Nc1ccc2ccccc2n1)c1ccc2cc3n(c2c1)CCCNC3=O] | 1-oxo-N-(quinolin-2-yl)-2,3,4,5-tetrahydro-1H-[1,4]diazepino[1,2-a]indole-8-carboxamide |
| 6 | 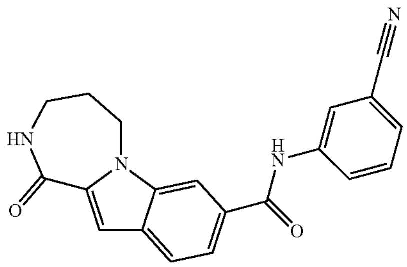 [SMILES: N#Cc1cccc(NC(=O)c2ccc3cc4n(c3c2)CCCNC4=O)c1] | N-(3-cyanophenyl)-1-oxo-2,3,4,5-tetrahydro-1H-[1,4]diazepino[1,2-a]indole-8-carboxamide |
| 7 | 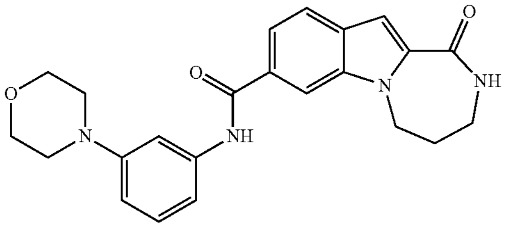 [SMILES: O=C(Nc1cccc(N2CCOCC2)c1)c1ccc2cc3n(c2c1)CCCNC3=O] | N-[3-(morpholin-4-yl)phenyl]-1-oxo-2,3,4,5-tetrahydro-1H-[1,4]diazepino[1,2-a]indole-8-carboxamide |
| 8 | 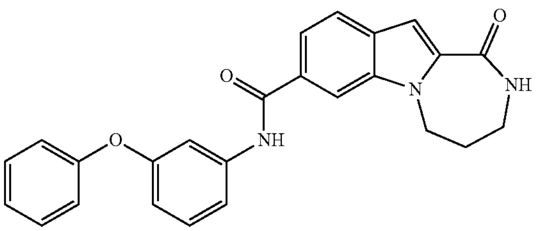 [SMILES: O=C(Nc1cccc(Oc2ccccc2)c1)c1ccc2cc3n(c2c1)CCCNC3=O] | 1-oxo-N-(3-phenoxyphenyl)-2,3,4,5-tetrahydro-1H-[1,4]diazepino[1,2-a]indole-8-carboxamide |

TABLE 1-continued

| Example | Structure | Name |
| --- | --- | --- |
| 9 | 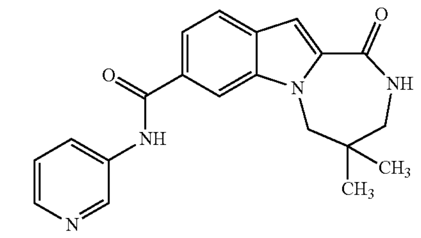 [SMILES: CC1(C)CNC(=O)c2cc3ccc(C(=O)Nc4cccnc4)cc3n2C1] | 4,4-dimethyl-1-oxo-N-(pyridin-3-yl)-2,3,4,5-tetrahydro-1H-[1,4]diazepino[1,2-a]indole-8-carboxamide |
| 10 | 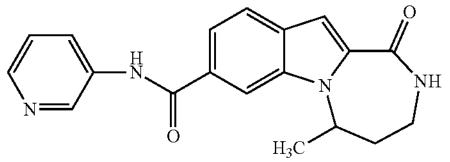 [SMILES: CC1CCNC(=O)c2cc3ccc(C(=O)Nc4cccnc4)cc3n21] | 5-methyl-1-oxo-N-(pyridin-3-yl)-2,3,4,5-tetrahydro-1H-[1,4]diazepino[1,2-a]indole-8-carboxamide |
| 11 | 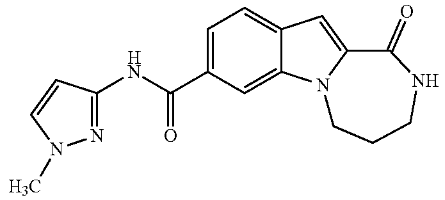 [SMILES: Cn1ccc(NC(=O)c2ccc3cc4n(c3c2)CCCNC4=O)n1] | N-(1-methyl-1H-pyrazol-3-yl)-1-oxo-2,3,4,5-tetrahydro-1H-[1,4]diazepino[1,2-a]indole-8-carboxamide |
| 12 | 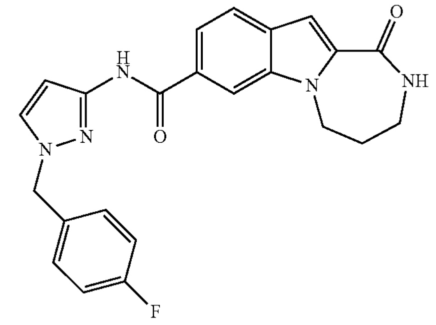 [SMILES: O=C(Nc1ccn(Cc2ccc(F)cc2)n1)c1ccc2cc3n(c2c1)CCCNC3=O] | N-[1-(4-fluorobenzyl)-1H-pyrazol-3-yl]-1-oxo-2,3,4,5-tetrahydro-1H-[1,4]diazepino[1,2-a]indole-8-carboxamide |
| 13 | 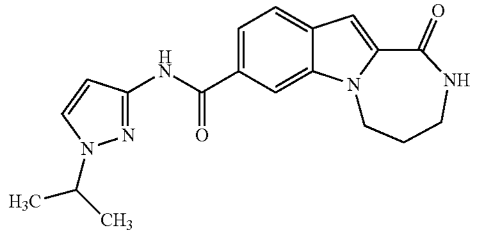 [SMILES: CC(C)n1ccc(NC(=O)c2ccc3cc4n(c3c2)CCCNC4=O)n1] | 1-oxo-N-[1-(propan-2-yl)-1H-pyrazol-3-yl]-2,3,4,5-tetrahydro-1H-[1,4]diazepino[1,2-a]indole-8-carboxamide |
| 14 | 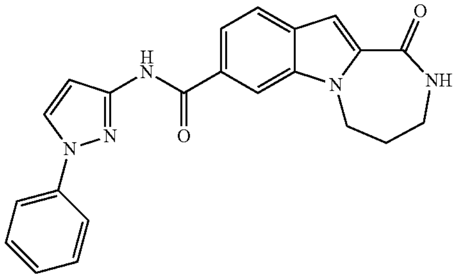 [SMILES: O=C(Nc1ccn(-c2ccccc2)n1)c1ccc2cc3n(c2c1)CCCNC3=O] | 1-oxo-N-(1-phenyl-1H-pyrazol-3-yl)-2,3,4,5-tetrahydro-1H-[1,4]diazepino[1,2-a]indole-8-carboxamide |

TABLE 1-continued

| Example | Structure | Name |
|---|---|---|
| 15 | 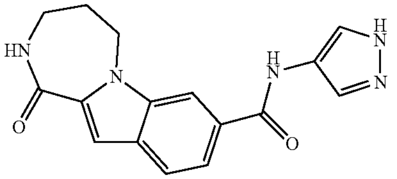 [SMILES: O=C(Nc1cn[nH]c1)c1ccc2cc3n(c2c1)CCCNC3=O] | 1-oxo-N-(1H-pyrazol-4-yl)-2,3,4,5-tetrahydro-1H-[1,4]diazepino[1,2-a]indole-8-carboxamide |
| 16 | 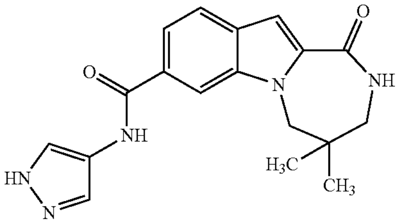 [SMILES: CC1(C)CNC(=O)c2cc3ccc(C(=O)Nc4cn[nH]c4)cc3n2C1] | 4,4-dimethyl-1-oxo-N-(1H-pyrazol-4-yl)-2,3,4,5-tetrahydro-1H-[1,4]diazepino[1,2-a]indole-8-carboxamide |
| 17 | 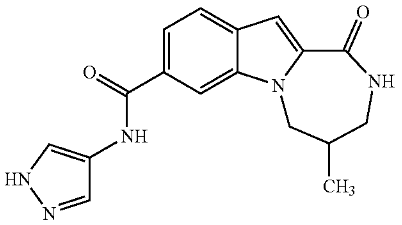 [SMILES: CC1CNC(=O)c2cc3ccc(C(=O)Nc4cn[nH]c4)cc3n2C1] | 4-methyl-1-oxo-N-(1H-pyrazol-4-yl)-2,3,4,5-tetrahydro-1H-[1,4]diazepino[1,2-a]indole-8-carboxamide |
| 18 | 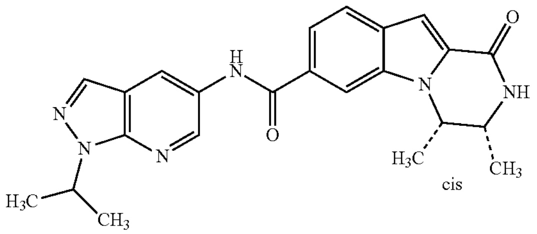 [SMILES: CC(C)n1ncc2cc(NC(=O)c3ccc4cc5n(c4c3)[C@@H](C)[C@@H](C)NC5=O)cnc21] | cis-3,4-dimethyl-1-oxo-N-[1-(propan-2-yl)-1H-pyrazolo[3,4-b]pyridin-5-yl]-1,2,3,4-tetrahydropyrazino[1,2-a]indole-7-carboxamide |
| 19 | 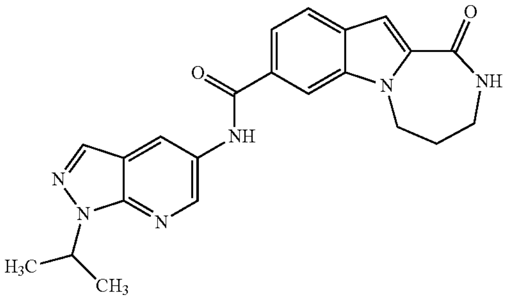 [SMILES: CC(C)n1ncc2cc(NC(=O)c3ccc4cc5n(c4c3)CCCNC5=O)cnc21] | 1-oxo-N-[1-(propan-2-yl)-1H-pyrazolo[3,4-b]pyridin-5-yl]-2,3,4,5-tetrahydro-1H-[1,4]diazepino[1,2-a]indole-8-carboxamide |
| 20 | 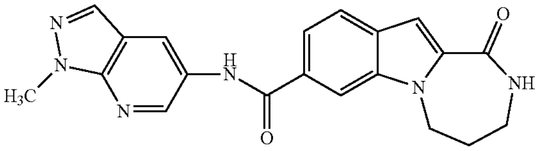 [SMILES: Cn1ncc2cc(NC(=O)c3ccc4cc5n(c4c3)CCCNC5=O)cnc21] | N-(1-methyl-1H-pyrazolo[3,4-b]pyridin-5-yl)-1-oxo-2,3,4,5-tetrahydro-1H-[1,4]diazepino[1,2-a]indole-8-carboxamide |
| 21 | 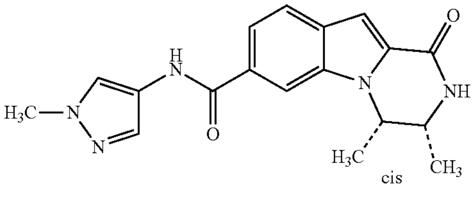 [SMILES: C[C@H]1NC(=O)c2cc3ccc(C(=O)Nc4cnn(C)c4)cc3n2[C@H]1C] | cis-3,4-dimethyl-N-(1-methyl-1H-pyrazol-4-yl)-1-oxo-1,2,3,4-tetrahydropyrazino[1,2-a]indole-7-carboxamide |

TABLE 1-continued

| Example | Structure | Name |
|---|---|---|
| 22 | 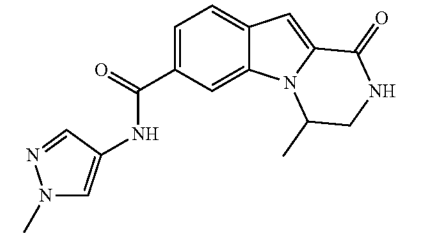 [SMILES: CC1CNC(=O)c2cc3ccc(C(=O)Nc4cnn(C)c4)cc3n21] | 4-methyl-N-(1-methyl-1H-pyrazol-4-yl)-1-oxo-1,2,3,4-tetrahydropyrazino[1,2-a]indole-7-carboxamide |
| 23 | 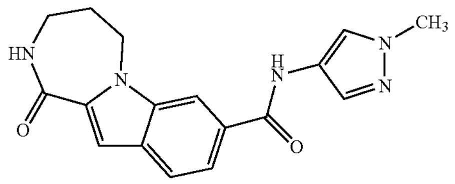 [SMILES: Cn1cc(NC(=O)c2ccc3cc4n(c3c2)CCCNC4=O)cn1] | N-(1-methyl-1H-pyrazol-4-yl)-1-oxo-2,3,4,5-tetrahydro-1H-[1,4]diazepino[1,2-a]indole-8-carboxamide |
| 24 | 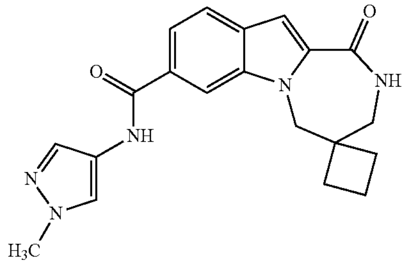 [SMILES: Cn1cc(NC(=O)c2ccc3cc4n(c3c2)CC2(CCC2)CNC4=O)cn1] | N-(1-methyl-1H-pyrazol-4-yl)-1'-oxo-2',3'-dihydro-1'H-spiro[cyclobutane-1,4'-[1,4]diazepino[1,2-a]indole]-8'-carboxamide |
| 25 | 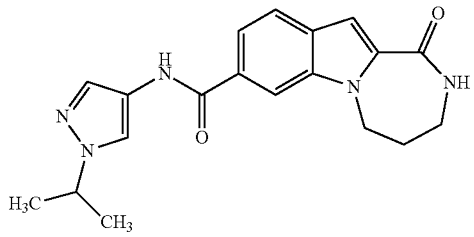 [SMILES: CC(C)n1cc(NC(=O)c2ccc3cc4n(c3c2)CCCNC4=O)cn1] | 1-oxo-N-[1-(propan-2-yl)-1H-pyrazol-4-yl]-2,3,4,5-tetrahydro-1H-[1,4]diazepino[1,2-a]indole-8-carboxamide |
| 26 | 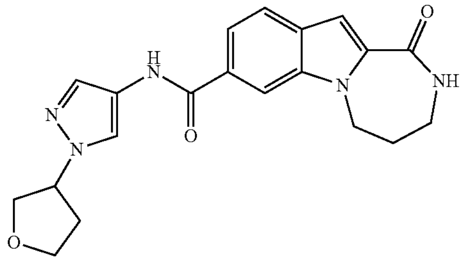 [SMILES: O=C(Nc1cnn(C2CCOC2)c1)c1ccc2cc3n(c2c1)CCCNC3=O] | 1-oxo-N-[1-(tetrahydrofuran-3-yl)-1H-pyrazol-4-yl]-2,3,4,5-tetrahydro-1H-[1,4]diazepino[1,2-a]indole-8-carboxamide |
| 27 | 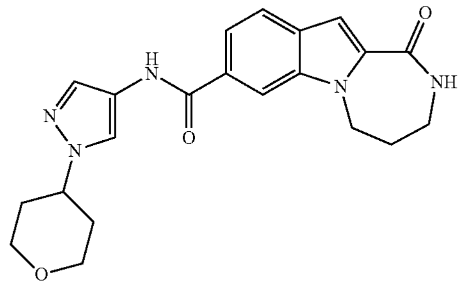 [SMILES: O=C(Nc1cnn(C2CCOCC2)c1)c1ccc2cc3n(c2c1)CCCNC3=O] | 1-oxo-N-[1-(tetrahydro-2H-pyran-4-yl)-1H-pyrazol-4-yl]-2,3,4,5-tetrahydro-1H-[1,4]diazepino[1,2-a]indole-8-carboxamide |

TABLE 1-continued

| Example | Structure | Name |
|---|---|---|
| 28 | 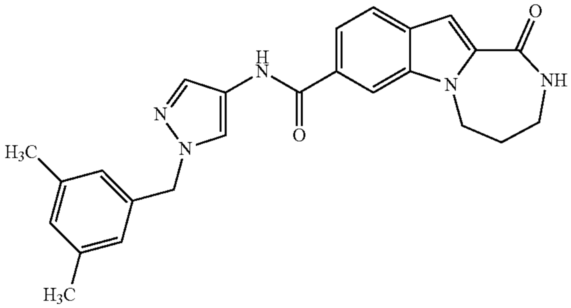 [SMILES: Cc1cc(C)cc(Cn2cc(NC(=O)c3ccc4cc5n(c4c3)CCCNC5=O)cn2)c1] | N-[1-(3,5-dimethylbenzyl)-1H-pyrazol-4-yl]-1-oxo-2,3,4,5-tetrahydro-1H-[1,4]diazepino[1,2-a]indole-8-carboxamide |
| 29 | 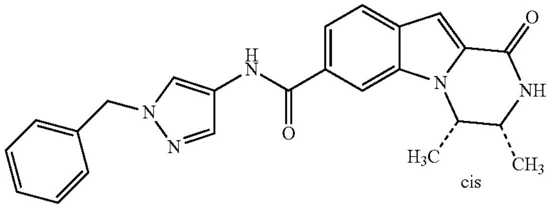 [SMILES: C[C@H]1NC(=O)c2cc3ccc(C(=O)Nc4cnn(Cc5ccccc5)c4)cc3n2[C@H]1C] cis | N-(1-benzyl-1H-pyrazol-4-yl)-cis-3,4-dimethyl-1-oxo-1,2,3,4-tetrahydropyrazino[1,2-a]indole-7-carboxamide |
| 30 | 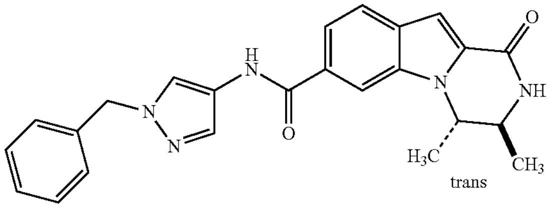 [SMILES: C[C@@H]1NC(=O)c2cc3ccc(C(=O)Nc4cnn(Cc5ccccc5)c4)cc3n2[C@H]1C] trans | N-(1-benzyl-1H-pyrazol-4-yl)-trans-3,4-dimethyl-1-oxo-1,2,3,4-tetrahydropyrazino[1,2-a]indole-7-carboxamide |
| 31 | 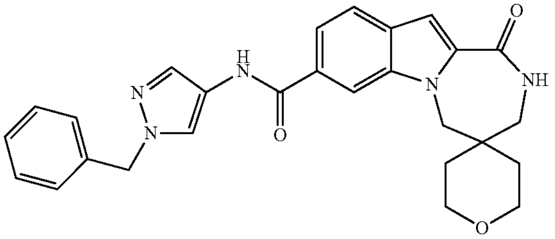 [SMILES: O=C(Nc1cnn(Cc2ccccc2)c1)c1ccc2cc3n(c2c1)CC1(CCOCC1)CNC3=O] | N-(1-benzyl-1H-pyrazol-4-yl)-1-oxo-2,2',3,3',5',6'-hexahydro-1H-spiro[1,4-diazepino[1,2-a]indole-4,4'-pyran]-8-carboxamide |
| 32 | 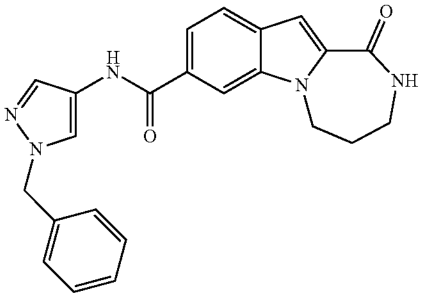 [SMILES: O=C(Nc1cnn(Cc2ccccc2)c1)c1ccc2cc3n(c2c1)CCCNC3=O] | N-(1-benzyl-1H-pyrazol-4-yl)-1-oxo-2,3,4,5-tetrahydro-1H-[1,4]diazepino[1,2-a]indole-8-carboxamide |
| 33 | 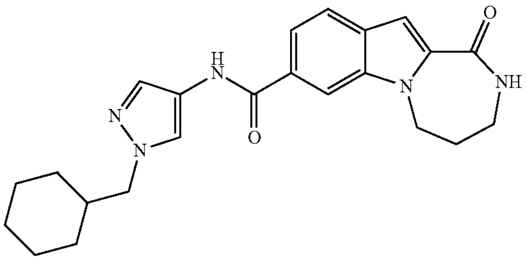 [SMILES: O=C(Nc1cnn(CC2CCCCC2)c1)c1ccc2cc3n(c2c1)CCCNC3=O] | N-[1-(cyclohexylmethyl)-1H-pyrazol-4-yl]-1-oxo-2,3,4,5-tetrahydro-1H-[1,4]diazepino[1,2-a]indole-8-carboxamide |

TABLE 1-continued

| Example | Structure | Name |
|---|---|---|
| 34 | 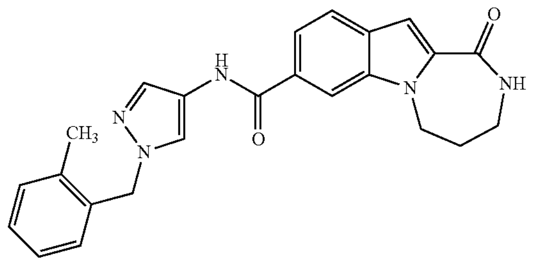 [SMILES: Cc1ccccc1Cn1cc(NC(=O)c2ccc3cc4n(c3c2)CCCNC4=O)cn1] | N-[1-(2-methylbenzyl)-1H-pyrazol-4-yl]-1-oxo-2,3,4,5-tetrahydro-1H-[1,4]diazepino[1,2-a]indole-8-carboxamide |
| 35 | 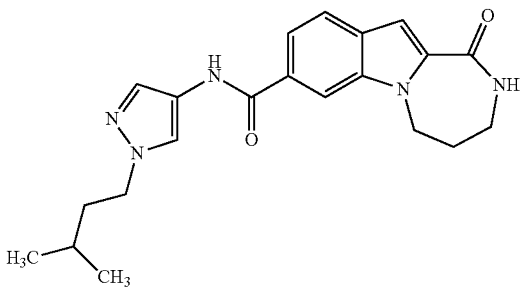 [SMILES: CC(C)CCn1cc(NC(=O)c2ccc3cc4n(c3c2)CCCNC4=O)cn1] | N-[1-(3-methylbutyl)-1H-pyrazol-4-yl]-1-oxo-2,3,4,5-tetrahydro-1H-[1,4]diazepino[1,2-a]indole-8-carboxamide |
| 36 | 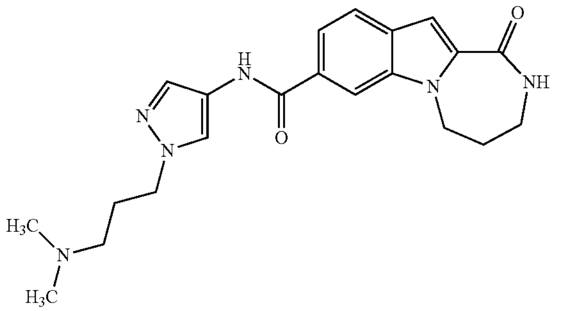 [SMILES: CN(C)CCCn1cc(NC(=O)c2ccc3cc4n(c3c2)CCCNC4=O)cn1] | N-{1-[3-(dimethylamino)propyl]-1H-pyrazol-4-yl}-1-oxo-2,3,4,5-tetrahydro-1H-[1,4]diazepino[1,2-a]indole-8-carboxamide |
| 37 | 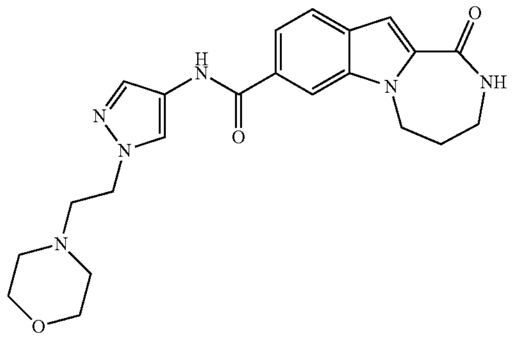 [SMILES: O=C(Nc1cnn(CCN2CCOCC2)c1)c1ccc2cc3n(c2c1)CCCNC3=O] | N-{1-[2-(morpholin-4-yl)ethyl]-1H-pyrazol-4-yl}-1-oxo-2,3,4,5-tetrahydro-1H-[1,4]diazepino[1,2-a]indole-8-carboxamide |
| 38 | 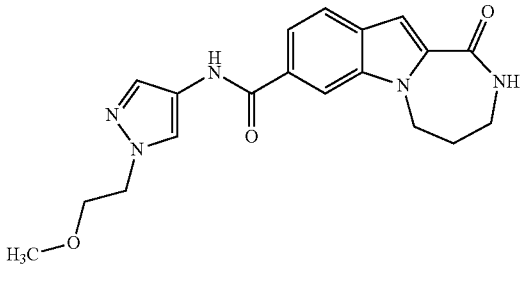 [SMILES: COCCn1cc(NC(=O)c2ccc3cc4n(c3c2)CCCNC4=O)cn1] | N-[1-(2-methoxyethyl)-1H-pyrazol-4-yl]-1-oxo-2,3,4,5-tetrahydro-1H-[1,4]diazepino[1,2-a]indole-8-carboxamide |

TABLE 1-continued

| Example | Structure | Name |
|---|---|---|
| 39 | 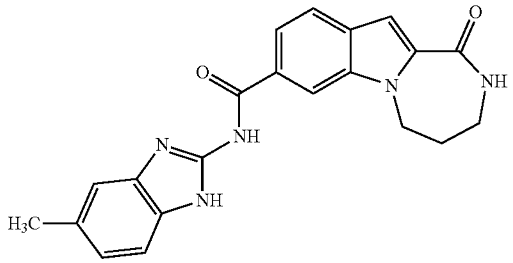 [SMILES: Cc1ccc2[nH]c(NC(=O)c3ccc4cc5n(c4c3)CCCNC5=O)nc2c1] | N-(5-methyl-1H-benzimidazol-2-yl)-1-oxo-2,3,4,5-tetrahydro-1H-[1,4]diazepino[1,2-a]indole-8-carboxamide |
| 40 | 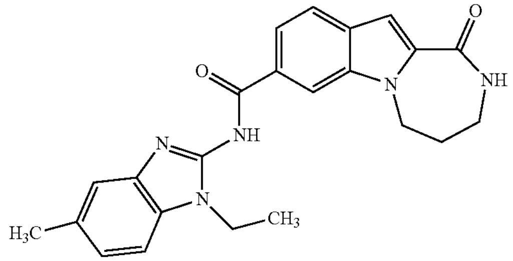 [SMILES: CCn1c(NC(=O)c2ccc3cc4n(c3c2)CCCNC4=O)nc2cc(C)ccc21] | N-(1-ethyl-5-methyl-1H-benzimidazol-2-yl)-1-oxo-2,3,4,5-tetrahydro-1H-[1,4]diazepino[1,2-a]indole-8-carboxamide |
| 41 | 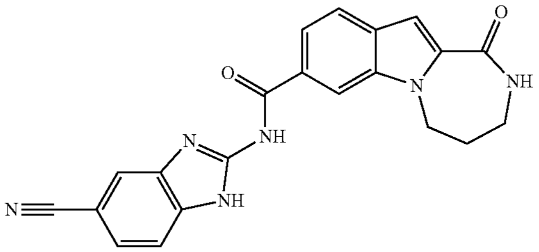 [SMILES: N#Cc1ccc2[nH]c(NC(=O)c3ccc4cc5n(c4c3)CCCNC5=O)nc2c1] | N-(5-cyano-1H-benzimidazol-2-yl)-1-oxo-2,3,4,5-tetrahydro-1H-[1,4]diazepino[1,2-a]indole-8-carboxamide |
| 42 | 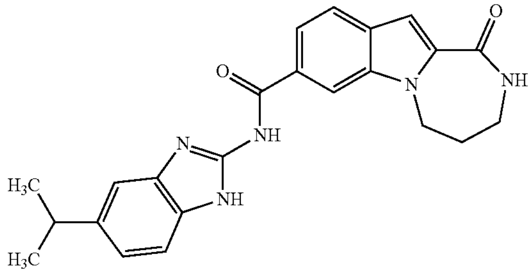 [SMILES: CC(C)c1ccc2[nH]c(NC(=O)c3ccc4cc5n(c4c3)CCCNC5=O)nc2c1] | 1-oxo-N-[5-(propan-2-yl)-1H-benzimidazol-2-yl]-2,3,4,5-tetrahydro-1H-[1,4]diazepino[1,2-a]indole-8-carboxamide |
| 43 | 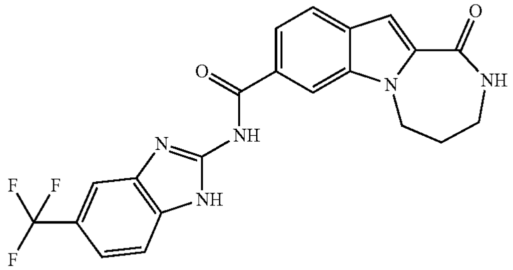 [SMILES: O=C(Nc1nc2cc(C(F)(F)F)ccc2[nH]1)c1ccc2cc3n(c2c1)CCCNC3=O] | 1-oxo-N-[5-(trifluoromethyl)-1H-benzimidazol-2-yl]-2,3,4,5-tetrahydro-1H-[1,4]diazepino[1,2-a]indole-8-carboxamide |
| 44 | 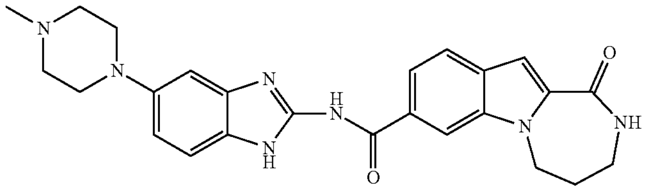 [SMILES: CN1CCN(c2ccc3[nH]c(NC(=O)c4ccc5cc6n(c5c4)CCCNC6=O)nc3c2)CC1] | N-[5-(4-methylpiperazin-1-yl)-1H-benzimidazol-2-yl]-1-oxo-2,3,4,5-tetrahydro-1H-[1,4]diazepino[1,2-a]indole-8-carboxamide |

TABLE 1-continued

| Example | Structure | Name |
|---|---|---|
| 45 | 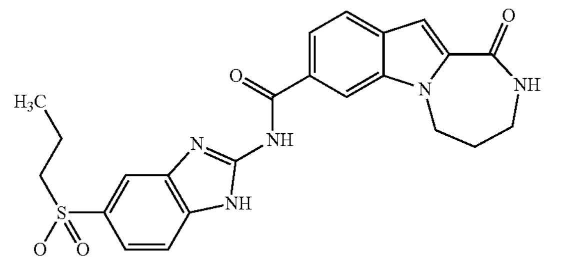 | 1-oxo-N-[5-(propylsulfonyl)-1H-benzimidazol-2-yl]-2,3,4,5-tetrahydro-1H-[1,4]diazepino[1,2-a]indole-8-carboxamide |
| 46 | 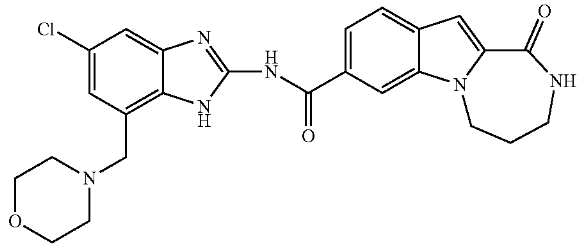 [SMILES: O=C(Nc1nc2cc(Cl)cc(CN3CCOCC3)c2[nH]1)c1ccc2cc3n(c2c1)CCCNC3=O] | N-[5-chloro-7-(morpholin-4-ylmethyl)-1H-benzimidazol-2-yl]-1-oxo-2,3,4,5-tetrahydro-1H-[1,4]diazepino[1,2-a]indole-8-carboxamide |
| 47 | 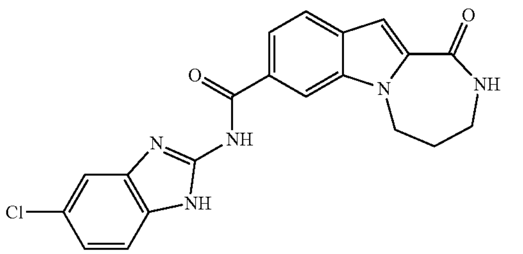 [SMILES: O=C(Nc1nc2cc(Cl)ccc2[nH]1)c1ccc2cc3n(c2c1)CCCNC3=O] | N-(5-chloro-1H-benzimidazol-2-yl)-1-oxo-2,3,4,5-tetrahydro-1H-[1,4]diazepino[1,2-a]indole-8-carboxamide |
| 48 | 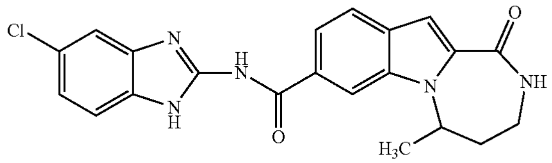 [SMILES: CC1CCNC(=O)c2cc3ccc(C(=O)Nc4nc5cc(Cl)ccc5[nH]4)cc3n21] | N-(5-chloro-1H-benzimidazol-2-yl)-5-methyl-1-oxo-2,3,4,5-tetrahydro-1H-[1,4]diazepino[1,2-a]indole-8-carboxamide |
| 49 | 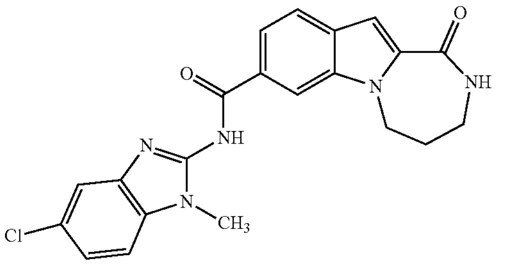 [SMILES: Cn1c(NC(=O)c2ccc3cc4n(c3c2)CCCNC4=O)nc2cc(Cl)ccc21] | N-(5-chloro-1-methyl-1H-benzimidazol-2-yl)-1-oxo-2,3,4,5-tetrahydro-1H-[1,4]diazepino[1,2-a]indole-8-carboxamide |
| 50 | 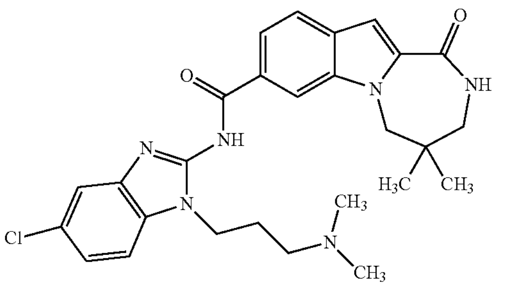 [SMILES: CN(C)CCCn1c(NC(=O)c2ccc3cc4n(c3c2)CC(C)(C)CNC4=O)nc2cc(Cl)ccc21] | N-{5-chloro-1-[3-(dimethylamino)propyl]-1H-benzimidazol-2-yl}-4,4-dimethyl-1-oxo-2,3,4,5-tetrahydro-1H-[1,4]diazepino[1,2-a]indole-8-carboxamide |

TABLE 1-continued

| Example | Structure | Name |
|---|---|---|
| 51 | 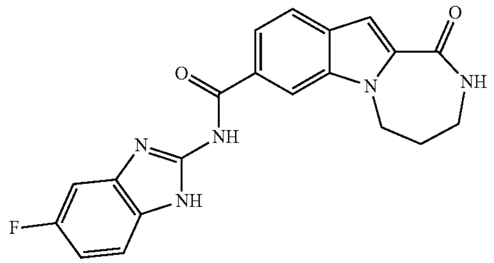 [SMILES: O=C(Nc1nc2cc(F)ccc2[nH]1)c1ccc2cc3n(c2c1)CCCNC3=O] | N-(5-fluoro-1H-benzimidazol-2-yl)-1-oxo-2,3,4,5-tetrahydro-1H-[1,4]diazepino[1,2-a]indole-8-carboxamide |
| 52 | 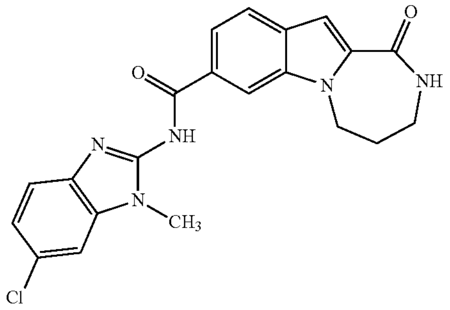 [SMILES: Cn1c(NC(=O)c2ccc3cc4n(c3c2)CCCNC4=O)nc2ccc(Cl)cc21] | N-(6-chloro-1-methyl-1H-benzimidazol-2-yl)-1-oxo-2,3,4,5-tetrahydro-1H-[1,4]diazepino[1,2-a]indole-8-carboxamide |
| 53 | 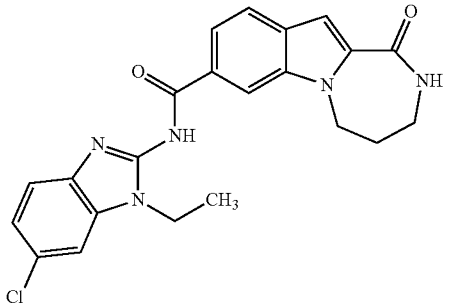 [SMILES: CCn1c(NC(=O)c2ccc3cc4n(c3c2)CCCNC4=O)nc2ccc(Cl)cc21] | N-(6-chloro-1-ethyl-1H-benzimidazol-2-yl)-1-oxo-2,3,4,5-tetrahydro-1H-[1,4]diazepino[1,2-a]indole-8-carboxamide |
| 54 | 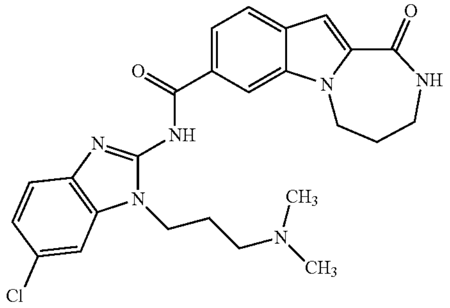 [SMILES: CN(C)CCCn1c(NC(=O)c2ccc3cc4n(c3c2)CCCNC4=O)nc2ccc(Cl)cc21] | N-{6-chloro-1-[3-(dimethylamino)propyl]-1H-benzimidazol-2-yl}-1-oxo-2,3,4,5-tetrahydro-1H-[1,4]diazepino[1,2-a]indole-8-carboxamide |
| 55 | 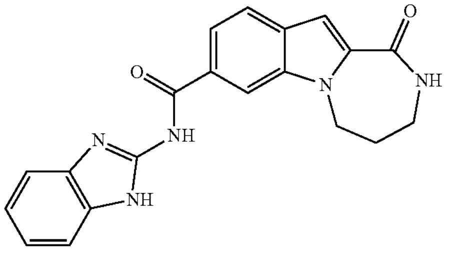 [SMILES: O=C(Nc1nc2ccccc2[nH]1)c1ccc2cc3n(c2c1)CCCNC3=O] | N-(1H-benzimidazol-2-yl)-1-oxo-2,3,4,5-tetrahydro-1H-[1,4]diazepino[1,2-a]indole-8-carboxamide |

TABLE 1-continued

| Example | Structure | Name |
|---|---|---|
| 56 | 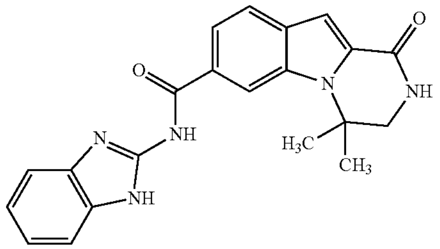 [SMILES: CC1(C)CNC(=O)c2cc3ccc(C(=O)Nc4nc5ccccc5[nH]4)cc3n21] | N-(1H-benzimidazol-2-yl)-4,4-dimethyl-1-oxo-1,2,3,4-tetrahydropyrazino[1,2-a]indole-7-carboxamide |
| 57 | 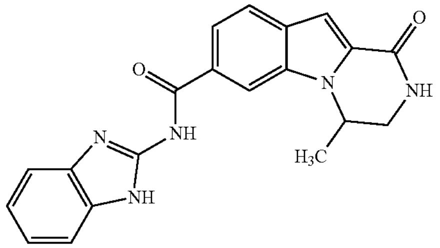 [SMILES: CC1CNC(=O)c2cc3ccc(C(=O)Nc4nc5ccccc5[nH]4)cc3n21] | N-(1H-benzimidazol-2-yl)-4-methyl-1-oxo-1,2,3,4-tetrahydropyrazino[1,2-a]indole-7-carboxamide |
| 58 | 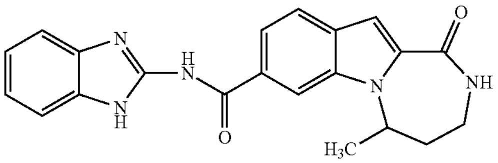 | N-(1H-benzimidazol-2-yl)-5-methyl-1-oxo-2,3,4,5-tetrahydro-1H-[1,4]diazepino[1,2-a]indole-8-carboxamide |
| 59 | 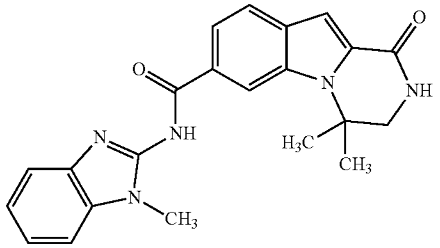 [SMILES: Cn1c(NC(=O)c2ccc3cc4n(c3c2)C(C)(C)CNC4=O)nc2ccccc21] | 4,4-dimethyl-N-(1-methyl-1H-benzimidazol-2-yl)-1-oxo-1,2,3,4-tetrahydropyrazino[1,2-a]indole-7-carboxamide |
| 60 | 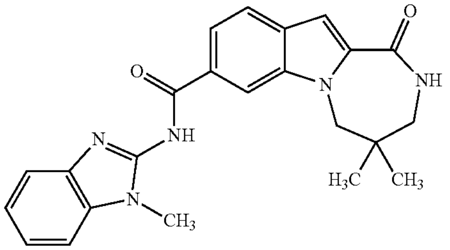 [SMILES: Cn1c(NC(=O)c2ccc3cc4n(c3c2)CC(C)(C)CNC4=O)nc2ccccc21] | 4,4-dimethyl-N-(1-methyl-1H-benzimidazol-2-yl)-1-oxo-2,3,4,5-tetrahydro-1H-[1,4]diazepino[1,2-a]indole-8-carboxamide |
| 61 | 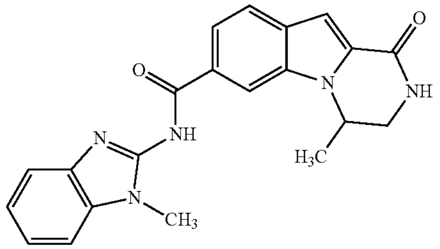 [SMILES: CC1CNC(=O)c2cc3ccc(C(=O)Nc4nc5ccccc5n4C)cc3n21] | 4-methyl-N-(1-methyl-1H-benzimidazol-2-yl)-1-oxo-1,2,3,4-tetrahydropyrazino[1,2-a]indole-7-carboxamide |

TABLE 1-continued

| Example | Structure | Name |
| --- | --- | --- |
| 62 | 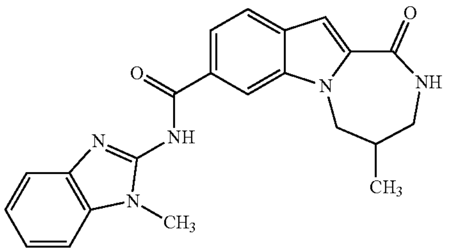 [SMILES: CC1CNC(=O)c2cc3ccc(C(=O)Nc4nc5ccccc5n4C)cc3n2C1] | 4-methyl-N-(1-methyl-1H-benzimidazol-2-yl)-1-oxo-2,3,4,5-tetrahydro-1H-[1,4]diazepino[1,2-a]indole-8-carboxamide |
| 63 | 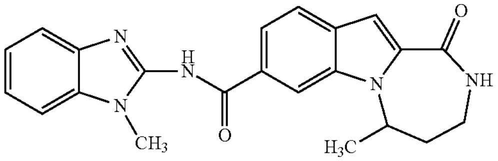 [SMILES: CC1CCNC(=O)c2cc3ccc(C(=O)Nc4nc5ccccc5n4C)cc3n21] | 5-methyl-N-(1-methyl-1H-benzimidazol-2-yl)-1-oxo-2,3,4,5-tetrahydro-1H-[1,4]diazepino[1,2-a]indole-8-carboxamide |
| 64 | 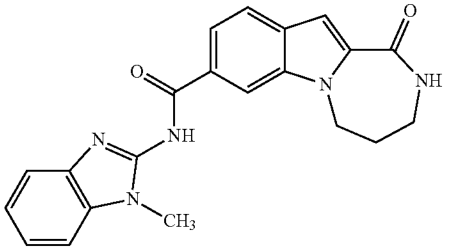 [SMILES: Cn1c(NC(=O)c2ccc3cc4n(c3c2)CCCNC4=O)nc2ccccc21] | N-(1-methyl-1H-benzimidazol-2-yl)-1-oxo-2,3,4,5-tetrahydro-1H-[1,4]diazepino[1,2-a]indole-8-carboxamide |
| 65 | 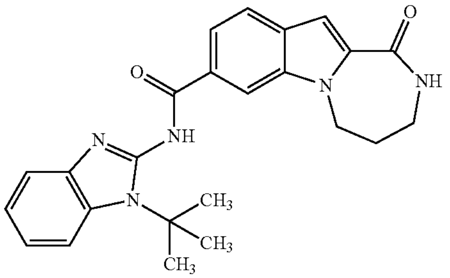 [SMILES: CC(C)(C)n1c(NC(=O)c2ccc3cc4n(c3c2)CCCNC4=O)nc2ccccc21] | N-(1-tert-butyl-1H-benzimidazol-2-yl)-1-oxo-2,3,4,5-tetrahydro-1H-[1,4]diazepino[1,2-a]indole-8-carboxamide |
| 66 | 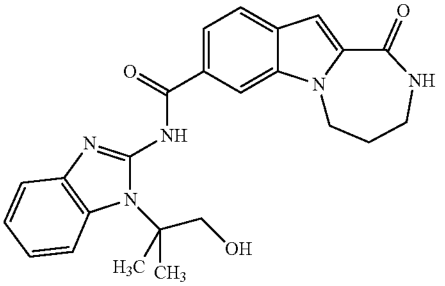 [SMILES: CC(C)(CO)n1c(NC(=O)c2ccc3cc4n(c3c2)CCCNC4=O)nc2ccccc21] | N-[1-(1-hydroxy-2-methylpropan-2-yl)-1H-benzimidazol-2-yl]-1-oxo-2,3,4,5-tetrahydro-1H-[1,4]diazepino[1,2-a]indole-8-carboxamide |
| 67 | 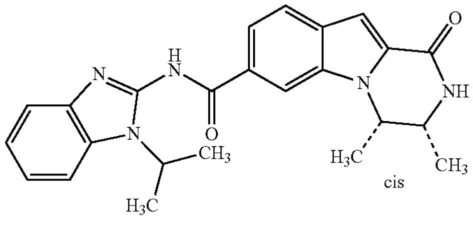 [SMILES: CC(C)n1c(NC(=O)c2ccc3cc4n(c3c2)[C@@H](C)[C@@H](C)NC4=O)nc2ccccc21] | cis-3,4-dimethyl-1-oxo-N-[1-(propan-2-yl)-1H-benzimidazol-2-yl]-1,2,3,4-tetrahydropyrazino[1,2-a]indole-7-carboxamide |

TABLE 1-continued

| Example | Structure | Name |
|---|---|---|
| 68 | 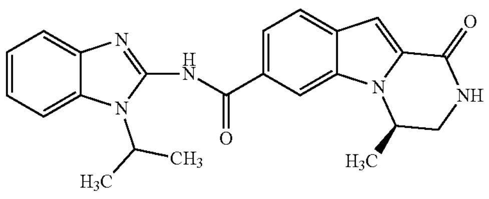 Chiral | (4R)-4-methyl-1-oxo-N-[1-(propan-2-yl)-1H-benzimidazol-2-yl]-1,2,3,4-tetrahydropyrazino[1,2-a]indole-7-carboxamide |
| 69 | 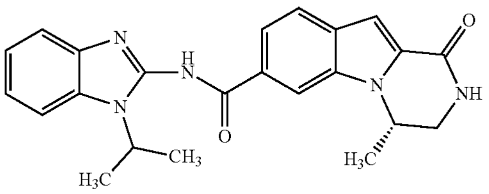 Chiral | (4S)-4-methyl-1-oxo-N-[1-(propan-2-yl)-1H-benzimidazol-2-yl]-1,2,3,4-tetrahydropyrazino[1,2-a]indole-7-carboxamide |
| 70 | 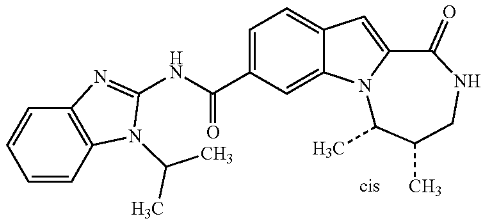 [SMILES: CC(C)n1c(NC(=O)c2ccc3cc4n(c3c2)[C@@H](C)[C@@H](C)CNC4=O)nc2ccccc21] | cis-4,5-dimethyl-1-oxo-N-[1-(propan-2-yl)-1H-benzimidazol-2-yl]-2,3,4,5-tetrahydro-1H-[1,4]diazepino[1,2-a]indole-8-carboxamide |
| 71 | 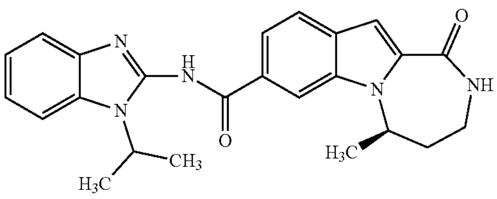 Chiral | (5R)-5-methyl-1-oxo-N-[1-(propan-2-yl)-1H-benzimidazol-2-yl]-2,3,4,5-tetrahydro-1H-[1,4]diazepino[1,2-a]indole-8-carboxamide |
| 72 | 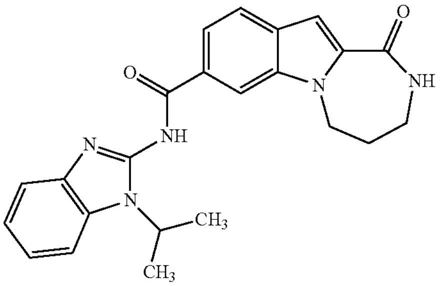 [SMILES: CC(C)n1c(NC(=O)c2ccc3cc4n(c3c2)CCCNC4=O)nc2ccccc21] | 1-oxo-N-[1-(propan-2-yl)-1H-benzimidazol-2-yl]-2,3,4,5-tetrahydro-1H-[1,4]diazepino[1,2-a]indole-8-carboxamide |
| 73 | 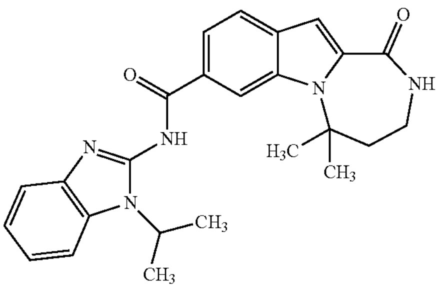 [SMILES: CC(C)n1c(NC(=O)c2ccc3cc4n(c3c2)C(C)(C)CCNC4=O)nc2ccccc21] | 4,4-dimethyl-1-oxo-N-[1-(propan-2-yl)-1H-benzimidazol-2-yl]-1,2,3,4-tetrahydropyrazino[1,2-a]indole-7-carboxamide |

TABLE 1-continued

| Example | Structure | Name |
|---|---|---|
| 74 | 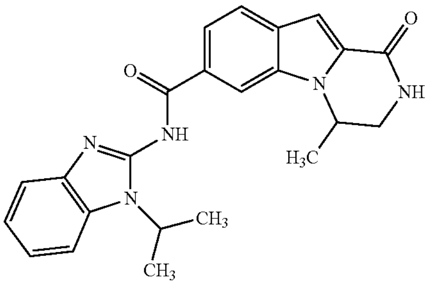 [SMILES: CC(C)n1c(NC(=O)c2ccc3cc4n(c3c2)C(C)CNC4=O)nc2ccccc21] | 4-methyl-1-oxo-N-[1-(propan-2-yl)-1H-benzimidazol-2-yl]-1,2,3,4-tetrahydropyrazino[1,2-a]indole-7-carboxamide |
| 75 | 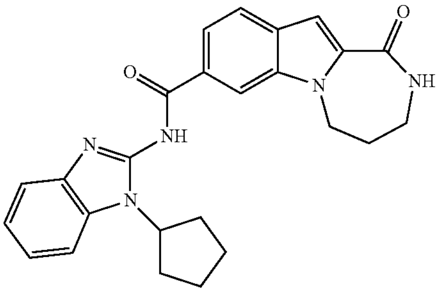 [SMILES: O=C(Nc1nc2ccccc2n1C1CCCC1)c1ccc2cc3n(c2c1)CCCNC3=O] | N-(1-cyclopentyl-1H-benzimidazol-2-yl)-1-oxo-2,3,4,5-tetrahydro-1H-[1,4]diazepino[1,2-a]indole-8-carboxamide |
| 76 | 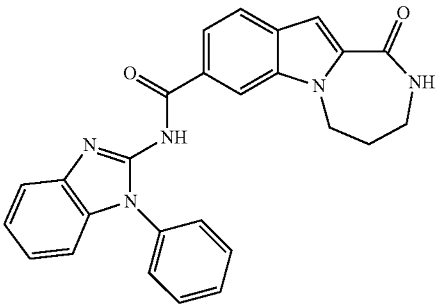 [SMILES: O=C(Nc1nc2ccccc2n1-c1ccccc1)c1ccc2cc3n(c2c1)CCCNC3=O] | 1-oxo-N-(1-phenyl-1H-benzimidazol-2-yl)-2,3,4,5-tetrahydro-1H-[1,4]diazepino[1,2-a]indole-8-carboxamide |
| 77 | 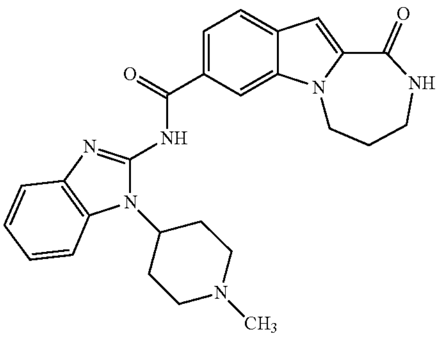 [SMILES: CN1CCC(n2c(NC(=O)c3ccc4cc5n(c4c3)CCCNC5=O)nc3ccccc32)CC1] | N-[1-(1-methylpiperidin-4-yl)-1H-benzimidazol-2-yl]-1-oxo-2,3,4,5-tetrahydro-1H-[1,4]diazepino[1,2-a]indole-8-carboxamide |

TABLE 1-continued

| Example | Structure | Name |
|---|---|---|
| 78 | 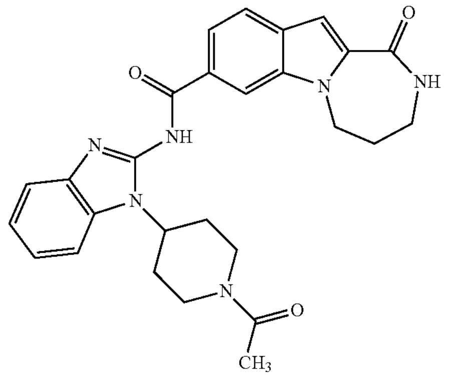 [SMILES: CC(=O)N1CCC(n2c(NC(=O)c3ccc4cc5n(c4c3)CCCNC5=O)nc3ccccc32)CC1] | N-[1-(1-acetylpiperidin-4-yl)-1H-benzimidazol-2-yl]-1-oxo-2,3,4,5-tetrahydro-1H-[1,4]diazepino[1,2-a]indole-8-carboxamide |
| 79 | 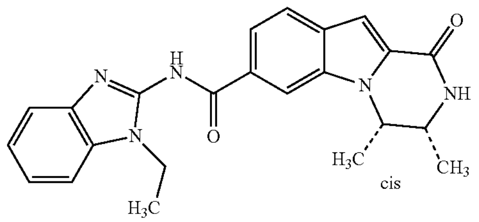 [SMILES: CCn1c(NC(=O)c2ccc3cc4n(c3c2)[C@@H](C)[C@@H](C)NC4=O)nc2ccccc21] | N-(1-ethyl-1H-benzimidazol-2-yl)-cis-3,4-dimethyl-1-oxo-1,2,3,4-tetrahydropyrazino[1,2-a]indole-7-carboxamide |
| 80 | 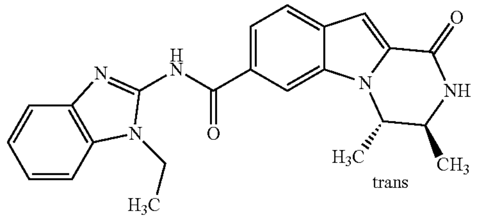 [SMILES: CCn1c(NC(=O)c2ccc3cc4n(c3c2)[C@@H](C)[C@H](C)NC4=O)nc2ccccc21] | N-(1-ethyl-1H-benzimidazol-2-yl)-trans-3,4-dimethyl-1-oxo-1,2,3,4-tetrahydropyrazino[1,2-a]indole-7-carboxamide |
| 81 | 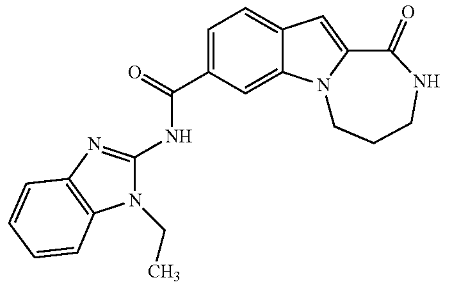 [SMILES: CCn1c(NC(=O)c2ccc3cc4n(c3c2)CCCNC4=O)nc2ccccc21] | N-(1-ethyl-1H-benzimidazol-2-yl)-1-oxo-2,3,4,5-tetrahydro-1H-[1,4]diazepino[1,2-a]indole-8-carboxamide |
| 82 | 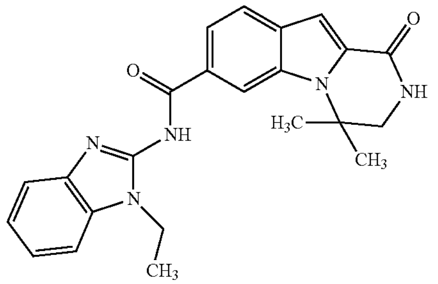 [SMILES: CCn1c(NC(=O)c2ccc3cc4n(c3c2)C(C)(C)CNC4=O)nc2ccccc21] | N-(1-ethyl-1H-benzimidazol-2-yl)-4,4-dimethyl-1-oxo-1,2,3,4-tetrahydropyrazino[1,2-a]indole-7-carboxamide |

TABLE 1-continued

| Example | Structure | Name |
|---|---|---|
| 83 | 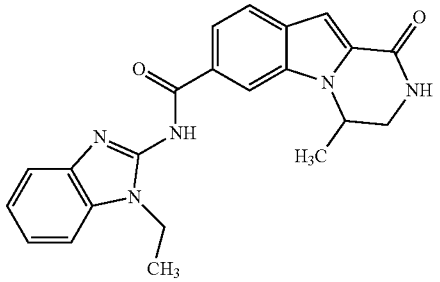 [SMILES: CCn1c(NC(=O)c2ccc3cc4n(c3c2)C(C)CNC4=O)nc2ccccc21] | N-(1-ethyl-1H-benzimidazol-2-yl)-4-methyl-1-oxo-1,2,3,4-tetrahydropyrazino[1,2-a]indole-7-carboxamide |
| 84 | 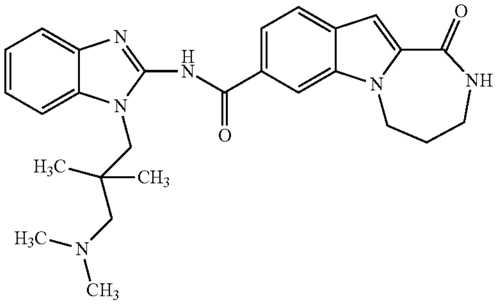 [SMILES: CN(C)CC(C)(C)Cn1c(NC(=O)c2ccc3cc4n(c3c2)CCCNC4=O)nc2ccccc21] | N-{1-[3-(dimethylamino)-2,2-dimethylpropyl]-1H-benzimidazol-2-yl}-1-oxo-2,3,4,5-tetrahydro-1H-[1,4]diazepino[1,2-a]indole-8-carboxamide |
| 85 | 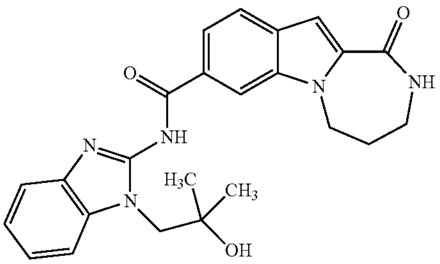 [SMILES: CC(C)(O)Cn1c(NC(=O)c2ccc3cc4n(c3c2)CCCNC4=O)nc2ccccc21] | N-[1-(2-hydroxy-2-methylpropyl)-1H-benzimidazol-2-yl]-1-oxo-2,3,4,5-tetrahydro-1H-[1,4]diazepino[1,2-a]indole-8-carboxamide |
| 86 | 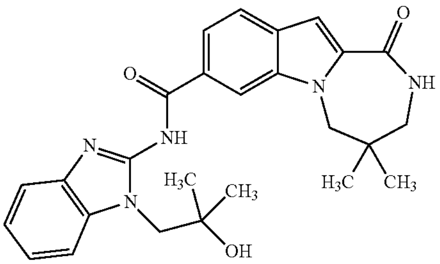 [SMILES: CC(C)(O)Cn1c(NC(=O)c2ccc3cc4n(c3c2)CC(C)(C)CNC4=O)nc2ccccc21] | N-[1-(2-hydroxy-2-methylpropyl)-1H-benzimidazol-2-yl]-4,4-dimethyl-1-oxo-2,3,4,5-tetrahydro-1H-[1,4]diazepino[1,2-a]indole-8-carboxamide |
| 87 | 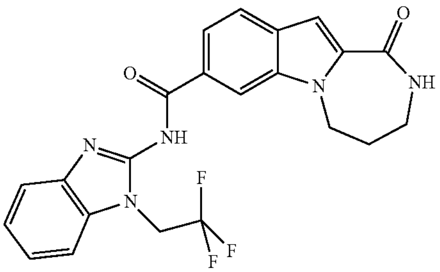 [SMILES: O=C(Nc1nc2ccccc2n1CC(F)(F)F)c1ccc2cc3n(c2c1)CCCNC3=O] | 1-oxo-N-[1-(2,2,2-trifluoroethyl)-1H-benzimidazol-2-yl]-2,3,4,5-tetrahydro-1H-[1,4]diazepino[1,2-a]indole-8-carboxamide |

TABLE 1-continued

| Example | Structure | Name |
|---|---|---|
| 88 | 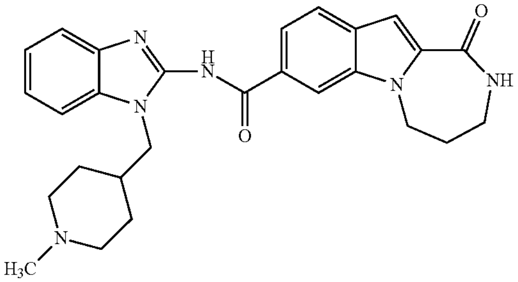 [SMILES: CN1CCC(Cn2c(NC(=O)c3ccc4cc5n(c4c3)CCCNC5=O)nc3ccccc32)CC1] | N-{1-[(1-methylpiperidin-4-yl)methyl]-1H-benzimidazol-2-yl}-1-oxo-2,3,4,5-tetrahydro-1H-[1,4]diazepino[1,2-a]indole-8-carboxamide |
| 89 | 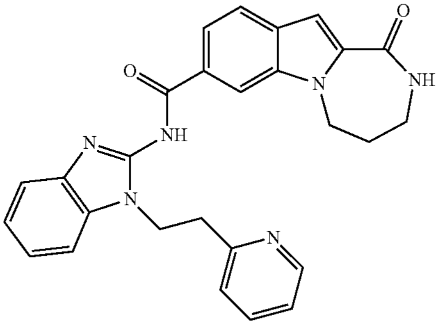 [SMILES: O=C(Nc1nc2ccccc2n1CCc1ccccn1)c1ccc2cc3n(c2c1)CCCNC3=O] | 1-oxo-N-{1-[2-(pyridin-2-yl)ethyl]-1H-benzimidazol-2-yl}-2,3,4,5-tetrahydro-1H-[1,4]diazepino[1,2-a]indole-8-carboxamide |
| 90 | 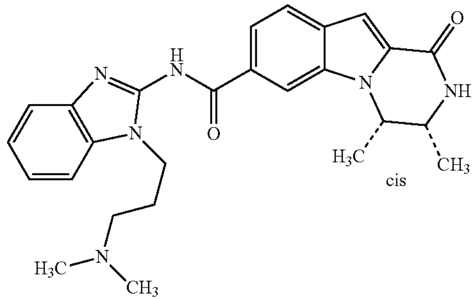 [SMILES: C[C@H]1NC(=O)c2cc3ccc(C(=O)Nc4nc5ccccc5n4CCCN(C)C)cc3n2[C@H]1C] | N-{1-[3-(dimethylamino)propyl]-1H-benzimidazol-2-yl}-cis-3,4-dimethyl-1-oxo-1,2,3,4-tetrahydropyrazino[1,2-a]indole-7-carboxamide |
| 91 | 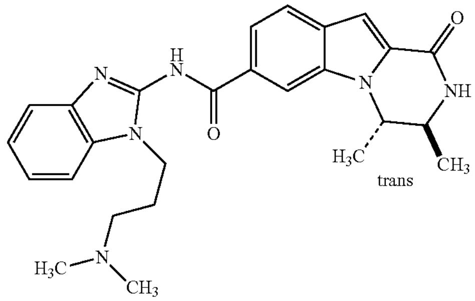 [SMILES: C[C@@H]1NC(=O)c2cc3ccc(C(=O)Nc4nc5ccccc5n4CCCN(C)C)cc3n2[C@H]1C] | N-{1-[3-(dimethylamino)propyl]-1H-benzimidazol-2-yl}-trans-3,4-dimethyl-1-oxo-1,2,3,4-tetrahydropyrazino[1,2-a]indole-7-carboxamide |
| 92 | 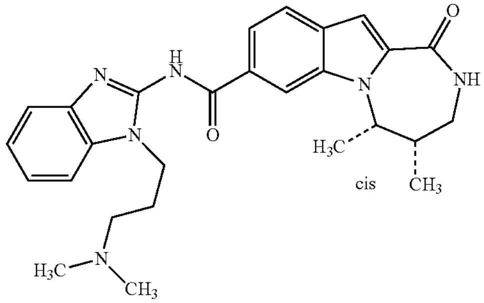 [SMILES: C[C@H]1CNC(=O)c2cc3ccc(C(=O)Nc4nc5ccccc5n4CCCN(C)C)cc3n2[C@H]1C] | N-{1-[3-(dimethylamino)propyl]-1H-benzimidazol-2-yl}-cis-4,5-dimethyl-1-oxo-2,3,4,5-tetrahydro-1H-[1,4]diazepino[1,2-a]indole-8-carboxamide |

TABLE 1-continued

| Example | Structure | Name |
|---|---|---|
| 93 | 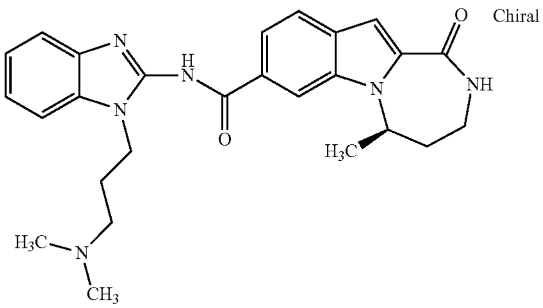 [SMILES: C[C@@H]1CCNC(=O)c2cc3ccc(C(=O)Nc4nc5ccccc5n4CCCN(C)C)cc3n21] Chiral | (5R)-N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide |
| 94 | 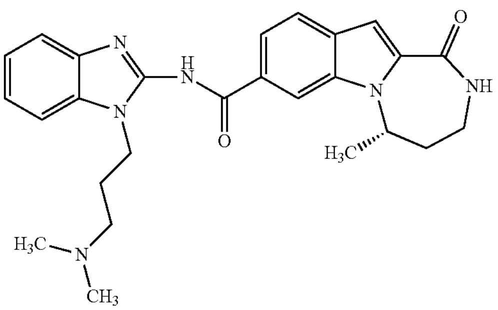 Chiral | (5S)-N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide |
| 95 | 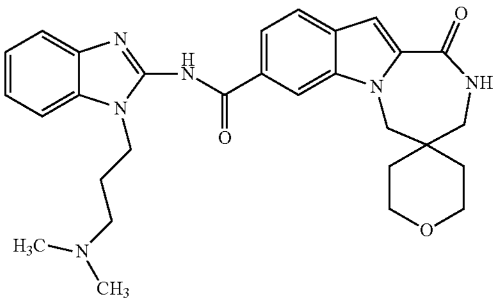 [SMILES: CN(C)CCCn1c(NC(=O)c2ccc3cc4n(c3c2)CC2(CCOCC2)CNC4=O)nc2ccccc21] | N-{1-[3-(dimethylamino)propyl]-1H-benzimidazol-2-yl}-1-oxo-2,2',3,3',5',6'-hexahydro-1H-spiro[1,4-diazepino[1,2-a]indole-4,4'-pyran]-8-carboxamide |
| 96 | 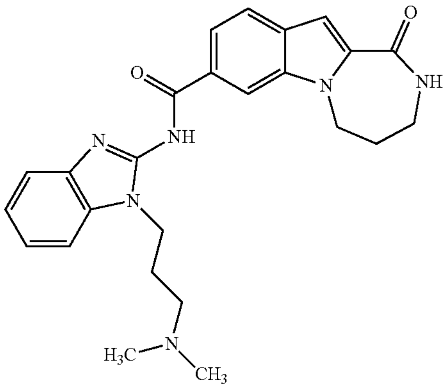 [SMILES: CN(C)CCCn1c(NC(=O)c2ccc3cc4n(c3c2)CCCNC4=O)nc2ccccc21] | N-{1-[3-(dimethylamino)propyl]-1H-benzimidazol-2-yl}-1-oxo-2,3,4,5-tetrahydro-1H-[1,4]diazepino[1,2-a]indole-8-carboxamide |

TABLE 1-continued

| Example | Structure | Name |
|---|---|---|
| 97 | 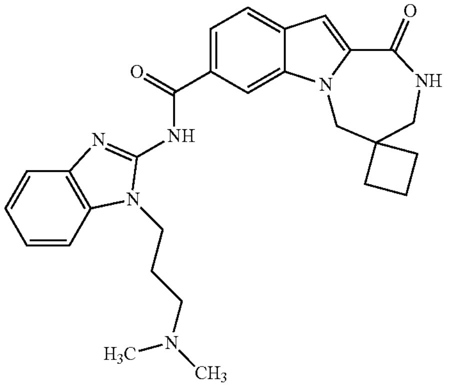 [SMILES: CN(C)CCCn1c(NC(=O)c2ccc3cc4n(c3c2)CC2(CCC2)CNC4=O)nc2ccccc21] | N-{1-[3-(dimethylamino)propyl]-1H-benzimidazol-2-yl}-1'-oxo-2',3'-dihydro-1'H-spiro[cyclobutane-1,4'-[1,4]diazepino[1,2-a]indole]-8'-carboxamide |
| 98 | 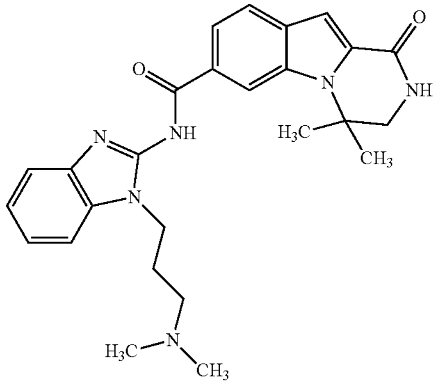 [SMILES: CN(C)CCCn1c(NC(=O)c2ccc3cc4n(c3c2)C(C)(C)CNC4=O)nc2ccccc21] | N-{1-[3-(dimethylamino)propyl]-1H-benzimidazol-2-yl}-4,4-dimethyl-1-oxo-1,2,3,4-tetrahydropyrazino[1,2-a]indole-7-carboxamide |
| 99 | 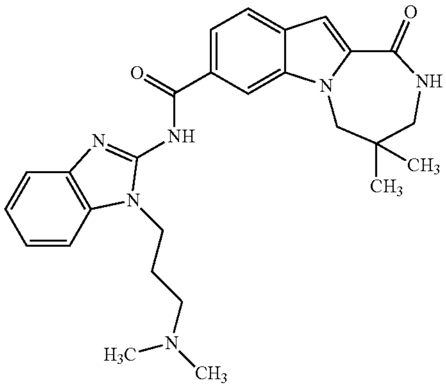 [SMILES: CN(C)CCCn1c(NC(=O)c2ccc3cc4n(c3c2)CC(C)(C)CNC4=O)nc2ccccc21] | N-{1-[3-(dimethylamino)propyl]-1H-benzimidazol-2-yl}-4,4-dimethyl-1-oxo-2,3,4,5-tetrahydro-1H-[1,4]diazepino[1,2-a]indole-8-carboxamide |
| 100 | 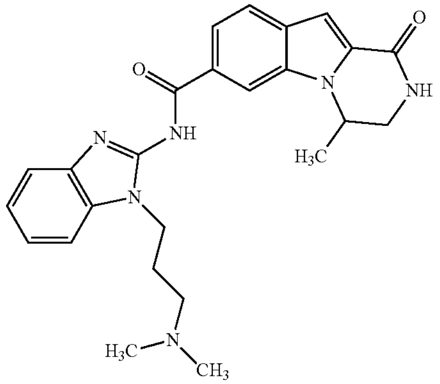 [SMILES: CC1CNC(=O)c2cc3ccc(C(=O)Nc4nc5ccccc5n4CCCN(C)C)cc3n21] | N-{1-[3-(dimethylamino)propyl]-1H-benzimidazol-2-yl}-4-methyl-1-oxo-1,2,3,4-tetrahydropyrazino[1,2-a]indole-7-carboxamide |

TABLE 1-continued

| Example | Structure | Name |
|---|---|---|
| 101 | 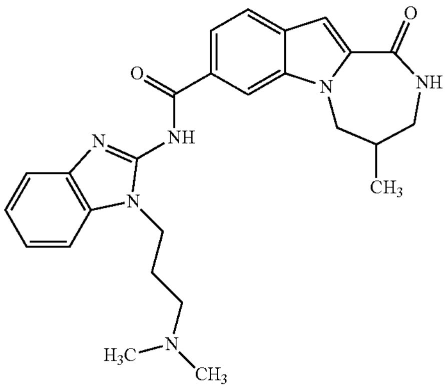 [SMILES: CC1CNC(=O)c2cc3ccc(C(=O)Nc4nc5ccccc5n4CCCN(C)C)cc3n2C1] | N-{1-[3-(dimethylamino)propyl]-1H-benzimidazol-2-yl}-4-methyl-1-oxo-2,3,4,5-tetrahydro-1H-[1,4]diazepino[1,2-a]indole-8-carboxamide |
| 102 | 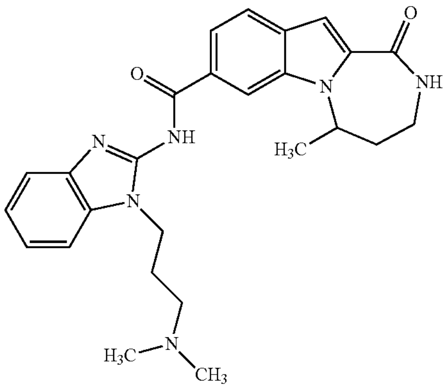 [SMILES: CC1CCNC(=O)c2cc3ccc(C(=O)Nc4nc5ccccc5n4CCCN(C)C)cc3n21] | N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide |
| 103 | 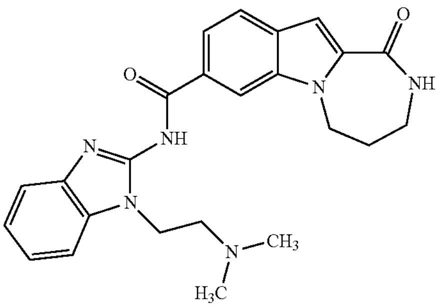 [SMILES: CN(C)CCn1c(NC(=O)c2ccc3cc4n(c3c2)CCCNC4=O)nc2ccccc21] | N-{1-[2-(dimethylamino)ethyl]-1H-benzimidazol-2-yl}-1-oxo-2,3,4,5-tetrahydro-1H-[1,4]diazepino[1,2-a]indole-8-carboxamide |
| 104 | 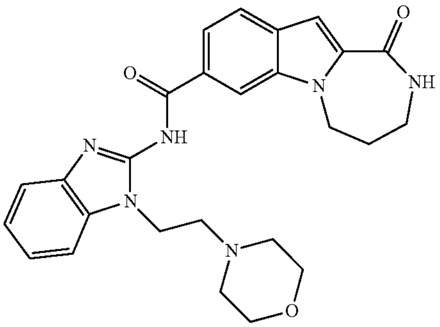 [SMILES: O=C(Nc1nc2ccccc2n1CCN1CCOCC1)c1ccc2cc3n(c2c1)CCCNC3=O] | N-{1-[2-(morpholin-4-yl)ethyl]-1H-benzimidazol-2-yl}-1-oxo-2,3,4,5-tetrahydro-1H-[1,4]diazepino[1,2-a]indole-8-carboxamide |

TABLE 1-continued

| Example | Structure | Name |
|---|---|---|
| 105 | 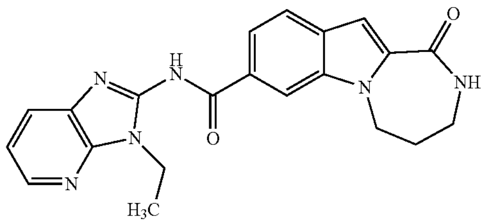 [SMILES: CCn1c(NC(=O)c2ccc3cc4n(c3c2)CCCNC4=O)nc2cccnc21] | N-(3-ethyl-3H-imidazo[4,5-b]pyridin-2-yl)-1-oxo-2,3,4,5-tetrahydro-1H-[1,4]diazepino[1,2-a]indole-8-carboxamide |
| 106 | 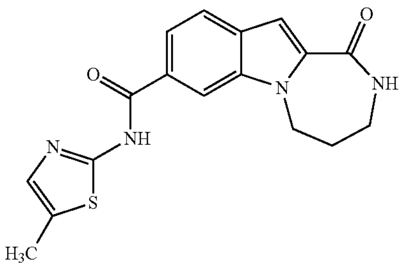 [SMILES: Cc1cnc(NC(=O)c2ccc3cc4n(c3c2)CCCNC4=O)s1] | N-(5-methyl-1,3-thiazol-2-yl)-1-oxo-2,3,4,5-tetrahydro-1H-[1,4]diazepino[1,2-a]indole-8-carboxamide |
| 107 | 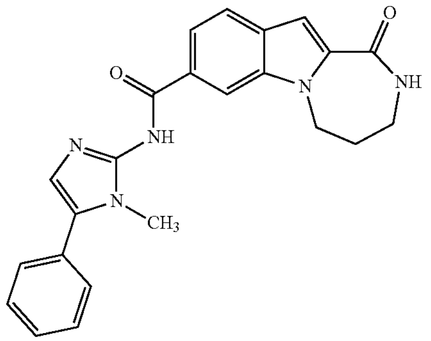 [SMILES: Cn1c(-c2ccccc2)cnc1NC(=O)c1ccc2cc3n(c2c1)CCCNC3=O] | N-(1-methyl-5-phenyl-1H-imidazol-2-yl)-1-oxo-2,3,4,5-tetrahydro-1H-[1,4]diazepino[1,2-a]indole-8-carboxamide |
| 108 | 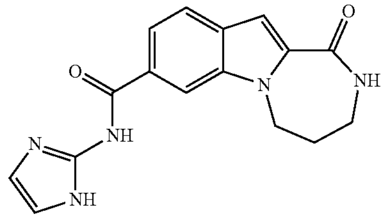 [SMILES: O=C(Nc1ncc[nH]1)c1ccc2cc3n(c2c1)CCCNC3=O] | N-(1H-imidazol-2-yl)-1-oxo-2,3,4,5-tetrahydro-1H-[1,4]diazepino[1,2-a]indole-8-carboxamide |
| 109 | 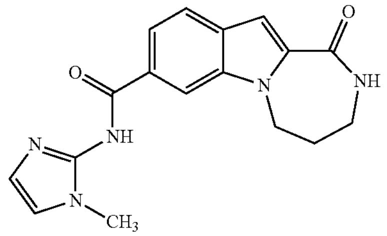 [SMILES: Cn1ccnc1NC(=O)c1ccc2cc3n(c2c1)CCCNC3=O] | N-(1-methyl-1H-imidazol-2-yl)-1-oxo-2,3,4,5-tetrahydro-1H-[1,4]diazepino[1,2-a]indole-8-carboxamide |
| 110 | 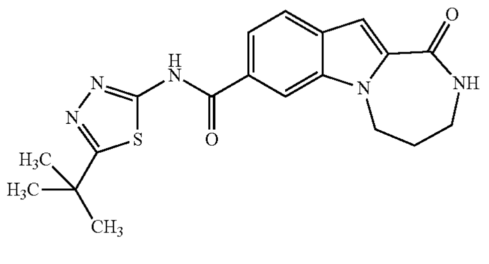 [SMILES: CC(C)(C)c1nnc(NC(=O)c2ccc3cc4n(c3c2)CCCNC4=O)s1] | N-(5-tert-butyl-1,3,4-thiadiazol-2-yl)-1-oxo-2,3,4,5-tetrahydro-1H-[1,4]diazepino[1,2-a]indole-8-carboxamide |

TABLE 1-continued

| Example | Structure | Name |
|---|---|---|
| 111 | 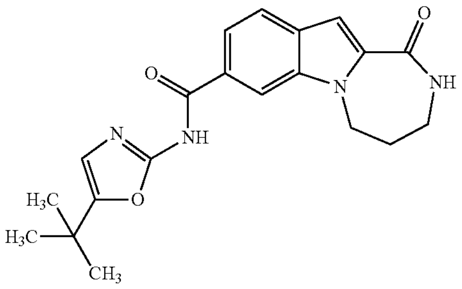 [SMILES: CC(C)(C)c1cnc(NC(=O)c2ccc3cc4n(c3c2)CCCNC4=O)o1] | N-(5-tert-butyl-1,3-oxazol-2-yl)-1-oxo-2,3,4,5-tetrahydro-1H-[1,4]diazepino[1,2-a]indole-8-carboxamide |
| 112 | 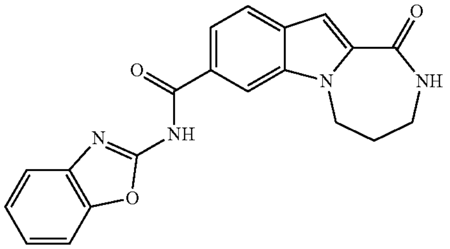 [SMILES: O=C(Nc1nc2ccccc2o1)c1ccc2cc3n(c2c1)CCCNC3=O] | N-(1,3-benzoxazol-2-yl)-1-oxo-2,3,4,5-tetrahydro-1H-[1,4]diazepino[1,2-a]indole-8-carboxamide |
| 113 | 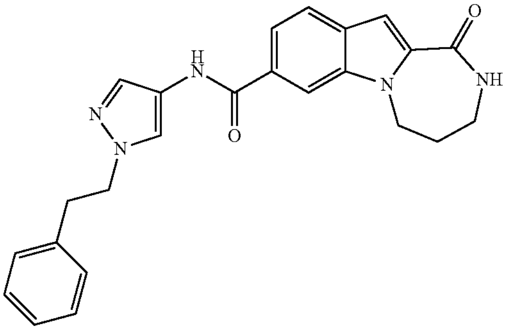 [SMILES: O=C(Nc1cnn(CCc2ccccc2)c1)c1ccc2cc3n(c2c1)CCCNC3=O] | 1-oxo-N-[1-(2-phenylethyl)-1H-pyrazol-4-yl]-2,3,4,5-tetrahydro-1H-[1,4]diazepino[1,2-a]indole-8-carboxamide |
| 114 | 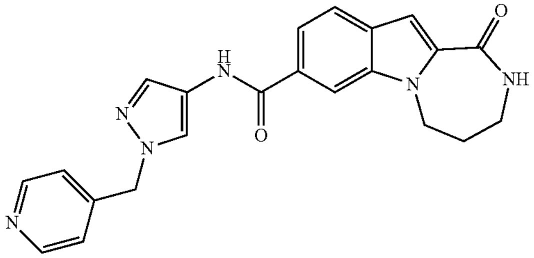 [SMILES: O=C(Nc1cnn(Cc2ccncc2)c1)c1ccc2cc3n(c2c1)CCCNC3=O] | 1-oxo-N-[1-(pyridin-4-ylmethyl)-1H-pyrazol-4-yl]-2,3,4,5-tetrahydro-1H-[1,4]diazepino[1,2-a]indole-8-carboxamide |
| 115 | 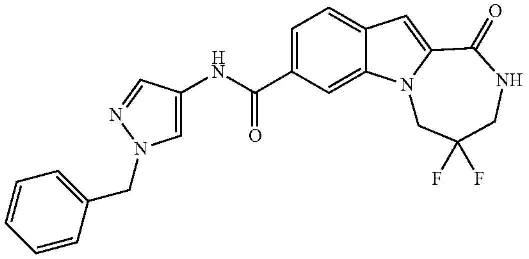 [SMILES: O=C(Nc1cnn(Cc2ccccc2)c1)c1ccc2cc3n(c2c1)CC(F)(F)CNC3=O] | N-(1-benzyl-1H-pyrazol-4-yl)-4,4-difluoro-1-oxo-2,3,4,5-tetrahydro-1H-[1,4]diazepino[1,2-a]indole-8-carboxamide |

TABLE 1-continued

| Example | Structure | Name |
|---|---|---|
| 116 | 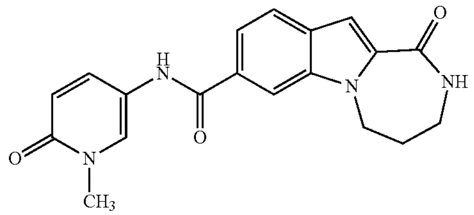 [SMILES: Cn1cc(NC(=O)c2ccc3cc4n(c3c2)CCCNC4=O)ccc1=O] | N-(1-methyl-6-oxo-1,6-dihydropyridin-3-yl)-1-oxo-2,3,4,5-tetrahydro-1H-[1,4]diazepino[1,2-a]indole-8-carboxamide |
| 117 | 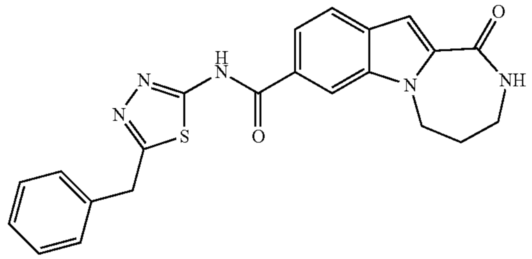 [SMILES: O=C(Nc1nnc(Cc2ccccc2)s1)c1ccc2cc3n(c2c1)CCCNC3=O] | N-(5-benzyl-1,3,4-thiadiazol-2-yl)-1-oxo-2,3,4,5-tetrahydro-1H-[1,4]diazepino[1,2-a]indole-8-carboxamide |
| 118 | 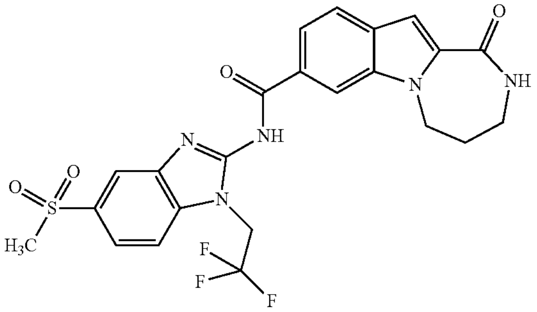 [SMILES: CS(=O)(=O)c1ccc2c(c1)nc(NC(=O)c1ccc3cc4n(c3c1)CCCNC4=O)n2CC(F)(F)F] | N-[5-(methylsulfonyl)-1-(2,2,2-trifluoroethyl)-1H-benzimidazol-2-yl]-1-oxo-2,3,4,5-tetrahydro-1H-[1,4]diazepino[1,2-a]indole-8-carboxamide |
| 119 | 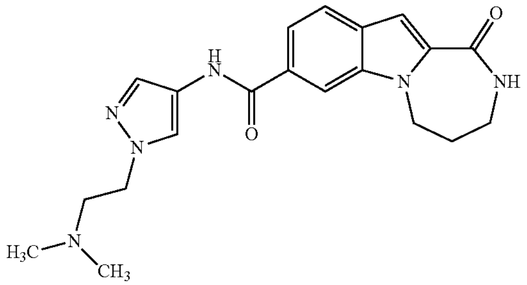 [SMILES: CN(C)CCn1cc(NC(=O)c2ccc3cc4n(c3c2)CCCNC4=O)cn1] | N-{1-[2-(dimethylamino)ethyl]-1H-pyrazol-4-yl}-1-oxo-2,3,4,5-tetrahydro-1H-[1,4]diazepino[1,2-a]indole-8-carboxamide |
| 120 | 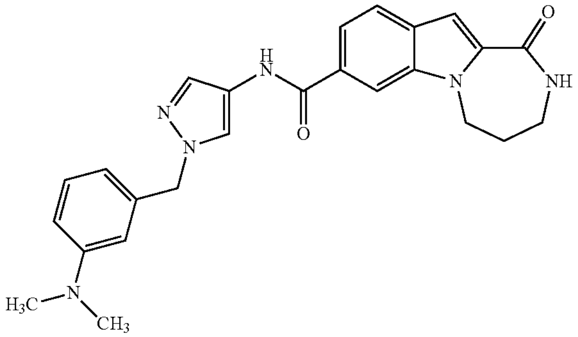 [SMILES: CN(C)c1cccc(Cn2cc(NC(=O)c3ccc4cc5n(c4c3)CCCNC5=O)cn2)c1] | N-{1-[3-(dimethylamino)benzyl]-1H-pyrazol-4-yl}-1-oxo-2,3,4,5-tetrahydro-1H-[1,4]diazepino[1,2-a]indole-8-carboxamide |

TABLE 1-continued

| Example | Structure | Name |
|---|---|---|
| 121 | 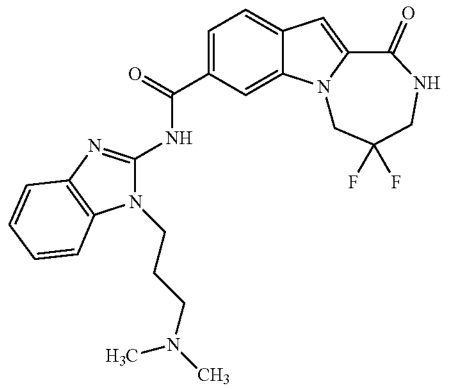 [SMILES: CN(C)CCCn1c(NC(=O)c2ccc3cc4n(c3c2)CC(F)(F)CNC4=O)nc2ccccc21] | N-{1-[3-(dimethylamino)propyl]-1H-benzimidazol-2-yl}-4,4-difluoro-1-oxo-2,3,4,5-tetrahydro-1H-[1,4]diazepino[1,2-a]indole-8-carboxamide |
| 122 | 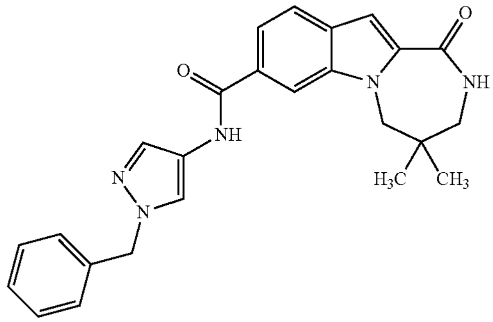 [SMILES: CC1(C)CNC(=O)c2cc3ccc(C(=O)Nc4cnn(Cc5ccccc5)c4)cc3n2C1] | N-(1-benzyl-1H-pyrazol-4-yl)-4,4-dimethyl-1-oxo-2,3,4,5-tetrahydro-1H-[1,4]diazepino[1,2-a]indole-8-carboxamide |
| 123 | 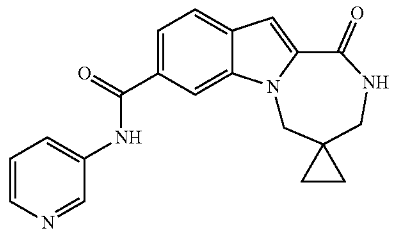 [SMILES: O=C(Nc1cccnc1)c1ccc2cc3n(c2c1)CC1(CC1)CNC3=O] | 1'-oxo-N-(pyridin-3-yl)-2',3'-dihydro-1'H-spiro[cyclopropane-1,4'-[1,4]diazepino[1,2-a]indole]-8'-carboxamide |
| 124 | 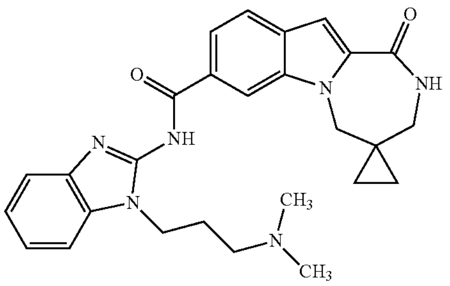 [SMILES: CN(C)CCCn1c(NC(=O)c2ccc3cc4n(c3c2)CC2(CC2)CNC4=O)nc2ccccc21] | N-{1-[3-(dimethylamino)propyl]-1H-benzimidazol-2-yl}-1'-oxo-2',3'-dihydro-1'H-spiro[cyclopropane-1,4'-[1,4]diazepino[1,2-a]indole]-8'-carboxamide |
| 125 | 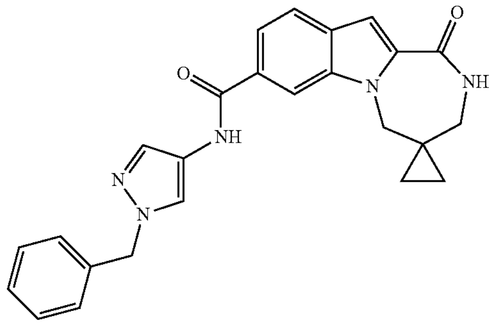 [SMILES: O=C(Nc1cnn(Cc2ccccc2)c1)c1ccc2cc3n(c2c1)CC1(CC1)CNC3=O] | N-(1-benzyl-1H-pyrazol-4-yl)-1'-oxo-2',3'-dihydro-1'H-spiro[cyclopropane-1,4'-[1,4]diazepino[1,2-a]indole]-8'-carboxamide |

TABLE 1-continued

| Example | Structure | Name |
|---|---|---|
| 126 | 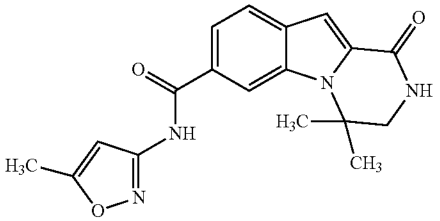 [SMILES: Cc1cc(NC(=O)c2ccc3cc4n(c3c2)C(C)(C)CNC4=O)no1] | 4,4-dimethyl-N-(5-methyl-1,2-oxazol-3-yl)-1-oxo-1,2,3,4-tetrahydropyrazino[1,2-a]indole-7-carboxamide |
| 127 | 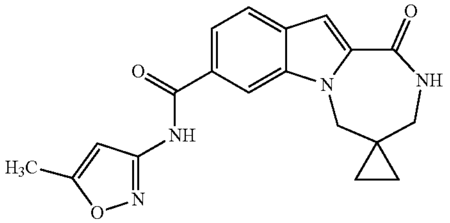 [SMILES: Cc1cc(NC(=O)c2ccc3cc4n(c3c2)CC2(CC2)CNC4=O)no1] | N-(5-methyl-1,2-oxazol-3-yl)-1'-oxo-2',3'-dihydro-1'H-spiro[cyclopropane-1,4'-[1,4]diazepino[1,2-a]indole]-8'-carboxamide |
| 128 | 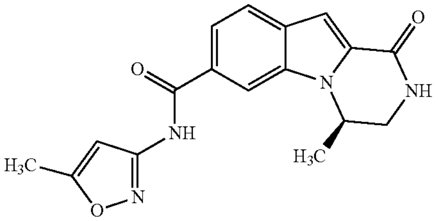 Chiral | (4R)-4-methyl-N-(5-methyl-1,2-oxazol-3-yl)-1-oxo-1,2,3,4-tetrahydropyrazino[1,2-a]indole-7-carboxamide |
| 129 | 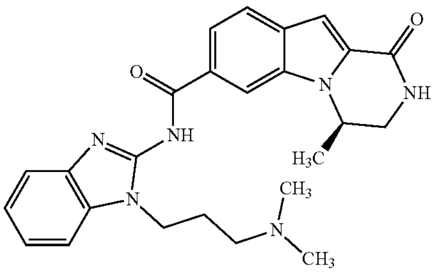 Chiral | (4R)-N-{1-[3-(dimethylamino)propyl]-1H-benzimidazol-2-yl}-4-methyl-1-oxo-1,2,3,4-tetrahydropyrazino[1,2-a]indole-7-carboxamide |
| 130 | 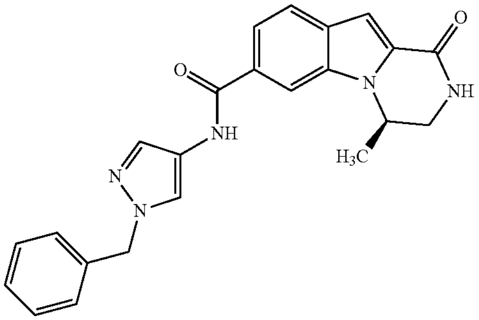 Chiral | (4R)-N-(1-benzyl-1H-pyrazol-4-yl)-4-methyl-1-oxo-1,2,3,4-tetrahydropyrazino[1,2-a]indole-7-carboxamide |
| 131 | 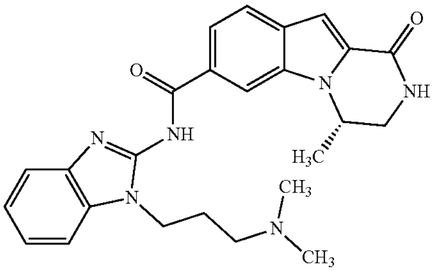 Chiral | (4S)-N-{1-[3-(dimethylamino)propyl]-1H-benzimidazol-2-yl}-4-methyl-1-oxo-1,2,3,4-tetrahydropyrazino[1,2-a]indole-7-carboxamide |

TABLE 1-continued

| Example | Structure | Name |
| --- | --- | --- |
| 132 | 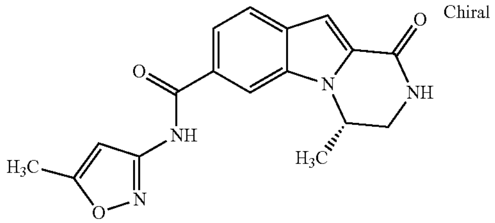 [SMILES: Cc1cc(NC(=O)c2ccc3cc4n(c3c2)[C@@H](C)CNC4=O)no1] | (4S)-4-methyl-N-(5-methyl-1,2-oxazol-3-yl)-1-oxo-1,2,3,4-tetrahydropyrazino[1,2-a]indole-7-carboxamide |
| 133 | 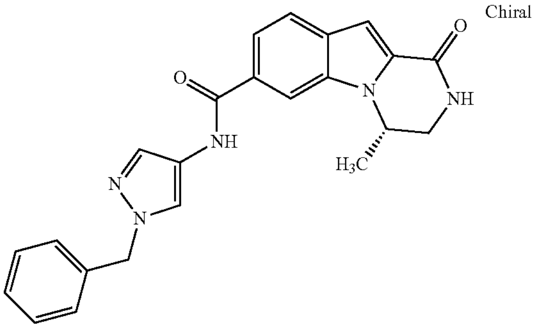 [SMILES: C[C@H]1CNC(=O)c2cc3ccc(C(=O)Nc4cnn(Cc5ccccc5)c4)cc3n21] | (4S)-N-(1-benzyl-1H-pyrazol-4-yl)-4-methyl-1-oxo-1,2,3,4-tetrahydropyrazino[1,2-a]indole-7-carboxamide |
| 134 | 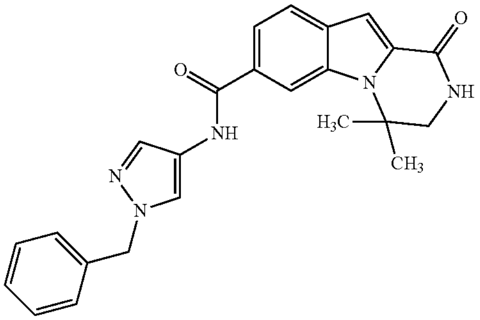 [SMILES: CC1(C)CNC(=O)c2cc3ccc(C(=O)Nc4cnn(Cc5ccccc5)c4)cc3n21] | N-(1-benzyl-1H-pyrazol-4-yl)-4,4-dimethyl-1-oxo-1,2,3,4-tetrahydropyrazino[1,2-a]indole-7-carboxamide |
| 135 | 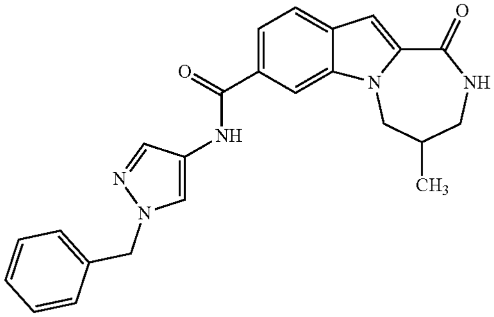 [SMILES: CC1CNC(=O)c2cc3ccc(C(=O)Nc4cnn(Cc5ccccc5)c4)cc3n2C1] | N-(1-benzyl-1H-pyrazol-4-yl)-4-methyl-1-oxo-2,3,4,5-tetrahydro-1H-[1,4]diazepino[1,2-a]indole-8-carboxamide |
| 136 | 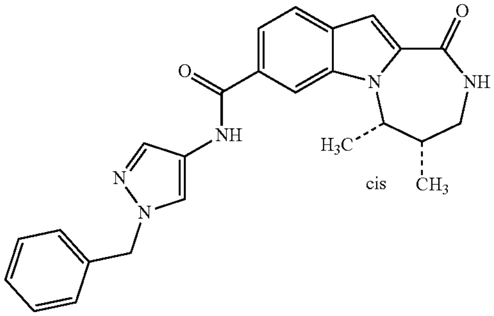 [SMILES: C[C@H]1CNC(=O)c2cc3ccc(C(=O)Nc4cnn(Cc5ccccc5)c4)cc3n2[C@H]1C] | N-(1-benzyl-1H-pyrazol-4-yl)-cis-4,5-dimethyl-1-oxo-2,3,4,5-tetrahydro-1H-[1,4]diazepino[1,2-a]indole-8-carboxamide |

TABLE 1-continued

| Example | Structure | Name |
|---|---|---|
| 137 | 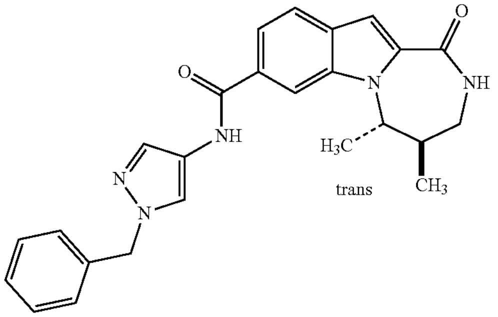 [SMILES: C[C@@H]1CNC(=O)c2cc3ccc(C(=O)Nc4cnn(Cc5ccccc5)c4)cc3n2[C@H]1C] | (4R,5S)-N-(1-benzyl-1H-pyrazol-4-yl)-trans-4,5-dimethyl-1-oxo-2,3,4,5-tetrahydro-1H-[1,4]diazepino[1,2-a]indole-8-carboxamide |
| 138 | 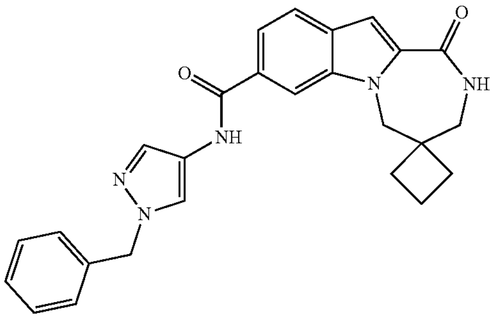 [SMILES: O=C(Nc1cnn(Cc2ccccc2)c1)c1ccc2cc3n(c2c1)CC1(CCC1)CNC3=O] | N-(1-benzyl-1H-pyrazol-4-yl)-1'-oxo-2',3'-dihydro-1'H-spiro[cyclobutane-1,4'-[1,4]diazepino[1,2-a]indole]-8'-carboxamide |
| 139 | 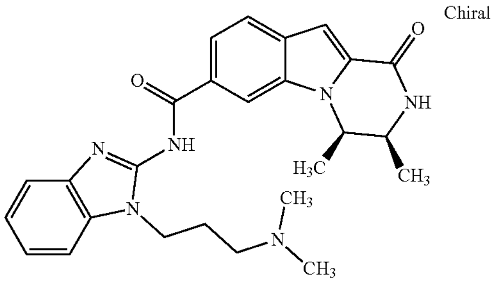 [SMILES: C[C@@H]1NC(=O)c2cc3ccc(C(=O)Nc4nc5ccccc5n4CCCN(C)C)cc3n2[C@@H]1C] | (3S,4R)-N-{1-[3-(dimethylamino)propyl]-1H-benzimidazol-2-yl}-3,4-dimethyl-1-oxo-1,2,3,4-tetrahydropyrazino[1,2-a]indole-7-carboxamide |
| 140 | 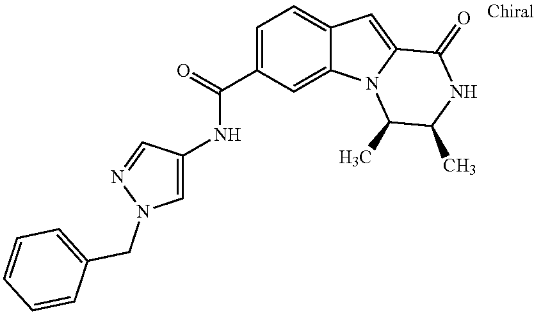 [SMILES: C[C@@H]1NC(=O)c2cc3ccc(C(=O)Nc4cnn(Cc5ccccc5)c4)cc3n2[C@@H]1C] | (3S,4R)-N-(1-benzyl-1H-pyrazol-4-yl)-3,4-dimethyl-1-oxo-1,2,3,4-tetrahydropyrazino[1,2-a]indole-7-carboxamide |
| 141 | 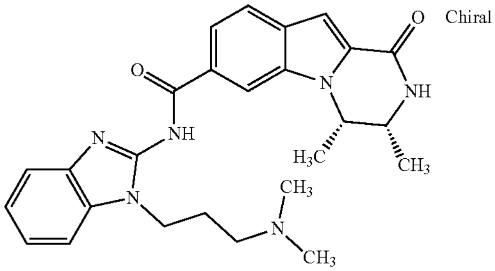 [SMILES: C[C@H]1NC(=O)c2cc3ccc(C(=O)Nc4nc5ccccc5n4CCCN(C)C)cc3n2[C@H]1C] | (3R,4S)-N-{1-[3-(dimethylamino)propyl]-1H-benzimidazol-2-yl}-3,4-dimethyl-1-oxo-1,2,3,4-tetrahydropyrazino[1,2-a]indole-7-carboxamide |

TABLE 1-continued

| Example | Structure | Name |
|---|---|---|
| 142 | 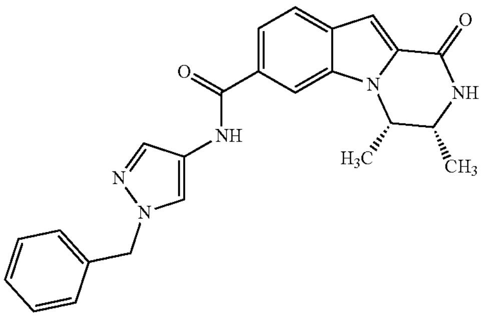 Chiral | (3R,4S)-N-(1-benzyl-1H-pyrazol-4-yl)-3,4-dimethyl-1-oxo-1,2,3,4-tetrahydropyrazino[1,2-a]indole-7-carboxamide |
| 143 | 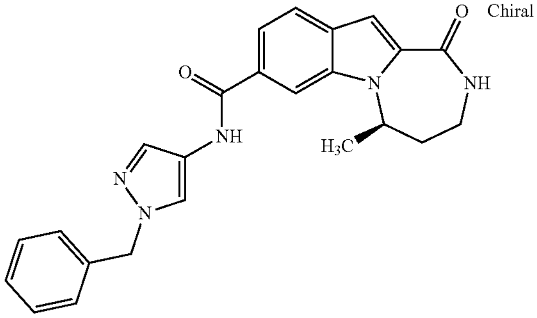 [SMILES: C[C@@H]1CCNC(=O)c2cc3ccc(C(=O)Nc4cnn(Cc5ccccc5)c4)cc3n21] Chiral | (5R)-N-(1-benzyl-1H-pyrazol-4-yl)-5-methyl-1-oxo-2,3,4,5-tetrahydro-1H-[1,4]diazepino[1,2-a]indole-8-carboxamide |
| 144 | 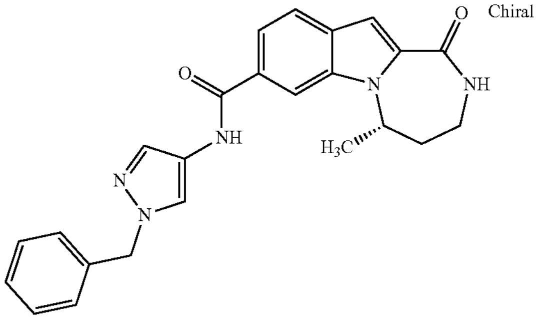 [SMILES: C[C@H]1CCNC(=O)c2cc3ccc(C(=O)Nc4cnn(Cc5ccccc5)c4)cc3n21] Chiral | (5S)-N-(1-benzyl-1H-pyrazol-4-yl)-5-methyl-1-oxo-2,3,4,5-tetrahydro-1H-[1,4]diazepino[1,2-a]indole-8-carboxamide |
| 145 | 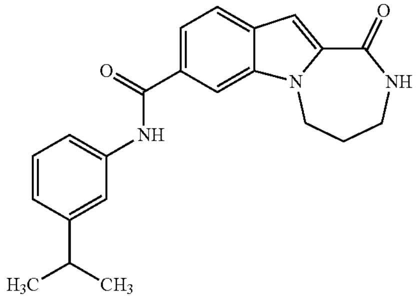 [SMILES: CC(C)c1cccc(NC(=O)c2ccc3cc4n(c3c2)CCCNC4=O)c1] | 1-oxo-N-[3-(propan-2-yl)phenyl]-2,3,4,5-tetrahydro-1H-[1,4]diazepino[1,2-a]indole-8-carboxamide |
| 146 | 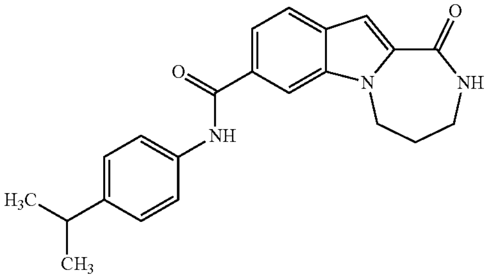 [SMILES: CC(C)c1ccc(NC(=O)c2ccc3cc4n(c3c2)CCCNC4=O)cc1] | 1-oxo-N-[4-(propan-2-yl)phenyl]-2,3,4,5-tetrahydro-1H-[1,4]diazepino[1,2-a]indole-8-carboxamide |

TABLE 1-continued

| Example | Structure | Name |
|---|---|---|
| 147 | 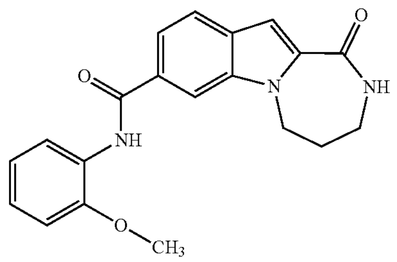 [SMILES: COc1ccccc1NC(=O)c1ccc2cc3n(c2c1)CCCNC3=O] | N-(2-methoxyphenyl)-1-oxo-2,3,4,5-tetrahydro-1H-[1,4]diazepino[1,2-a]indole-8-carboxamide |
| 148 | 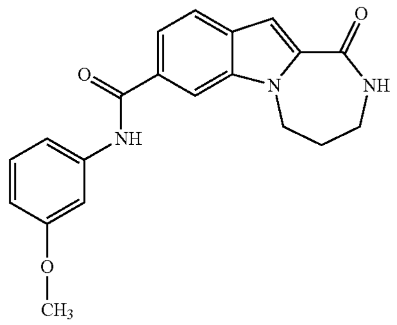 [SMILES: COc1cccc(NC(=O)c2ccc3cc4n(c3c2)CCCNC4=O)c1] | N-(3-methoxyphenyl)-1-oxo-2,3,4,5-tetrahydro-1H-[1,4]diazepino[1,2-a]indole-8-carboxamide |
| 149 | 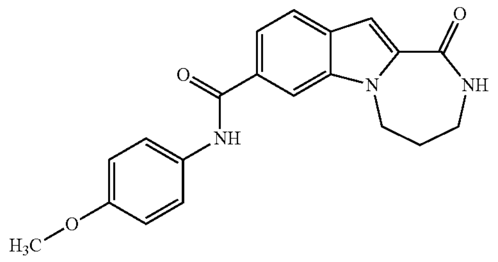 [SMILES: COc1ccc(NC(=O)c2ccc3cc4n(c3c2)CCCNC4=O)cc1] | N-(4-methoxyphenyl)-1-oxo-2,3,4,5-tetrahydro-1H-[1,4]diazepino[1,2-a]indole-8-carboxamide |
| 150 | 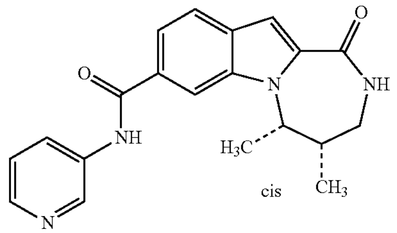 [SMILES: C[C@H]1CNC(=O)c2cc3ccc(C(=O)Nc4cccnc4)cc3n2[C@H]1C] | Cis-4,5-dimethyl-1-oxo-N-(pyridin-3-yl)-2,3,4,5-tetrahydro-1H-[1,4]diazepino[1,2-a]indole-8-carboxamide |
| 151 | 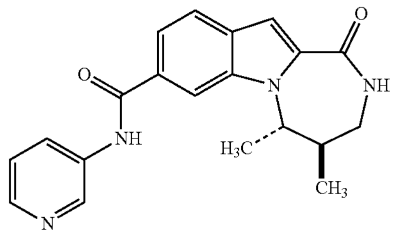 [SMILES: C[C@@H]1CNC(=O)c2cc3ccc(C(=O)Nc4cccnc4)cc3n2[C@H]1C] | Trans-4,5-dimethyl-1-oxo-N-(pyridin-3-yl)-2,3,4,5-tetrahydro-1H-[1,4]diazepino[1,2-a]indole-8-carboxamide |
| 152 | 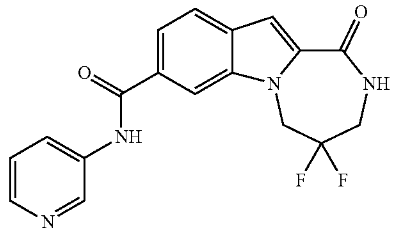 [SMILES: O=C(Nc1cccnc1)c1ccc2cc3n(c2c1)CC(F)(F)CNC3=O] | 4,4-difluoro-1-oxo-N-(pyridin-3-yl)-2,3,4,5-tetrahydro-1H-[1,4]diazepino[1,2-a]indole-8-carboxamide |

TABLE 1-continued

| Example | Structure | Name |
|---|---|---|
| 153 | 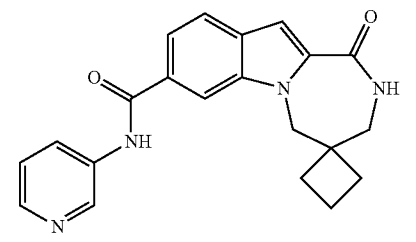 [SMILES: O=C(Nc1cccnc1)c1ccc2cc3n(c2c1)CC1(CCC1)CNC3=O] | 1'-oxo-N-(pyridin-3-yl)-2',3'-dihydro-1'H-spiro[cyclobutane-1,4'-[1,4]diazepino[1,2-a]indole]-8'-carboxamide |
| 154 | 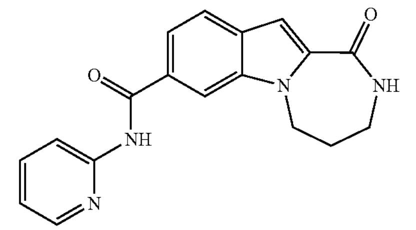 [SMILES: O=C(Nc1ccccn1)c1ccc2cc3n(c2c1)CCCNC3=O] | 1-oxo-N-(pyridin-2-yl)-2,3,4,5-tetrahydro-1H-[1,4]diazepino[1,2-a]indole-8-carboxamide |
| 155 | 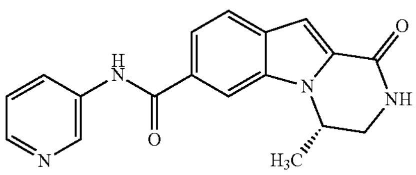 [SMILES: C[C@H]1CNC(=O)c2cc3ccc(C(=O)Nc4cccnc4)cc3n21] | (4S)-4-methyl-1-oxo-N-(pyridin-3-yl)-1,2,3,4-tetrahydropyrazino[1,2-a]indole-7-carboxamide |
| 156 | 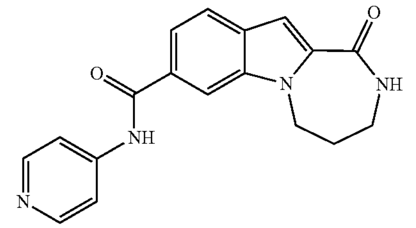 [SMILES: O=C(Nc1ccncc1)c1ccc2cc3n(c2c1)CCCNC3=O] | 1-oxo-N-(pyridin-4-yl)-2,3,4,5-tetrahydro-1H-[1,4]diazepino[1,2-a]indole-8-carboxamide |
| 157 | 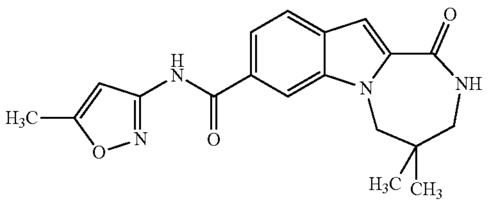 [SMILES: Cc1cc(NC(=O)c2ccc3cc4n(c3c2)CC(C)(C)CNC4=O)no1] | 4,4-dimethyl-N-(5-methyl-1,2-oxazol-3-yl)-1-oxo-2,3,4,5-tetrahydro-1H-[1,4]diazepino[1,2-a]indole-8-carboxamide |
| 158 | 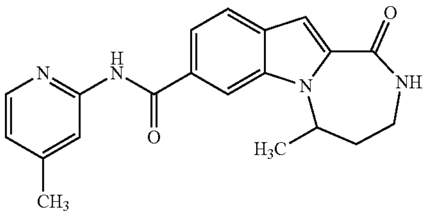 [SMILES: Cc1ccnc(NC(=O)c2ccc3cc4n(c3c2)C(C)CCNC4=O)c1] | 5-methyl-N-(4-methylpyridin-2-yl)-1-oxo-2,3,4,5-tetrahydro-1H-[1,4]diazepino[1,2-a]indole-8-carboxamide |
| 159 | 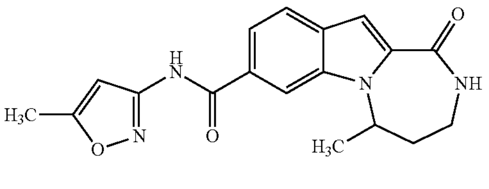 [SMILES: Cc1cc(NC(=O)c2ccc3cc4n(c3c2)C(C)CCNC4=O)no1] | 5-methyl-N-(5-methyl-1,2-oxazol-3-yl)-1-oxo-2,3,4,5-tetrahydro-1H-[1,4]diazepino[1,2-a]indole-8-carboxamide |

TABLE 1-continued

| Example | Structure | Name |
|---|---|---|
| 160 | 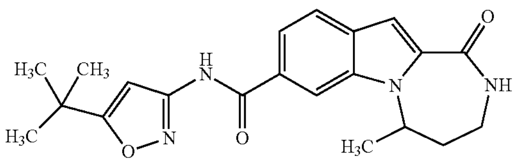 [SMILES: CC1CCNC(=O)c2cc3ccc(C(=O)Nc4cc(C(C)(C)C)on4)cc3n21] | N-(5-tert-butyl-1,2-oxazol-3-yl)-5-methyl-1-oxo-2,3,4,5-tetrahydro-1H-[1,4]diazepino[1,2-a]indole-8-carboxamide |
| 161 | 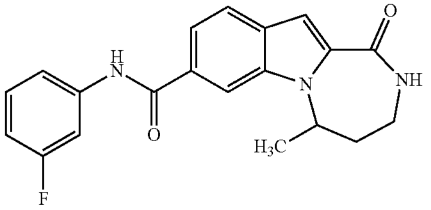 [SMILES: CC1CCNC(=O)c2cc3ccc(C(=O)Nc4cccc(F)c4)cc3n21] | N-(3-fluorophenyl)-5-methyl-1-oxo-2,3,4,5-tetrahydro-1H-[1,4]diazepino[1,2-a]indole-8-carboxamide |
| 162 | 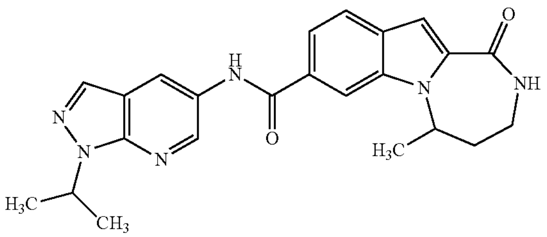 [SMILES: CC(C)n1ncc2cc(NC(=O)c3ccc4cc5n(c4c3)C(C)CCNC5=O)cnc21] | 5-methyl-1-oxo-N-[1-(propan-2-yl)-1H-pyrazolo[3,4-b]pyridin-5-yl]-2,3,4,5-tetrahydro-1H-[1,4]diazepino[1,2-a]indole-8-carboxamide |
| 163 | 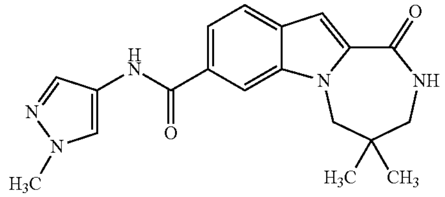 [SMILES: Cn1cc(NC(=O)c2ccc3cc4n(c3c2)CC(C)(C)CNC4=O)cn1] | 4,4-dimethyl-N-(1-methyl-1H-pyrazol-4-yl)-1-oxo-2,3,4,5-tetrahydro-1H-[1,4]diazepino[1,2-a]indole-8-carboxamide |
| 164 | 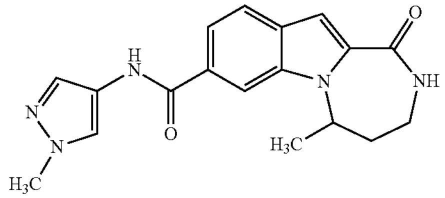 [SMILES: CC1CCNC(=O)c2cc3ccc(C(=O)Nc4cnn(C)c4)cc3n21] | 5-methyl-N-(1-methyl-1H-pyrazol-4-yl)-1-oxo-2,3,4,5-tetrahydro-1H-[1,4]diazepino[1,2-a]indole-8-carboxamide |
| 165 | 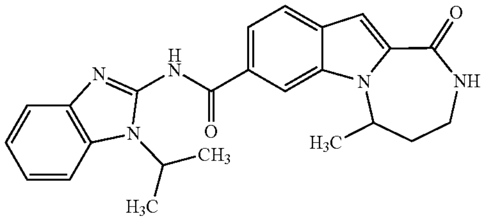 | 5-methyl-1-oxo-N-[1-(propan-2-yl)-1H-benzimidazol-2-yl]-2,3,4,5-tetrahydro-1H-[1,4]diazepino[1,2-a]indole-8-carboxamide |
| 166 | 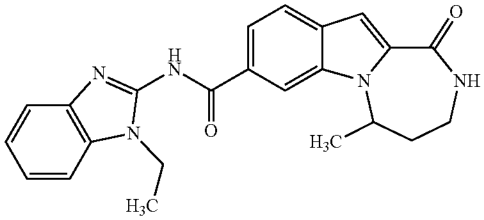 [SMILES: CCn1c(NC(=O)c2ccc3cc4n(c3c2)C(C)CCNC4=O)nc2ccccc21] | N-(1-ethyl-1H-benzimidazol-2-yl)-5-methyl-1-oxo-2,3,4,5-tetrahydro-1H-[1,4]diazepino[1,2-a]indole-8-carboxamide |

TABLE 1-continued

| Example | Structure | Name |
|---|---|---|
| 167 | 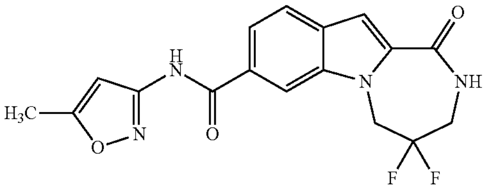 [SMILES: Cc1cc(NC(=O)c2ccc3cc4n(c3c2)CC(F)(F)CNC4=O)no1] | 4,4-difluoro-N-(5-methyl-1,2-oxazol-3-yl)-1-oxo-2,3,4,5-tetrahydro-1H-[1,4]diazepino[1,2-a]indole-8-carboxamide |
| 168 | 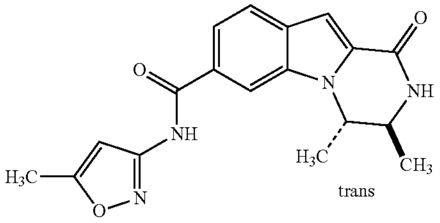 [SMILES: Cc1cc(NC(=O)c2ccc3cc4n(c3c2)[C@@H](C)[C@H](C)NC4=O)no1] | Trans-3,4-dimethyl-N-(5-methyl-1,2-oxazol-3-yl)-1-oxo-1,2,3,4-tetrahydropyrazino[1,2-a]indole-7-carboxamide |
| 169 | 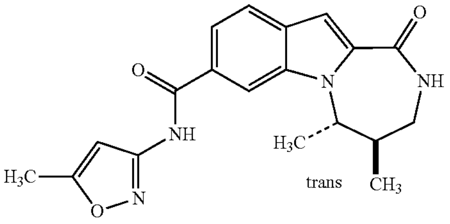 [SMILES: Cc1cc(NC(=O)c2ccc3cc4n(c3c2)[C@@H](C)[C@H](C)CNC4=O)no1] | Trans-4,5-dimethyl-N-(5-methyl-1,2-oxazol-3-yl)-1-oxo-2,3,4,5-tetrahydro-1H-[1,4]diazepino[1,2-a]indole-8-carboxamide |
| 170 | 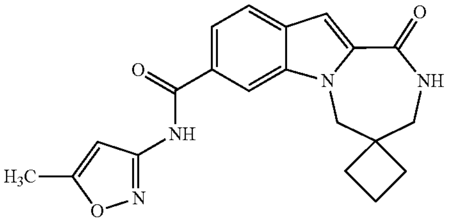 [SMILES: Cc1cc(NC(=O)c2ccc3cc4n(c3c2)CC2(CCC2)CNC4=O)no1] | N-(5-methyl-1,2-oxazol-3-yl)-1'-oxo-2',3'-dihydro-1'H-spiro[cyclobutane-1,4'-[1,4]diazepino[1,2-a]indole]-8'-carboxamide |
| 171 | 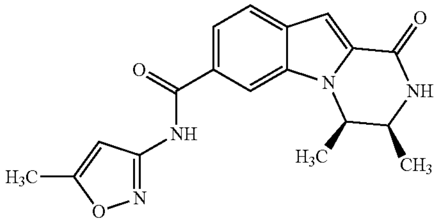 Chiral | (3S,4R)-3,4-dimethyl-N-(5-methyl-1,2-oxazol-3-yl)-1-oxo-1,2,3,4-tetrahydropyrazino[1,2-a]indole-7-carboxamide |
| 172 | 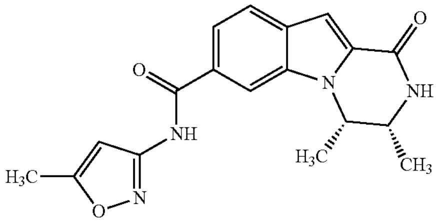 Chiral | (3R,4S)-3,4-dimethyl-N-(5-methyl-1,2-oxazol-3-yl)-1-oxo-1,2,3,4-tetrahydropyrazino[1,2-a]indole-7-carboxamide |
| 173 | 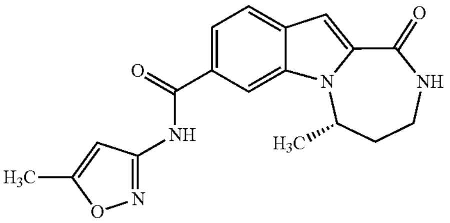 Chiral | (5S)-5-methyl-N-(5-methyl-1,2-oxazol-3-yl)-1-oxo-2,3,4,5-tetrahydro-1H-[1,4]diazepino[1,2-a]indole-8-carboxamide |

TABLE 1-continued

| Example | Structure | Name |
|---|---|---|
| 174 | 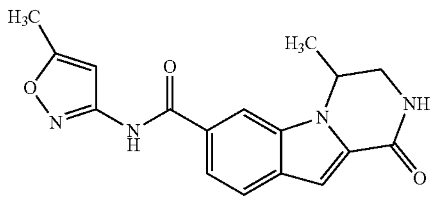 [SMILES: Cc1cc(NC(=O)c2ccc3cc4n(c3c2)C(C)CNC4=O)no1] | 4-methyl-N-(5-methyl-1,2-oxazol-3-yl)-1-oxo-1,2,3,4-tetrahydropyrazino[1,2-a]indole-7-carboxamide |
| 175 | 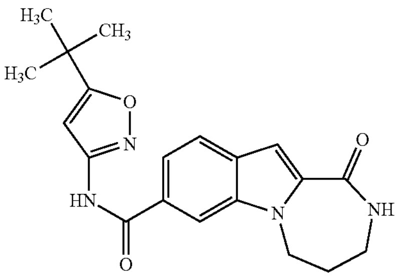 [SMILES: CC(C)(C)c1cc(NC(=O)c2ccc3cc4n(c3c2)CCCNC4=O)no1] | N-(5-tert-butyl-1,2-oxazol-3-yl)-1-oxo-2,3,4,5-tetrahydro-1H-[1,4]diazepino[1,2-a]indole-8-carboxamide |
| 176 | 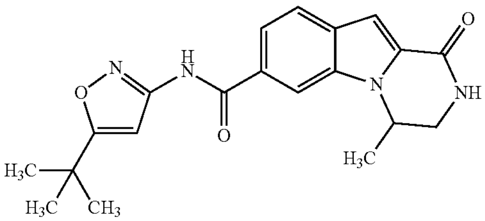 [SMILES: CC1CNC(=O)c2cc3ccc(C(=O)Nc4cc(C(C)(C)C)on4)cc3n21] | N-(5-tert-butyl-1,2-oxazol-3-yl)-4-methyl-1-oxo-1,2,3,4-tetrahydropyrazino[1,2-a]indole-7-carboxamide |
| 177 | 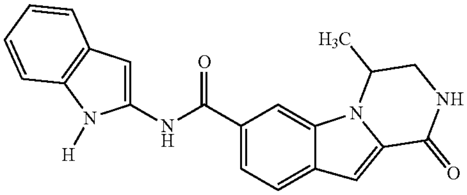 [SMILES: CC1CNC(=O)c2cc3ccc(C(=O)Nc4cc5ccccc5[nH]4)cc3n21] | N-(1H-indol-2-yl)-4-methyl-1-oxo-1,2,3,4-tetrahydropyrazino[1,2-a]indole-7-carboxamide |
| 178 | 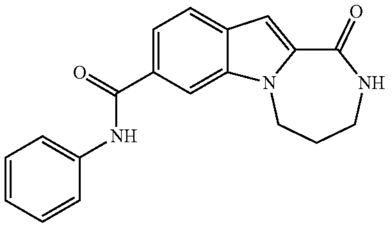 [SMILES: O=C(Nc1ccccc1)c1ccc2cc3n(c2c1)CCCNC3=O] | 1-oxo-N-phenyl-2,3,4,5-tetrahydro-1H-[1,4]diazepino[1,2-a]indole-8-carboxamide |
| 179 | 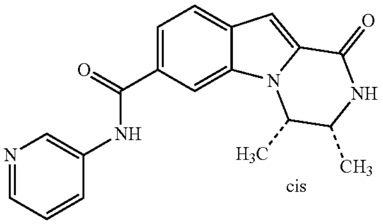 [SMILES: C[C@H]1NC(=O)c2cc3ccc(C(=O)Nc4cccnc4)cc3n2[C@H]1C] cis | Cis-3,4-dimethyl-1-oxo-N-(pyridin-3-yl)-1,2,3,4-tetrahydropyrazino[1,2-a]indole-7-carboxamide |

TABLE 1-continued

| Example | Structure | Name |
|---|---|---|
| 180 | 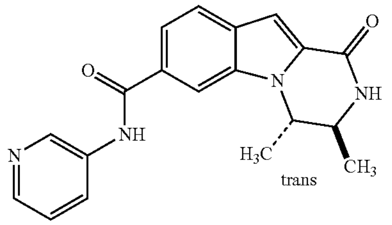 [SMILES: C[C@@H]1NC(=O)c2cc3ccc(C(=O)Nc4cccnc4)cc3n2[C@H]1C] | Trans-3,4-dimethyl-1-oxo-N-(pyridin-3-yl)-1,2,3,4-tetrahydropyrazino[1,2-a]indole-7-carboxamide |
| 181 | 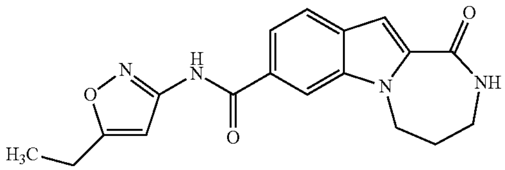 [SMILES: CCc1cc(NC(=O)c2ccc3cc4n(c3c2)CCCNC4=O)no1] | N-(5-ethyl-1,2-oxazol-3-yl)-1-oxo-2,3,4,5-tetrahydro-1H-[1,4]diazepino[1,2-a]indole-8-carboxamide |
| 182 | 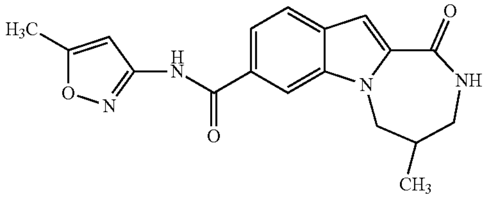 [SMILES: Cc1cc(NC(=O)c2ccc3cc4n(c3c2)CC(C)CNC4=O)no1] | 4-methyl-N-(5-methyl-1,2-oxazol-3-yl)-1-oxo-2,3,4,5-tetrahydro-1H-[1,4]diazepino[1,2-a]indole-8-carboxamide |
| 183 | 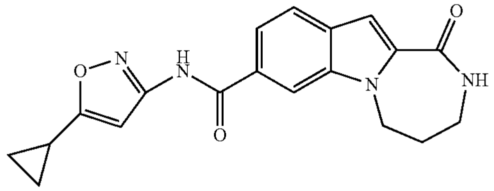 [SMILES: O=C(Nc1cc(C2CC2)on1)c1ccc2cc3n(c2c1)CCCNC3=O] | N-(5-cyclopropyl-1,2-oxazol-3-yl)-1-oxo-2,3,4,5-tetrahydro-1H-[1,4]diazepino[1,2-a]indole-8-carboxamide |
| 184 | 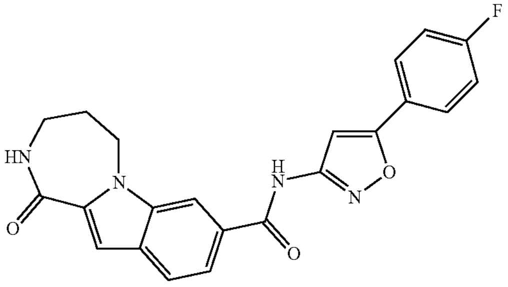 [SMILES: O=C(Nc1cc(-c2ccc(F)cc2)on1)c1ccc2cc3n(c2c1)CCCNC3=O] | N-[5-(4-fluorophenyl)-1,2-oxazol-3-yl]-1-oxo-2,3,4,5-tetrahydro-1H-[1,4]diazepino[1,2-a]indole-8-carboxamide |
| 185 | 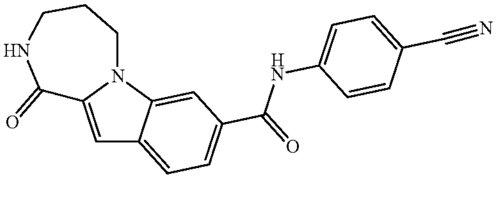 [SMILES: N#Cc1ccc(NC(=O)c2ccc3cc4n(c3c2)CCCNC4=O)cc1] | N-(4-cyanophenyl)-1-oxo-2,3,4,5-tetrahydro-1H-[1,4]diazepino[1,2-a]indole-8-carboxamide |
| 186 | 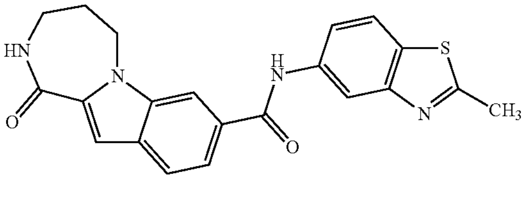 [SMILES: Cc1nc2cc(NC(=O)c3ccc4cc5n(c4c3)CCCNC5=O)ccc2s1] | N-(2-methyl-1,3-benzothiazol-5-yl)-1-oxo-2,3,4,5-tetrahydro-1H-[1,4]diazepino[1,2-a]indole-8-carboxamide |

TABLE 1-continued

| Example | Structure | Name |
|---|---|---|
| 187 | 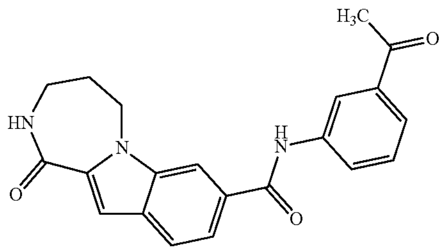 [SMILES: CC(=O)c1cccc(NC(=O)c2ccc3cc4n(c3c2)CCCNC4=O)c1] | N-(3-acetylphenyl)-1-oxo-2,3,4,5-tetrahydro-1H-[1,4]diazepino[1,2-a]indole-8-carboxamide |
| 188 | 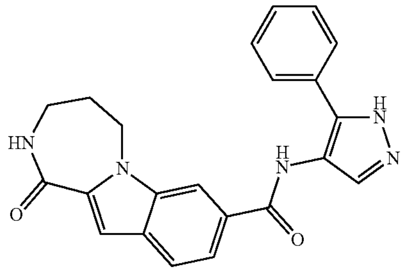 [SMILES: O=C(Nc1cn[nH]c1-c1ccccc1)c1ccc2cc3n(c2c1)CCCNC3=O] | 1-oxo-N-(5-phenyl-1H-pyrazol-4-yl)-2,3,4,5-tetrahydro-1H-[1,4]diazepino[1,2-a]indole-8-carboxamide |
| 189 | 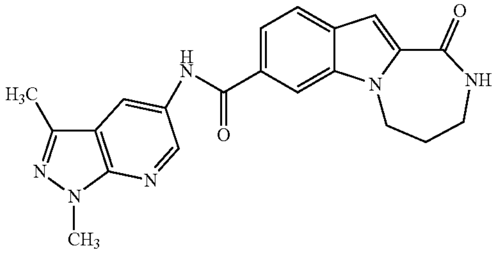 [SMILES: Cc1nn(C)c2ncc(NC(=O)c3ccc4cc5n(c4c3)CCCNC5=O)cc12] | N-(1,3-dimethyl-1H-pyrazolo[3,4-b]pyridin-5-yl)-1-oxo-2,3,4,5-tetrahydro-1H-[1,4]diazepino[1,2-a]indole-8-carboxamide |
| 190 | 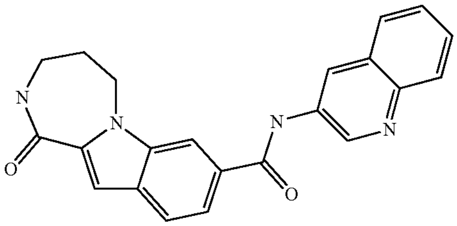 [SMILES: O=C(Nc1cnc2ccccc2c1)c1ccc2cc3n(c2c1)CCCNC3=O] | 1-oxo-N-(quinolin-3-yl)-2,3,4,5-tetrahydro-1H-[1,4]diazepino[1,2-a]indole-8-carboxamide |
| 191 | 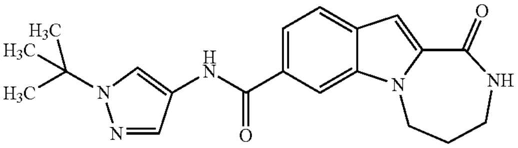 [SMILES: CC(C)(C)n1cc(NC(=O)c2ccc3cc4n(c3c2)CCCNC4=O)cn1] | N-(1-tert-butyl-1H-pyrazol-4-yl)-1-oxo-2,3,4,5-tetrahydro-1H-[1,4]diazepino[1,2-a]indole-8-carboxamide |
| 192 | 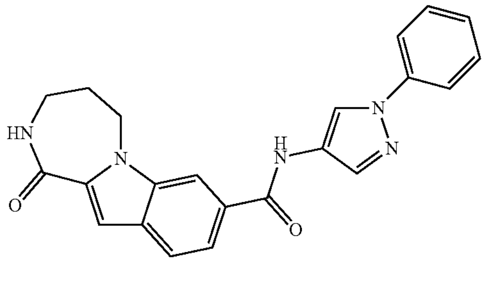 [SMILES: O=C(Nc1cnn(-c2ccccc2)c1)c1ccc2cc3n(c2c1)CCCNC3=O] | 1-oxo-N-(1-phenyl-1H-pyrazol-4-yl)-2,3,4,5-tetrahydro-1H-[1,4]diazepino[1,2-a]indole-8-carboxamide |

TABLE 1-continued

| Example | Structure | Name |
| --- | --- | --- |
| 193 | 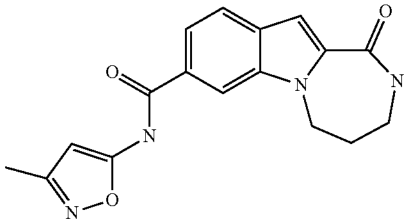 [SMILES: Cc1cc(NC(=O)c2ccc3cc4n(c3c2)CCCNC4=O)on1] | N-(3-methyl-1,2-oxazol-5-yl)-1-oxo-2,3,4,5-tetrahydro-1H-[1,4]diazepino[1,2-a]indole-8-carboxamide |
| 194 | 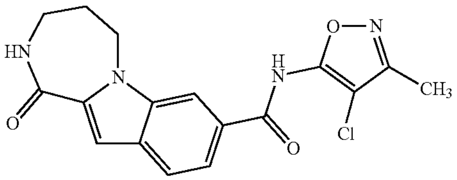 [SMILES: Cc1noc(NC(=O)c2ccc3cc4n(c3c2)CCCNC4=O)c1Cl] | N-(4-chloro-3-methyl-1,2-oxazol-5-yl)-1-oxo-2,3,4,5-tetrahydro-1H-[1,4]diazepino[1,2-a]indole-8-carboxamide |
| 195 | 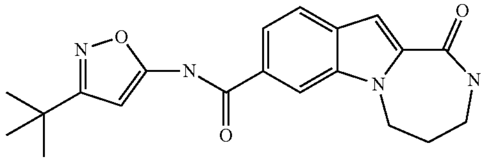 [SMILES: CC(C)(C)c1cc(NC(=O)c2ccc3cc4n(c3c2)CCCNC4=O)on1] | N-(3-tert-butyl-1,2-oxazol-5-yl)-1-oxo-2,3,4,5-tetrahydro-1H-[1,4]diazepino[1,2-a]indole-8-carboxamide |
| 196 | 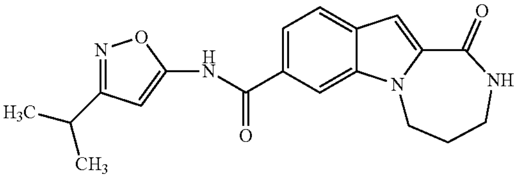 [SMILES: CC(C)c1cc(NC(=O)c2ccc3cc4n(c3c2)CCCNC4=O)on1] | 1-oxo-N-[3-(propan-2-yl)-1,2-oxazol-5-yl]-2,3,4,5-tetrahydro-1H-[1,4]diazepino[1,2-a]indole-8-carboxamide |
| 197 | 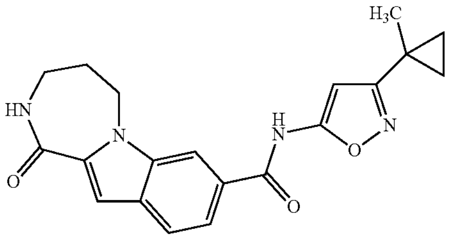 [SMILES: CC1(c2cc(NC(=O)c3ccc4cc5n(c4c3)CCCNC5=O)on2)CC1] | N-[3-(1-methylcyclopropyl)-1,2-oxazol-5-yl]-1-oxo-2,3,4,5-tetrahydro-1H-[1,4]diazepino[1,2-a]indole-8-carboxamide |
| 198 | 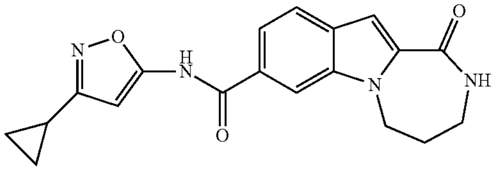 [SMILES: O=C(Nc1cc(C2CC2)no1)c1ccc2cc3n(c2c1)CCCNC3=O] | N-(3-cyclopropyl-1,2-oxazol-5-yl)-1-oxo-2,3,4,5-tetrahydro-1H-[1,4]diazepino[1,2-a]indole-8-carboxamide |
| 199 | 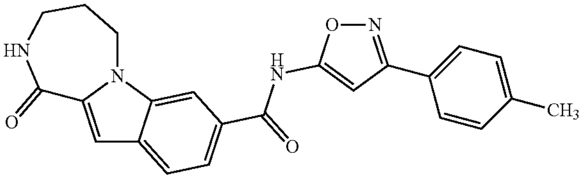 [SMILES: Cc1ccc(-c2cc(NC(=O)c3ccc4cc5n(c4c3)CCCNC5=O)on2)cc1] | N-[3-(4-methylphenyl)-1,2-oxazol-5-yl]-1-oxo-2,3,4,5-tetrahydro-1H-[1,4]diazepino[1,2-a]indole-8-carboxamide |
| 200 | 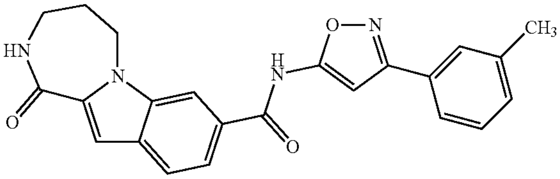 [SMILES: Cc1cccc(-c2cc(NC(=O)c3ccc4cc5n(c4c3)CCCNC5=O)on2)c1] | N-[3-(3-methylphenyl)-1,2-oxazol-5-yl]-1-oxo-2,3,4,5-tetrahydro-1H-[1,4]diazepino[1,2-a]indole-8-carboxamide |

TABLE 1-continued

| Example | Structure | Name |
| --- | --- | --- |
| 201 | 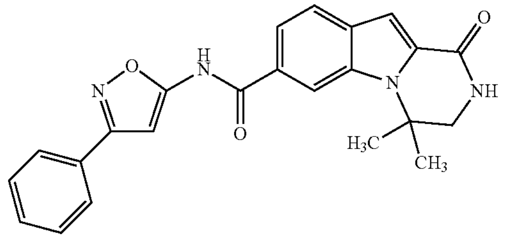 [SMILES: CC1(C)CNC(=O)c2cc3ccc(C(=O)Nc4cc(-c5ccccc5)no4)cc3n21] | 4,4-dimethyl-1-oxo-N-(3-phenyl-1,2-oxazol-5-yl)-1,2,3,4-tetrahydropyrazino[1,2-a]indole-7-carboxamide |
| 202 | 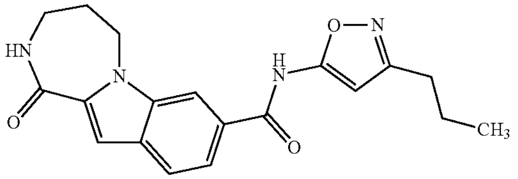 [SMILES: CCCc1cc(NC(=O)c2ccc3cc4n(c3c2)CCCNC4=O)on1] | 1-oxo-N-(3-propyl-1,2-oxazol-5-yl)-2,3,4,5-tetrahydro-1H-[1,4]diazepino[1,2-a]indole-8-carboxamide |
| 203 | 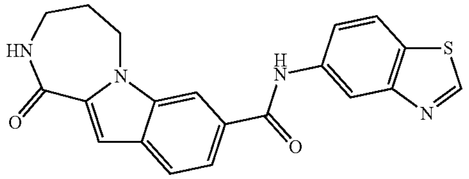 [SMILES: O=C(Nc1ccc2scnc2c1)c1ccc2cc3n(c2c1)CCCNC3=O] | N-(1,3-benzothiazol-5-yl)-1-oxo-2,3,4,5-tetrahydro-1H-[1,4]diazepino[1,2-a]indole-8-carboxamide |
| 204 | 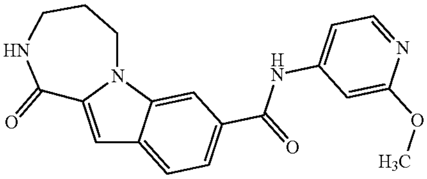 [SMILES: COc1cc(NC(=O)c2ccc3cc4n(c3c2)CCCNC4=O)ccn1] | N-(2-methoxypyridin-4-yl)-1-oxo-2,3,4,5-tetrahydro-1H-[1,4]diazepino[1,2-a]indole-8-carboxamide |
| 205 | 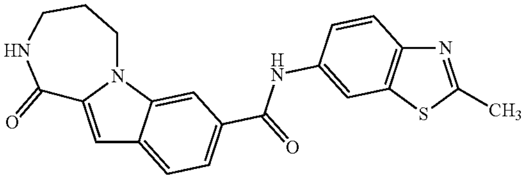 [SMILES: Cc1nc2ccc(NC(=O)c3ccc4cc5n(c4c3)CCCNC5=O)cc2s1] | N-(2-methyl-1,3-benzothiazol-6-yl)-1-oxo-2,3,4,5-tetrahydro-1H-[1,4]diazepino[1,2-a]indole-8-carboxamide |
| 206 | 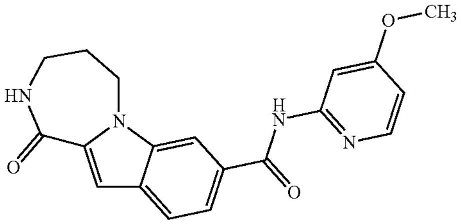 [SMILES: COc1ccnc(NC(=O)c2ccc3cc4n(c3c2)CCCNC4=O)c1] | N-(4-methoxypyridin-2-yl)-1-oxo-2,3,4,5-tetrahydro-1H-[1,4]diazepino[1,2-a]indole-8-carboxamide |
| 207 | 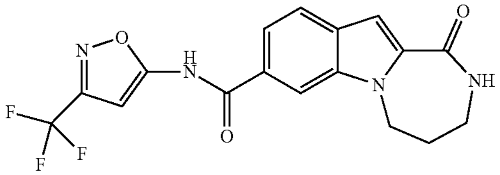 [SMILES: O=C(Nc1cc(C(F)(F)F)no1)c1ccc2cc3n(c2c1)CCCNC3=O] | 1-oxo-N-[3-(trifluoromethyl)-1,2-oxazol-5-yl]-2,3,4,5-tetrahydro-1H-[1,4]diazepino[1,2-a]indole-8-carboxamide |
| 208 | 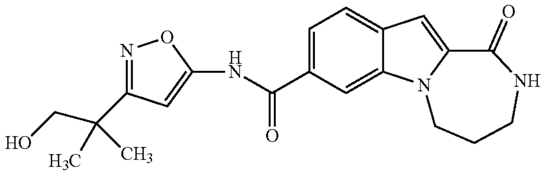 [SMILES: CC(C)(CO)c1cc(NC(=O)c2ccc3cc4n(c3c2)CCCNC4=O)on1] | N-[3-(1-hydroxy-2-methylpropan-2-yl)-1,2-oxazol-5-yl]-1-oxo-2,3,4,5-tetrahydro-1H-[1,4]diazepino[1,2-a]indole-8-carboxamide |

TABLE 1-continued

| Example | Structure | Name |
|---|---|---|
| 209 | 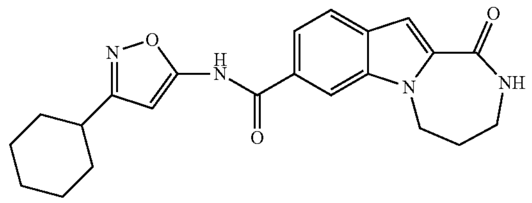 [SMILES: O=C(Nc1cc(C2CCCCC2)no1)c1ccc2cc3n(c2c1)CCCNC3=O] | N-(3-cyclohexyl-1,2-oxazol-5-yl)-1-oxo-2,3,4,5-tetrahydro-1H-[1,4]diazepino[1,2-a]indole-8-carboxamide |
| 210 | 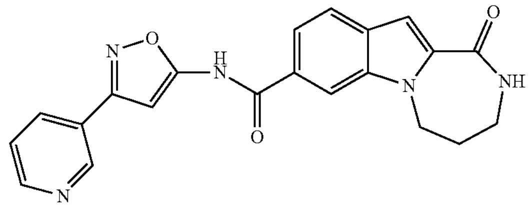 [SMILES: O=C(Nc1cc(-c2cccnc2)no1)c1ccc2cc3n(c2c1)CCCNC3=O] | 1-oxo-N-[3-(pyridin-3-yl)-1,2-oxazol-5-yl]-2,3,4,5-tetrahydro-1H-[1,4]diazepino[1,2-a]indole-8-carboxamide |
| 211 | 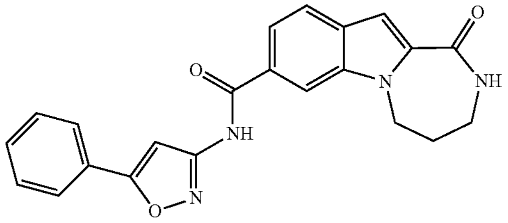 [SMILES: O=C(Nc1cc(-c2ccccc2)on1)c1ccc2cc3n(c2c1)CCCNC3=O] | 1-oxo-N-(5-phenyl-1,2-oxazol-3-yl)-2,3,4,5-tetrahydro-1H-[1,4]diazepino[1,2-a]indole-8-carboxamide |
| 212 | 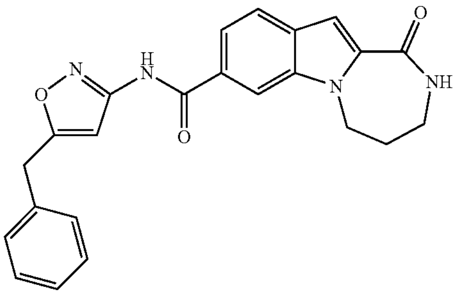 [SMILES: O=C(Nc1cc(Cc2ccccc2)on1)c1ccc2cc3n(c2c1)CCCNC3=O] | N-(5-benzyl-1,2-oxazol-3-yl)-1-oxo-2,3,4,5-tetrahydro-1H-[1,4]diazepino[1,2-a]indole-8-carboxamide |
| 213 | 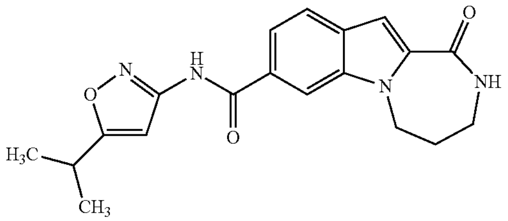 [SMILES: CC(C)c1cc(NC(=O)c2ccc3cc4n(c3c2)CCCNC4=O)no1] | 1-oxo-N-[5-(propan-2-yl)-1,2-oxazol-3-yl]-2,3,4,5-tetrahydro-1H-[1,4]diazepino[1,2-a]indole-8-carboxamide |
| 214 | 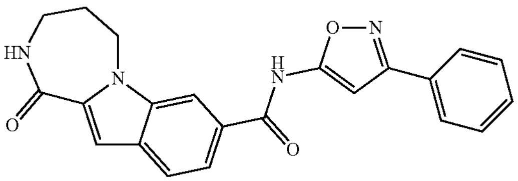 [SMILES: O=C(Nc1cc(-c2ccccc2)no1)c1ccc2cc3n(c2c1)CCCNC3=O] | 1-oxo-N-(3-phenyl-1,2-oxazol-5-yl)-2,3,4,5-tetrahydro-1H-[1,4]diazepino[1,2-a]indole-8-carboxamide |
| 215 | 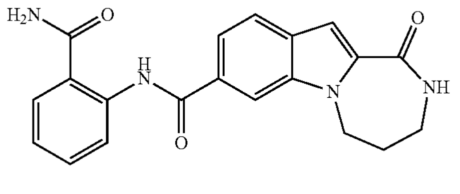 [SMILES: NC(=O)c1ccccc1NC(=O)c1ccc2cc3n(c2c1)CCCNC3=O] | N-(2-carbamoylphenyl)-1-oxo-2,3,4,5-tetrahydro-1H-[1,4]diazepino[1,2-a]indole-8-carboxamide |

TABLE 1-continued

| Example | Structure | Name |
|---|---|---|
| 216 | 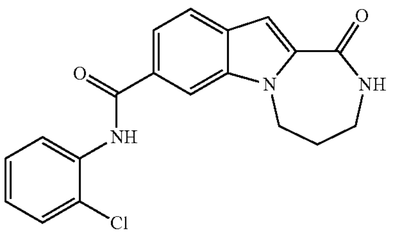 [SMILES: O=C(Nc1ccccc1Cl)c1ccc2cc3n(c2c1)CCCNC3=O] | N-(2-chlorophenyl)-1-oxo-2,3,4,5-tetrahydro-1H-[1,4]diazepino[1,2-a]indole-8-carboxamide |
| 217 | 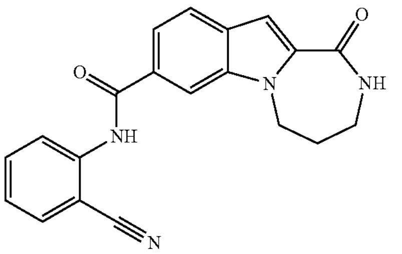 [SMILES: N#Cc1ccccc1NC(=O)c1ccc2cc3n(c2c1)CCCNC3=O] | N-(2-cyanophenyl)-1-oxo-2,3,4,5-tetrahydro-1H-[1,4]diazepino[1,2-a]indole-8-carboxamide |
| 218 | 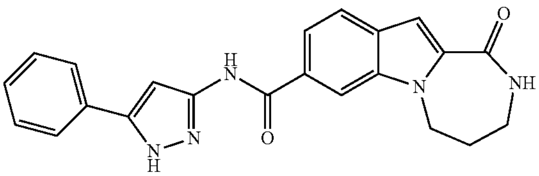 [SMILES: O=C(Nc1cc(-c2ccccc2)[nH]n1)c1ccc2cc3n(c2c1)CCCNC3=O] | 1-oxo-N-(5-phenyl-1H-pyrazol-3-yl)-2,3,4,5-tetrahydro-1H-[1,4]diazepino[1,2-a]indole-8-carboxamide |
| 219 | 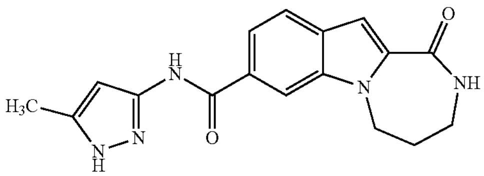 [SMILES: Cc1cc(NC(=O)c2ccc3cc4n(c3c2)CCCNC4=O)n[nH]1] | N-(5-methyl-1H-pyrazol-3-yl)-1-oxo-2,3,4,5-tetrahydro-1H-[1,4]diazepino[1,2-a]indole-8-carboxamide |
| 220 | 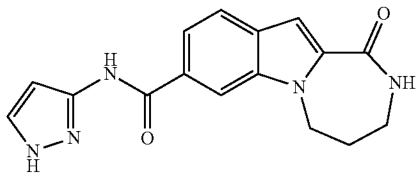 [SMILES: O=C(Nc1cc[nH]n1)c1ccc2cc3n(c2c1)CCCNC3=O] | 1-oxo-N-(1H-pyrazol-3-yl)-2,3,4,5-tetrahydro-1H-[1,4]diazepino[1,2-a]indole-8-carboxamide |
| 221 | 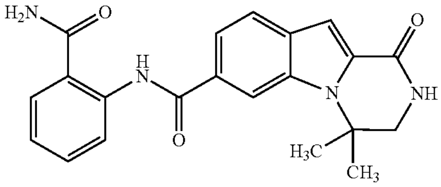 [SMILES: CC1(C)CNC(=O)c2cc3ccc(C(=O)Nc4ccccc4C(N)=O)cc3n21] | N-(2-carbamoylphenyl)-4,4-dimethyl-1-oxo-1,2,3,4-tetrahydropyrazino[1,2-a]indole-7-carboxamide |
| 222 | 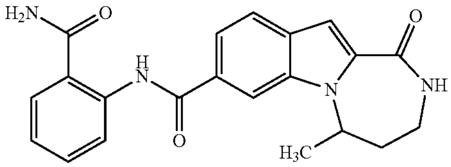 [SMILES: CC1CCNC(=O)c2cc3ccc(C(=O)Nc4ccccc4C(N)=O)cc3n21] | N-(2-carbamoylphenyl)-5-methyl-1-oxo-2,3,4,5-tetrahydro-1H-[1,4]diazepino[1,2-a]indole-8-carboxamide |
| 223 | 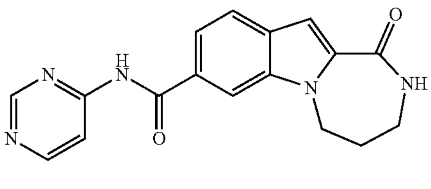 [SMILES: O=C(Nc1ccncn1)c1ccc2cc3n(c2c1)CCCNC3=O] | 1-oxo-N-(pyrimidin-4-yl)-2,3,4,5-tetrahydro-1H-[1,4]diazepino[1,2-a]indole-8-carboxamide |

TABLE 1-continued

| Example | Structure | Name |
|---|---|---|
| 224 | 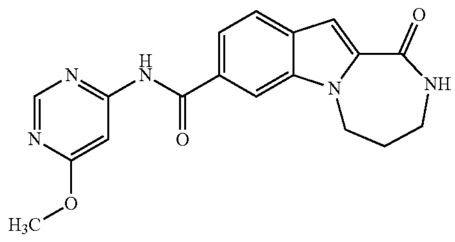 [SMILES: COc1cc(NC(=O)c2ccc3cc4n(c3c2)CCCNC4=O)ncn1] | N-(6-methoxypyrimidin-4-yl)-1-oxo-2,3,4,5-tetrahydro-1H-[1,4]diazepino[1,2-a]indole-8-carboxamide |
| 225 | 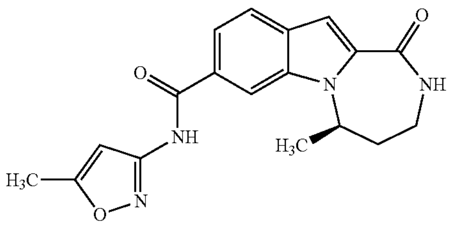 Chiral | (5R)-5-methyl-N-(5-methyl-1,2-oxazol-3-yl)-1-oxo-2,3,4,5-tetrahydro-1H-[1,4]diazepino[1,2-a]indole-8-carboxamide |
| 226 | 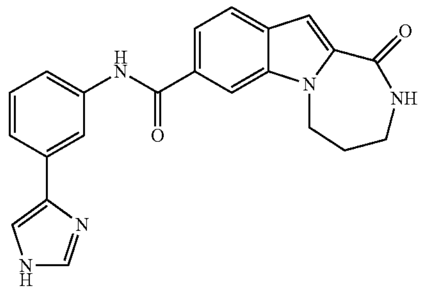 [SMILES: O=C(Nc1cccc(-c2c[nH]cn2)c1)c1ccc2cc3n(c2c1)CCCNC3=O] | N-[3-(1H-imidazol-4-yl)phenyl]-1-oxo-2,3,4,5-tetrahydro-1H-[1,4]diazepino[1,2-a]indole-8-carboxamide |
| 227 | 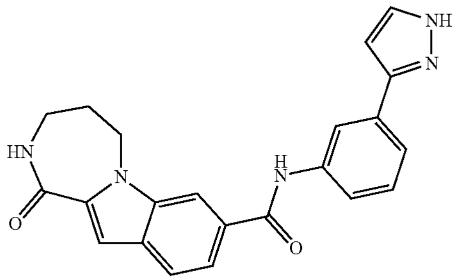 [SMILES: O=C(Nc1cccc(-c2cc[nH]n2)c1)c1ccc2cc3n(c2c1)CCCNC3=O] | 1-oxo-N-[3-(1H-pyrazol-3-yl)phenyl]-2,3,4,5-tetrahydro-1H-[1,4]diazepino[1,2-a]indole-8-carboxamide |
| 228 | 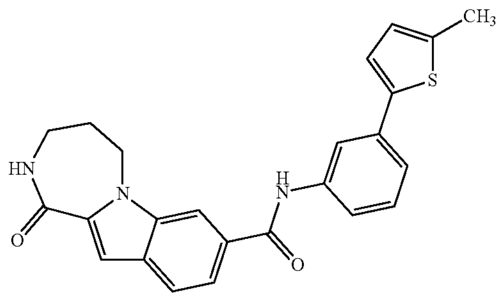 [SMILES: Cc1ccc(-c2cccc(NC(=O)c3ccc4cc5n(c4c3)CCCNC5=O)c2)s1] | N-[3-(5-methylthiophen-2-yl)phenyl]-1-oxo-2,3,4,5-tetrahydro-1H-[1,4]diazepino[1,2-a]indole-8-carboxamide |
| 229 | 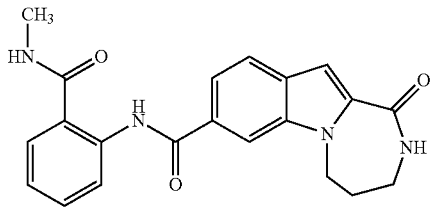 [SMILES: CNC(=O)c1ccccc1NC(=O)c1ccc2cc3n(c2c1)CCCNC3=O] | N-[2-(methylcarbamoyl)phenyl]-1-oxo-2,3,4,5-tetrahydro-1H-[1,4]diazepino[1,2-a]indole-8-carboxamide |

TABLE 1-continued

| Example | Structure | Name |
|---|---|---|
| 230 | 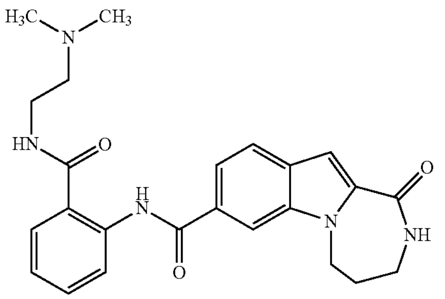 [SMILES: CN(C)CCNC(=O)c1ccccc1NC(=O)c1ccc2cc3n(c2c1)CCCNC3=O] | N-(2-{[2-(dimethylamino)ethyl]carbamoyl}phenyl)-1-oxo-2,3,4,5-tetrahydro-1H-[1,4]diazepino[1,2-a]indole-8-carboxamide |
| 231 | 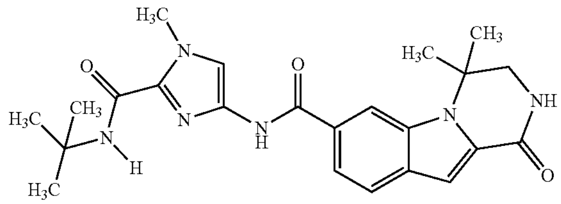 [SMILES: Cn1cc(NC(=O)c2ccc3cc4n(c3c2)C(C)(C)CNC4=O)nc1C(=O)NC(C)(C)C] | N-[2-(tert-butylcarbamoyl)-1-methyl-1H-imidazol-4-yl]-4,4-dimethyl-1-oxo-1,2,3,4-tetrahydropyrazino[1,2-a]indole-7-carboxamide |
| 232 | 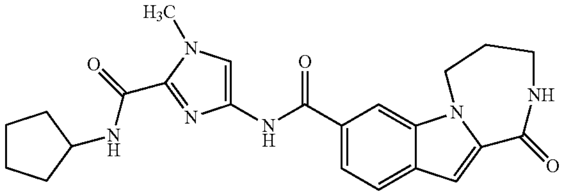 [SMILES: Cn1cc(NC(=O)c2ccc3cc4n(c3c2)CCCNC4=O)nc1C(=O)NC1CCCC1] | N-[2-(cyclopentylcarbamoyl)-1-methyl-1H-imidazol-4-yl]-1-oxo-2,3,4,5-tetrahydro-1H-[1,4]diazepino[1,2-a]indole-8-carboxamide |
| 233 | 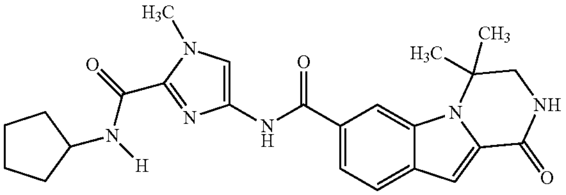 [SMILES: Cn1cc(NC(=O)c2ccc3cc4n(c3c2)C(C)(C)CNC4=O)nc1C(=O)NC1CCCC1] | N-[2-(cyclopentylcarbamoyl)-1-methyl-1H-imidazol-4-yl]-4,4-dimethyl-1-oxo-1,2,3,4-tetrahydropyrazino[1,2-a]indole-7-carboxamide |
| 234 | 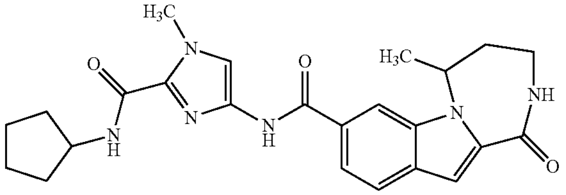 [SMILES: CC1CCNC(=O)c2cc3ccc(C(=O)Nc4cn(C)c(C(=O)NC5CCCC5)n4)cc3n21] | N-[2-(cyclopentylcarbamoyl)-1-methyl-1H-imidazol-4-yl]-5-methyl-1-oxo-2,3,4,5-tetrahydro-1H-[1,4]diazepino[1,2-a]indole-8-carboxamide |
| 235 | 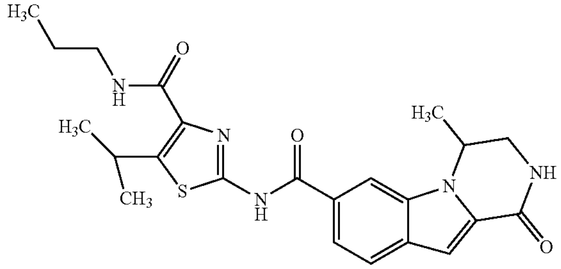 [SMILES: CCCNC(=O)c1nc(NC(=O)c2ccc3cc4n(c3c2)C(C)CNC4=O)sc1C(C)C] | 4-methyl-1-oxo-N-[5-(propan-2-yl)-4-(propylcarbamoyl)-1,3-thiazol-2-yl]-1,2,3,4-tetrahydropyrazino[1,2-a]indole-7-carboxamide |

TABLE 1-continued

| Example | Structure | Name |
|---|---|---|
| 236 | 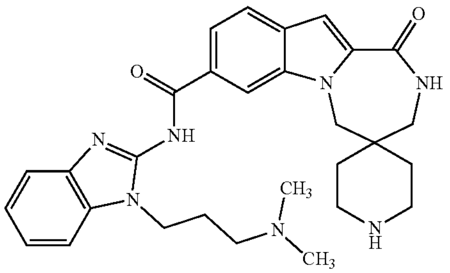 [SMILES: CN(C)CCCn1c(NC(=O)c2ccc3cc4n(c3c2)CC2(CCNCC2)CNC4=O)nc2ccccc21] | N-{1-[3-(dimethylamino)propyl]-1H-benzimidazol-2-yl}-1-oxo-2,3-dihydro-1H-spiro[1,4-diazepino[1,2-a]indole-4,4'-piperidine]-8-carboxamide |
| 237 | 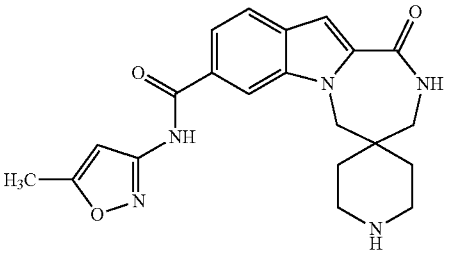 [SMILES: Cc1cc(NC(=O)c2ccc3cc4n(c3c2)CC2(CCNCC2)CNC4=O)no1] | N-(5-methyl-1,2-oxazol-3-yl)-1-oxo-2,3-dihydro-1H-spiro[1,4-diazepino[1,2-a]indole-4,4'-piperidine]-8-carboxamide |
| 238 | 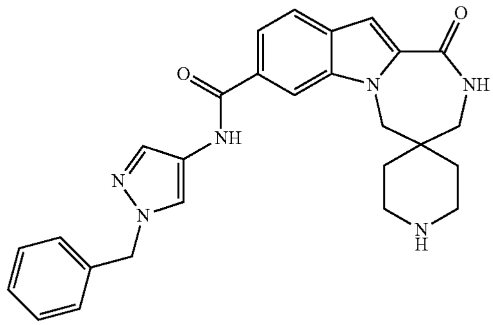 [SMILES: O=C(Nc1cnn(Cc2ccccc2)c1)c1ccc2cc3n(c2c1)CC1(CCNCC1)CNC3=O] | N-(1-benzyl-1H-pyrazol-4-yl)-1-oxo-2,3-dihydro-1H-spiro[1,4-diazepino[1,2-a]indole-4,4'-piperidine]-8-carboxamide |
| 239 | 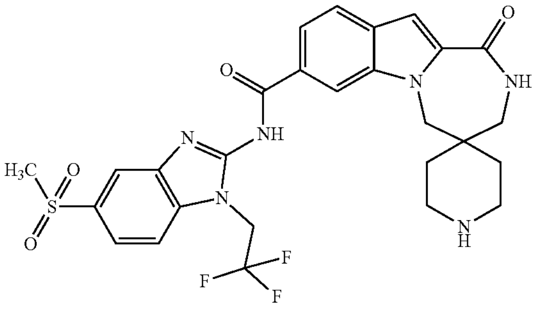 [SMILES: CS(=O)(=O)c1ccc2c(c1)nc(NC(=O)c1ccc3cc4n(c3c1)CC1(CCNCC1)CNC4=O)n2CC(F)(F)F] | N-[5-(methylsulfonyl)-1-(2,2,2-trifluoroethyl)-1H-benzimidazol-2-yl]-1-oxo-2,3-dihydro-1H-spiro[1,4-diazepino[1,2-a]indole-4,4'-piperidine]-8-carboxamide |

For all compounds disclosed hereinabove in this application, in the event the nomenclature is in conflict with the structure, it shall be understood that the compound is defined by the structure.

In one embodiment, the invention relates to a compound selected from the group consisting of:

N-(2-methoxypyridin-4-yl)-1-oxo-2,3,4,5-tetrahydro-1H-[1,4]diazepino[1,2-a]indole-8-carboxamide;

N-(1-ethyl-1H-benzimidazol-2-yl)-4,4-dimethyl-1-oxo-1,2,3,4-tetrahydropyrazino[1,2-a]indole-7-carboxamide;

N-(1-ethyl-1H-benzimidazol-2-yl)-cis-3,4-dimethyl-1-oxo-1,2,3,4-tetrahydropyrazino[1,2-a]indole-7-carboxamide;

4R)—N-{1-[3-(dimethylamino)propyl]-1H-benzimidazol-2-yl}-4-methyl-1-oxo-1,2,3,4-tetrahydropyrazino[1,2-a]indole-7-carboxamide;

N-(1-ethyl-1H-benzimidazol-2-yl)-5-methyl-1-oxo-2,3,4,5-tetrahydro-1H-[1,4]diazepino[1,2-a]indole-8-carboxamide;

5-methyl-1-oxo-N-[1-(propan-2-yl)-1H-benzimidazol-2-yl]-2,3,4,5-tetrahydro-1H-[1,4]diazepino[1,2-a]indole-8-carboxamide;

(4R)—N-(1-benzyl-1H-pyrazol-4-yl)-4-methyl-1-oxo-1,2,3,4-tetrahydropyrazino[1,2-a]indole-7-carboxamide;

N-(1H-benzimidazol-2-yl)-4,4-dimethyl-1-oxo-1,2,3,4-tetrahydropyrazino[1,2-a]indole-7-carboxamide;

(3S,4R)—N-(1-benzyl-1H-pyrazol-4-yl)-3,4-dimethyl-1-oxo-1,2,3,4-tetrahydropyrazino[1,2-a]indole-7-carboxamide;

N-(1H-benzimidazol-2-yl)-4-methyl-1-oxo-1,2,3,4-tetrahydropyrazino[1,2-a]indole-7-carboxamide;

4,4-dimethyl-N-(1-methyl-1H-benzimidazol-2-yl)-1-oxo-1,2,3,4-tetrahydropyrazino[1,2-a]indole-7-carboxamide;

N-{1-[3-(dimethylamino)propyl]-1H-benzimidazol-2-yl}-4,4-dimethyl-1-oxo-1,2,3,4-tetrahydropyrazino[1,2-a]indole-7-carboxamide;

4-methyl-N-(1-methyl-1H-benzimidazol-2-yl)-1-oxo-1,2,3,4-tetrahydropyrazino[1,2-a]indole-7-carboxamide;

(5R)-5-methyl-1-oxo-N-[1-(propan-2-yl)-1H-benzimidazol-2-yl]-2,3,4,5-tetrahydro-1H-[1,4]diazepino[1,2-a]indole-8-carboxamide;

N-(1-ethyl-1H-benzimidazol-2-yl)-4-methyl-1-oxo-1,2,3,4-tetrahydropyrazino[1,2-a]indole-7-carboxamide;

N-(1H-benzimidazol-2-yl)-5-methyl-1-oxo-2,3,4,5-tetrahydro-1H-[1,4]diazepino[1,2-a]indole-8-carboxamide;

(5R)—N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide;

N-{1-[3-(dimethylamino)propyl]-1H-benzimidazol-2-yl}-1'-oxo-2',3'-dihydro-1'H-spiro[cyclopropane-1,4'-[1,4]diazepino[1,2-a]indole]-8'-carboxamide;

(5R)—N-(1-benzyl-1H-pyrazol-4-yl)-5-methyl-1-oxo-2,3,4,5-tetrahydro-1H-[1,4]diazepino[1,2-a]indole-8-carboxamide;

N-(1-benzyl-1H-pyrazol-4-yl)-cis-3,4-dimethyl-1-oxo-1,2,3,4-tetrahydropyrazino[1,2-a]indole-7-carboxamide;

N-{1-[3-(dimethylamino)propyl]-1H-benzimidazol-2-yl}-cis-3,4-dimethyl-1-oxo-1,2,3,4-tetrahydropyrazino[1,2-a]indole-7-carboxamide;

(3S,4R)—N-{1-[3-(dimethylamino)propyl]-1H-benzimidazol-2-yl}-3,4-dimethyl-1-oxo-1,2,3,4-tetrahydropyrazino[1,2-a]indole-7-carboxamide;

N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide;

N-(1-ethyl-1H-benzimidazol-2-yl)-1-oxo-2,3,4,5-tetrahydro-1H-[1,4]diazepino[1,2-a]indole-8-carboxamide;

N-(5-chloro-1H-benzimidazol-2-yl)-5-methyl-1-oxo-2,3,4,5-tetrahydro-1H-[1,4]diazepino[1,2-a]indole-8-carboxamide;

N-(1-ethyl-5-methyl-1H-benzimidazol-2-yl)-1-oxo-2,3,4,5-tetrahydro-1H-[1,4]diazepino[1,2-a]indole-8-carboxamide;

cis-3,4-dimethyl-1-oxo-N-[1-(propan-2-yl)-1H-benzimidazol-2-yl]-1,2,3,4-tetrahydropyrazino[1,2-a]indole-7-carboxamide;

N-(1-benzyl-1H-pyrazol-4-yl)-4,4-difluoro-1-oxo-2,3,4,5-tetrahydro-1H-[1,4]diazepino[1,2-a]indole-8-carboxamide;

4,4-dimethyl-1-oxo-N-[1-(propan-2-yl)-1H-benzimidazol-2-yl]-1,2,3,4-tetrahydropyrazino[1,2-a]indole-7-carboxamide; and the pharmaceutically acceptable salts thereof.

In another embodiment, the invention relates to a compound selected from the group consisting of:

5-methyl-N-(1-methyl-1H-benzimidazol-2-yl)-1-oxo-2,3,4,5-tetrahydro-1H-[1,4]diazepino[1,2-a]indole-8-carboxamide; N-(1-benzyl-1H-pyrazol-4-yl)-4,4-dimethyl-1-oxo-1,2,3,4-tetrahydropyrazino[1,2-a]indole-7-carboxamide;

N-[2-(cyclopentylcarbamoyl)-1-methyl-1H-imidazol-4-yl]-5-methyl-1-oxo-2,3,4,5-tetrahydro-1H-[1,4]diazepino[1,2-a]indole-8-carboxamide;

N-(1H-indol-2-yl)-4-methyl-1-oxo-1,2,3,4-tetrahydropyrazino[1,2-a]indole-7-carboxamide;

N-(5-methyl-1H-benzimidazol-2-yl)-1-oxo-2,3,4,5-tetrahydro-1H-[1,4]diazepino[1,2-a]indole-8-carboxamide;

1-oxo-N-[1-(2,2,2-trifluoroethyl)-1H-benzimidazol-2-yl]-2,3,4,5-tetrahydro-1H-[1,4]diazepino[1,2-a]indole-8-carboxamide;

(4S)-4-methyl-1-oxo-N-[1-(propan-2-yl)-1H-benzimidazol-2-yl]-1,2,3,4-tetrahydropyrazino[1,2-a]indole-7-carboxamide;

N-{1-[3-(dimethylamino)propyl]-1H-benzimidazol-2-yl}-4-methyl-1-oxo-1,2,3,4-tetrahydropyrazino[1,2-a]indole-7-carboxamide;

5-methyl-N-(1-methyl-1H-benzimidazol-2-yl)-1-oxo-2,3,4,5-tetrahydro-1H-[1,4]diazepino[1,2-a]indole-8-carboxamide;

N-[2-(cyclopentylcarbamoyl)-1-methyl-1H-imidazol-4-yl]-4,4-dimethyl-1-oxo-1,2,3,4-tetrahydropyrazino[1,2-a]indole-7-carboxamide;

N-{1-[3-(dimethylamino)benzyl]-1H-pyrazol-4-yl}-1-oxo-2,3,4,5-tetrahydro-1H-[1,4]diazepino[1,2-a]indole-8-carboxamide;

cis-4,5-dimethyl-1-oxo-N-[1-(propan-2-yl)-1H-benzimidazol-2-yl]-2,3,4,5-tetrahydro-1H-[1,4]diazepino[1,2-a]indole-8-carboxamide;

N-(5-chloro-1H-benzimidazol-2-yl)-1-oxo-2,3,4,5-tetrahydro-1H-[1,4]diazepino[1,2-a]indole-8-carboxamide;

N-[2-(tert-butylcarbamoyl)-1-methyl-1H-imidazol-4-yl]-4,4-dimethyl-1-oxo-1,2,3,4-tetrahydropyrazino[1,2-a]indole-7-carboxamide;

N-(6-methoxypyrimidin-4-yl)-1-oxo-2,3,4,5-tetrahydro-1H-[1,4]diazepino[1,2-a]indole-8-carboxamide;

N-(1-ethyl-1H-benzimidazol-2-yl)-trans-3,4-dimethyl-1-oxo-1,2,3,4-tetrahydropyrazino[1,2-a]indole-7-carboxamide;

(3S,4R)-3,4-dimethyl-N-(5-methyl-1,2-oxazol-3-yl)-1-oxo-1,2,3,4-tetrahydropyrazino[1,2-a]indole-7-carboxamide;

4-methyl-1-oxo-N-[1-(propan-2-yl)-1H-benzimidazol-2-yl]-1,2,3,4-tetrahydropyrazino[1,2-a]indole-7-carboxamide;

N-(1-benzyl-1H-pyrazol-4-yl)-cis-4,5-dimethyl-1-oxo-2,3,4,5-tetrahydro-1H-[1,4]diazepino[1,2-a]indole-8-carboxamide;

N-(2-carbamoylphenyl)-4,4-dimethyl-1-oxo-1,2,3,4-tetrahydropyrazino[1,2-a]indole-7-carboxamide;

N-[1-(2-hydroxy-2-methylpropyl)-1H-benzimidazol-2-yl]-4,4-dimethyl-1-oxo-2,3,4,5-tetrahydro-1H-[1,4]diazepino[1,2-a]indole-8-carboxamide;

N-(3-ethyl-3H-imidazo[4,5-b]pyridin-2-yl)-1-oxo-2,3,4,5-tetrahydro-1H-[1,4]diazepino[1,2-a]indole-8-carboxamide;

N-(1-benzyl-1H-pyrazol-4-yl)-1'-oxo-2',3'-dihydro-1'H-spiro[cyclopropane-1,4'-[1,4]diazepino[1,2-a]indole]-8'-carboxamide;

1-oxo-N-[5-(propan-2-yl)-1H-benzimidazol-2-yl]-2,3,4,5-tetrahydro-1H-[1,4]diazepino[1,2-a]indole-8-carboxamide;

cis-3,4-dimethyl-1-oxo-N-[1-(propan-2-yl)-1H-pyrazolo[3,4-b]pyridin-5-yl]-1,2,3,4-tetrahydropyrazino[1,2-a]indole-7-carboxamide;

4,4-dimethyl-1-oxo-N-(3-phenyl-1,2-oxazol-5-yl)-1,2,3,4-tetrahydropyrazino[1,2-a]indole-7-carboxamide;

N-{1-[3-(dimethylamino)propyl]-1H-benzimidazol-2-yl}-cis-4,5-dimethyl-1-oxo-2,3,4,5-tetrahydro-1H-[1,4]diazepino[1,2-a]indole-8-carboxamide;

N-(6-chloro-1-ethyl-1H-benzimidazol-2-yl)-1-oxo-2,3,4,5-tetrahydro-1H-[1,4]diazepino[1,2-a]indole-8-carboxamide;

1-oxo-N-[1-(pyridin-4-ylmethyl)-1H-pyrazol-4-yl]-2,3,4,5-tetrahydro-1H-[1,4]diazepino[1,2-a]indole-8-carboxamide;

N-(1-benzyl-1H-pyrazol-4-yl)-1-oxo-2,3,4,5-tetrahydro-1H-[1,4]diazepino[1,2-a]indole-8-carboxamide;

(5S)—N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide; and the pharmaceutically acceptable salts thereof.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The invention includes pharmaceutically acceptable derivatives of compounds depicted in Table 1. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

DETAILED DESCRIPTION OF THE INVENTION

Synthetic Examples

Compounds depicted in Table 1 are prepared as illustrated by the examples below. Retention times for the compounds are obtained on an HPLC system using the conditions shown in Table 2 below.

TABLE 2

| Method | Time (min) | Water + 0.1% $HCO_2H$ | $CH_3CN$ + 0.1% $HCO_2H$ | Flow (mL/min) | Column |
|---|---|---|---|---|---|
| V1 | 0 | 88 | 12 | 1.5 | Agilent SB-C18 |
| | 0.25 | 70 | 30 | 1.5 | 1.8 um |
| | 0.3 | 60 | 40 | 1.5 | 3 × 50 mm column |
| | 1.19 | 5 | 95 | 1.5 | |
| | 1.75 | 0 | 100 | 1.5 | |
| A1 | 0 | 95 | 5 | 2.5 | Agilent Zorbax C18 SB |
| | 1.7 | 5 | 95 | 2.5 | 3.5 um 4.6 × 30 mm |
| | 2 | 5 | 95 | 2.5 | cartridge |
| | 2.1 | 95 | 5 | 2.5 | |
| | 2.3 | 95 | 5 | 2.5 | |
| H1 | 0 | 90 | 10 | 0.8 | Waters BEH 2.1 × 50 mm |
| | 1.19 | 5 | 95 | 0.8 | C18 1.7 um column |
| | 1.7 | 5 | 95 | 0.8 | |
| U2 | 0 | 90 | 10 | 0.8 | Waters BEH 2.1 × 50 mm |
| | 4.5 | 5 | 95 | 0.8 | C18 1.7 um column |
| A2 | 0 | 99 | 1 | 1.5 | Agilent Zorbax Eclipse |
| | 2 | 80 | 20 | 1.5 | XDB-C8 5 um |
| | 7 | 5 | 95 | 1.5 | 4.6 × 150 mm column |
| | 9 | 5 | 95 | 1.5 | |
| | 9.3 | 99 | 1 | 1.5 | |
| | 10 | 99 | 1 | 1.5 | |

Intermediate A: Diethyl 1H-indole-2,6-dicarboxylate

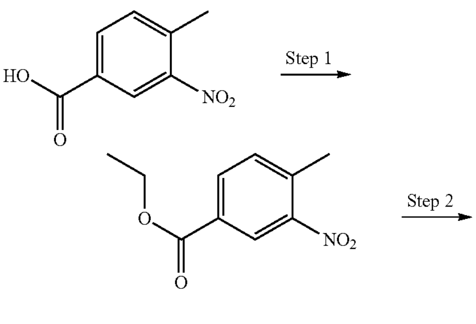

-continued

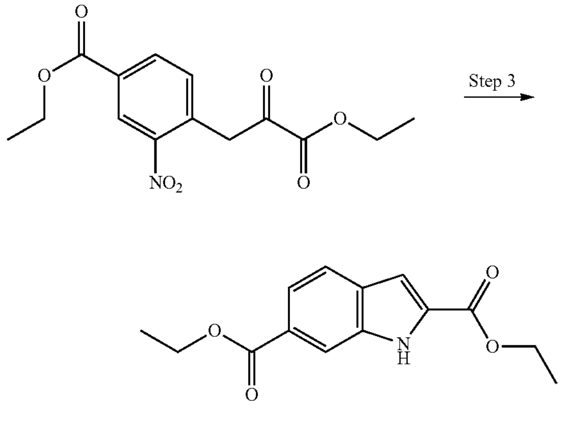

Step 1: Synthesis of ethyl 4-methyl-3-nitrobenzoate

4-Methyl-3-nitrobenzoic acid (71 g, 0.39 mol) is dissolved in dry ethanol (600 mL) and dry HCl gas is bubbled into the solution for 5 min. The reaction mixture is heated to 90° C. under $N_2$ for 20 h. The solvent is removed under vacuum to afford the title compound as a straw-colored liquid (80.0 g, 98%).

Step 2: Synthesis of ethyl 4-(3-ethoxy-2,3-dioxopropyl)-3-nitrobenzoate

To a solution of ethyl 4-methyl-3-nitrobenzoate (80 g, 0.38 mol) and oxalic acid diethyl ester (57 mL, 0.42 mol) in ethanol (1000 mL) is added sodium ethoxide (430 mL, 1.15 mol, 21% in ethanol). The resulting brown solution is stirred at room temperature for 16 h. The reaction is quenched with 3N HCl to neutral pH and diluted with water (2000 mL). The resulting white precipitate is filtered and dried in vacuum to afford the title compound (91 g, 77%).

Step 3: Synthesis of diethyl 1H-indole-2,6-dicarboxylate

Ethyl 4-(3-ethoxy-2,3-dioxopropyl)-3-nitrobenzoate (91 g, 0.29 mol) is suspended in 800 mL of acetic acid and it is heated with stirring to 75° C. Once the solid is dissolved, water (600 mL) is added. Zinc dust (189 g, 2.9 mol) is added carefully in small portions and the reaction temperature is kept below 85° C. The mixture is then stirred vigorously for 1 hour after the addition. EtOAc (1500 mL) is added and the mixture was filtered through Celite. The solid is washed with more EtOAc (1500 mL) and the filtrates are combined, washed twice with water (1500 mL), four times with saturated $NaHCO_3$ (1000 mL), and once with brine (1000 mL). The filtrate is dried ($Na_2SO_4$), filtered, and concentrated to afford the crude compound which was recrystallized from toluene to afford the title compound (44.6 g, 58%) as a yellow powder.

Intermediate B: 4-Methyl-1-oxo-1,2,3,4-tetrahydropyrazino[1,2-a]indole-7-carboxylic acid

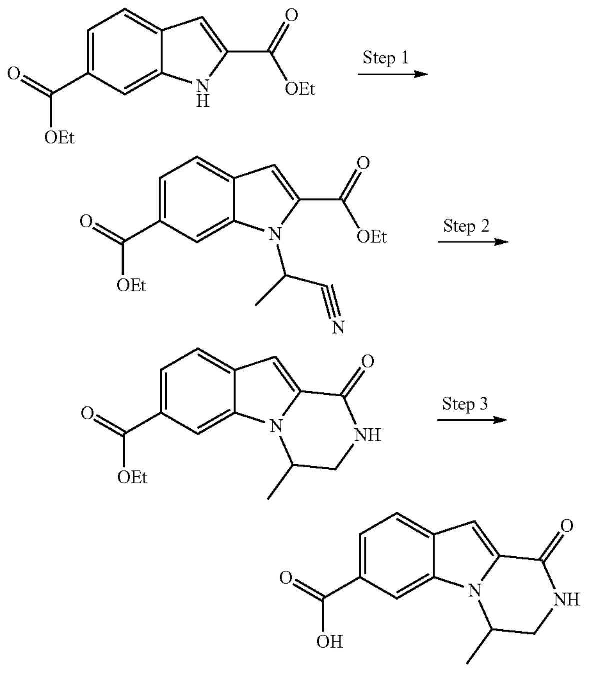

Step 1: Synthesis of diethyl 1-(1-cyanoethyl)-1H-indole-2,6-dicarboxylate

A mixture of $K_2CO_3$ (7.9 g, 57.4 mmol) and diethyl 1H-indole-2,6-dicarboxylate (Intermediate A, 5.0 g, 19.1 mmol) in DMF (30 mL) is stirred at room temperature for 30 min. A solution of 2-bromo-propionitrile (3.4 mL, 38.3 mmol) in DMF (10 mL) is added. The reaction mixture is warmed to 80° C. for 6 h and then cooled to room temperature and stirred for another 16 h. Solvent is removed and the residue is partitioned between EtOAc and water. The organic layer is separated, dried and concentrated to afford crude compound which is purified by flash column chromatography using EtOAc in hexanes followed by trituration with acetonitrile to afford the title compound (5.5 g, 91%).

Step 2: Synthesis of ethyl 4-methyl-1-oxo-1,2,3,4-tetrahydropyrazino[1,2-a]indole-7-carboxylate To a solution of diethyl 1-(1-cyanoethyl)-1H-indole-2,6-dicarboxylate (3.9 g, 12.4 mmol) in ethanol (500 mL) is added platinum oxide (2.0 g, 8.8 mmol). The reaction mixture is then shaken under 50 psi of $H_2$ for 4 h. Additional platinum oxide (700 mg, 3.1 mmol) is added along with more ethanol (10 mL) and the mixture is shaken under 50 psi of $H_2$ for another 16 h. The reaction mixture is filtered through Celite under a flow of $N_2$ and the Celite is rinsed with EtOAc. The filtrates are combined and concentrated to afford the title compound (3.2 g, 95%) which is used in the next step without further purification.

Step 3: Synthesis of 4-methyl-1-oxo-1,2,3,4-tetrahydropyrazino[1,2-α]indole-7-carboxylic acid To a suspension of ethyl 4-methyl-1-oxo-1,2,3,4-tetrahydropyrazino[1,2-a]indole-7-carboxylate (3.2 g, 11.8 mmol) in THF:ethanol (1:1, 50 mL) is added 1N NaOH solution (43 mL, 43 mmol). The reaction mixture is heated at 75° C. for 18 h. The solvents are removed and the residue is dissolved in water. The aqueous solution is washed with ether and acidified to pH 4 using 3N HCl solution. The resulting white solid is filtered and rinsed more ether to afford the title compound (2.2 g, 76%).

Intermediate C: (4R)-4-methyl-1-oxo-1,2,3,4-tetrahydropyrazino[1,2-a]indole-7-carboxylic acid

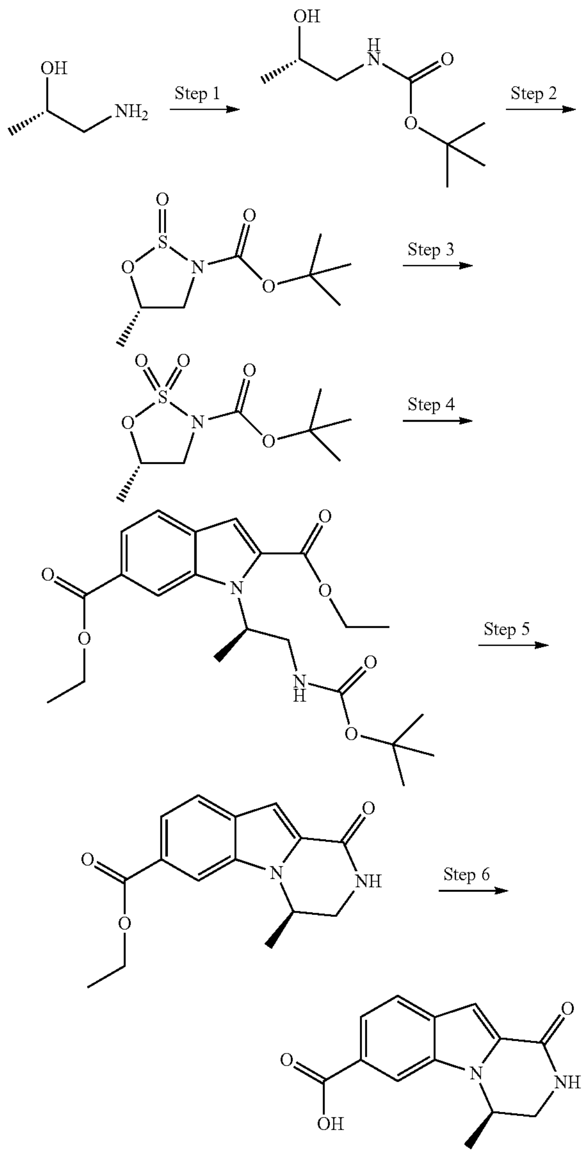

Step 1: Synthesis of tert-butyl [(2S)-2-hydroxypropyl]carbamate

To a stirred solution of (2S)-1-aminopropan-2-ol (2.0 g, 26.6 mmol) in $CH_2Cl_2$ (50 mL) is added a solution of di-tert-butyl dicarbonate (6.1 g, 28 mmol) in $CH_2Cl_2$ (50 mL). The reaction mixture is stirred for 18 h. The solution is washed with citric acid and $NaHCO_3$, dried ($Na_2SO_4$) and evaporated to afford the title compound (5.1 g, crude) as colorless oil.

Step 2: Synthesis of tert-butyl (5S)-5-methyl-1,2,3-oxathiazolidine-3-carboxylate 2-oxide A stirred solution of thionyl chloride (4.8 mL, 66.3 mmol) in acetonitrile (30 mL) is cooled down to −45° C. and a solution of tert-butyl [(2S)-2-hydroxypropyl]carbamate (5.1 g, 26.6 mmol) in acetonitrile (40 mL) is added by an addition funnel over about 20 min, keeping the internal temperature below −40° C. Then 4-dimethylaminopyridine (324 mg, 2.6 mmol) is added followed by the dropwise addition of pyridine (10.7 mL, 133.7 mmol), keeping the temperature below −40° C. The addition takes 1.5 h. Ethyl acetate (100 mL) is added to the suspension. The mixture is filtered at −35° C. to remove the solid and the solid is washed with EtOAc before it is discarded. Saturated $Na_2HPO_4$ solution (40 mL) is added to the filtrate and the mixture is stirred vigorously for 30 min. The organic layer is separated, washed with 1M $NaHSO_4$ to remove residual pyridine, dried ($Na_2SO_4$) and concentrated to afford a clear oil. The residue was taken up in diethyl ether, a small amount of insoluble material was removed and the filtrate was concentrated to afford the title compound (5.7 g, crude) as an oil.

Step 3: Synthesis of tert-butyl (5S)-5-methyl-1,2,3-oxathiazolidine-3-carboxylate 2,2-dioxide To a solution of tert-butyl (5S)-5-methyl-1,2,3-oxathiazolidine-3-carboxylate 2-oxide (5.7 g, 25.8 mmol) in acetonitrile (60 mL) and water (30 mL) is added sodium periodate (8.3 g, 38.7 mmol) in one portion. After 5 min, a few crystals of $RuCl_3$ is added. The reaction is stirred for 3 h and the resulting thick slurry is diluted with water (100 mL) and ethyl acetate (20 mL) and is passed through a bed of Celite, rinsing with additional EtOAc. The filtrate is concentrated to remove the organic solvents and the resulting solid is isolated by filtration to afford the title compound (6.0 g, 97%).

Step 4: Synthesis of diethyl 1-{(2R)-1-[(tert-butoxycarbonyl)amino]propan-2-yl}-1H-indole-2,6-dicarboxylate A stirred suspension of 60% NaH (371 mg, 9.3 mmol) in DMF (10 mL) is cooled in an ice bath, and a solution of diethyl 1H-indole-2,6-dicarboxylate (Intermediate A, 2.6 g, 10.1 mmol) in DMF (10 mL) is added. The mixture is stirred for 20 min, then a solution of tert-butyl (5S)-5-methyl-1,2,3-oxathiazolidine-3-carboxylate 2,2-dioxide (2.0 g, 8.4 mmol) in DMF (10 mL) is added. The reaction mixture is stirred for 30 min at 0° C. and then warmed to room temperature and stirred for 48 h. The reaction is poured into ice water and the resultant solid is removed by filtration. The filtrate is acidified to pH 3 with 1N aqueous HCl and extracted with EtOAc. The combined extracts are washed with water, brine, dried ($Na_2SO_4$) and concentrated to afford the title compound (2.7 g, crude) as an oil.

Step 5: Synthesis of ethyl (4R)-4-methyl-1-oxo-1,2,3,4-tetrahydropyrazino[1,2-a]indole-7-carboxylate To a solution of diethyl 1-{(2R)-1-[(tert-butoxycarbonyl)amino]propan-2-yl}-1H-indole-2,6-dicarboxylate (2.7 g, 6.4 mmol) in $CH_2Cl_2$ (10 mL) is added TFA (10 mL). The reaction mixture is stirred for 2 h and the solvent is removed under vacuum. To a solution of the residue in ethanol (30 mL) is added $K_2CO_3$ (4.5 g, 32.3 mmol) and the reaction mixture is stirred at room temperature for 16 h. The solvent is evaporated and the residue is taken up in water. To the mixture is added a small amount of diethyl ether followed by heptanes (100 mL). The suspension is filtered to afford the title compound (1.3 g, 57% for two steps) as a solid.

Step 6: Synthesis of (4R)-4-methyl-1-oxo-1,2,3,4-tetrahydropyrazino[1,2-a]indole-7-carboxylic acid To a solution of ethyl (4R)-4-methyl-1-oxo-1,2,3,4-tetrahydropyrazino[1,2-α]indole-7-carboxylate (1.3 g, 4.8 mmol) in ethanol (60 mL) is added 1M NaOH solution (12 mL, 12 mmol). The reaction mixture is refluxed for 1.5 h. Then the reaction mixture is acidified with 1M HCl and ethanol is removed under vacuum. The resulting solid is filtered, washed with water, and dried to afford the title compound (1.1 g, 98%) as a solid.

Intermediate D: (4S)-4-methyl-1-oxo-1,2,3,4-tetrahydropyrazino[1,2-a]indole-7-carboxylic acid

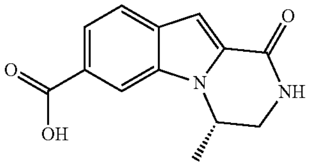 [SMILES: C[C@H]1CNC(=O)c2cc3ccc(C(=O)O)cc3n21]

This compound is synthesized using the similar procedure used to prepare (4R)-4-methyl-1-oxo-1,2,3,4-tetrahydropyrazino[1,2-a]indole-7-carboxylic acid (Intermediate C), replacing (2S)-1-aminopropan-2-ol with (2R)-1-aminopropan-2-ol in Step 1.

Intermediate E: 4,4-dimethyl-1-oxo-1,2,3,4-tetrahydropyrazino[1,2-a]indole-7-carboxylic acid

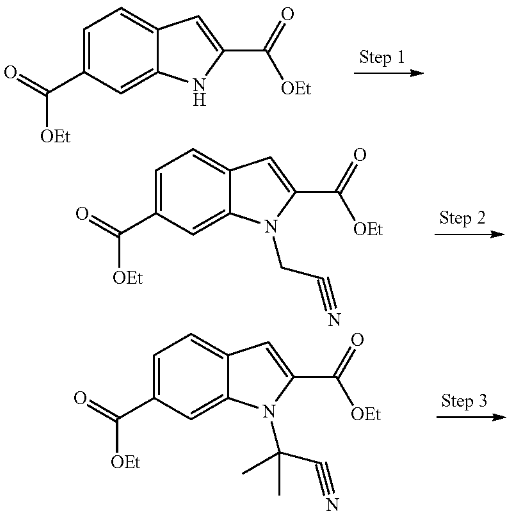

-continued

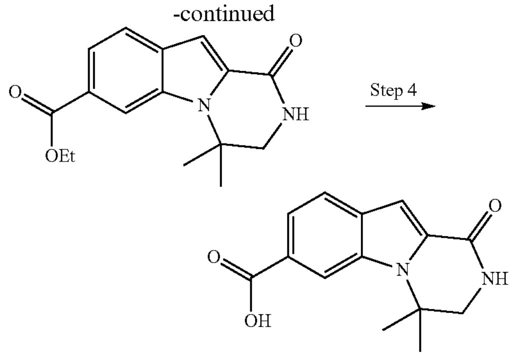

Step 1: Synthesis of diethyl 1-(cyanomethyl)-1H-indole-2,6-dicarboxylate

To a solution of diethyl 1H-indole-2,6-dicarboxylate (Intermediate A, 4.0 g, 15.3 mmol) in dry DMF (50 mL) is added $K_2CO_3$ (6.3 g, 45.9 mmol). The reaction mixture is stirred under $N_2$ for 30 min. Bromoacetonitrile (2.1 mL, 30.6 mmol) is added and the reaction mixture is heated to 80° C. for 4 h. After cooling, the reaction mixture is taken up in EtOAc (300 mL) and washed with water, then brine, dried ($Na_2SO_4$) and concentrated. The residue is recrystallized from ethanol to afford the title compound (3.9 g, 84%) as fine off-white needles.

Step 2: Synthesis of diethyl 1-(2-cyanopropan-2-yl)-1H-indole-2,6-dicarboxylate

To a solution of diethyl 1-(cyanomethyl)-1H-indole-2,6-dicarboxylate (2.0 g, 6.8 mmol) in THF (60 mL) is added methyl iodide (1.7 mL, 27.2 mmol) at 0° C. A solution of 1.0M sodium bis(trimethylsilyl)amide in THF (20.4 mL, 20.4 mmol) is added at 0° C. The reaction mixture is warmed to room temperature and stirred for 24 h. The reaction is quenched with saturated aqueous $NH_4Cl$ solution, diluted with EtOAc (100 mL) and the aqueous phase is separated and extracted twice with EtOAc. The combined organic layers are washed with brine, dried ($MgSO_4$) and concentrated to afford the crude compound which is purified by flash column chromatography using EtOAc in hexanes to afford the title compound (1.4 g, 61%).

Step 3: Synthesis of ethyl 4,4-dimethyl-1-oxo-1,2,3,4-tetrahydropyrazino[1,2-a]indole-7-carboxylate A mixture of diethyl 1-(2-cyanopropan-2-yl)-1H-indole-2,6-dicarboxylate (9.3 g, 23.3 mmol) and Raney Ni (4 g of 50% wet catalyst) and water (5 mL) water is heated to 50° C. under 250 psi of $H_2$. The mixture is stirred for 18 h. LCMS shows complete reaction with high purity. The mixture is filtered through Celite, keeping the catalyst wet until properly disposed. The solvent was removed under reduced pressure to afford the title compound (7.7 g, 95%) as a white solid.

Step 4: Synthesis of 4,4-dimethyl-1-oxo-1,2,3,4-tetrahydropyrazino[1,2-a]indole-7-carboxylic acid To a suspension of ethyl 4,4-dimethyl-1-oxo-1,2,3,4-tetrahydropyrazino[1,2-a]indole-7-carboxylate (2.7 g, 9.3 mmol) in methanol (30 mL) is added 3N NaOH solution (15.5 mL, 46.5 mmol). The reaction mixture is heated at 65° C. for 16 h. The reaction mixture is diluted with water and acidified to pH 2 using 2N HCl solution at 0° C. The resulting white solid is filtered, rinsed with water and dried to afford the title compound (2.1 g, 88%) as a white solid.

Intermediate F: cis-3,4-dimethyl-1-oxo-1,2,3,4-tetrahydropyrazino[1,2-a]indole-7-carboxylic acid Intermediate G: trans-3,4-dimethyl-1-oxo-1,2,3,4-tetrahydropyrazino[1,2-a]indole-7-carboxylic acid

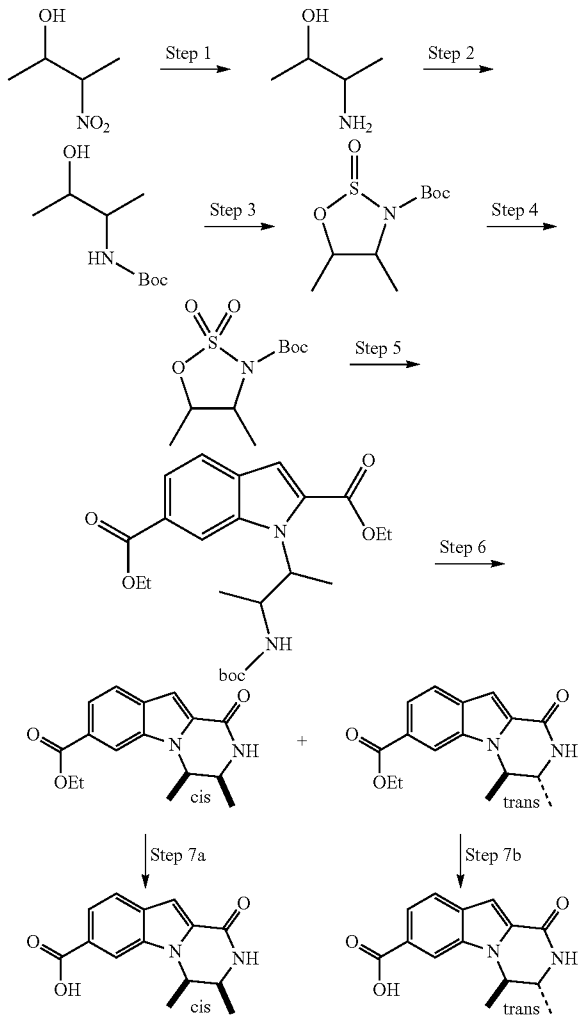

Step 1: Synthesis of 3-aminobutan-2-ol

Ammonium formate (9.0 g, 142.9 mmol) is added to a solution of 3-nitrobutan-2-ol (2.5 g, 21.0 mmol) in methanol (20 mL). Palladium on carbon (250 mg) is then added as a slurry in methanol. The reaction mixture is stirred at room temperature for 18 h. Celite is added and the mixture is filtered though a plug of more Celite. The solid is washed with methanol and the filtrates are combined and concentrated to afford the title compound (2.42 g, 129%) which is used in the next step without purification.

Step 2: Synthesis of tert-butyl (3-hydroxybutan-2-yl)carbamate

To a stirred solution of crude 3-amino-butan-2-ol from the preceding reaction (2.42 g) in $CH_2Cl_2$ (20 mL) is added a solution of di-tert-butyl dicarbonate (4.7 g, 21.4 mmol) in $CH_2Cl_2$ (20 mL). The reaction mixture is stirred for 18 h and then the solution is washed with 1M $NaHSO_4$ and $NaHCO_3$. The organic layer is separated, dried over ($MgSO_4$) and concentrated to afford the title crude compound as a colorless oil (4.33 g, 105% over 2 steps).

Step 3: Synthesis of tert-butyl 4,5-dimethyl-1,2,3-oxathiazolidine-3-carboxylate 2-oxide To a stirred solution of thionyl chloride (4.1 mL, 56.8 mmol) in acetonitrile (30 mL) cooled to −45° C. is added a solution of tert-butyl (3-hydroxybutan-2-yl)carbamate (4.30 g, 22.7 mmol) in acetonitrile (40 mL) by syringe over 10 min, keeping the internal temperature below −40° C. When the addition is complete, 4-dimethylamino pyridine (277.5 mg, 2.3 mmol) is added followed by the dropwise addition of pyridine (9.2 mL, 113.6 mmol), keeping the temperature below −40° C. The reaction mixture is stirred at −40° C. for 1 h. Ethyl acetate (70 mL) is added to the suspension and the mixture is filtered at −35° C. The solid is washed with EtOAc and the filtrates are combined. Saturated $Na_2HPO_4$ solution (40 mL) is added and the mixture is stirred vigorously for 30 min. The organic layer is separated, washed with 1M $NaHSO_4$, dried ($MgSO_4$) and concentrated to afford the title crude compound (4.83 g, 90%) as an oil.

Step 4: Synthesis of tert-butyl 4,5-dimethyl-1,2,3-oxathiazolidine-3-carboxylate 2,2-dioxide To a solution of tert-butyl 4,5-dimethyl-1,2,3-oxathiazolidine-3-carboxylate 2-oxide in acetonitrile (50 mL) and water (30 mL) cooled to 0° C. is added sodium periodate (6.4 g, 30.0 mmol). After 5 min, the pH of the mixture is adjusted to 7-8 by addition of saturated $Na_2HPO_4$ solution. Then the solution of $RuCl_3$ (41.5 mg, 0.2 mmol) in water (0.5 mL) is added. The pH of the reaction mixture is kept between 6 and 9 by addition of $Na_2HPO_4$ solution. After stirring for 2 h, water (100 mL) is added and the pH is adjusted to 6 by addition of 2 M HCl solution. The mixture is extracted with EtOAc and the organic layer is separated, washed with $NaHCO_3$ and brine. The aqueous washing layers are back extracted once with EtOAc. The combined organic layers are dried ($MgSO_4$) and concentrated to afford the crude compound which is purified by flash column chromatography using EtOAc in hexanes to afford the title compound (4.48 g, 85% for 4 steps).

Step 5: Synthesis of diethyl 1-[3-[(tert-butoxycarbonyl)amino]butan-2-yl]-1H-indole-2,6-dicarboxylate To a stirred suspension of 60% NaH dispersion in mineral oil (596 mg, 14.9 mmol) in DMF (14 mL) at 0° C. is added a solution of diethyl 1H-indole-2,6-dicarboxylate (Intermediate A, 3.9 g, 14.9 mmol) in DMF (14 mL). The mixture is stirred for 40 min, then a solution of tert-butyl 4,5-dimethyl-1,2,3-oxathiazolidine-3-carboxylate 2,2-dioxide (3.8 g, 14.9 mmol) in DMF (7 mL) is added. The reaction mixture is stirred for 30 min at 0° C. and then is warmed to room temperature and stirred for 65 h. Water is added and the mixture is stirred for 15 min before EtOAc (50 mL) is added. Then the organic layer is separated, washed with aqueous $NH_4Cl$ solution, water, and brine, dried ($MgSO_4$) and concentrated to afford the crude title compound, which was used directly in the next reaction.

Step 6: Synthesis of ethyl cis-3,4-dimethyl-1-oxo-1,2,3,4-tetrahydropyrazino[1,2-α]indole-7-carboxylate and ethyl trans-3,4-dimethyl-1-oxo-1,2,3,4-tetrahydropyrazino[1,2-α]indole-7-carboxylate To a solution of the crude diethyl 1-{3-[(tert-butoxycarbonyl)amino]butan-2-yl}-1H-indole-2,6-dicarboxylate from the preceding reaction in $CH_2Cl_2$ (10 mL) is added TFA (10 mL). The mixture is stirred for 1 h at room temperature. The solvent is removed and the residue is dried in vacuo for 1 h. To a solution of the residue in ethanol (100 mL) is added $K_2CO_3$ (6.2 g, 44.8 mmol). The reaction mixture is refluxed for 1 h. After cooling to room temperature, the solvent is removed under vacuum and the residue is partitioned between EtOAc and water. The organic layer is separated, washed with brine, dried ($MgSO_4$) and concentrated to afford the crude compound which is purified by flash column chromatography using EtOAc in heptane to afford ethyl trans-3,4-dimethyl-1-oxo-1,2,3,4-tetrahydropyrazino[1,2-α]indole-7-carboxylate (870 mg, 20% for 2 steps) and ethyl cis-3,4-dimethyl-1-oxo-1,2,3,4-tetrahydropyrazino[1,2-a]indole-7-carboxylate (1.9 g, 45% for 2 steps).

Step 7a: Synthesis of cis-3,4-dimethyl-1-oxo-1,2,3,4-tetrahydropyrazino[1,2-α]indole-7-carboxylic acid To a suspension of ethyl cis-3,4-dimethyl-1-oxo-1,2,3,4-tetrahydropyrazino[1,2-α]indole-7-carboxylate (2.1 g, 7.3 mmol) in ethanol (60 mL) is added 1M NaOH solution (20 mL, 20 mmol). The reaction mixture is heated at 80° C. for 1 h and then cooled to room temperature. The reaction mixture is acidified using concentrated HCl and ethanol is removed under vacuum. The resulting solid is filtered, rinsed with water and dried to afford the title compound (1.8 g, 96%).

Step 7b: Synthesis of trans-3,4-dimethyl-1-oxo-1,2,3,4-tetrahydropyrazino[1,2-a]indole-7-carboxylic acid To a suspension of ethyl trans-3,4-dimethyl-1-oxo-1,2,3,4-tetrahydropyrazino[1,2-a]indole-7-carboxylate (930 mg, 3.2 mmol) in ethanol (40 mL) is added 1M NaOH solution (10 mL, 10 mmol). The reaction mixture is heated at 80° C. for 1 h and then cooled to room temperature. The reaction mixture is acidified using concentrated HCl and ethanol is removed under vacuum. The resulting solid is filtered, rinsed with water and dried to afford the title compound (782 mg, 93%).

Intermediate H: (3S,4R)-3,4-Dimethyl-1-oxo-1,2,3,4-tetrahydro-pyrazino[1,2-a]indole-7-carboxylic acid Intermediate I: (3R,4S)-3,4-Dimethyl-1-oxo-1,2,3,4-tetrahydro-pyrazino[1,2-a]indole-7-carboxylic acid

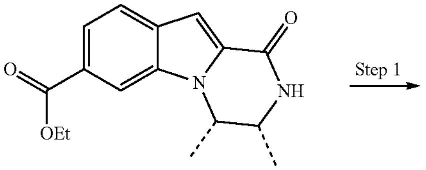

-continued

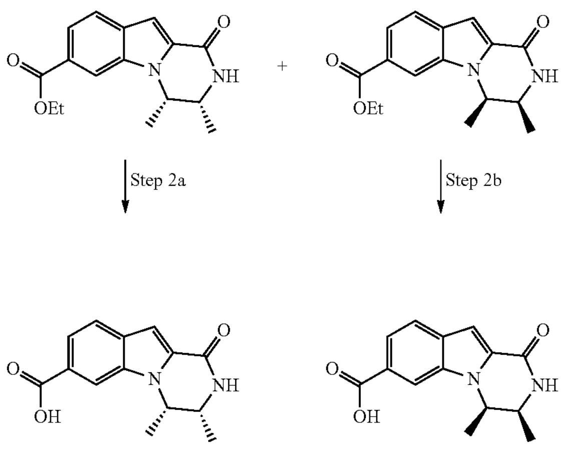

Step 1: Separation of ethyl (3R,4S)-3,4-dimethyl-1-oxo-1,2,3,4-tetrahydropyrazino[1,2-a]indole-7-carboxylate and ethyl (3S,4R)-3,4-dimethyl-1-oxo-1,2,3,4-tetrahydropyrazino[1,2-a]indole-7-carboxylate Racemic cis-3,4-dimethyl-1-oxo-1,2,3,4-tetrahydropyrazino[1,2-a]indole-7-carboxylic acid (Intermediate F, 1.9 g, 6.7 mmol) is separated on a preparative chiral column (Chiralpak AD, 5 cm×50 cm, 20 u, Chiral Technologies, West Chester, Pa.) using Gilson preparative HPLC (Mobile Phase: 12% isopropanol in heptane; Flow rate: 100 mL/min) to afford ethyl (3S,4R)-3,4-dimethyl-1-oxo-1,2,3,4-tetrahydropyrazino[1,2-a]indole-7-carboxylate (870 mg, 46%) and ethyl (3R,4S)-3,4-dimethyl-1-oxo-1,2,3,4-tetrahydropyrazino[1,2-a]indole-7-carboxylate (852 mg, 45%).

Step 2a: Synthesis of (3R,4S)-3,4-dimethyl-1-oxo-1,2,3,4-tetrahydro-pyrazino[1,2-a]indole-7-carboxylic acid To a solution of ethyl (3R,4S)-3,4-dimethyl-1-oxo-1,2,3,4-tetrahydropyrazino[1,2-a]indole-7-carboxylate (851 mg, 3.0 mmol) in ethanol (20 mL) is added 1M NaOH solution (7.0 mL, 7.0 mmol). The reaction mixture is heated at 70° C. for 2 h. The solvent is removed and the residue is acidified using 1M HCl solution until the pH is 5. The resulting white solid is filtered and dried to afford the title compound (697 mg, 91%).

Step 2b: Synthesis of (3S,4R)-3,4-Dimethyl-1-oxo-1,2,3,4-tetrahydro-pyrazino[1,2-a]indole-7-carboxylic acid Ethyl (3S,4R)-3,4-dimethyl-1-oxo-1,2,3,4-tetrahydropyrazino[1,2-a]indole-7-carboxylate (870 mg, 3.0 mmol) is suspended in ethanol (25 mL) and 1M NaOH solution (7.6 mL, 7.6 mmol) is added. The reaction mixture is heated at 80° C. for 1 h and then cooled to room temperature. The mixture is acidified with 1M HCl solution and ethanol is removed. The resulting solid is filtered, rinsed with water and dried to afford the title compound (760 mg, 97%).

Intermediate J: 1-oxo-2,3,4,5-tetrahydro-1H-[1,4]diazepino[1,2-a]indole-8-carboxylic acid

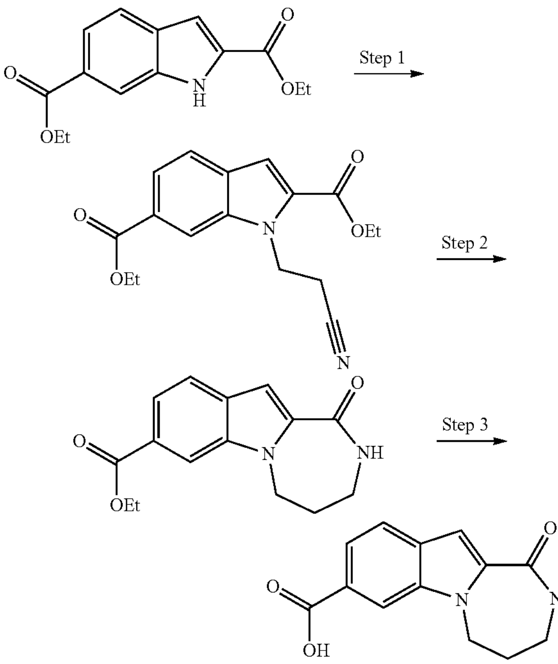

Step 1: Synthesis of diethyl 1-(2-cyanoethyl)-1H-indole-2,6-dicarboxylate

A 40% solution of Triton B in methanol (0.50 mL, 1.1 mmol) is added to a suspension of diethyl 1H-indole-2,6-dicarboxylate (Intermediate A, 2.6 g, 10.0 mmol) and acrylonitrile (2.2 mL, 33.4 mmol) in 1,4-dioxane (25 mL). The reaction mixture is warmed to 55° C. for 30 min and then it is stirred at room temperature for 18 h. Water (30 mL) is added and the mixture is extracted with EtOAc. The organic layer is washed with water, brine, dried ($Na_2SO_4$) and concentrated to afford the title crude compound (3.0 g, 96%) as a yellow solid which is used in the next step without purification.

Step 2: Synthesis of ethyl 1-oxo-2,3,4,5-tetrahydro-1H-[1,4]diazepino[1,2-a]indole-8-carboxylate To a suspension of diethyl 1-(2-cyanoethyl)-1H-indole-2,6-dicarboxylate (1.5 g, 4.8 mmol) in THF (12 mL) and methanol (16 mL) is added $CoCl_2$ (1.3 g, 9.6 mmol). The bright blue suspension/solution is cooled to 0° C., and $NaBH_4$ (1.8 g, 48.0 mmol) is carefully added in small portions. As each portion is added $H_2$ is formed violently and the suspension becomes black. After the addition of $NaBH_4$ is complete, the mixture is warmed up room temperature for 60 min and is then heated at reflux for 16 h. The mixture is cooled to room temperature and is diluted with EtOAc. The mixture is filtered through Celite, and the gummy solids are washed with EtOAc. The combined EtOAc filtrate is washed with 3M HCl, water, $NaHCO_3$, brine, dried ($Na_2SO_4$) and concentrated to afford the title crude compound (1.1 g, 85%) which is used in the next step without purification.

Step 3: Synthesis of 1-oxo-2,3,4,5-tetrahydro-1H-[1,4]diazepino[1,2-a]indole-8-carboxylic acid To a suspension of ethyl 1-oxo-2,3,4,5-tetrahydro-1H-[1,4]diazepino[1,2-a]indole-8-carboxylate (900 mg, 3.3 mmol) in THF:methanol (1:1, 20 mL) is added 1N NaOH (9.0 mL, 9.0 mmol). The reaction mixture is heated at 70° C. for 2 h. The reaction mixture is cooled to room temperature, diluted with water (80 mL) and is acidified with 3N HCl to pH 2-3. The resulting yellow precipitate is filtered, washed with water and dried in vacuo oven at 60° C. to afford the title compound (540 mg, 67%).

Intermediate K: 5-methyl-1-oxo-2,3,4,5-tetrahydro-1H-[1,4]diazepino[1,2-a]indole-8-carboxylic acid

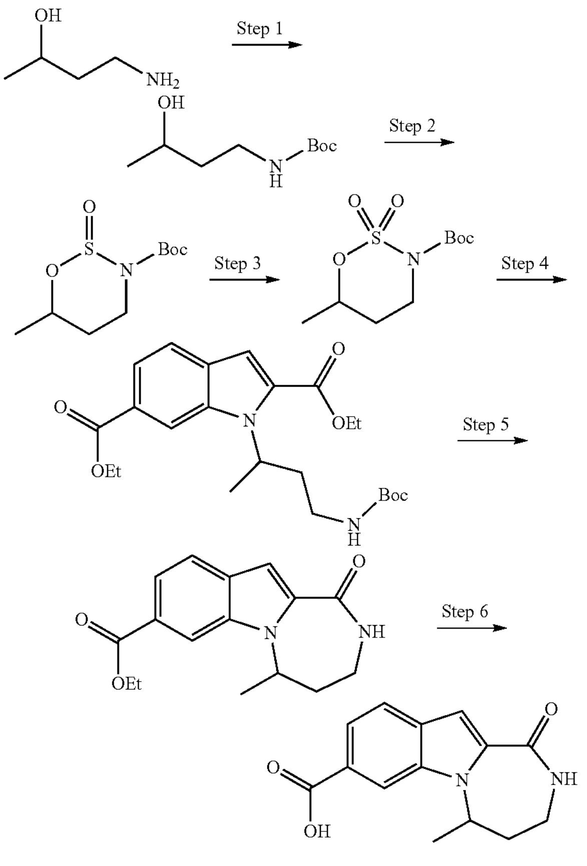

Step 1: Synthesis of tert-butyl (3-hydroxybutyl)carbamate

To a stirred solution of 4-aminobutan-2-ol (1.0 g, 11.2 mmol) in $CH_2Cl_2$ (20 mL) is added a solution of di-tert-butyl dicarbonate (2.45 g, 11.2 mmol) in $CH_2Cl_2$ (20 mL). The reaction mixture is stirred for 18 h. The solution is washed with citric acid and $NaHCO_3$, dried ($MgSO_4$) and evaporated to afford the title compound (2.1 g, 99%) as colorless oil.

Step 2: Synthesis of tert-butyl 6-methyl-1,2,3-oxathiazinane-3-carboxylate 2-oxide To a stirred solution of thionyl chloride (2.0 mL, 27.9 mmol) in acetonitrile (15 mL) cooled to −45° C. is added a solution of tert-butyl (3-hydroxybutyl)carbamate (2.1 g, 11.2 mmol) in acetonitrile (20 mL) by syringe over 10 min, keeping the internal temperature below −40° C. 4-Dimethylaminopyridine (136 mg, 1.1 mmol) is added followed by the dropwise addition of pyridine (4.5 mL, 55.8 mmol, keeping the temperature below −40° C. The addition takes 90 min. Ethyl acetate (50 mL) is added to the suspension and the mixture is filtered at −35° C. to remove the solid and the solid which is washed with EtOAc before it is discarded. The filtrates are combined, and saturated $Na_2HPO_4$ solution (20 mL) is added. The mixture is stirred vigorously for 30 min and the organic layer is separated, washed with 1M $NaHSO_4$ to remove residual pyridine, dried ($MgSO_4$) and concentrated to afford the title compound (2.52 g, 96%) as an oil.

Step 3: Synthesis of tert-butyl 6-methyl-1,2,3-oxathiazinane-3-carboxylate 2,2-dioxide To a solution of tert-butyl 6-methyl-1,2,3-oxathiazinane-3-carboxylate 2-oxide (2.52 g, 10.7 mmol) in acetonitrile (25 mL) and water (15 mL) cooled to 0° C. is added sodium periodate (3.4 g, 16.1 mmol) in one portion. After 5 min, the pH is adjusted to 7-8 by addition of saturated $Na_2HPO_4$ solution. A solution of $RuCl_3$ (22 mg, 0.11 mmol) in water (0.5 mL) is added and the pH is kept between 6 and 9 by addition of $Na_2HPO_4$ solution. After 2 h, water (100 mL) is added and pH is adjusted to 6 by addition of 2M HCl solution. The reaction mixture is extracted with EtOAc and the organic layer is washed with $NaHCO_3$ and brine and the washes are back-extracted once with EtOAc. Then the combined organic layers are dried ($MgSO_4$), filtered and concentrated. The crude compound is purified by flash column chromatography to afford the title compound (1.63 g, 61%).

Step 4: Synthesis of diethyl 1-{4-[(tert-butoxycarbonyl)amino]butan-2-yl}-1H-indole-2,6-dicarboxylate To a stirred suspension of 60% NaH dispersion in mineral oil (78.8 mg, 2.0 mmol) in DMF (2.5 mL) cooled to 0° C. is added a solution of diethyl 1H-indole-2,6-dicarboxylate (Intermediate A, 561 mg, 2.1 mmol) in DMF (3 mL). The mixture is stirred for 20 min and a solution of tert-butyl 6-methyl-1,2,3-oxathiazinane-3-carboxylate 2,2-dioxide (450 mg, 1.8 mmol) in DMF (2.5 mL) is added. The reaction mixture is stirred for 30 min at 0° C. and it is warmed to room temperature and stirred for 48 h. Saturated $NH_4Cl$ solution is added and the reaction mixture is extracted with EtOAc. The organic layer is separated, washed with water, then brine, dried ($MgSO_4$) and concentrated to afford the title compound (1.04 g, 50% pure) as an oil.

Step 5: Synthesis of ethyl 5-methyl-1-oxo-2,3,4,5-tetrahydro-1H-[1,4]diazepino[1,2-a]indole-8-carboxylate To a solution of diethyl 1-{4-[(tert-butoxycarbonyl)amino]butan-2-yl}-1H-indole-2,6-dicarboxylate (1.04 g, 1.8 mmol) in $CH_2Cl_2$ (4 mL) is added TFA (4 mL). The reaction mixture is stirred for 1 h and the solvent is removed under vacuum. To a solution of the residue in ethanol (10 mL) is added triethylamine (0.75 mL, 5.4 mmol) and $K_2CO_3$ (742 mg, 5.4 mmol). The reaction mixture is refluxed for 3 h. Then the solvent is evaporated, the residue is partitioned between EtOAc and water. The organic layer is then separated, dried ($MgSO_4$) and concentrated to afford crude compound which is purified by flash column chromatography to afford the title compound (300 mg, 59% for two steps).

Step 6: Synthesis of 5-methyl-1-oxo-2,3,4,5-tetrahydro-1H-[1,4]diazepino[1,2-a]indole-8-carboxylic acid 1 NaOH solution (60 mL, 60 mmol) is added to a solution of ethyl 5-methyl-1-oxo-2,3,4,5-tetrahydro-1H-[1,4]diazepino[1,2-a]indole-8-carboxylate (7.0 g, 24 mmol) in ethanol (75 mL). The reaction mixture is refluxed for 1.5 h. Then the reaction mixture is acidified with 1M HCl and ethanol is removed under vacuum. The resulting solid is filtered, washed with water and dried to afford the title compound (5.8 g, 92%) as a solid.

Intermediate L: (5R)-5-methyl-1-oxo-2,3,4,5-tetrahydro-1H-[1,4]diazepino[1,2-a]indole-8-carboxylic acid

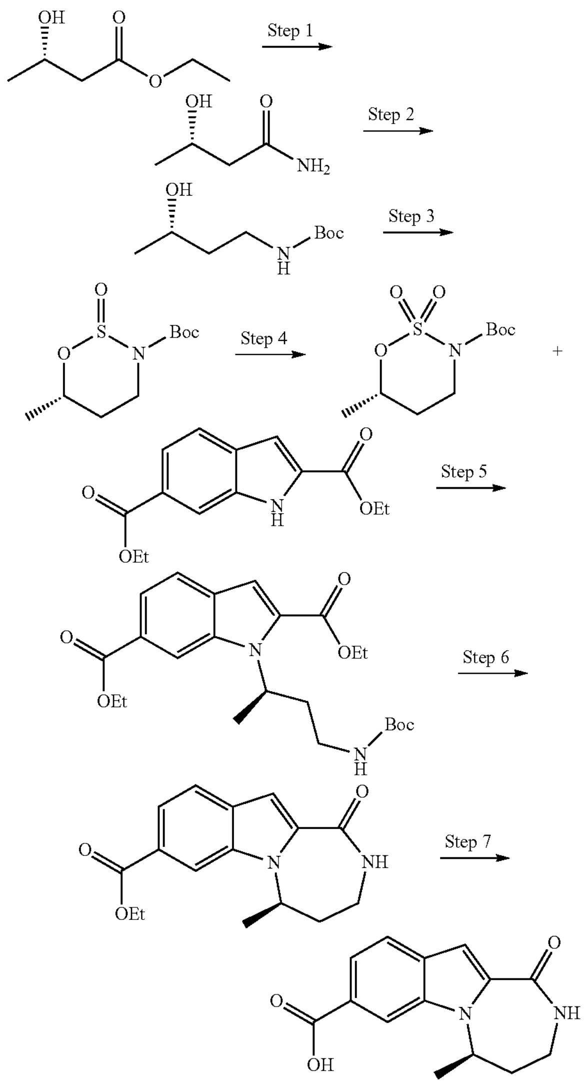

Step 1: Synthesis of (3S)-3-hydroxybutanamide

Ethyl (3S)-3-hydroxybutanoate (200 g, 1.5 mol) is added to 25% $NH_4OH$ aqueous solution (2.0 L) in a sealed tube. The reaction mixture is heated at 60° C. for 16 h. The solvent is removed azeotropically with toluene to afford the title crude compound (176 g, 82%) as a white crystalline solid which is used in the next step without purification.

Step 2: Synthesis of tert-butyl [(3S)-3-hydroxybutyl]carbamate

Sodium borohydride (220 g, 5.9 mol) is added portionwise to a solution of (3S)-3-hydroxybutanamide (200 g, 1.9 mol) in dry THF (1.0 L) at 0° C. A solution of 50% $BF_3OEt_2$ (755 mL, 6.0 mol) in ether is added and the reaction mixture is warmed to room temperature and stirred for 16 h. 2M NaOH solution is added at 0° C. until the pH is about 8 followed by additional THF (320 mL). Di-tert-butyl dicarbonate (940 mL, 3.9 mol) is added and the reaction mixture is stirred for another 16 h at room temperature. The reaction mixture is diluted with EtOAc and water. The organic layer is separated, dried ($Na_2SO_4$) and concentrated to afford the crude compound which is purified by flash column chromatography using 20% EtOAc in hexane to afford the title compound (100 g, 28%) as pale yellow liquid.

Step 3: Synthesis of tert-butyl (6S)-6-methyl-1,2,3-oxathiazinane-3-carboxylate 2-oxide To a solution of thionyl chloride (192 mL, 2.6 mol) in acetonitrile (1.0 L) at −40° C. is added dropwise a solution of tert-butyl [(3S)-3-hydroxybutyl]carbamate (200 g, 1.1 mol) in acetonitrile (2.5 L). The mixture is stirred for 10 min and 4-dimethylaminopyridine (12.9 g, 105.66 mmol) is added. After stirring for another 10 min, pyridine (427 mL, 5.3 mol) is added over 90 min, keeping the temperature below −40° C. EtOAc is added at −40° C. and the suspension is filtered to remove the solid. To the filtrate is added saturated $Na_2HPO_4$ solution and the mixture is stirred vigorously for 30 minutes at room temperature. The organic layer is separated, washed with 1M $NaHSO_4$ solution, dried ($Na_2SO_4$) and concentrated to afford the title crude compound (250 g) as an oil which is used in the next step without purification.

Step 4: Synthesis of tert-butyl (6S)-6-methyl-1,2,3-oxathiazinane-3-carboxylate 2,2-dioxide Sodium periodate (341 g, 1.6 mol) is added to a solution of tert-butyl (6S)-6-methyl-1,2,3-oxathiazinane-3-carboxylate 2-oxide (250 g, 1062 mmol) in acetonitrile (2.5 L) and water (1.5 L) at 0° C. The pH of the mixture is adjusted to 7 by the addition of saturated $Na_2HPO_4$ solution. A solution of $RuCl_33H_2O$ (2.20 g, 10.62 mmol) is added at 5° C. and the pH of mixture is kept at 7 by addition of saturated $Na_2HPO_4$ solution. The reaction is stirred at room temperature for 2 h. Water is added and pH is adjusted to 6 by addition of 2.0 M HCl solution. EtOAc (1.0 L) is added and the aqueous layer is separated and extracted with EtOAc (2×500 mL). The organic layers are combined, washed with saturated $NaHCO_3$ solution and brine, dried ($Na_2SO_4$) and concentrated to afford the crude compound which is purified by flash column chromatography using EtOAc in hexane to afford the title compound (140 g, 52%) as a pale yellow oil.

Step 5: Synthesis of diethyl 1-{(2R)-4-[(tert-butoxycarbonyl)amino]butan-2-yl}-1H-indole-2,6-dicarboxylate A stirred suspension of 60% NaH (840 mg, 21 mmol) in NMP (40 mL) is cooled in an ice bath, and a solution of diethyl 1H-indole-2,6-dicarboxylate (Intermediate A, 5.8 g, 22 mmol) in NMP (20 mL) is added. The mixture is stirred for 20 min, then a solution of tert-butyl (6S)-6-methyl-1,2,3-oxathiazinane-3-carboxylate 2,2-dioxide (5.0 g, 20 mmol) in NMP (20 mL) is added. The reaction mixture is stirred for 30 min at 0° C. and is warmed to room temperature and stirred for 48 h. The reaction is poured into ice water and the resultant solid is isolated by filtration. The filtrate is acidified to pH 3 with 1N aqueous HCl and extracted with EtOAc. The combined extracts are washed with water 4 times, then brine, dried ($Na_2SO_4$) and concentrated to afford the title compound (6.0 g, crude) as an oil which was used in the next step without purification.

Step 6: Synthesis of ethyl (5R)-5-methyl-1-oxo-2,3,4,5-tetrahydro-1H-[1,4]diazepino[1,2-a]indole-8-carboxylate To a solution of 1-((R)-3-tert-butoxycarbonylamino-1-methyl-propyl)-1H-indole-2,6-dicarboxylic acid diethyl ester (6.0 g, crude) in $CH_2Cl_2$ (27 mL) is added TFA (18.1 mL). The reaction mixture is stirred for 1 hour and the solvent is removed under vacuum. To a solution of the residue in ethanol (90 mL) is added $K_2CO_3$ (4.6 g, 33.3 mmol) and the reaction mixture is heated to reflux for 2 hours. The cooled reaction mixture is poured into ice water and extracted with EtOAc. The combined extracts are washed with water, brine, dried ($Na_2SO_4$) and concentrated to afford the title compound (3.65 g, crude) as a brown oil.

Step 7: Synthesis of (5R)-5-methyl-1-oxo-2,3,4,5-tetrahydro-1H-[1,4]diazepino[1,2-a]indole-8-carboxylic acid To a solution of (5R)-5-methyl-1-oxo-2,3,4,5-tetrahydro-1H-[1,4]diazepino[1,2-a]indole-8-carboxylate (3.65 g, crude) in ethanol (30 mL) is added 1M NaOH solution (13.8 mL, 13.8 mmol). The reaction mixture is refluxed for 2 h. The reaction mixture is acidified with 1M HCl and ethanol is removed under vacuum. The resulting solid is collected by filtration, is washed with water and dried to afford the title compound (2.1 g, 41% for 3 steps) as a solid.

Intermediate M: (5S)-5-methyl-1-oxo-2,3,4,5-tetrahydro-1H-[1,4]diazepino[1,2-a]indole-8-carboxylic acid

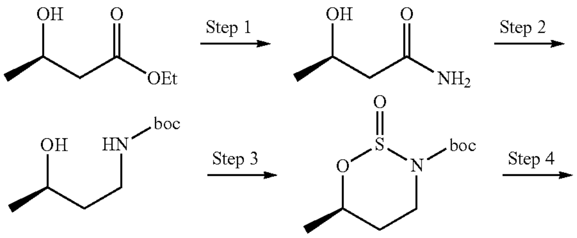

-continued

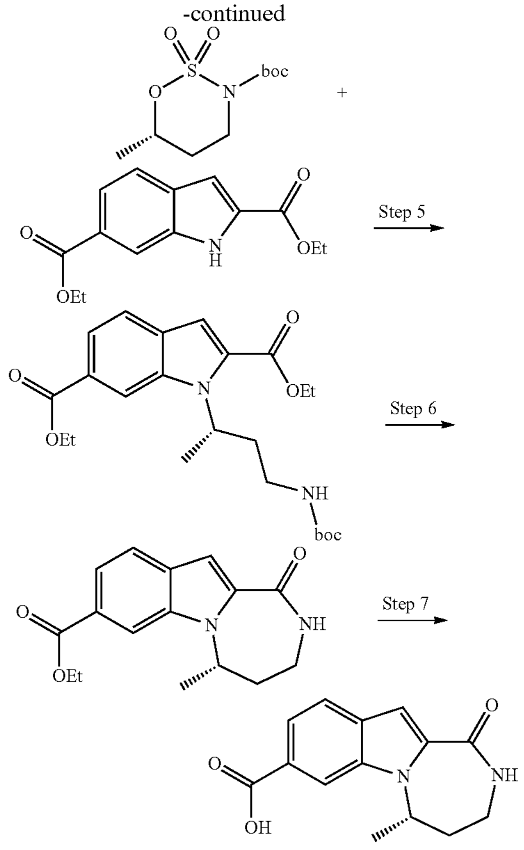

Step 1: Synthesis of (3R)-3-hydroxybutanamide

Ammonium hydroxide 28% aqueous solution (25 mL) is mixed with ethyl (3R)-3-hydroxybutanoate (4.4 g, 33.5 mmol) in a screw-top flask. The flask is sealed and the mixture is heated at 60° C. for 7 h and stirred at room temperature for 48 h. The solvent is removed and the residue is dried to afford the title crude compound (4.0 g) which is used in the next step without purification.

Step 2: Synthesis of tert-butyl [(3R)-3-hydroxybutyl]carbamate

To a suspension of (3R)-3-hydroxybutanamide (2.0 g, 19.4 mmol) in THF (30 mL) is added neat borane-methyl sulfide (9.2 mL, 97.0 mmol). The reaction mixture is refluxed for 2 h. After cooling to room temperature, 6M HCl solution (3 mL) is added cautiously. The reaction mixture is refluxed for 2 h and is then basified to pH 9 by addition of $Na_2CO_3$ solution. A solution of di-tert-butyl dicarbonate (4.7 g, 21.3 mmol) in THF (10 mL) is added and the reaction mixture is stirred at room temperature for 48 h. Then the reaction mixture is partitioned between EtOAc and aqueous $Na_2CO_3$. The organic layer is separated, washed with water and brine, dried ($MgSO_4$) and concentrated to afford the crude compound which is purified by flash column chromatography using EtOAc in hexanes to afford the title compound (1.6 g, 43% for two steps).

Step 3: Synthesis of tert-butyl (6R)-6-methyl-1,2,3-oxathiazinane-3-carboxylate 2-oxide To a stirred solution of thionyl chloride (2.9 g, 24.3 mmol) in acetonitrile (15 mL) is cooled to −45° C. is added a solution of tert-butyl [(3R)-3-hydroxybutyl]carbamate (1.8 g, 9.7 mmol) in acetonitrile (20 mL) by syringe over 10 min, keeping the internal temperature below −40° C. 4-Dimethylaminopyridine (119 mg, 0.97 mmol) is added followed by the slow addition of pyridine (3.9 mL, 48.6 mmol), keeping the temperature below −40° C. Ethyl acetate (50 mL) is added to the suspension and the mixture at −35° C. is filtered. The solid is washed with EtOAc and the filtrates are combined. Saturated $Na_2HPO_4$ solution (20 mL) is added into the filtrates and the mixture is stirred vigorously for 30 min. The organic layer is separated, washed with 1M $NaHSO_4$, dried ($MgSO_4$) and concentrated to afford the title compound (2.3 g, 99%) which is used in the next step without purification.

Step 4: Synthesis of tert-butyl (6R)-6-methyl-1,2,3-oxathiazinane-3-carboxylate 2,2-dioxide To a solution of tert-butyl (6R)-6-methyl-1,2,3-oxathiazinane-3-carboxylate 2-oxide (2.3 g, 9.6 mmol) in acetonitrile (25 mL) and water (15 mL) cooled to 0° C. is added sodium periodate (3.1 g, 14.3 mmol) in one portion. After 5 min, the pH of the mixture is adjusted to 7-8 by addition of saturated $Na_2HPO_4$ solution. A solution of $RuCl_3$ (9.9 mg, 0.05 mmol) in water (0.5 mL) is added and the reaction mixture is stirred for 2 h, keeping the pH between 6 and 9 by addition of $Na_2HPO_4$ solution. Water (100 mL) is added and the pH is adjusted to 6 by addition of 2M HCl solution. EtOAc is added and the organic layer is separated, washed with $NaHCO_3$ and brine. The combined aqueous layers are back extracted once with EtOAc. The combined organic phases are dried ($MgSO_4$) and concentrated to afford the crude compound which is purified by flash column chromatography using EtOAc in hexanes affords the title compound (1.13 g, 47%).

Step 5: Synthesis of diethyl 1-{(2S)-4-[(tert-butoxycarbonyl)amino]butan-2-yl}-1H-indole-2,6-dicarboxylate To a suspension of hexane washed 60% sodium hydride in mineral oil (91 mg, 2.3 mmol) in DMF (2.5 mL) under nitrogen atmosphere to 0° C. is added a solution of diethyl 1H-indole-2,6-dicarboxylate (619 mg, 2.4 mmol) in DMF (4 mL). The mixture is stirred for 20 min at 0° C. and a solution of tert-butyl (6R)-6-methyl-1,2,3-oxathiazinane-3-carboxylate 2,2-dioxide (518 mg, 2.1 mmol) in DMF (2.5 mL) is added. The reaction mixture is stirred for 30 min at 0° C. and is warmed to room temperature and stirred for 72 h. Water and $NH_4Cl$ solution are added and the mixture is stirred for 15 min. The aqueous mixture is extracted with EtOAc (50 mL) and the organic layer is washed with water, brine, dried ($MgSO_4$) and concentrated to afford the title crude compound (1.1 g) which is used in the next step without purification.

Step 6: Synthesis of ethyl (5S)-5-methyl-1-oxo-2,3,4,5-tetrahydro-1H-[1,4]diazepino[1,2-a]indole-8-carboxylate To a solution of diethyl 1-{(2S)-4-[(tert-butoxycarbonyl)amino]butan-2-yl}-1H-indole-2,6-dicarboxylate (891 mg, 2.1 mmol) in $CH_2Cl_2$ (4 mL) is added TFA (3 mL). The mixture is stirred at room temperature for 1 h then the solvent is evaporated. To a solution of the residue in ethanol (10 mL) is added $K_2CO_3$ (854 mg, 6.2 mmol). The reaction mixture is refluxed for 4 h with vigorous stifling. EtOAc is added and the organic layer is washed with water, brine, dried ($MgSO_4$) and concentrated to afford crude compound which is purified by flash column chromatography using EtOAc in hexanes then methanol in $CH_2Cl_2$ to afford the title compound (269 mg, 46%).

Step 7: Synthesis of (5S)-5-methyl-1-oxo-2,3,4,5-tetrahydro-1H-[1,4]diazepino[1,2-a]indole-8-carboxylic acid To a solution of ethyl (5S)-5-methyl-1-oxo-2,3,4,5-tetrahydro-1H-[1,4]diazepino[1,2-a]indole-8-carboxylate (1.9 g, 6.7 mmol) in ethanol (75 mL) is added 1N NaOH solution (16 mL, 16 mmol). The reaction mixture is refluxed for 1.5 h and cooled to room temperature. The ethanol is removed under vacuum and the residue is diluted with water. The mixture is acidified with aqueous 1N HCl solution the resulting solid is collected by filtration, rinsed with water and dried to afford the title compound (1.7 g, 99%).

Intermediate N: 4-methyl-1-oxo-2,3,4,5-tetrahydro-1H-[1,4]diazepino[1,2-a]indole-8-carboxylic acid

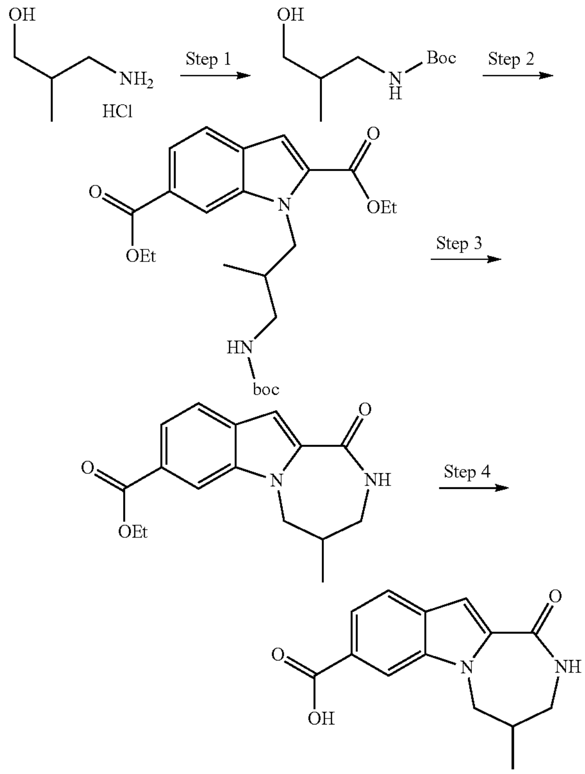

Step 1: Synthesis of tert-butyl (3-hydroxy-2-methylpropyl)carbamate

To a stirred solution of 3-amino-2-methylpropan-1-ol hydrochloride salt (2.0 g, 15.9 mmol) in $CH_2Cl_2$ (100 mL) are added triethylamine (3.3 mL, 23.9 mmol) and di-tert-butyl dicarbonate (3.8 g, 17.5 mmol). The mixture is stirred for 36 h and then saturated $NH_4Cl$ solution (150 mL) is added. The mixture is stirred for 10 min and the organic layer is separated and washed with saturated $NaHCO_3$, dried ($Na_2SO_4$) and concentrated to afford the title compound which is used in next step without purification.

Step 2: Synthesis of diethyl 1-{3-[(tert-butoxycarbonyl)amino]-2-methylpropyl}-1H-indole-2,6-dicarboxylate To a solution of diethyl 1H-indole-2,6-dicarboxylate (Intermediate A, 1.9 g, 7.4 mmol), tert-butyl (3-hydroxy-2-methylpropyl)carbamate (2.8 g, 14.8 mmol) and triphenylphosphine (4.9 g, 18.5 mmol) in THF (35 mL) at 0° C. is added diisopropyl azodicarboxylate (3.8 mL, 18.5 mmol). The mixture is stirred for 16 h at room temperature and then the solvent is removed. The residue is filtered through a pad of silica (300 g, 240-400 mesh) using 30% EtOAc in heptane to afford of mixture of the title compound and diethyl 1H-indole-2,6-dicarboxylate (3.2 g) which is used in the next step without further purification.

Step 3: Synthesis of ethyl 4-methyl-1-oxo-2,3,4,5-tetrahydro-1H-[1,4]diazepino[1,2-a]indole-8-carboxylate To a mixture of diethyl 1-{3-[(tert-butoxycarbonyl)amino]-2-methylpropyl}-1H-indole-2,6-dicarboxylate and diethyl 1H-indole-2,6-dicarboxylate (3.2 g, 7.4 mmol) in $CH_2Cl_2$ (70 mL) is added TFA (30 mL). The mixture is stirred at room temperature for 2 h. The reaction is concentrated and the residue is dried in vacuo for 1 h. To a solution of the residue in ethanol (150 mL) are added triethylamine (3.1 mL, 22.2 mmol) and $K_2CO_3$ (6.1 g, 44.2 mmol). The mixture is heated at 80° C. for 5 h. Water (300 mL) is added and the mixture is extracted with EtOAc (3×200 mL). The organic layers are combined, dried ($Na_2SO_4$) and concentrated and the crude compound is purified by flash column chromatography to afford the title compound (1.4 g, 66% for 3 steps).

Step 4: Synthesis of 4-methyl-1-oxo-2,3,4,5-tetrahydro-1H-[1,4]diazepino[1,2-a]indole-8-carboxylic acid To a solution ethyl 4-methyl-1-oxo-2,3,4,5-tetrahydro-1H-[1,4]diazepino[1,2-a]indole-8-carboxylate (1.4 g, 4.9 mmol) in ethanol (50 mL) is added 1M NaOH (12.5 mL, 12.5 mmol) and the mixture is heated at 80° C. for 2 h. Acetic acid (10 mL) and water (650 mL) are added and the resulting solid is filtered and rinsed with water to afford the title compound (751 mg, 58%) as a white solid.

Intermediate O: trans-4,5-dimethyl-1-oxo-2,3,4,5-tetrahydro-1H-[1,4]diazepino[1,2-a]indole-8-carboxylic acid

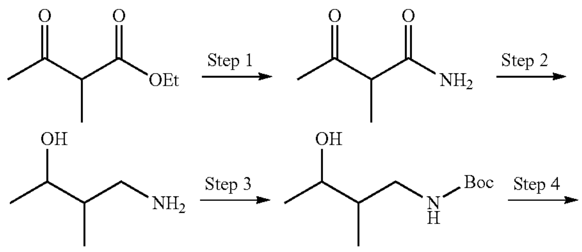

-continued

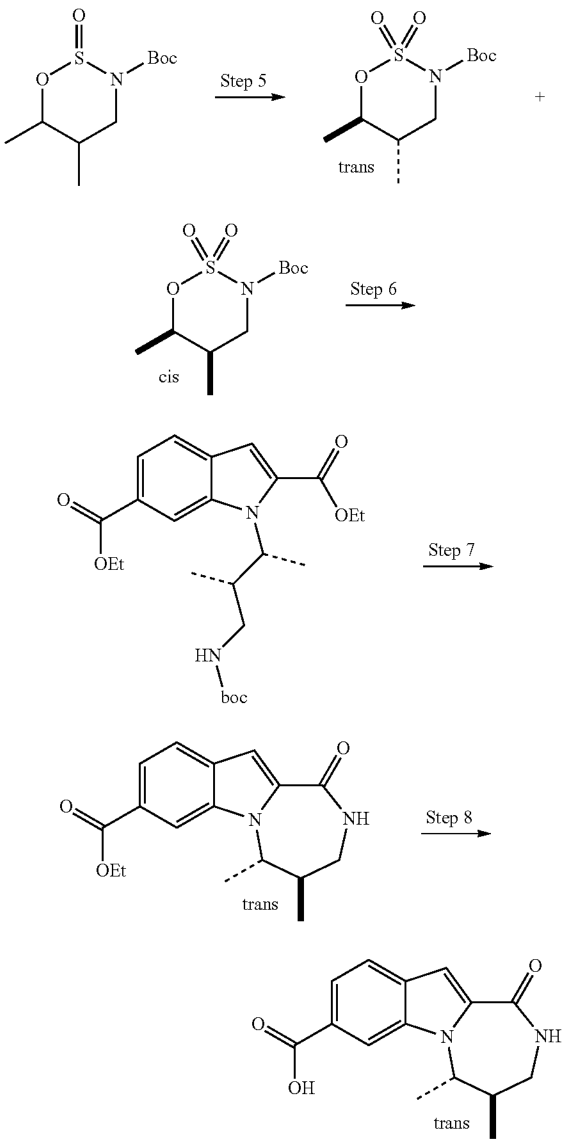

Step 1: Synthesis of 2-methyl-3-oxobutanamide

A suspension of ethyl 2-methyl-3-oxobutanoate (72 g, 499 mmol) in ammonium hydroxide (300 mL) is stirred vigorously at room temperature for 4 days. The resulting crystalline precipitate is filtered and discarded. The filtrate is concentrated under vacuum to afford an oil that crystallizes on standing. The solid is collected and dried to afford the title compound (26.7 g, 46%).

Step 2: Synthesis of 4-amino-3-methylbutan-2-ol

To a suspension of solid $LiAlH_4$ (4.9 g, 130 mmol) in ether (150 mL) cooled to −60° C. under a nitrogen atmosphere is added a solution of 2-methyl-3-oxobutanamide (3.0 g, 26.1 mmol) in THF (30 mL). When addition is complete, the reaction mixture is warmed up slowly to room temperature for 1 h. The mixture is then refluxed for 3 h, is cooled to room temperature and stirred for another 16 h. Water (4.9 mL) is added cautiously followed by the addition of 15% NaOH solution (4.9 mL). After gas evolution subsides, more water (14.7 mL) is added. The mixture is stirred for 1 h and the resulting solid is filtered and washed well with ether. The filtrate is concentrated to afford the title compound (2.38 g, 89%) as a colorless oil.

Step 3: Synthesis of tert-butyl (3-hydroxy-2-methylbutyl)carbamate

To a stirred solution of 4-amino-3-methylbutan-2-ol (2.4 g, 23.1 mmol) in $CH_2Cl_2$ (30 mL) is added a solution of di-tert-butyl dicarbonate (5.0 g, 23.1 mmol) in $CH_2Cl_2$ (20 mL). The reaction is stirred for 18 h at room temperature. The solution is washed with 1M $NaHSO_4$, dried over ($MgSO_4$) and concentrated. Purification of the residue by flash column chromatography using EtOAc in hexanes affords the title compound (3.4 g, 73%) as a colorless oil.

Step 4: Synthesis of tert-butyl 5,6-dimethyl-1,2,3-oxathiazinane-3-carboxylate 2-oxide To a stirred solution of thionyl chloride (5.4 g, 45.4 mmol) in acetonitrile (25 mL) cooled to −45° C. is added a solution of tert-butyl (3-hydroxy-2-methylbutyl)carbamate (3.7 g, 18.1 mmol) in acetonitrile (35 mL) by syringe over about 15 min, keeping the internal temperature below −40° C. When the addition is completed, solid 4-dimethylamino pyridine (222 mg, 1.8 mmol) is added in one portion followed by pyridine (7.3 mL, 90.8 mmol), keeping the temperature below −40° C. The mixture is stirred at −40° C. to −35° C. for 1 h. Ethyl acetate (100 mL) is added and the mixture is filtered at −35° C. The solid is washed with EtOAc and discarded. To the filtrate is added saturated $Na_2HPO_4$ solution (20 mL) and the mixture is stirred vigorously for 3 h. The organic layer is separated, washed with 1M $NaHSO_4$, dried ($MgSO_4$) and concentrated to afford the title compound (4.4 g) which is used in the next step without purification.

Step 5: Synthesis of tert-butyl cis-5,6-dimethyl-1,2,3-oxathiazinane-3-carboxylate 2,2-dioxide To a solution of tert-butyl 5,6-dimethyl-1,2,3-oxathiazinane-3-carboxylate 2-oxide (4.4 g, 17.6 mmol) in acetonitrile (45 mL) and water (25 mL) cooled to 0° C. is added sodium periodate (5.6 g, 26.4 mmol) in one portion. After 5 min, the pH is adjusted to 7-8 by addition of saturated $Na_2HPO_4$ solution. A solution of $RuCl_3$ (36 mg, 0.18 mmol) in water (0.5 mL) is added and the pH is kept between 6 and 9 by addition of $Na_2HPO_4$ solution. After 2 h, water (100 mL) is added, and pH is adjusted to 6 by addition of 2M HCl solution. The mixture is extracted with EtOAc and the organic layer is separated, washed with $NaHCO_3$ and brine. The aqueous layers are back extracted once with EtOAc. The combined organic layers are dried ($MgSO_4$) and concentrated. The residue is purified by flash column chromatography using EtOAc in hexanes to afford the diastereoisomers of tert-butyl-5,6-dimethyl-1,2,3-oxathiazinane-3-carboxylate 2,2-dioxide (Trans: 530 mg, 11%, first eluted; C is: 1.2 g, 25%, second eluted; mixed fractions (0.70 g, 15%). Assignment is based on $^1H$ NMR assignment and coupling constants.

Step 6: Synthesis of diethyl 1-{(2,3-syn)-4-[(tert-butoxycarbonyl)amino]-3-methylbutan-2-yl}-1H-indole-2,6-dicarboxylate A suspension of 60% sodium hydride (119 mg, 3.0 mmol) in DMF (3 mL) is cooled to 0° C. and a solution of diethyl 1H-indole-2,6-dicarboxylate (Intermediate A, 934 mg, 3.6 mmol) is added. After the mixture is stirred for 20 min at 0° C., a solution of tert-butyl cis-5,6-dimethyl-1,2,3-oxathiazinane-3-carboxylate 2,2-dioxide (790 mg, 3.0 mmol) in DMF (2.0 mL) is added. The reaction mixture is warmed to room temperature and stirred for 16 h. Water is added and the mixture is extracted with EtOAc. The organic layer is washed with brine, dried ($Na_2SO_4$) and concentrated to afford the title crude compound (1.6 g) which is used in the next step without purification.

Step 7: Synthesis of ethyl trans-4,5-dimethyl-1-oxo-2,3,4,5-tetrahydro-1H-[1,4]diazepino[1,2-a]indole-8-carboxylate To a solution of diethyl 1-{(2,3-syn)-4-[(tert-butoxycarbonyl)amino]-3-methylbutan-2-yl}-1H-indole-2,6-dicarboxylate (1.6 g) in $CH_2Cl_2$ (10 mL) is added TFA (1.0 mL). The mixture is stirred at room temperature for 4 h and the solvent is removed under vacuum. The residue is dissolved in ethanol (10 mL) and $Na_2CO_3$ (1.63 g, 12 mmol) is added and the mixture is refluxed for 3 h. Then the reaction mixture is filtered and the solid is washed with $CH_2Cl_2$. The combined filtrate is concentrated and the crude compound is purified by flash column chromatography using methanol in $CH_2Cl_2$ to afford the title compound (592 mg, 66% for 3 steps).

Step 8: Synthesis of trans-4,5-dimethyl-1-oxo-2,3,4,5-tetrahydro-1H-[1,4]diazepino[1,2-a]indole-8-carboxylic acid A mixture of ethyl trans-4,5-dimethyl-1-oxo-2,3,4,5-tetrahydro-1H-[1,4]diazepino[1,2-a]indole-8-carboxylate (363 mg, 1.2 mmol) and LiOH monohydrate (76 mg, 1.8 mmol) in dioxane:water (1:1, 10 mL) is stirred at room temperature for 6 h. The solvents are removed and water is added. The solution is acidified to pH 5 with 1M HCl and the resulting white solid is filtered and dried to afford the title compound (201 mg, 61%) as a white solid.

Intermediate P: cis-4,5-dimethyl-1-oxo-2,3,4,5-tetrahydro-1H-[1,4]diazepino[1,2-a]indole-8-carboxylic acid

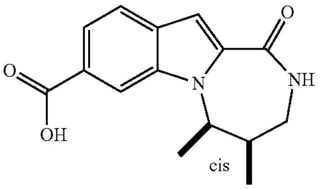 [SMILES: C[C@@H]1CNC(=O)c2cc3ccc(C(=O)O)cc3n2[C@@H]1C]

This compound is synthesized using the similar procedure used to prepare trans-4,5-dimethyl-1-oxo-2,3,4,5-tetrahydro-1H-[1,4]diazepino[1,2-a]indole-8-carboxylic acid (Intermediate O), replacing the tert-butyl cis-5,6-dimethyl-1,2,3-oxathiazinane-3-carboxylate 2,2-dioxide with tert-butyl trans-5,6-dimethyl-1,2,3-oxathiazinane-3-carboxylate 2,2-dioxide in step 6.

Intermediate Q: 4,4-dimethyl-1-oxo-2,3,4,5-tetrahydro-1H-[1,4]diazepino[1,2-a]indole-8-carboxylic acid

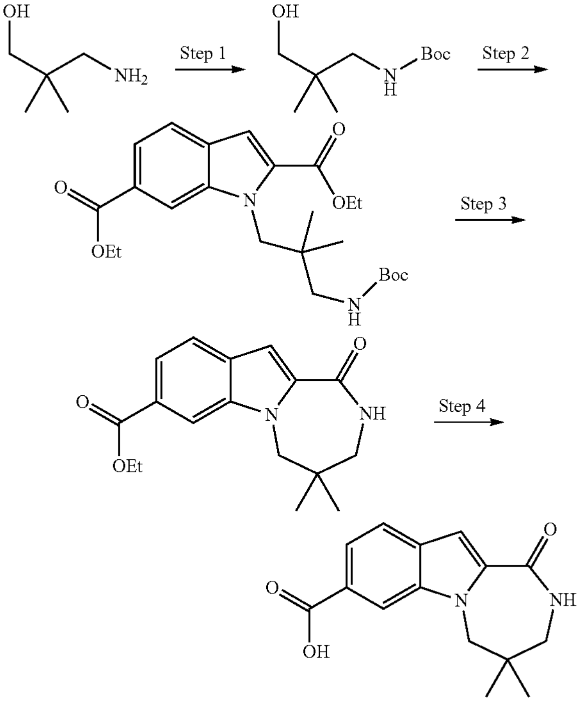

Step 1: Synthesis of tert-butyl (3-hydroxy-2,2-dimethylpropyl)carbamate

To a stirred solution of 3-amino-2,2-dimethylpropan-1-ol (10 g, 96.9 mmol) in $CH_2Cl_2$ (700 mL) is added di-tert-butyl dicarbonate (23.3 g, 106.6 mmol). The mixture is stirred for 40 h and then 300 mL of saturated $NH_4Cl$ solution is added. The mixture is stirred for another 10 min and the organic layer is separated. Then it is washed with saturated $NaHCO_3$, dried ($Na_2SO_4$) and concentrated to afford the title crude compound (19 g) which is used in next step without purification.

Step 2: Synthesis of diethyl 1-{3-[(tert-butoxycarbonyl)amino]-2,2-dimethylpropyl}-1H-indole-2,6-dicarboxylate To a solution of diethyl 1H-indole-2,6-dicarboxylate (25.3 g, 97 mmol), tert-butyl (3-hydroxy-2,2-dimethylpropyl)carbamate (19.7, 97 mmol) and triphenylphosphine (50.9 g, 194 mmol) in THF (200 mL) is added and diisopropyl azodicarboxylate (40.2 mL, 194 mmol). The mixture is stirred for 60 h at room temperature and then the solvent is removed. The residue is separated into two portions and each of them is filtered through a short plug of silica gel (400 g) using 20% EtOAc in heptane. A mixture of diethyl 1-{3-[(tert-butoxycarbonyl)amino-]-2,2-dimethylpropyl}-1H-indole-2,6-dicarboxylate and diethyl 1H-indole-2,6-dicarboxylate (55 g) is obtained and the mixture is used in the next step without further purification.

Step 3: Synthesis of ethyl 4,4-dimethyl-1-oxo-2,3,4,5-tetrahydro-1H-[1,4]diazepino[1,2-a]indole-8-carboxylate To a mixture of diethyl 1-{3-[(tert-butoxycarbonyl)amino-]-2,2-dimethylpropyl}-1H-indole-2,6-dicarboxylate and diethyl 1H-indole-2,6-dicarboxylate (Intermediate A, 21.9 g, 49 mmol) in $CH_2Cl_2$ (400 mL) is added TFA (100 mL). The mixture is stirred at room temperature for 2 h and then all the solvent is evaporated. The residue is dissolved in EtOAc (300 mL) and is washed with saturated $NaHCO_3$ solution until the pH is about 7. The aqueous layer is extracted with EtOAc (100 mL) and the organic layers are combined, dried ($Na_2SO_4$) and concentrated. To a solution of the residue in ethanol (1000 mL) are added triethylamine (20.5 mL, 147 mmol) and $K_2CO_3$ (20.3 g, 147 mmol). The mixture is heated at 80° C. for 2 h and then cooled to room temperature and stirred for 16 h. The solid formed the reaction mixture is filtered off and set aside. The filtrate is concentrated and the residue is purified by flash column chromatography using methanol in $CH_2Cl_2$ to afford the title compound (7.6 g, 66% for 3 steps).

Step 4: Synthesis of 4,4-dimethyl-1-oxo-2,3,4,5-tetrahydro-1H-[1,4]diazepino[1,2-a]indole-8-carboxylic acid Ethyl 4,4-dimethyl-1-oxo-2,3,4,5-tetrahydro-1H-[1,4]diazepino[1,2-a]indole-8-carboxylate (7.6 g, 25.3 mmol) is dissolved in ethanol (250 mL) and 1M NaOH solution (88.6 mL, 88.6 mmol) is added. The reaction mixture is heated at 80° C. for 2 h. Acetic acid (40 mL) and water (350 mL) are added and the resulting solid is filtered and rinsed with water to afford the title compound (3.1 g, 45%) as an off-white solid.

Intermediate R: 4,4-difluoro-1-oxo-2,3,4,5-tetrahydro-1H-[1,4]diazepino[1,2-a]indole-8-carboxylic acid

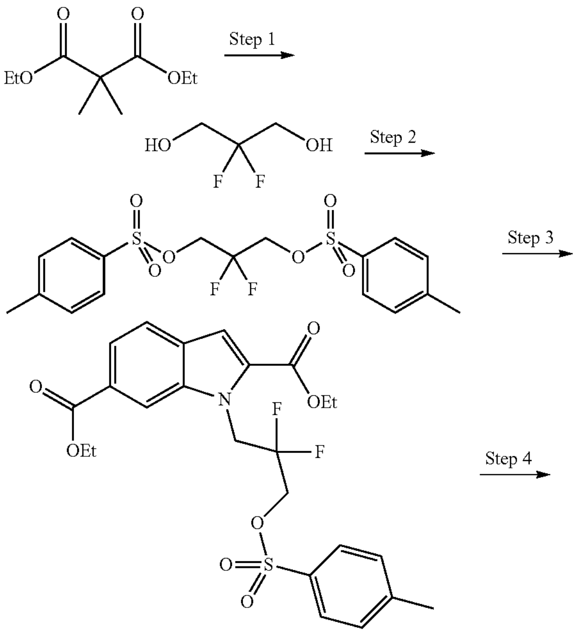

-continued

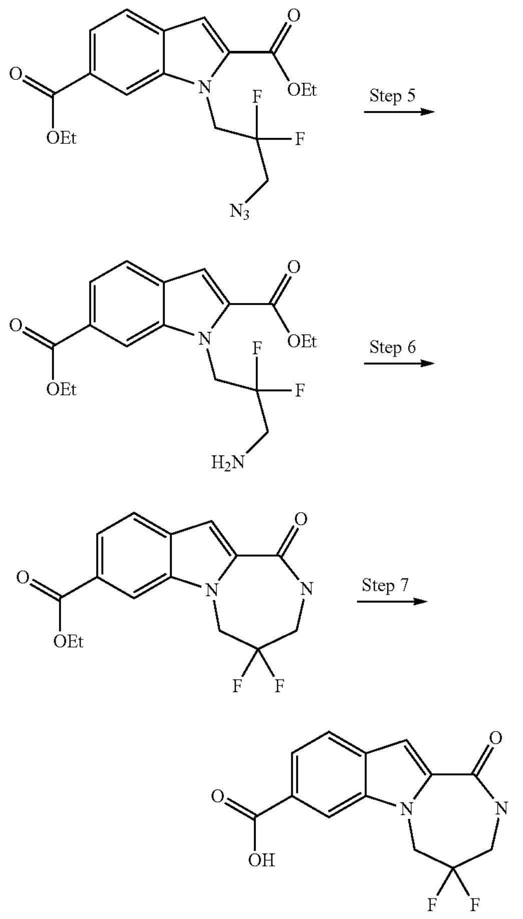

Step 1: Synthesis of 2,2-difluoropropane-1,3-diol

To a solution of diethyl difluoropropanedioate (5.0 g, 24.7 mmol) in THF (150 mL) at 0° C. is added 1.0 M $LiAlH_4$ THF solution (39.5 mL, 39.5 mmol). The reaction mixture is warmed to room temperature and stirred for 16 h. Water (300 mL) is added carefully and the pH is adjusted to 3 by adding 1M HCl solution. The water is removed in vacuo and the residue is extracted with EtOAc (3×300 mL). The organic layers are combined, dried ($Na_2SO_4$) and concentrated to afford the title compound (2.5 g, 89%).

Step 2: Synthesis of 2,2-difluoropropane-1,3-diyl bis(4-methylbenzenesulfonate)

To a solution of 2,2-difluoropropane-1,3-diol (2.5 g, 22.3 mmol) in $CH_2Cl_2$ (100 mL) is added triethylamine (14.3 mL, 111.5 mmol) followed by 4-methyl-benzenesulfonyl chloride (12.8 g, 66.9 mmol). The reaction mixture is stirred for 16 h at room temperature. Water (35 mL) is added and the organic layer is separated and washed with more water (2×35 mL). The organic layer is concentrated and the crude compound is purified by flash column chromatography using EtOAc in heptane to afford the title compound (6.7 g, 71%).

Step 3: Synthesis of diethyl 1-(2,2-difluoro-3-{[(4-methylphenyl)sulfonyl]oxy}propyl)-1H-indole-2,6-dicarboxylate Diethyl 1H-indole-2,6-dicarboxylate (Intermediate A, 3.5 g, 13.6 mmol), 2,2-difluoropropane-1,3-diyl bis(4-methylbenzenesulfonate) (6.0 g, 14.3 mmol) and $K_2CO_3$ (3.9 g, 28.5 mmol) are mixed in DMF (36 mL) and the reaction mixture is separated into 3 fractions. Each fraction is heated in a microwave reactor at 135° C. for 1 h. The 3 fractions are combined, and water (300 mL) and EtOAc (300 mL) are added. The aqueous layer is separated and extracted with EtOAc (3×100 mL). The organic layers are combined, washed with water (3×200 mL), dried ($Na_2SO_4$) and concentrated. The crude compound is purified by flash column chromatography using EtOAc in heptane to afford the title compound (4.7 g, 59% pure, 38% yield).

Step 4: Synthesis of diethyl 1-(3-azido-2,2-difluoropropyl)-1H-indole-2,6-dicarboxylate To a solution of diethyl 1-(2,2-difluoro-3-{[(4-methylphenyl)sulfonyl]oxy}propyl)-1H-indole-2,6-dicarboxylate (4.7 g, 59% pure, 5.5 mmol) in DMF (40 mL) is added sodium azide (908 mg, 13.8 mmol). The mixture is heated at 95° C. for 40 h. Water (250 mL) is added and the mixture is extracted with EtOAc (3×250 mL). The organic layers are combined, washed with water (3×250 mL), dried ($Na_2SO_4$) and concentrated to afford the title crude compound (2.5 g) which is used in the next step without purification.

Step 5: Synthesis of diethyl 1-(3-amino-2,2-difluoropropyl)-1H-indole-2,6-dicarboxylate To a solution of diethyl 1-(3-azido-2,2-difluoropropyl)-1H-indole-2,6-dicarboxylate (2.5 g, 7.8 mmol) in methanol: $CH_2Cl_2$ (1:1, 60 mL) is added 10% palladium on carbon (1.4 g, 1.3 mmol). The reaction mixture is stirred for 3.5 h under $H_2$ atmosphere. The reaction mixture is filtered and the filtrate is concentrated to afford the title crude compound (2.3 g) which is used in the next step without purification.

Step 6: Synthesis of ethyl 4,4-difluoro-1-oxo-2,3,4,5-tetrahydro-1H-[1,4]diazepino[1,2-a]indole-8-carboxylate To a solution of diethyl 1-(3-amino-2,2-difluoropropyl)-1H-indole-2,6-dicarboxylate (2.3 g) in ethanol (160 mL) are added triethylamine (2.7 mL, 19.0 mmol) and $K_2CO_3$ (1.3 g, 9.5 mmol). The mixture is heated at 80° C. for 16 h. Ethanol is removed under vacuum and water (100 mL) is added. The resulting light yellow solid is filtered and dried to afford the title compound (1.2 g, 70% for 3 steps).

Step 7: Synthesis of 4,4-difluoro-1-oxo-2,3,4,5-tetrahydro-1H-[1,4]diazepino[1,2-a]indole-8-carboxylic acid Ethyl 4,4-difluoro-1-oxo-2,3,4,5-tetrahydro-1H-[1,4]diazepino[1,2-a]indole-8-carboxylate (470 mg, 1.5 mmol) is suspended in ethanol (17 mL) and 1M NaOH solution (4.8 mL, 4.8 mmol) is added. The reaction mixture is heated at 60° C. for 1 h 50 min. Acetic acid (15 mL) and water (100 mL) are added and the resulting white solid is filtered and rinsed with water to afford the title compound (350 mg, 82%).

Intermediate S: 1'-oxo-2',3'-dihydro-1'H-spiro[cyclopropane-1,4'-[1,4]diazepino[1,2-a]indole]-8'-carboxylic acid

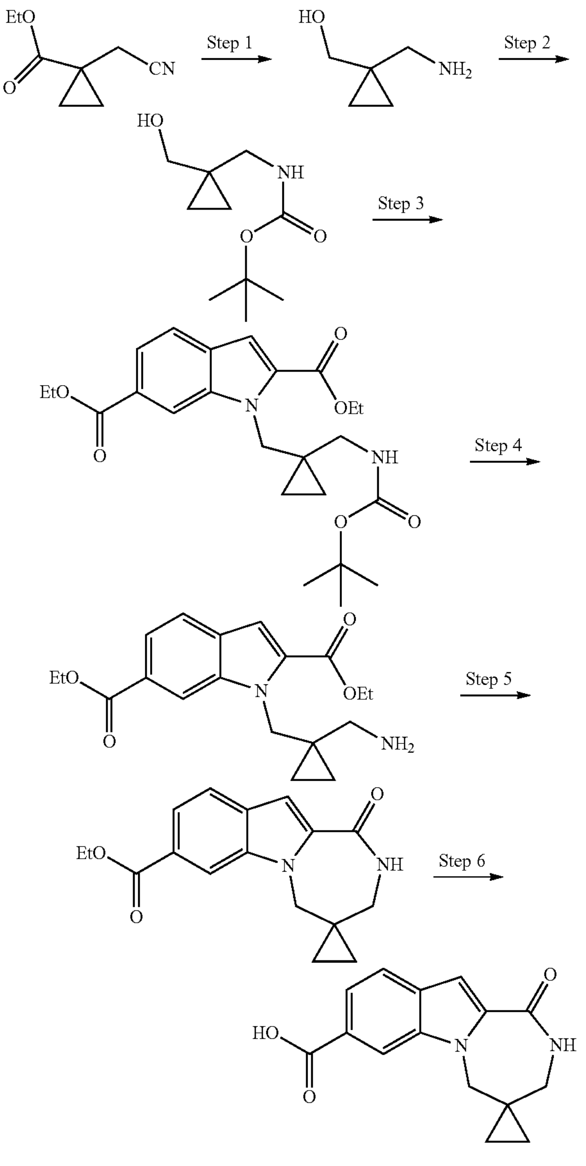

Step 1: Synthesis of [1-(aminomethyl)cyclopropyl]methanol

To a suspension of lithium aluminum hydride (34 g, 899 mmol) in THF (400 mL) is added a solution of ethyl 1-(cyanomethyl)cyclopropanecarboxylate (25 g, 179 mmol) in THF (100 mL) at 0° C. The reaction mixture is stirred at room temperature for 4 h. The reaction mixture is cooled to 0° C. and ice cold water (60 mL) is added. The mixture is extracted with EtOAc (2×300 mL). The organic layers are combined, dried ($Na_2SO_4$) and concentrated to afford the title crude compound (20 g) which is used in the next step without purification.

Step 2: Synthesis of tert-butyl {[1-(hydroxymethyl) cyclopropyl]methyl}carbamate Di-tert-butyl dicarbonate (40.5 mL, 197 mmol) is added to a stirred solution of [1-(aminomethyl)cyclopropyl]methanol (20 g, 198 mmol) in $CH_2Cl_2$ (600 mL) at room temperature. The reaction mixture is stirred at same temperature for 40 h. Then saturated $NH_4Cl$ solution (250 mL) is added and the reaction mixture is stirred for another 10 min. The organic layer is separated, washed with saturated $NaHCO_3$ solution (100 mL), dried ($Na_2SO_4$) and concentrated to afford the title compound (20 g, 56% for 2 steps) as a white solid.

Step 3: Synthesis of diethyl 1-[(1-{[(tert-butoxycarbonyl)amino]methyl}cyclopropyl)methyl]-1H-indole-2,6-dicarboxylate To a solution of tert-butyl {[1-(hydroxymethyl)cyclopropyl]methyl}carbamate (20 g, 99.5 mmol), diethyl 1H-indole-2,6-dicarboxylate (26 g, 99.5 mmol) and triphenylphosphine (52 g, 199 mmol) in THF (300 mL) is added diisopropyl azodicarboxylate (31 mL, 199 mmol) at room temperature. The reaction mixture is stirred for 60 h and the solvent is evaporated. The residue is purified by flash column chromatography using 12% EtOAc in petroleum ether to afford a mixture of diethyl 1-[(1-{[(tert-butoxycarbonyl)amino]methyl}cyclopropyl)methyl]-1H-indole-2,6-dicarboxylate and diethyl 1H-indole-2,6-dicarboxylate (36 g) as a white solid. The mixture is used in the next step without further purification.

Step 4: Synthesis of diethyl 1-{[1-(aminomethyl) cyclopropyl]methyl}-1H-indole-2,6-dicarboxylate TFA (120 mL) is added to a solution of crude diethyl 1-[(1-{[(tert-butoxycarbonyl)amino]methyl}cyclopropyl) methyl]-1H-indole-2,6-dicarboxylate (36 g, 81 mmol) in $CH_2Cl_2$ (700 mL) at room temperature. The reaction mixture is stirred for 2 h and the solvent is evaporated. The residue is dissolved in EtOAc (600 mL) and is washed with saturated $NaHCO_3$ until the pH is about 7. The aqueous layer is extracted with EtOAc (2×100 mL) and the combined organic layers are dried ($Na_2SO_4$), and concentrated to afford the title compound (30 g, >99%) as a light yellow colored oil which is used in the next step without purification.

Step 5: Synthesis of ethyl 1'-oxo-2',3'-dihydro-1'H-spiro[cyclopropane-1,4'-[1,4]diazepino[1,2-a]indole]-8'-carboxylate Triethylamine (36.3 mL, 260.8 mmol) is added to the mixture of crude diethyl 1-{[1-(aminomethyl)cyclopropyl]methyl}-1H-indole-2,6-dicarboxylate (30 g, 86.9 mmol) and $K_2CO_3$ (36 g, 260.8 mmol) in ethanol (800 mL). The reaction mixture is heated at 80° C. for 2 h and it is cooled to room temperature and stirred for another 16 h. Solid $K_2CO_3$ is removed by filtration and the filtrate is concentrated to afford the crude compound which is purified by flash column chromatography using 3% methanol in $CH_2Cl_2$ to afford the title compound (9.2 g, 31% for 3 steps) as a white solid.

Step 6: Synthesis of 1'-oxo-2',3'-dihydro-1'H-spiro [cyclopropane-1,4'-[1,4]diazepino[1,2-a]indole]-8'-carboxylic acid A solution of NaOH (3 g, 75 mmol) in water (75 mL) is added to a suspension of ethyl 1'-oxo-2',3'-dihydro-1'H-spiro[cyclopropane-1,4'-[1,4]diazepino[1,2-a]indole]-8'-carboxylate (9 g, 30.2 mmol) in ethanol (300 mL). The reaction mixture is heated at 80° C. for 2 h. Acetic acid (48 mL) and water (250 mL) are added and the resulting solid is filtered, rinsed with water and dried to afford the title compound (5.4 g, 66%) as a white solid.

Intermediate T: 1'-oxo-2',3'-dihydro-1'H-spiro[cyclobutane-1,4'-[1,4]diazepino[1,2-a]indole]-8'-carboxylic acid

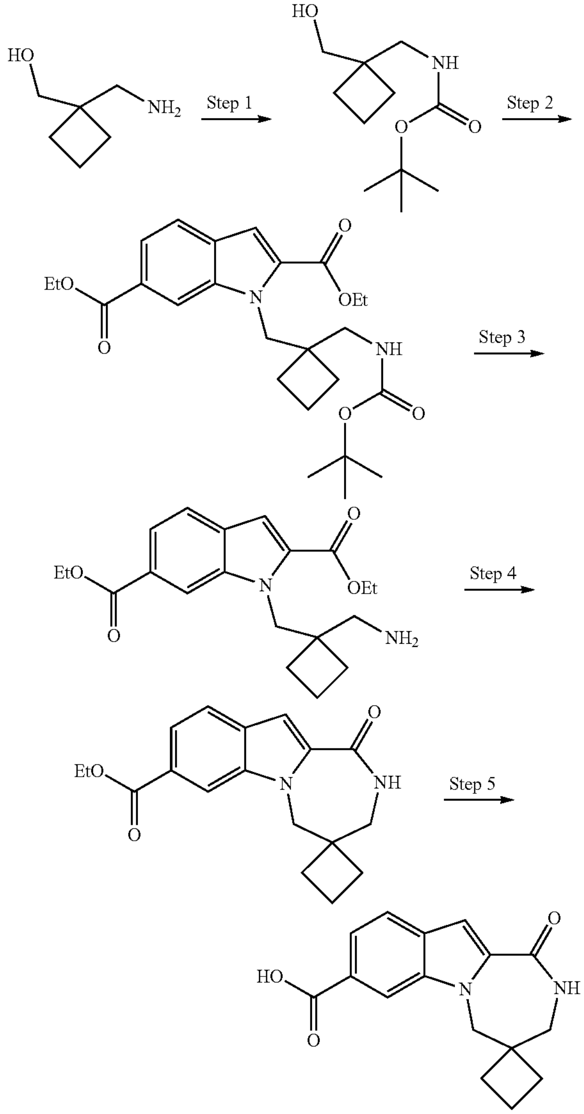

Step 1: Synthesis of tert-butyl {[1-(hydroxymethyl) cyclobutyl]methyl}carbamate

Di-tert-butyl dicarbonate (23.19 mL, 104 mmol) is added to a stirred solution of [1-(aminomethyl)cyclobutyl]methanol (12 g, 104 mmol) in $CH_2Cl_2$ (700 mL) and the reaction mixture is stirred for 40 h at room temperature. Saturated $NH_4Cl$ (300 mL) is added and the mixture is stirred for another 10 min. The organic layer is separated, washed with saturated NaHCO$_3$ (100 mL), dried (Na$_2$SO$_4$) and concentrated to afford the title compound (20 g, 89%) as a white solid.

Step 2: Synthesis of diethyl 1-[(1-{[(tert-butoxycarbonyl)amino]methyl}cyclobutyl)methyl]-1H-indole-2,6-dicarboxylate To a solution of tert-butyl {[1-(hydroxymethyl)cyclobutyl]methyl}carbamate (12 g, 55.76 mmol), diethyl 1H-indole-2,6-dicarboxylate (14.56 g, 55.76 mmol) and triphenylphosphine (29.2 g, 111.5 mmol.) in THF (110 mL) is added diisopropyl azodicarboxylate (22.41 mL, 111.5 mmol) at room temperature and the reaction mixture is stirred for 60 h. The solvent is evaporated and the residue is purified by flash column chromatography using 12% EtOAc in petroleum ether to afford diethyl 1-[(1-{[(tert-butoxycarbonyl)amino]methyl}cyclobutyl)methyl]-1H-indole-2,6-dicarboxylate contaminated with un-reacted diethyl 1H-indole-2,6-dicarboxylate. The mixture is used in the next step without further purification.

Step 3: Synthesis of diethyl 1-{[1-(aminomethyl)cyclobutyl]methyl}-1H-indole-2,6-dicarboxylate TFA (100 mL) is added to the solution of crude diethyl 1-[1-{[(tert-butoxycarbonyl)amino]methyl}cyclobutyl)methyl]-1H-indole-2,6-dicarboxylate from the preceding step in CH$_2$Cl$_2$ (450 mL). The reaction mixture is stirred at room temperature for 2 h and the solvent is removed in vacuo. The residue is dissolved in EtOAc (300 mL) and it is washed with saturated NaHCO$_3$ until the pH is about 7. Then the aqueous layer is separated and extracted with EtOAc (3×100 mL). The organic layers are combined, dried (Na$_2$SO$_4$) and concentrated to afford the title compound which is used in the next step without purification.

Step 4: Synthesis of ethyl 1'-oxo-2',3'-dihydro-1'H-spiro[cyclobutane-1,4'-[1,4]diazepino[1,2-a]indole]-8'-carboxylate Triethylamine (23.3 mL, 167.5 mmol) is added to a mixture of crude 1-(1-aminomethyl-cyclobutylmethyl)-1H-indole-2,6-dicarboxylic acid diethyl ester from the preceding step and K$_2$CO$_3$ (23.16 g, 167.5 mmol) in ethanol (1.2 L). The reaction mixture is heated at 80° C. for 2 h then is cooled down to room temperature and stirred for another 16 h. The solid K$_2$CO$_3$ is removed by filtration and the filtrate is concentrated to afford the crude compound which is purified by flash column chromatography using 3% methanol in CH$_2$Cl$_2$ to afford the title compound (7 g, 40% for 3 steps) as a white solid.

Step 5: Synthesis of 1'-oxo-2',3'-dihydro-1'H-spiro[cyclobutane-1,4'-[1,4]diazepino[1,2-a]indole]-8'-carboxylic acid To a solution of ethyl 1'-oxo-2',3'-dihydro-1'H-spiro[cyclobutane-1,4'-[1,4]diazepino[1,2-a]indole]-8'-carboxylate (7 g, 22.4 mmol) in ethanol (240 mL) is added a solution of NaOH (2.24 g, 56 mmol) in water (56 mL). The reaction mixture is heated at 80° C. for 2 h. Acetic acid (35.8 mL) and water (314 mL) are added and the resulting solid is filtered, rinsed with water and dried to afford the title compound (4 g, 64%) as a white solid.

Intermediate U: 1-oxo-2,2',3,3',5',6'-hexahydro-1H-spiro[1,4-diazepino[1,2-a]indole-4,4'-pyran]-8-carboxylic acid

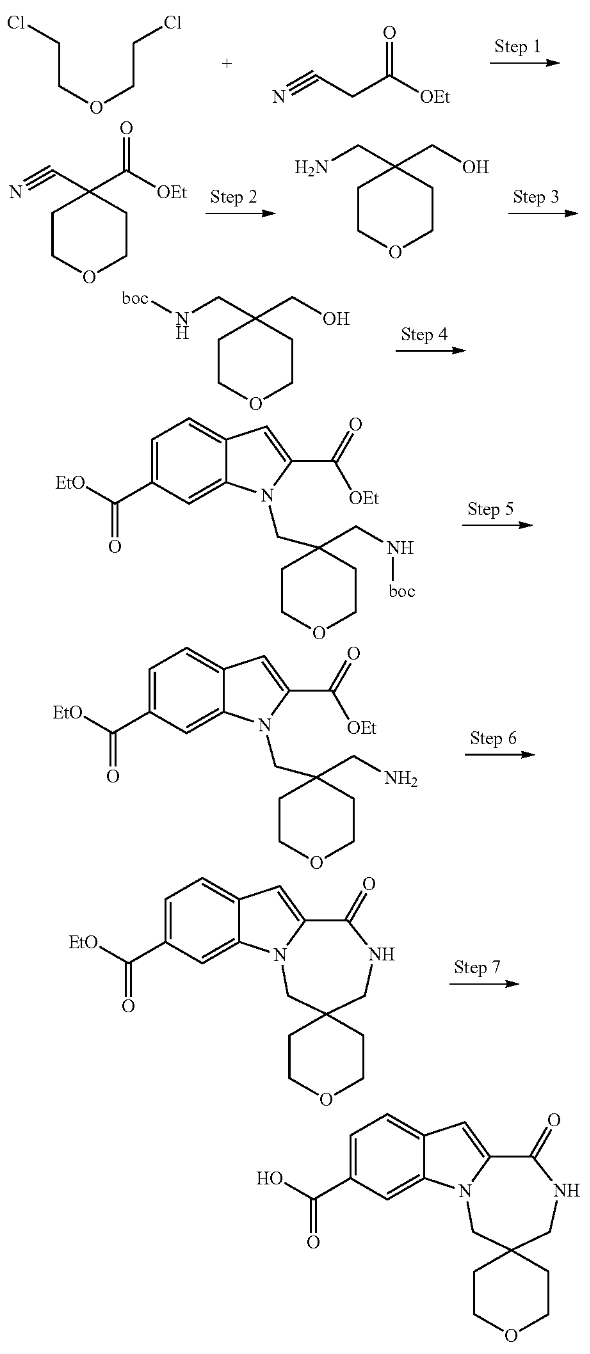

Step 1: Synthesis of ethyl 4-cyanotetrahydro-2H-pyran-4-carboxylate

To a suspension of NaH (22.11 g, 552.1 mmol) in DMF (350 mL) is added ethyl cyanoacetate (23.5 mL, 195 mmol) at 0° C. over 25 min. The reaction mixture is warmed to room temperature for 2 h and it is cooled down to 0° C. again. A solution of 1-chloro-2-(2-chloroethoxy)ethane (31.1 mL, 265.4 mmol) in DMF (50 mL) is added and the reaction mixture is warmed to room temperature for 1 h. Then the reaction mixture is heated at 90° C. for 16 h before the reaction is quenched with ice cold water (180 mL). The mixture is extracted with EtOAc (2×200 mL) and the organic layers are combined, dried ($Na_2SO_4$) and concentrated. The crude compound is purified by fractional distillation under high vacuum to afford the title compound (10 g, 25%) as a colorless oil.

Step 2: Synthesis of [4-(aminomethyl)tetrahydro-2H-pyran-4-yl]methanol

A solution of ethyl 4-cyanotetrahydro-2H-pyran-4-carboxylate (10 g, 54.64 mmol) in THF (50 mL) is added dropwise to a suspension of lithium aluminum hydride (8.26 g, 218.5 mmol) in THF (100 mL) at 0° C. The reaction mixture is warmed to room temperature and stirred for 4 h. The mixture is cooled to 0° C. and ice cold water (30 mL) is added slowly. The mixture is extracted with EtOAc (2×200 mL) and the organic layers are combined, dried ($Na_2SO_4$) and concentrated to afford the title crude compound (8 g, >99%) which is used in the next step without purification.

Step 3: Synthesis of tert-butyl {[4-(hydroxymethyl)tetrahydro-2H-pyran-4-yl]methyl}carbamate Di-tert-butyl dicarbonate (12.27 mL, 55.17 mmol) is added to a stirred solution of [4-(aminomethyl)tetrahydro-2H-pyran-4-yl]methanol (8 g, 55.17 mmol) in $CH_2Cl_2$ (350 mL) at room temperature. The reaction mixture is stirred for 40 h before saturated $NH_4Cl$ solution (150 mL) is added. The mixture is stirred for another 10 min and the organic layer is separated, washed with saturated $NaHCO_3$ (60 mL), dried ($Na_2SO_4$) and concentrated to afford the title compound (13 g, 96%) as a white solid.

Step 4: Synthesis of diethyl 1-[(4-{[(tert-butoxycarbonyl)amino]methyl}tetrahydro-2H-pyran-4-yl)methyl]-1H-indole-2,6-dicarboxylate To a solution of tert-butyl {[4-(hydroxymethyl)tetrahydro-2H-pyran-4-yl]methyl}carbamate (10 g, 40.81 mmol), diethyl 1H-indole-2,6-dicarboxylate (Intermediate A, 10.65 g, 40.81 mmol) and triphenylphosphine (21.3 g, 81.63 mmol) in THF (110 mL) at room temperature is added diisopropyl azodicarboxylate (16 mL, 81.63 mmol). The reaction mixture is stirred for 60 h and the solvent is removed under vacuum. The residue is purified by flash column chromatography using 12% EtOAc in petroleum ether to afford a mixture of diethyl 1-[(4-{[(tert-butoxycarbonyl)amino]methyl}tetrahydro-2H-pyran-4-yl)methyl]-1H-indole-2,6-dicarboxylate and un-reacted diethyl 1H-indole-2,6-dicarboxylate as a white solid. The mixture is used in the next step without further purification.

Step 5: Synthesis of diethyl 1-{[4-(aminomethyl)tetrahydro-2H-pyran-4-yl]methyl}-1H-indole-2,6-dicarboxylate TFA (60 mL) is added to a solution of crude diethyl 1-[(4-{[(tert-butoxycarbonyl)amino]methyl}tetrahydro-2H-pyran-4-yl)methyl]-1H-indole-2,6-dicarboxylate from the preceding step in $CH_2Cl_2$ (400 mL). The reaction mixture is stirred at room temperature for 2 h. Then the solvent is removed under vacuum and the residue is dissolved in EtOAc (300 mL) and washed with saturated $NaHCO_3$ solution until the pH is about 7. The aqueous layer is separated and it is extracted with EtOAc (100 mL). The organic layers are combined, dried over $Na_2SO_4$ and concentrated to afford the crude title compound which is used in the next step without purification.

Step 6: Synthesis of ethyl 1-oxo-2,2',3,3',5',6'-hexahydro-1H-spiro[1,4-diazepino[1,2-a]indole-4,4'-pyran]-8-carboxylate To a solution of the crude diethyl 1-{[4-(aminomethyl)tetrahydro-2H-pyran-4-yl]methyl}-1H-indole-2,6-dicarboxylate from the preceding step in ethanol (800 mL) is added triethylamine (16.16 mL, 115.9 mmol) and $K_2CO_3$ (16.1 g, 115.9 mmol). The reaction mixture is heated at 80° C. for 2 h and is cooled to room temperature and stirred for an additional 16 h. The solid $K_2CO_3$ is removed by filtration and the filtrate is concentrated. The crude compound is purified by flash column chromatography using 3% methanol in $CH_2Cl_2$ to afford the title compound (4.2 g, 30% for 3 steps) as a white solid.

Step 7: Synthesis of 1-oxo-2,2',3,3',5',6'-hexahydro-1H-spiro[1,4-diazepino[1,2-a]indole-4,4'-pyran]-8-carboxylic acid To a suspension of ethyl 1-oxo-2,2',3,3',5',6'-hexahydro-1H-spiro[1,4-diazepino[1,2-a]indole-4,4'-pyran]-8-carboxylate (4.2 g, 12.2 mmol) in ethanol (120 mL) is added NaOH (1.22 g, 30.5 mmol) and water (30 mL). The reaction mixture is heated at 80° C. for 2 h. Acetic acid (19 mL) and water (180 mL) are added and the resulting solid is collected by filtration, washed with water and dried to afford the title compound (2.42 g, 64%) as a white solid.

Intermediate V: 1'-(tert-butoxycarbonyl)-1-oxo-2,3-dihydro-1H-spiro[1,4-diazepino[1,2-a]indole-4,4'-piperidine]-8-carboxylic acid

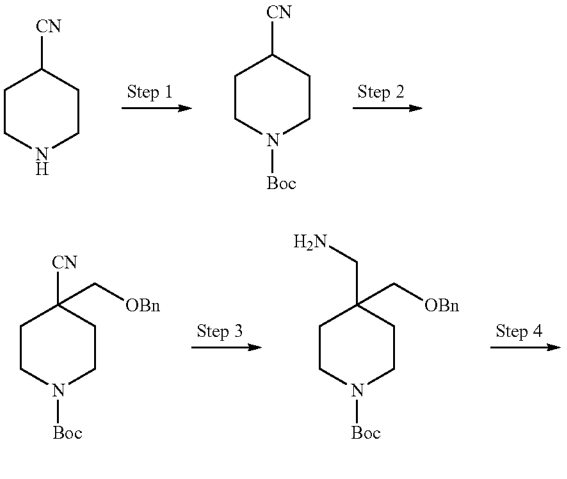

-continued

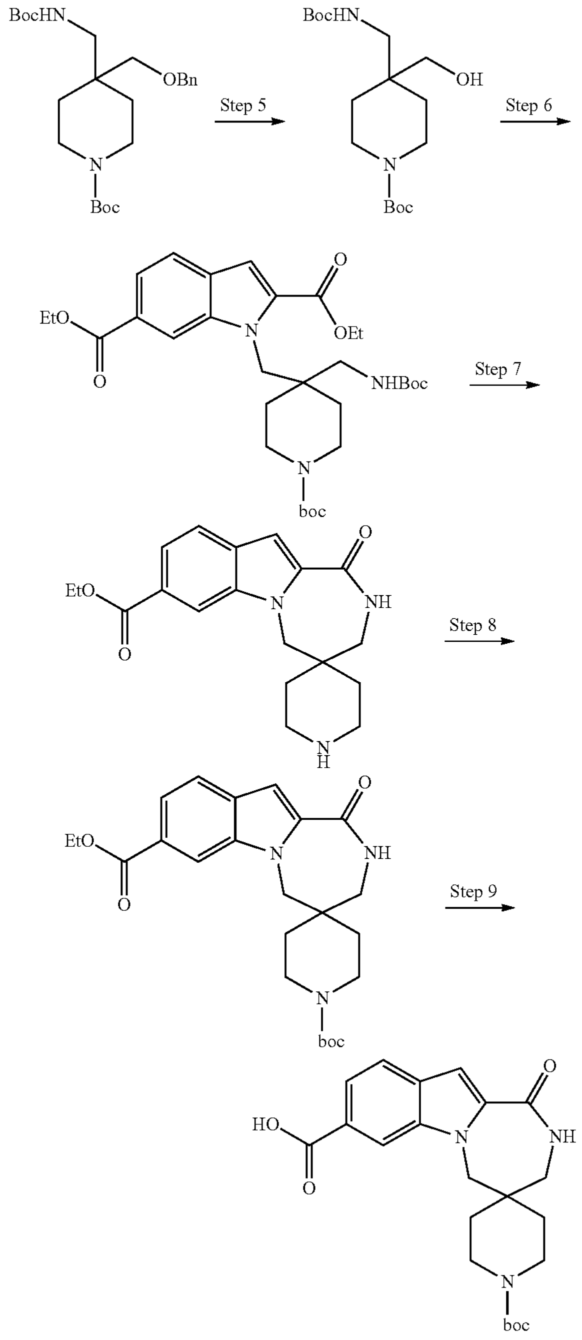

Step 1: Synthesis of tert-butyl 4-cyanopiperidine-1-carboxylate

Di-tert-butyl dicarbonate (26.4 mL, 109.0 mmol) is added dropwise to a solution of piperidine-4-carbonitrile (10 g, 90.9 mmol) in $CH_2Cl_2$ (120 mL) at 0° C. The reaction mixture is warmed to room temperature and stirred for 1 h. The solvent is evaporated, a small amount of n-hexane is added and the mixture is cooled to 0° C. for 1 h. The resulting solid is collected by filtration and dried to afford the title compound (14 g, 73.6%) as a white solid.

Step 2: Synthesis of tert-butyl 4-[(benzyloxy)methyl]-4-cyanopiperidine-1-carboxylate To a solution of tert-butyl 4-cyanopiperidine-1-carboxylate (4 g, 19 mmol) in THF (70 mL) cooled to 0° C. is added 0.5 M KHMDS (57 mL, 28.5 mmol) in toluene dropwise. The reaction mixture is warmed to room temperature and stirred for 1 h. Chloromethoxymethyl-benzene (4.46 g, 28.5 mmol) is added and the reaction mixture is stirred for another 1 h at room temperature. Water and ethyl acetate are added and the aqueous layer is separated and extracted with ethyl acetate (2×50 mL). The organic layers are combined, washed with brine, dried ($Na_2SO_4$) and concentrated to afford the title compound (3 g, 48.3%) as a light yellow liquid.

Step 3: Synthesis of tert-butyl 4-(aminomethyl)-4-[(benzyloxy)methyl]piperidine-1-carboxylate To a slurry of Raney nickel (1 g, 10% w/w) in methanol are added tert-butyl 4-[(benzyloxy)methyl]-4-cyanopiperidine-1-carboxylate (10 g, 30.3 mmol) and methanol/$NH_3$ (1 mL). The reaction mixture is stirred at room temperature under 60 psi of $H_2$ for 16 h. Then the reaction mixture is filtered through a pad of Celite and the filtrate is concentrated to afford the title compound (8 g, 79%) as a colorless liquid.

Step 4: Synthesis of tert-butyl 4-[(benzyloxy)methyl]-4-{[(tert-butoxycarbonyl)amino]methyl}piperidine-1-carboxylate Di-tert-butyl dicarbonate (3.4 mL, 14.28 mmol) is added dropwise to a solution of tert-butyl 4-(aminomethyl)-4-[(benzyloxy)methyl]piperidine-1-carboxylate (4 g, 11.9 mmol) in $CH_2Cl_2$ (130 mL) at 0° C. The reaction mixture is warmed to room temperature and stirred for 1 h. The mixture is concentrated and the residue is purified by flash column chromatography using 20% EtOAc/petroleum ether to afford the title compound (3 g, 65%) as a white solid.

Step 5: Synthesis of tert-butyl 4-{[(tert-butoxycarbonyl)amino]methyl}-4-(hydroxymethyl)piperidine-1-carboxylate To a slurry of 10% palladium on carbon (700 mg, 0.66 mmol) in methanol is added tert-butyl butyl 4-[(benzyloxy)methyl]-4-{[(tert-butoxycarbonyl)amino]methyl}piperidine-1-carboxylate (7 g, 16.1 mmol). The reaction mixture is stirred at room temperature under 60 psi of $H_2$ for 16 h. Then the reaction mixture is filtered through a pad of Celite and the filtrate is concentrated to afford the title compound (4 g, 73%) as a white solid.

Step 6: Synthesis of diethyl 1-{[1-(tert-butoxycarbonyl)-4-{[(tert-butoxycarbonyl)amino]methyl}piperidin-4-yl]methyl}-1H-indole-2,6-dicarboxylate A solution of triphenylphosphine (19.4 g, 74.1 mmol) and DIAD (14.05 mL, 74.1 mmol) in THF (700 mL) is cooled to 0° C. and stirred for 10 min. Diethyl 1H-indole-2,6-dicarboxylate (15.47 g, 59.3 mmol) is added and reaction mixture is stirred for another 10 min. tert-Butyl 4-{[(tert-butoxycarbonyl)amino]methyl}-4-(hydroxymethyl)piperidine-1-carboxylate (17 g, 49.4 mmol) is added and the reaction mixture is stirred for 48 h at room temperature. The mixture is partitioned between water and ethyl acetate. and the organic layer is separated. The aqueous layer is extracted with ethyl acetate (2×200 mL). The combined organic layers are dried ($Na_2SO_4$), and concentrated. The residue is purified by flash column chromatography using 15% EtOAc in petroleum ether to afford the title compound (17 g, 32%) as a dark brown oil.

Step 7: Synthesis of ethyl 1-oxo-2,3-dihydro-1H-spiro[1,4-diazepino[1,2-a]indole-4,4'-piperidine]-8-carboxylate Trifluoroacetic acid (13.4 mL, 173.8 mmol) is added dropwise to the solution of diethyl 1-{[1-(tert-butoxycarbonyl)-4-{[(tert-butoxycarbonyl)amino]methyl}piperidin-4-yl]methyl}-1H-indole-2,6-dicarboxylate (17 g, 29.0 mmol) in $CH_2Cl_2$ (200 mL) at 0° C. The reaction mixture is stirred for 3 h at room temperature and then is basified with aqueous $K_2CO_3$ solution until the pH is 8. The aqueous layer is separated and extracted with $CH_2Cl_2$ (2×250 mL). The organic layers are combined, washed with brine, dried ($Na_2SO_4$) and concentrated. The crude material is recrystallized using diethyl ether to afford the title compound (6 g, 61%) as a white solid.

Step 8: Synthesis of 1'-tert-butyl 8-ethyl 1-oxo-2,3-dihydro-1H,1'H-spiro[1,4-diazepino[1,2-a]indole-4,4'-piperidine]-1',8-dicarboxylate To a solution of ethyl 1-oxo-2,3-dihydro-1H-spiro[1,4-diazepino[1,2-a]indole-4,4'-piperidine]-8-carboxylate (8 g, 23.5 mmol) in THF (150 mL) at 0° C. is added triethylamine (5.07 mL, 35.19 mmol). After stirring for 10 min, di-tert-butyl dicarbonate (8.5 mL, 35.2 mmol) is added and reaction mixture is warmed to room temperature for 1 h. The mixture is partitioned between water and ethyl acetate. The aqueous layer is separated and is extracted with ethyl acetate (2×100 mL). The organic layers are combined, dried ($Na_2SO_4$) and concentrated to afford the title compound (4 g, 38.8%) as a white solid.

Step 9: Synthesis of 1'-(tert-butoxycarbonyl)-1-oxo-2,3-dihydro-1H-spiro[1,4-diazepino[1,2-a]indole-4,4'-piperidine]-8-carboxylic acid To a solution of 1'-tert-butyl 8-ethyl 1-oxo-2,3-dihydro-1H,1'H-spiro[1,4-diazepino[1,2-a]indole-4,4'-piperidine]-1',8-dicarboxylate (5.0 g, 11.3 mmol) in ethanol (120 mL) at 0° C. is added 1M NaOH solution (34 mL, 34 mmol). The reaction mixture is warmed to room temperature and is stirred for 16 h. The solvent is evaporated and water is added into the residue. The mixture is cooled to 0° C. and acidified with 10% acetic acid. The resulting solid is collected by filtration, washed with water and dried to afford the title compound (3.3 g, 72%) as an off white solid.

Intermediate W: 3-methyl-1-oxo-2,3,4,5-tetrahydro-1H-[1,4]diazepino[1,2-a]indole-8-carboxylic acid

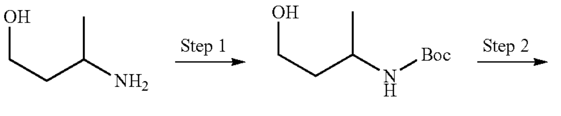

-continued

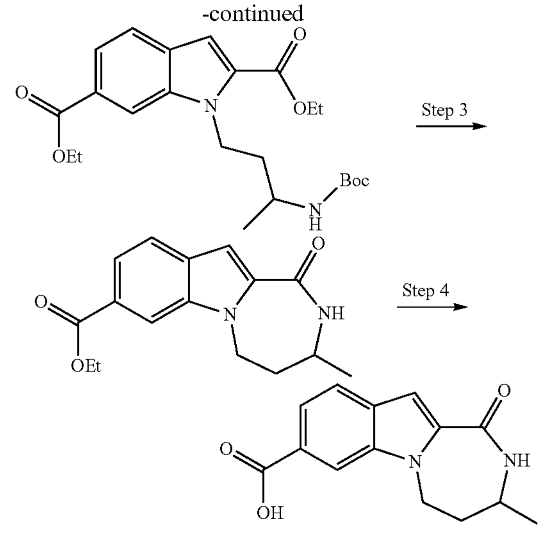

Step 1: Synthesis of tert-butyl (4-hydroxybutan-2-yl)carbamate

To a solution of 3-aminobutan-1-ol (1.0 g, 11.2 mmol), 4-dimethylamino pyridine (137.0 mg, 1.1 mmol) and triethylamine (1.7 mL, 12.3 mmol) in acetonitrile (20 mL) is added di-tert-butyl dicarbonate (2.9 g, 13.5 mmol). The reaction mixture is stirred for 40 h at room temperature. The solvent is removed and the residue is partitioned between $CH_2Cl_2$ and saturated $NaHCO_3$. The aqueous is extracted with $CH_2Cl_2$ and the combined organic layers are dried ($Na_2SO_4$) and concentrated. The crude residue is purified by flash column chromatography using methanol in $CH_2Cl_2$ to afford the title compound (680 mg, 32%).

Step 2: Synthesis of diethyl 1-{3-[(tert-butoxycarbonyl)amino]butyl}-1H-indole-2,6-dicarboxylate To solution of diethyl 1H-indole-2,6-dicarboxylate (Intermediate A, 729 mg, 2.8 mmol), triphenylphosphine (879 mg, 3.3 mmol) and tert-butyl (4-hydroxybutan-2-yl)carbamate (634 mg, 3.3 mmol) in $CH_2Cl_2$ (10 mL) cooled to 0° C. is added diisopropyl azodicarboxylate (0.69 mL, 3.3 mmol). The reaction mixture is warmed to room temperature and stirred for 16 h. The solvent is removed and the residue is purified by flash column chromatography using methanol in $CH_2Cl_2$ to afford the mixture of diethyl 1-{3-[(tert-butoxycarbonyl)amino]butyl}-1H-indole-2,6-dicarboxylate and unreacted diethyl 1H-indole-2,6-dicarboxylate (604 mg). The mixture is used in the next step without further purification.

Step 3: Synthesis of ethyl 3-methyl-1-oxo-2,3,4,5-tetrahydro-1H-[1,4]diazepino[1,2-a]indole-8-carboxylate To a mixture of diethyl 1-{3-[(tert-butoxycarbonyl)amino]butyl}-1H-indole-2,6-dicarboxylate and diethyl 1H-indole-2,6-dicarboxylate (600 mg) in $CH_2Cl_2$ (10 mL) is added TFA (5 mL). The reaction mixture is stirred for 2 h at room temperature. The solvent is evaporated and the residue dried in vacuo. To a solution of the residue in ethanol (10 mL) is added $K_2CO_3$ (500 mg, 3.6 mmol) and triethylamine (0.02 mL, 0.14 mmol). The reaction mixture is heated to 80° C. for 36 h. The mixture is diluted with water (10 mL) and is extracted with EtOAc. The organic layers are dried ($Na_2SO_4$) and concentrated and the residue is purified by flash column chromatography using EtOAc in heptane to afford the title compound (120 mg, 15% for 3 steps).

Step 4: Synthesis of 3-methyl-1-oxo-2,3,4,5-tetrahydro-1H-[1,4]diazepino[1,2-a]indole-8-carboxylic acid To a solution of ethyl 3-methyl-1-oxo-2,3,4,5-tetrahydro-1H-[1,4]diazepino[1,2-a]indole-8-carboxylate (120 mg, 0.42 mmol) in ethanol (10 mL) is added 1M NaOH solution (1.0 mL, 1.0 mmol). The reaction mixture is heated at 80° C. for 2 h. Acetic acid (3 mL) is and water (60 mL) are added and the mixture is concentrated. The residue is purified by preparative HPLC to afford the title compound (63 mg, 58%).

Intermediate X: 3,3-dimethyl-1-oxo-2,3,4,5-tetrahydro-1H-[1,4]diazepino[1,2-a]indole-8-carboxylic acid

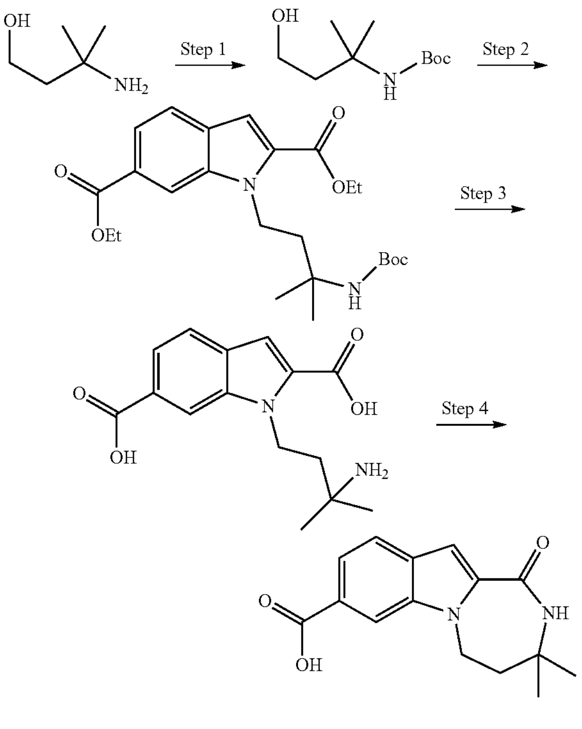

Step 1: Synthesis of tert-butyl (4-hydroxy-2-methylbutan-2-yl)carbamate

To a solution of 3-amino-3-methylbutan-1-ol (1.0 g, 9.7 mmol) in EtOAc (5 mL) is added di-tert-butyl dicarbonate (2.1 g, 9.7 mmol). The mixture is stirred for 16 h and the solvent is evaporated to afford the crude title compound which is used in the next step without purification.

Step 2: Synthesis of diethyl 1-{3-[(tert-butoxycarbonyl)amino]-3-methylbutyl}-1H-indole-2,6-dicarboxylate To a solution of diethyl 1H-indole-2,6-dicarboxylate (Intermediate A, 100 mg, 0.38 mmol), crude tert-butyl (4-hydroxy-2-methylbutan-2-yl)carbamate (155 mg, 0.76 mmol) and triphenylphospine (251 mg, 0.96 mmol) in THF (1.5 mL) is added diisopropyl azodicarboxylate (0.20 mL, 0.96 mmol). The mixture is stirred for 16 h at room temperature. The solvent is evaporated and the residue is purified by flash column chromatography to afford a mixture of diethyl 1-{3-[(tert-butoxycarbonyl)amino]-3-methylbutyl}-1H-indole-2,6-dicarboxylate and diethyl 1H-indole-2,6-dicarboxylate (131 mg) which is used in the next step without purification.

Step 3: Synthesis of 1-(3-amino-3-methylbutyl)-1H-indole-2,6-dicarboxylic acid

To the mixture of the crude diethyl 1-{3-[(tert-butoxycarbonyl)amino-]-3-methylbutyl}-1H-indole-2,6-dicarboxylate from the preceding step in $CH_2Cl_2$ (3 mL) is added TFA (1.5 mL). The mixture is stirred at room temperature for 2 h. The solvent is evaporated and the residue dried in vacuo. To a solution of the residue in ethanol (8 mL). is added triethylamine (0.13 mL, 0.90 mmol) and $K_2CO_3$ (124 mg, 0.90 mmol). The mixture is heated at 80° C. for 2 h and at 100° C. for 64 h. Water (20 mL) and acetic acid (1 mL) are added and the mixture is extracted with EtOAc. The organic layers are dried ($Na_2SO_2$) and concentrated to afford the title compound which is used in the next step without purification.

Step 4: Synthesis of 3,3-dimethyl-1-oxo-2,3,4,5-tetrahydro-1H-[1,4]diazepino[1,2-a]indole-8-carboxylic acid To a solution of the crude 1-(3-Amino-3-methylbutyl)-1H-indole-2,6-dicarboxylic acid from the preceding step in THF (9.0 mL) is added 1,1'-carbonyldiimidazole (162 mg, 0.90 mmol) followed by 1,8-diazabicyclo[5.4.0] undec-7-ene (0.14 mL, 0.90 mmol). The mixture is stirred at room temperature for 2 h. Acetic acid (0.3 mL) and water (50 mL) are added and the mixture is extracted with EtOAc. The organic layers are dried ($Na_2SO_4$) and concentrated. The crude compound is purified by flash column chromatography using 10% methanol in $CH_2Cl_2$ to afford the title compound (17 mg, 16% for three steps).

Intermediate Y: 5-phenyl-1,2-oxazol-3-amine

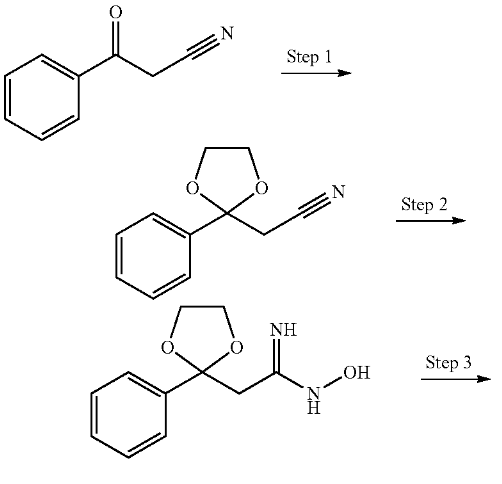

-continued

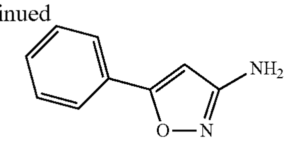

Step 1: Synthesis of (2-phenyl-1,3-dioxolan-2-yl)acetonitrile

To a solution of 3-oxo-3-phenylpropanenitrile (10 g, 68.8 mmol) and PTSA (0.027 g, 1.37 mmol) in toluene (120 mL) is added ethylene glycol (120 mL, 2057 mmol). The mixture is heated at 150° C. for 14 h. The solvent is evaporated under reduced pressure and the residue is washed with 10% NaOH solution. The aqueous layer is extracted with diethyl ether (2×100 mL) and the combined organic layers are dried ($Na_2SO_4$) and evaporated to provide the crude compound. The crude material is purified over neutral alumina eluting with 1% of ethyl acetate/hexane to afford the title compound as an off white solid (10 g, 77%).

Step 2: Synthesis of N-hydroxy-2-(2-phenyl-1,3-dioxolan-2-yl)ethanimidamide

Sodium hydroxide (3.1 g, 77 mmol) is added to hydroxylamine hydrochloride (5.2 g, 75 mmol) at 0° C. and is stirred for 15 min. A solution of (2-phenyl-1,3-dioxolan-2-yl)acetonitrile (7 g, 37 mmol) in methanol (25 mL) is added dropwise to the reaction mixture at 0° C. The reaction mixture is allowed to warm to room temperature and is heated at 90° C. for 16 h. The solvent was evaporated under reduced pressure to afford the title compound as a brown solid (7 g, 85%) which is used in the next step without purification.

Step 3: Synthesis of 5-phenyl-1,2-oxazol-3-amine

Ethanol (125 mL) and water (25 mL) are added to N-hydroxy-2-(2-phenyl-1,3-dioxolan-2-yl)ethanimidamide (7 g, 32 mmol). The pH is adjusted to 1 with the addition conc.

HCl and the reaction mixture is heated at 90° C. for 2 h. The solvent is evaporated to dryness and the resulting residue is neutralized using phosphate buffer. The mixture is extracted with ethyl acetate and the combined organic phases are dried ($Na_2SO_4$) and concentrated in vacuo. The crude residue is purified over neutral alumina eluting with 30% ethyl acetate/hexane to afford the title compound as an off-white solid (1.7 g, 34%).

Intermediates Z-AD in the table below are synthesized according to the procedure for Intermediate Y, substituting the appropriate commercially available reagents.

| Structure | Intermediate | Name |
|---|---|---|
| 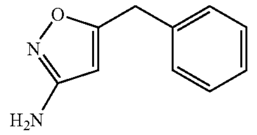 [SMILES: Nc1cc(Cc2ccccc2)on1] | Z | 5-benzyl-1,2-oxazol-3-amine |
| 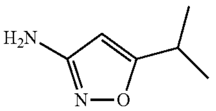 | AA | 5-(propan-2-yl)-1,2-oxazol-3-amine |

-continued

| Structure | Intermediate | Name |
|---|---|---|
| 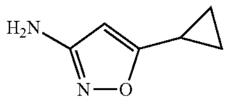 | AB | 5-cyclopropyl-1,2-oxazol-3-amine |
| 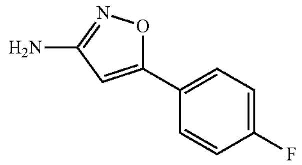 [SMILES: Nc1cc(-c2ccc(F)cc2)on1] | AC | 5-(4-fluorophenyl)-1,2-oxazol-3-amine |
| 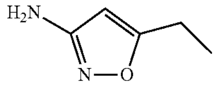 | AD | 5-ethyl-1,2-oxazol-3-amine |

Intermediate AE: 1-(pyridin-4-ylmethyl)-1H-pyrazol-4-amine

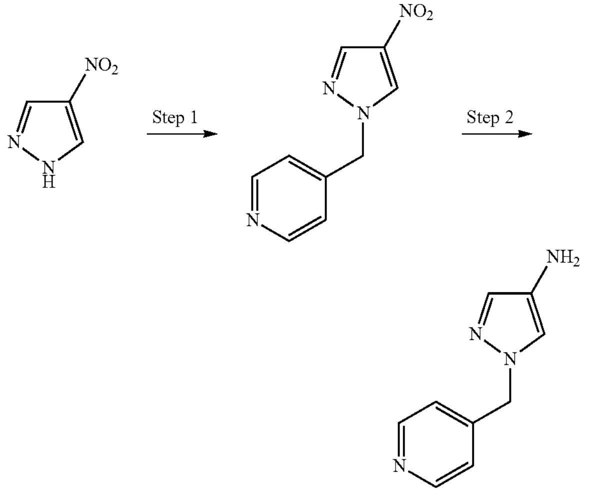

Step 1. Synthesis of 4-[(4-nitro-1H-pyrazol-1-yl)methyl]pyridine

To a stirred solution of 4-nitro-1H-pyrazole (211 mg, 1.87 mmol), pyridine-4-methanol (0.28 mL, 2.56 mmol), and triphenylphosphine (538 mg, 2.05 mmol) in THF (10 mL) under nitrogen is added di-t-butyl azodicarboxylate (472 mg, 2.05 mmol) over 3 min. The reaction mixture was stirred for 16 h at room temperature. The mixture is concentrated and is purified by flash column chromatography using a gradient of 0-3% methanol in $CH_2Cl_2$ to afford the title compound as a yellow oil (247 mg, 65%).

Step 2. Synthesis of 1-(pyridin-4-ylmethyl)-1H-pyrazol-4-amine

A solution of 4-[(4-nitro-1H-pyrazol-1-yl)methyl]pyridine (247 mg, 1.21 mmol) in methanol (10 mL) is hydrogenated over 10% palladium on carbon (30 mg) under balloon pressure for 3 h. The mixture is filtered through Celite and the filtrate is concentrated. The residue is purified by flash column chromatography using a gradient of 0-10% methanol in $CH_2Cl_2$ to afford the title compound as a brown oil (198 mg, 94%).

Intermediates AF-AQ in the table below are synthesized according to the procedure for Intermediate AE, substituting the appropriate commercially available reagents.

| Structure | Intermediate | Name |
|---|---|---|
| 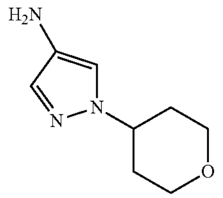 [SMILES: Nc1cnn(C2CCOCC2)c1] | AF | 1-(tetrahydro-2H-pyran-4-yl)-1H-pyrazol-4-amine |
| 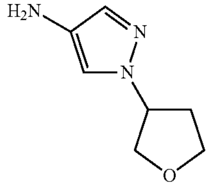 [SMILES: Nc1cnn(C2CCOC2)c1] | AG | 1-(tetrahydrofuran-3-yl)-1H-pyrazol-4-amine |
| 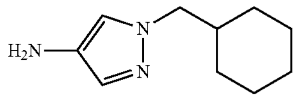 [SMILES: Nc1cnn(CC2CCCCC2)c1] | AH | 1-(cyclohexylmethyl)-1H-pyrazol-4-amine |
| 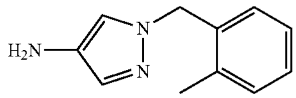 | AI | 1-(2-methylbenzyl)-1H-pyrazol-4-amine |
| 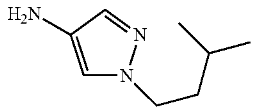 | AJ | 1-(3-methylbutyl)-1H-pyrazol-4-amine |
| 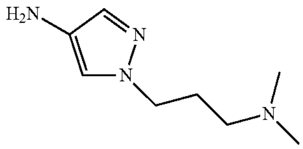 | AK | 1-[3-(dimethylamino)propyl]-1H-pyrazol-4-amine |
| 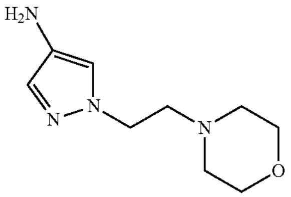 [SMILES: Nc1cnn(CCN2CCOCC2)c1] | AL | 1-[2-(morpholin-4-yl)ethyl]-1H-pyrazol-4-amine |
| 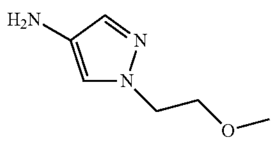 | AM | 1-(2-methoxyethyl)-1H-pyrazol-4-amine |
| 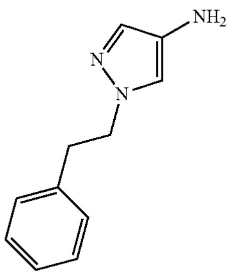 [SMILES: Nc1cnn(CCc2ccccc2)c1] | AN | 1-(2-phenylethyl)-1H-pyrazol-4-amine |

-continued

| Structure | Intermediate | Name |
|---|---|---|
| 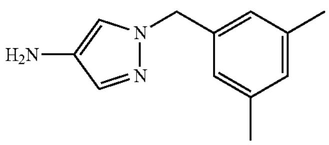 | AO | 1-(3,5-dimethylbenzyl)-1H-pyrazol-4-amine |
| 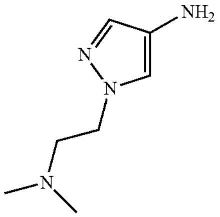 | AP | 1-[2-(dimethylamino)ethyl]-1H-pyrazol-4-amine |
| 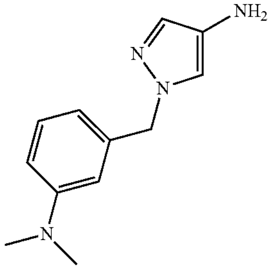 [SMILES: CN(C)c1cccc(Cn2cc(N)cn2)c1] | AQ | 1-[3-(dimethylamino)benzyl]-1H-pyrazol-4-amine |

Intermediate AR: 1-methyl-1H-pyrazolo[3,4-b]pyridin-5-amine

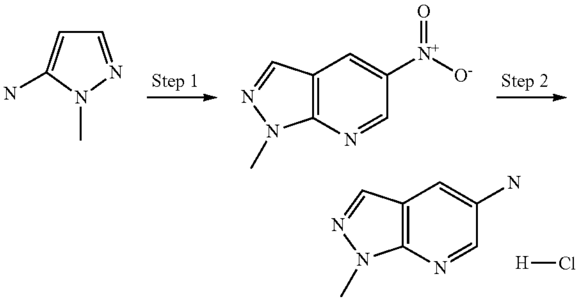

Step 1: Synthesis of 1-methyl-5-nitro-1H-pyrazolo[3,4-b]pyridine

To a solution of 1-methyl-1H-pyrazol-5-amine (291 mg, 3.00 mmol) in acetic acid (3 mL) is added nitromalonaldehyde sodium salt (474 mg, 3.00 mmol) and reaction mixture is heated to 108° C. for 1 h. The reaction mixture is allowed to cool to room temperature and is stirred for 16 h. The solvent is evaporated under reduced pressure and the residue is purified by flash column chromatography using a gradient of 0-100% ethyl acetate in heptane to afford the title compound as a solid (100 mg, 19%).

Step 2: Synthesis of 1-methyl-1H-pyrazolo[3,4-b]pyridin-5-amine

To a solution of 1-methyl-5-nitro-1H-pyrazolo[3,4-b]pyridine (90 mg, 0.51 mmol) in $CH_2Cl_2$ (1 mL) is added zinc (200 mg, 3.06 mmol) and acetic acid (250 µL). The mixture is heated at 45° C. for 5 h. The zinc is removed by filtration and the filtrate was evaporated under reduced pressure. The residue is purified by flash column chromatography using a gradient of 0-10% methanol in $CH_2Cl_2$. 1N HCl in ether is added to the residue to afford the title compound as the hydrochloride salt (43 mg, 46%).

Intermediate AS: 3-ethyl-3H-imidazo[4,5-b]pyridin-2-amine

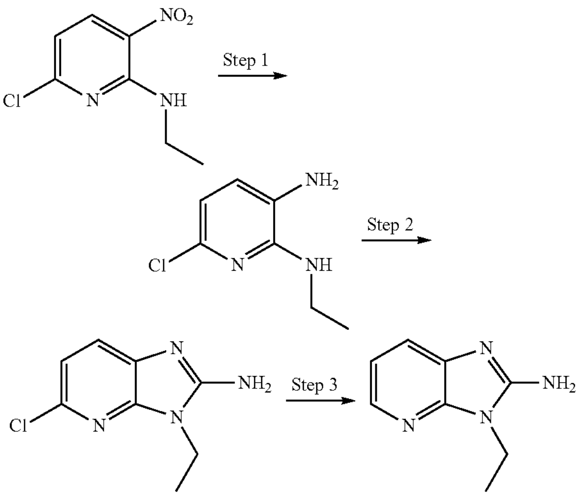

Step 1. Synthesis of 6-chloro-$N^2$-ethylpyridine-2,3-diamine

To a solution of 6-chloro-N-ethyl-3-nitropyridin-2-amine (1.82 g, 9.04 mmol) in ethanol (20 mL) is added iron powder (2.52 g, 45.2 mmol) followed by a solution of ammonium chloride (2.42 g, 45.2 mmol) in water (8 mL). The mixture is heated in a microwave reactor at 140° C. for 30 min. The mixture is diluted with EtOAc, filtered and evaporated to afford the title compound as a brown oil (1.55 g, 100%) which was used in the next step without purification.

Step 2. Synthesis of 5-chloro-3-ethyl-3H-imidazo[4,5-b]pyridin-2-amine

To a solution of 6-chloro-$N^2$-ethylpyridine-2,3-diamine (401 mg, 2.34 mmol) in ethanol (10 mL) is added a 3M solution of cyanogen bromide in DCM (0.93 mL, 2.8 mmol). The solution is stirred for 6 h at room temperature. The solution is basified with ammonia in methanol and evaporated. The residue is purified via flash column chromatography using a gradient of 0-15% methanol in $CH_2Cl_2$ containing 1% $NH_4OH$ to afford the title compound (212 mg, 46%).

Step 3. Synthesis of 3-ethyl-3H-imidazo[4,5-b]pyridin-2-amine

Ammonium formate (1.55 g, 24.6 mmol) is added to a solution of 5-chloro-3-ethyl-3H-imidazo[4,5-b]pyridin-2-amine (410 mg, 2.09 mmol) in ethanol (10 mL) containing 10% palladium on carbon (40 mg). The mixture is stirred for 16 h, filtered, and concentrated. The residue is purified via flash column chromatography using a gradient of 0-10% methanol in $CH_2Cl_2$ to afford the title compound (192 mg, 57%).

Intermediate AT: 1-methyl-5-phenyl-1H-imidazol-2-amine

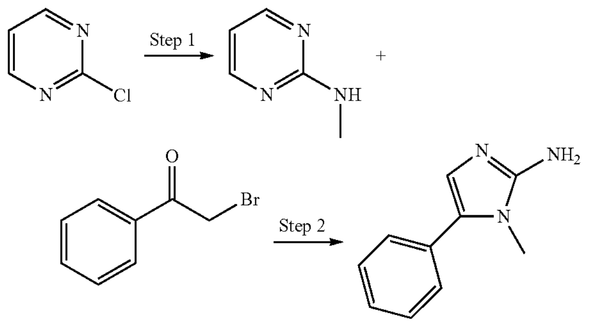

Step 1: Synthesis of N-methylpyrimidin-2-amine

To a solution of 2-chloropyrimidine (1 g, 8.7 mmol) in methanol (10 mL) is added a 2M solution of methylamine (13.2 mL, 26.2 mmol) in methanol, followed by $K_2CO_3$ (2.5 g, 18 mmol). The reaction flask is sealed and heated to 80° C. overnight. The reaction is then cooled to room temperature and concentrated to remove volatiles. The residue is partitioned between water and $CH_2Cl_2$. The organic layer is dried ($Na_2SO_4$) and concentrated to afford the title compound (290 mg, 30%) as a brown oil.

Step 2: Synthesis of 1-methyl-5-phenyl-1H-imidazol-2-amine

To a microwave vial containing a solution of N-methylpyrimidin-2-amine (290 mg, 2.7 mmol) in acetonitrile (5 mL) is added 2-bromo-1-phenylethanone (714 mg, 3.6 mmol). The vial is sealed and heated in a microwave reactor at 130° C. for 20 minutes and is cooled to room temperature. The mixture is treated with hydrazine hydrate (0.65 mL, 13.3 mmol) and is then heated in a microwave reactor at 100° C. for 5 minutes. The reaction is poured into water (30 mL) and filtered to afford the title compound (192 mg, 42%) as a solid.

Intermediate AU: 1-methyl-1H-imidazol-2-amine

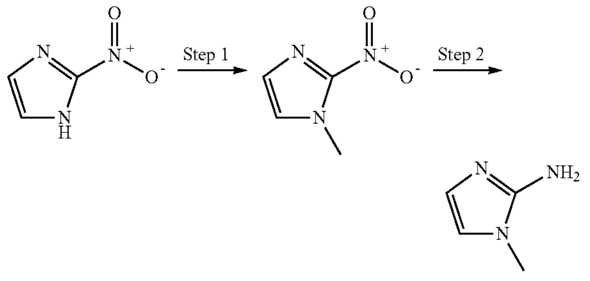

Step 1: Synthesis of 1-methyl-2-nitro-1H-imidazole

To a solution of 2-nitro-1H-imidazole (500 mg, 4.4 mmol) in DMF (50 mL) is added cesium carbonate (1.7 g, 5.3 mmol) and the mixture is heated to 50° C. for 30 minutes. The resulting suspension is cooled to room temperature and MeI (0.33 mL, 5.3 mmol) is added. The reaction is heated to 50° C. for 2 hours is then cooled to room temperature and filtered through a bed of Celite. The filtrate is poured over ice water and extracted ethyl acetate. The organic layer is washed with water, brine, dried ($Na_2SO_4$) and concentrated to afford the title compound (485 mg, 86%) as a yellow solid.

Step 2: Synthesis of 1-methyl-1H-imidazol-2-amine

To a solution of 1-methyl-2-nitro-1H-imidazole (485 mg, 3.8 mmol) in ethanol (10 mL) under a nitrogen atmosphere is carefully 20% palladium on carbon (50 mg, Degussa type) followed by ammonium formate (1.4 g, 23 mmol). The reaction is stirred for 16 h. The suspension is carefully filtered through a bed of Celite and the filtrate is rinsed with additional ethanol (10 mL). The filtrate is concentrated and the residue is partitioned between water and ethyl acetate. The organic layer is dried ($Na_2SO_4$) and concentrated and the residue is purified by chromatography through a short bed of silica gel using 5% methanol in CH2Cl2 to afford the title compound (552 mg, 80%) as an oil.

Intermediate AV: 5-tert-butyl-1,3-oxazol-2-amine

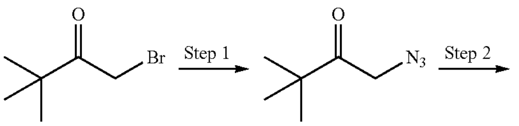

-continued

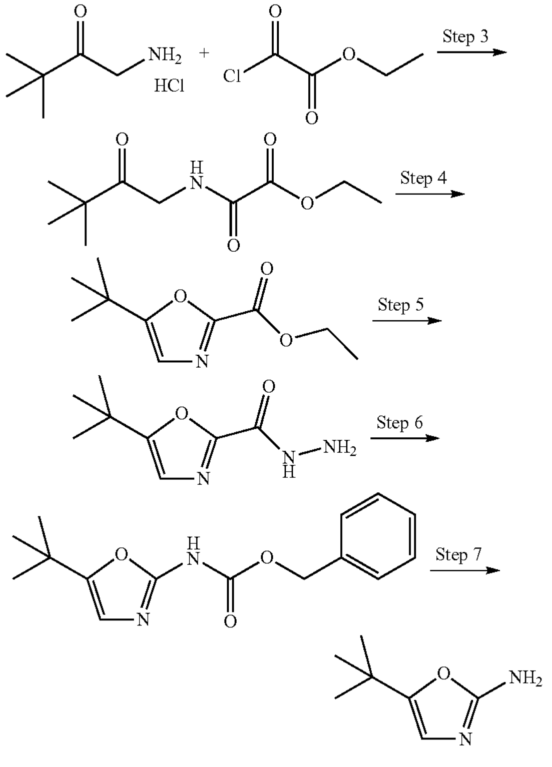

Step 1: Synthesis of 1-azido-3,3-dimethylbutan-2-one

To a solution of 1-bromo-3,3-dimethylbutan-2-one (50 g, 279 mmol) in acetone (400 mL) is added $NaN_3$ (22 g, 335 mmol) at 0° C. The reaction mixture is warmed to room temperature for 7 h. The reaction mixture is filtered and the filtrate is concentrated. The residue is diluted with EtOAc and washed with water and brine. The organic layer is dried ($Na_2SO_4$) and concentrated to afford the title crude compound which is used in the next step without purification.

Step 2: Synthesis of 1-amino-3,3-dimethylbutan-2-one

To a solution of the crude 1-azido-3,3-dimethylbutan-2-one from the preceding step in methanol (500 mL) is added concentrated HCl (30 mL) and 5% palladium on carbon (4.0 g, 1.9 mmol). The reaction mixture is stirred at room temperature under 400 psi hydrogen atmosphere for 14 h. The reaction mixture is filtered through Celite and the filtrate is concentrated. The crude material is washed with diethyl ether to afford the title compound (35.8 g, 85% for 2 steps) as the hydrochloride salt.

Step 3: Synthesis of ethyl[(3,3-dimethyl-2-oxobutyl)amino](oxo)acetate

To a mixture of 1-amino-3,3-dimethylbutan-2-one hydrochloride salt (35 g, 231 mmol) in $CH_2Cl_2$ (500 mL) at 0° C. are added N,N-diisopropylethylamine (74 g, 577 mmol) and ethyl chloro(oxo)acetate (31.5 g, 231 mmol) slowly over a period of 15 min. The reaction mixture is stirred at room temperature for 2 h and is filtered through Celite. The filtrate is concentrated to afford the title compound (40 g, 81%).

Step 4: Synthesis of ethyl 5-tert-butyl-1,3-oxazole-2-carboxylate

To a mixture of ethyl[(3,3-dimethyl-2-oxobutyl)amino](oxo)acetate (40 g, 162 mmol) in toluene (350 mL) is added phosphorous oxychloride (75 g, 488 mmol). The reaction mixture is heated at 120° C. for 14 h. Then the solvent is removed and the residue is diluted with ether. The ether layer is washed with saturated aqueous $NaHCO_3$ solution, brine, dried ($Na_2SO_4$) and concentrated to afford the title compound (28 g, 87%).

Step 5: Synthesis of 5-tert-butyl-1,3-oxazole-2-carbohydrazide

To a mixture of ethyl 5-tert-butyl-1,3-oxazole-2-carboxylate (28 g, 142 mmol) in ethanol (200 mL) is added hydrazine hydrate (7.1 g, 142 mmol). The reaction mixture is heated at 85° C. for 3 h. The solvent is evaporated and the residue is washed with n-pentane to afford the title compound (25 g, 96%) as a white solid.

Step 6: Synthesis of benzyl (5-tert-butyl-1,3-oxazol-2-yl)carbamate

To a mixture of 5-tert-butyl-1,3-oxazole-2-carbohydrazide (15 g, 82 mmol) in diethyl ether (250 mL) at 0° C. are added 6N aqueous HCl solution (210 mL, 1.26 mol) and $NaNO_2$ (9.6 g, 139 mmol) aqueous solution over a period of 15 min. The reaction mixture is stirred at 0° C. for 1 h and saturated $NaHCO_3$ solution is added to quench the reaction. The mixture is extracted with diethyl ether (3×100 mL) and the ether layers are combined, washed with brine, dried ($Na_2SO_4$) and concentrated. The residue is diluted with xylene (70 mL) and benzyl alcohol (27 g, 246 mmol) is added. The reaction mixture is refluxed for another 3 h and the solvent is removed under vacuum. The residue is purified by flash column chromatography to afford the title compound (5.0 g, 22%).

Step 7: Synthesis of 5-tert-butyl-1,3-oxazol-2-amine

To a solution of benzyl (5-tert-butyl-1,3-oxazol-2-yl)carbamate (5.0 g, 18.2 mmol) in methanol (100 mL) is added 10% palladium on carbon (500 mg, 0.5 mmol). The reaction is stirred at room temperature for 3 h under hydrogen atmosphere. The reaction mixture is filtered through Celite and the filtrate is concentrated. The residue is purified by flash column chromatography to afford the title compound (1.7 g, 68%) as a light brown solid.

Intermediate AW: 1-(propan-2-yl)-1H-benzimidazol-2-amine; hydrobromide

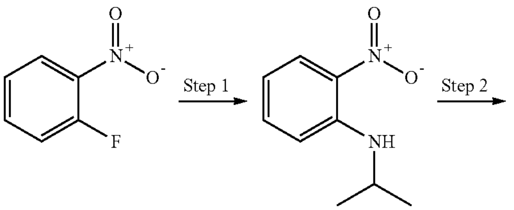

-continued

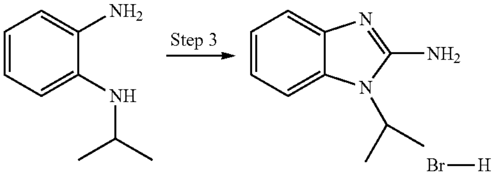

Step 1: Synthesis of 2-nitro-N-(propan-2-yl)aniline

To a solution of 1-fluoro-2-nitrobenzene (0.5 mL, 4.7 mmol) in DMSO (10 mL) is added isopropylamine (0.6 mL, 7.1 mmol), followed by Hunig's base (1.2 mL, 7.1 mmol). The reaction flask is sealed and heated to 80° C. 16 h. The reaction is cooled to room temperature and is poured over ice water and extracted ethyl acetate. The organic layer is washed with water, brine, dried ($Na_2SO_4$) and concentrated to afford the title compound (828 mg, 97%) as an orange oil.

Step 2: Synthesis of N-(propan-2-yl)benzene-1,2-diamine

To a solution of 2-nitro-N-(propan-2-yl)aniline (828 mg, 4.6 mmol) in ethanol (10 mL) under a nitrogen atmosphere is carefully 20% palladium on carbon (50 mg, Degussa type) followed by ammonium formate (1.4 g, 23 mmol) and the reaction is stirred overnight. The suspension is carefully filtered through a bed of Celite and the filtrate is rinsed with additional ethanol (10 mL). The filtrate is concentrated and the residue is partitioned between water and ethyl acetate. The organic layer is dried ($Na_2SO_4$) and concentrated.

The crude material is purified by chromatography through a short bed of silica gel using 5% methanol in $CH_2Cl_2$ to afford the title compound (552 mg, 80%) as an oil.

Step 3: Synthesis of 1-(propan-2-yl)-1H-benzimidazol-2-amine; hydrobromide

To a solution of N-(propan-2-yl)benzene-1,2-diamine (552 mg, 3.4 mmol) in ethanol (10 mL) is added a 3M solution of cyanogen bromide (1.35 mL, 4.04 mmol) in $CH_2Cl_2$. The reaction is stirred for 16 h and is then concentrated. The crude residue is triturated with diethyl ether and the suspension is filtered to afford the title compound (870 mg, 92%) as a purple solid.

Intermediates AX-BE in the table below are synthesized according to the procedure for Intermediate AX, substituting the appropriate commercially available reagents.

| Structure | Intermediate | Name |
|---|---|---|
| 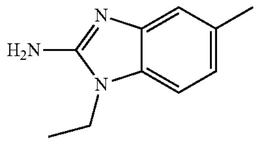 | AX | 1-ethyl-5-methyl-1H-benzimidazol-2-amine |

-continued

| Structure | Intermediate | Name |
|---|---|---|
| 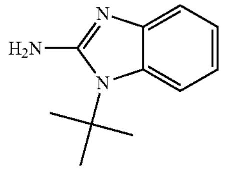 | AY | 1-tert-butyl-1H-benzimidazol-2-amine |
| 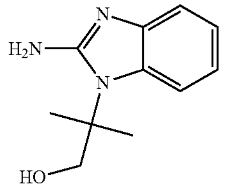 | AZ | 2-(2-amino-1H-benzimidazol-1-yl)-2-methyl-propan-1-ol |
| 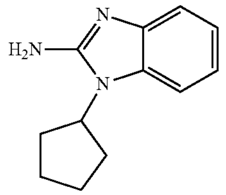 [SMILES: Nc1nc2ccccc2n1C1CCCC1] | BA | 1-cyclopentyl-1H-benzimidazol-2-amine |
| 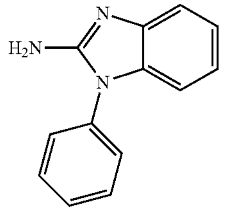 [SMILES: Nc1nc2ccccc2n1-c1ccccc1] | BB | 1-phenyl-1H-benzimidazol-2-amine |
| 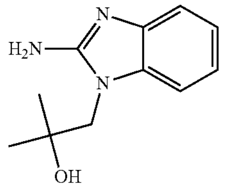 | BC | 1-(2-amino-1H-benzimidazol-1-yl)-2-methyl-propan-2-ol |
| 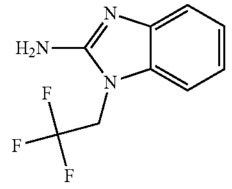 [SMILES: Nc1nc2ccccc2n1CC(F)(F)F] | BD | 1-(2,2,2-trifluoroethyl)-1H-benzimidazol-2-amine |
| 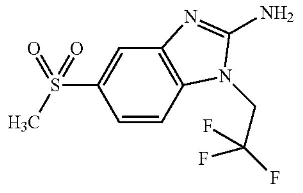 [SMILES: CS(=O)(=O)c1ccc2c(c1)nc(N)n2CC(F)(F)F] | BE | 5-(methylsulfonyl)-1-(2,2,2-trifluoroethyl)-1H-benzimidazol-2-amine |

Intermediate BG: 5-chloro-1-methyl-1H-benzimidazol-2-amine; hydrobromide

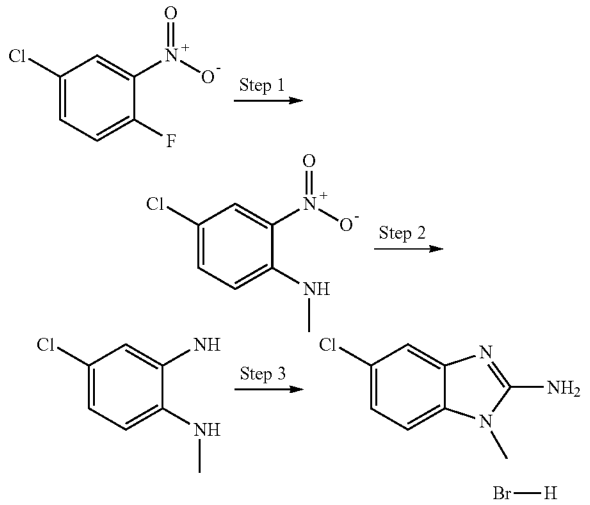

Step 1: Synthesis of 4-chloro-N-methyl-2-nitroaniline

To a solution of 4-chloro-1-fluoro-2-nitrobenzene (832 mg, 4.7 mmol) in DMSO (10 mL) is added a 2M solution of methylamine (3.56 mL, 7.1 mmol) in tetrahydrofuran, followed by Hunig's base (1.2 mL, 7.1 mmol). The reaction flask is sealed and heated to 80° C. for 16 h. The reaction is cooled to room temperature and poured over ice water. The resulting solid is isolated by filtration to afford the title compound (713 mg, 81%).

Step 2: Synthesis of 4-chloro-$N^1$-methylbenzene-1,2-diamine

To a solution of 4-chloro-N-methyl-2-nitroaniline (713 mg, 3.8 mmol) in ethanol (10 mL) is added ammonium formate (1.2 g, 19 mmol) followed by zinc dust (745 mg, 11.5 mmol). The reaction is heated to 50° C. for 2 h. The room temperature suspension is filtered through a bed of Celite and the filtrate is rinsed with additional methanol (10 mL). The filtrate is concentrated to afford the title compound (592 mg, 89%) as an oil which was used in the next step without purification Step 3: Synthesis of 5-chloro-1-methyl-1H-benzimidazol-2-amine; hydrobromide To a solution of 4-chloro-$N^1$-methylbenzene-1,2-diamine (592 mg, 3.4 mmol) in ethanol (10 mL) is added a 3M solution of cyanogen bromide (1.35 mL, 4.04 mmol) in $CH_2Cl_2$. The reaction is stirred for several days and is diluted with diethyl ether. The resulting solid is collected by filtration to afford the title compound (663 mg, 66%).

Intermediates BH-BJ in the table below are synthesized according to the procedure for Intermediate BG, substituting the appropriate commercially available reagents.

| Structure | Intermediate | Name |
|---|---|---|
| 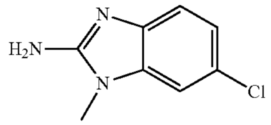 | BH | 6-chloro-1-methyl-1H-benzimidazol-2-amine |
| 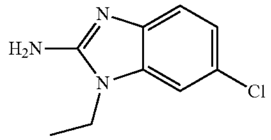 | BI | 6-chloro-1-ethyl-1H-benzimidazol-2-amine |
| 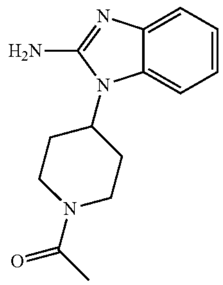 [SMILES: CC(=O)N1CCC(n2c(N)nc3ccccc32)CC1] | BJ | 1-[4-(2-amino-1H-benzimidazol-1-yl)piperidin-1-yl]-ethanone |

Intermediate BK: 1-[3-(dimethylamino)-2,2-dimethylpropyl]-1H-benzimidazol-2-amine; dihydrobromide

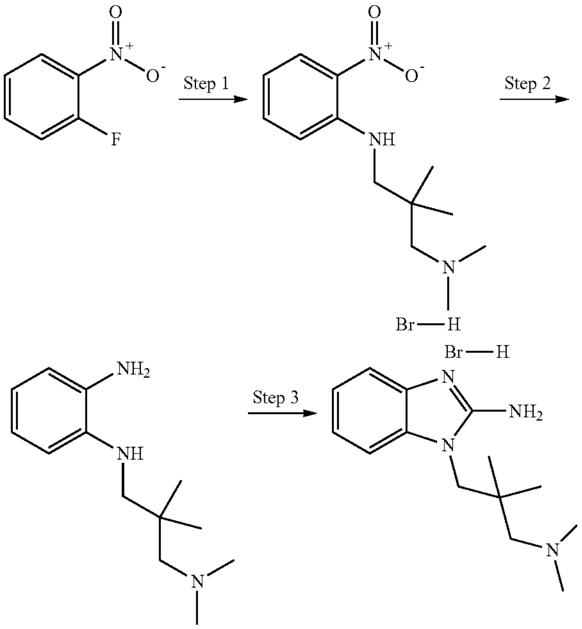

Step 1: Synthesis of N,N,2,2-tetramethyl-N'-(2-nitrophenyl)propane-1,3-diamine

To a solution of 1-fluoro-2-nitrobenzene (353 mg, 2.5 mmol) in DMSO (5 mL) is added 2,2,N*1*,N*1*-Tetramethyl-propane-1,3-diamine (391 mg, 3 mmol), followed by Hunig's base (0.65 mL, 3.8 mmol). The reaction flask is sealed and heated to 80° C. for 16 h. The reaction is cooled to room temperature, is poured over ice water and is extracted with $CH_2Cl_2$. The organic layer is washed with water, brine, is dried ($Na_2SO_4$) and concentrated to afford the title crude compound (635 mg, crude) as an orange oil.

Step 2: Synthesis of N-[3-(dimethylamino)-2,2-dimethylpropyl]benzene-1,2-diamine To a flask containing a solution of tin (II) chloride dehydrate (1.71 g, 7.6 mmol) in concentrated HCl (5 mL) is added a solution of N,N,2,2-tetramethyl-N'-(2-nitrophenyl)propane-1,3-diamine (635 mg, 2.5 mmol). The reaction is stirred for 16 h and is neutralized by the addition of 4M aqueous NaOH. The mixture is extracted with $CH_2Cl_2$ and the organic layer is separated, dried ($Na_2SO_4$) and concentrated to afford the title compound (504 mg, 90%) as an oil.

Step 3: Synthesis of 1-[3-(dimethylamino)-2,2-dimethylpropyl]-1H-benzimidazol-2-amine; dihydrobromide To a solution of N-[3-(dimethylamino)-2,2-dimethylpropyl]benzene-1,2-diamine (504 mg, 2.3 mmol) in ethanol (5 mL) is added a 48% aqueous HBr solution (0.26 mL, 2.3 mmol) followed by a 3M solution of cyanogen bromide (1.14 mL, 3.4 mmol) in CH2Cl2. The reaction is stirred for 48 h and is then diluted with diethyl ether. The resulting solid is isolated by filtration to afford the title compound (885 mg, 95%).

Intermediates BL-BR in the table below are synthesized according to the procedure for Intermediate BK, substituting the appropriate commercially available reagents.

| Structure | Intermediate | Name |
|---|---|---|
| 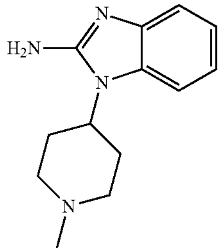 [SMILES: CN1CCC(n2c(N)nc3ccccc32)CC1] | BL | 1-(1-methyl-piperidin-4-yl)-1H-benzimidazol-2-amine |
| 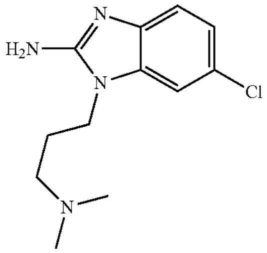 [SMILES: CN(C)CCCn1c(N)nc2ccc(Cl)cc21] | BM | 6-chloro-1-[3-(dimethylamino)-propyl]-1H-benzimidazol-2-amine |
| 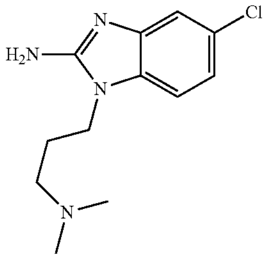 [SMILES: CN(C)CCCn1c(N)nc2cc(Cl)ccc21] | BN | 5-chloro-1-[3-(dimethylamino)-propyl]-1H-benzimidazol-2-amine |

-continued

| Structure | Intermediate | Name |
|---|---|---|
| 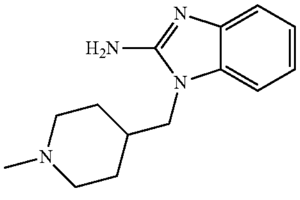 [SMILES: CN1CCC(Cn2c(N)nc3ccccc32)CC1] | BO | 1-[(1-methyl-piperidin-4-yl)methyl]-1H-benzimidazol-2-amine |
| 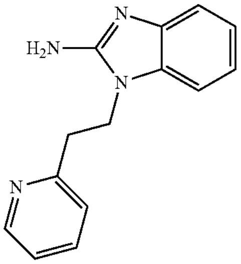 [SMILES: Nc1nc2ccccc2n1CCc1ccccn1] | BP | 1-[2-(pyridin-2-yl)ethyl]-1H-benzimidazol-2-amine |
| 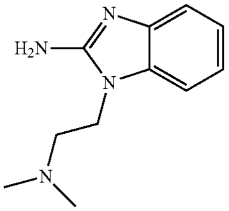 | BQ | 1-[2-(dimethylamino)-ethyl]-1H-benzimidazol-2-amine |
| 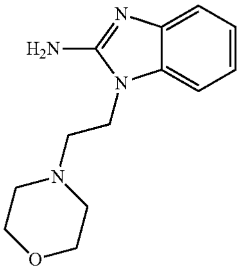 [SMILES: Nc1nc2ccccc2n1CCN1CCOCC1] | BR | 1-[2-(morpholin-4-yl)ethyl]-1H-benzimidazol-2-amine |

Intermediate BS: 5-(4-methylpiperazin-1-yl)-1H-benzimidazol-2-amine; bistrifluoroacetate

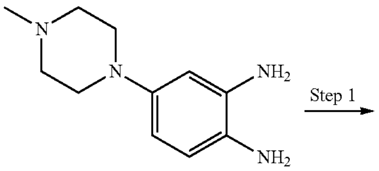

-continued

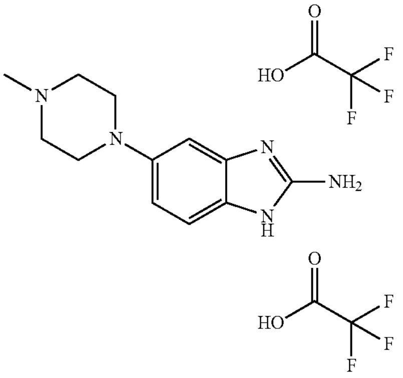

To a solution of 4-(4-methylpiperazin-1-yl)benzene-1,2-diamine (206 mg, 1 mmol) in ethanol (5 mL) is added a 3M solution of cyanogen bromide (0.5 mL, 1.5 mmol) in $CH_2Cl_2$. The reaction is stirred overnight and then diluted with diethyl ether. The resulting solid is isolated by filtration and then purified by preparative HPLC using 5-90% acetonitrile/water with 0.1% TFA to afford the title compound (60 mg, 13%).

Intermediate BT: 5-chloro-7-(morpholin-4-ylmethyl)-1H-benzimidazol-2-amine; dihydrobromide

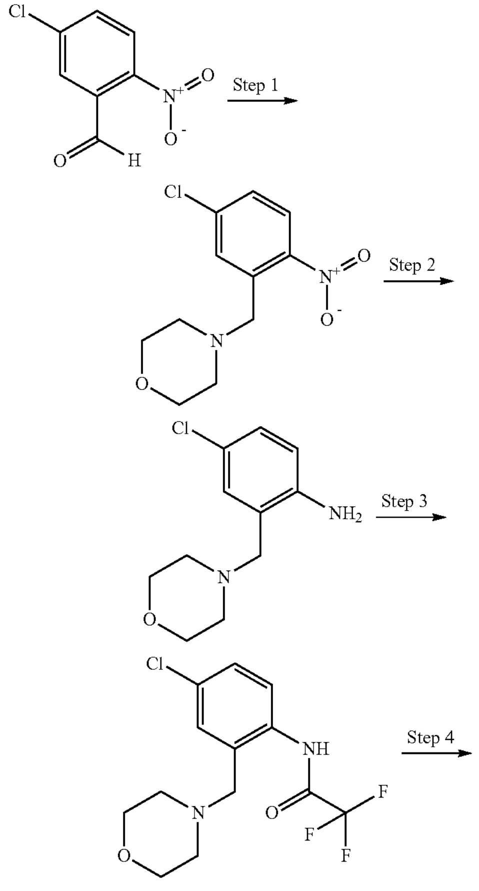

-continued

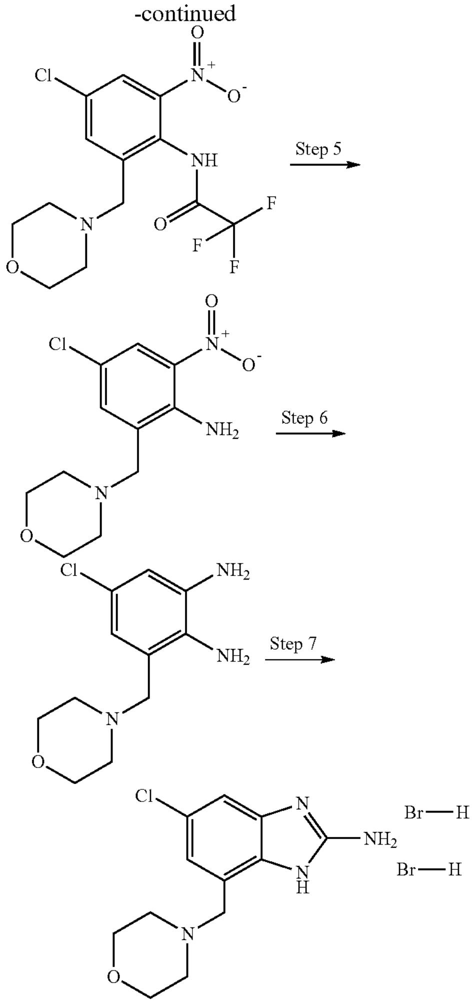

Step 1: Synthesis of 4-(5-chloro-2-nitrobenzyl)morpholine

To a solution of morpholine (2.8 mL, 32.3 mmol) in THF (100 mL) is added 5-chloro-2-nitrobenzaldehyde (5 g, 26.9 mmol) followed by sodium triacetoxyborohydride (11.4 g, 53.9 mmol) and HOAc (3.2 mL, 53.9 mmol). The reaction is stirred for 16 h. The reaction is poured into a saturated aqueous $Na_2CO_3$ solution and extracted with ethyl acetate. The combined extracts are washed with water, brine, dried ($Na_2SO_4$) and concentrated to afford a clear oil. The residue is taken up in 1N aqueous HCl and the insoluble material is removed by filtration. The filtrate is neutralized with 2M aqueous $K_2CO_3$ and partitioned into ethyl acetate. The organic layer is dried ($Na_2SO_4$) and concentrated to afford the title compound (5.1 g, 74%) as an oil.

Step 2: Synthesis of 4-chloro-2-(morpholin-4-ylmethyl)aniline

To a solution of 4-(5-chloro-2-nitrobenzyl)morpholine (5.1 g, 19.9 mmol) in HOAc (75 mL) is carefully added zinc dust (3.9 g, 59.6 mmol). After 2 h, the reaction is filtered through a bed of Celite and the filtrate is concentrated to remove most of the HOAc. The residue is then taken up in 2M aqueous $K_2CO_3$ and extracted with ethyl acetate. The organic layer is dried ($Na_2SO_4$) and concentrated to afford a brown oil. The crude material is partially purified by flash chromatography using a gradient of 0-5% methanol in $CH_2Cl_2$ to afford the title compound (4.0 g, 62%, 70% purity).

Step 3: Synthesis of N-[4-chloro-2-(morpholin-4-ylmethyl)phenyl]-2,2,2-trifluoroacetamide To a solution of 4-chloro-2-(morpholin-4-ylmethyl)aniline (4.0 g, 12.4 mmol) in 1,4-dioxane (75 mL) cooled in an ice bath is added trifluoroacetic anhydride (2.4 mL, 17.4 mmol) and the reaction is warmed to room temperature overnight. The reaction is diluted with diethyl ether and the insoluble material is removed by filtration. The filtrate is concentrated and partitioned between 2M aqueous $K_2CO_3$ and diethyl ether. The organic layer is separated, dried ($Na_2SO_4$) and concentrated to afford the title compound (3.8 g, 95%) as an orange oil which was used in the next step without purification.

Step 4: Synthesis of N-[4-chloro-2-(morpholin-4-ylmethyl)-6-nitrophenyl]-2,2,2-trifluoroacetamide To a mixture of N-[4-chloro-2-(morpholin-4-ylmethyl) phenyl]-2,2,2-trifluoroacetamide (3.8 g, 11.8 mmol) in concentrated sulfuric acid (35 mL) cooled to 0° C. is added potassium nitrate (1.4 g, 14.1 mmol). The reaction is slowly warmed to room temperature over a period of 2 h and is then poured into ice water. The mixture is neutralized with saturated aqueous $K_2CO_3$ and the resulting solid is isolated by filtration to afford the title compound (3.6 g, 82%).

Step 5: Synthesis of 4-chloro-2-(morpholin-4-ylmethyl)-6-nitroaniline

To a solution of N-[4-chloro-2-(morpholin-4-ylmethyl)-6-nitrophenyl]-2,2,2-trifluoroacetamide (3.6 g, 9.6 mmol) in ethanol (60 mL) is added a 10% aqueous NaOH solution (60 mL, 150 mmol) and the reaction is heated to 80° C. for 3 h. The mixture is cooled to room temperature and is stirred an additional 16 h. Most of the ethanol is evaporated under reduced pressure and the resulting solid is isolated by filtration to afford the title compound (2 g, 77%).

Step 6: Synthesis of 5-chloro-3-(morpholin-4-ylmethyl)benzene-1,2-diamine

To a flask containing a solution of tin (II) chloride (1.1 g, 6 mmol) in concentrated HCl (1.5 mL) is added a solution of 4-chloro-2-(morpholin-4-ylmethyl)-6-nitroaniline (543 mg, 2 mmol) in concentrated HCl (1 mL). The reaction is stirred for 1 h. The thick slurry is filtered and the filter cake rinsed with HCl. The filter cake is dissolved in water (10 mL), is treated with 2M aqueous $K_2CO_3$ and is extracted with $CH_2Cl_2$. The organic layer is separated, dried ($Na_2SO_4$) and concentrated to afford the title compound (458 mg, 95%) as an oil.

Step 7: Synthesis of 5-chloro-7-(morpholin-4-ylmethyl)-1H-benzimidazol-2-amine; dihydrobromide To a solution of 5-chloro-3-(morpholin-4-ylmethyl)benzene-1,2-diamine (458 mg, 1.9 mmol) in ethanol (5 mL) is added a 48% aqueous HBr solution (0.21 mL, 1.9 mmol) followed by a 3M solution of cyanogen bromide (0.95 mL, 2.8 mmol) in $CH_2Cl_2$. After stirring for 48 h the mixture is diluted with diethyl ether. The resulting solid is isolated by filtration to afford the title compound (595 mg, 73%).

Example 1

N-(3-chlorophenyl)-1-oxo-2,3,4,5-tetrahydro-1H-[1,4]diazepino[1,2-a]indole-8-carboxamide

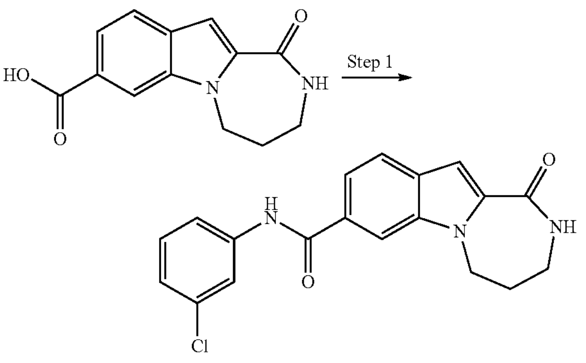

To a solution of 1-oxo-2,3,4,5-tetrahydro-1H-[1,4]diazepino[1,2-a]indole-8-carboxylic acid (Intermediate J, 49 mg, 0.2 mmol) in DMF (1 mL) is added [(benzotriazol-1-yloxy)-dimethylamino-methylene]dimethyl-ammonium tetrafluoroborate (TBTU) (77 mg, 0.24 mmol) and the reaction is stirred for 10 minutes. The reaction is then treated with 3-chloro-phenylamine (28 mg, 0.22 mmol) followed by triethylamine (0.10 mL, 0.7 mmol) and is stirred for 16 h. The reaction is poured into water (20 mL) and the resulting solid is filtered. The solid is dried, suspended in MTBE (20 mL) and filtered again to afford the title compound (40 mg, 56%) as an off-white solid.

Examples 2-156 are synthesized according to the procedure for Example 1, substituting either commercially available reagents or the appropriate intermediates described above.

Example 157

4,4-dimethyl-N-(5-methyl-1,2-oxazol-3-yl)-1-oxo-2,3,4,5-tetrahydro-1H-[1,4]diazepino[1,2-a]indole-8-carboxamide

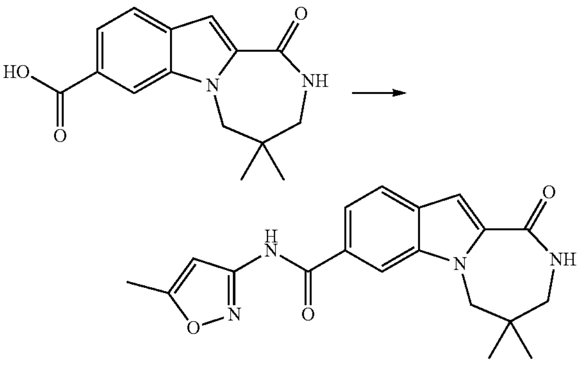

To a solution of 4,4-dimethyl-1-oxo-2,3,4,5-tetrahydro-1H-[1,4]diazepino[1,2-a]indole-8-carboxylic acid (100 mg, 0.37 mmol) in THF (2 mL) is added 1,1'-carbonyldiimidazole (149 mg, 0.92 mmol). The reaction mixture is heated at 55° C. for 1 h. The mixture is cooled to room temperature and 5-methyl-3-aminoisoxazole (144 mg, 1.47 mmol) is added. After stifling 10 min, 1,8-diazabicycloundec-7-ene (0.14 mL, 0.92 mmol) is added and the reaction is heated at 60° C. for 16 h. After cooling to room temperature, the solvent is evaporated and the residue is purified by preparative HPLC using 10-85% acetonitrile/water with 0.1% TFA to afford the title compound (79 mg, 61%). LCMS (ESMS): m/z 353.45 ($M+H^+$).

Examples 158-173 are synthesized according to the procedure for Example 157, substituting either commercially available reagents or the appropriate intermediates described above.

Example 174

4-methyl-N-(5-methyl-1,2-oxazol-3-yl)-1-oxo-1,2,3,4-tetrahydropyrazino[1,2-a]indole-7-carboxamide

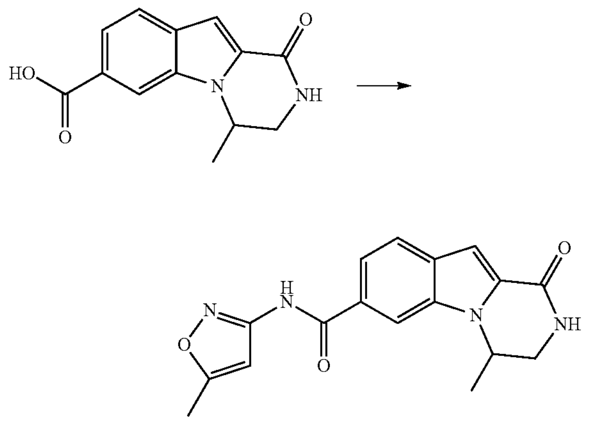

To a solution of 4-methyl-1-oxo-1,2,3,4-tetrahydropyrazino[1,2-a]indole-7-carboxylic acid (50 mg, 0.21 mmol) in DMF (1 mL) are added N-hydroxybenzotriazole (39 mg, 0.29 mmol) and 1-ethyl-3-(3-dimethylaminopropyl)carbodiimide (61 mg, 0.32 mmol). After stirring for 10 min, 5-methyl-3-aminoisoxazole (38 mg, 0.39 mmol), N,N-diisopropylethylamine (0.07 mL, 0.42 mmol) and 4-dimethylaminopyridine (2.6 mg, 0.02 mmol) are added. The reaction mixture is heated at 50° C. for 15 h and simultaneously a stream of $N_2$ is blown over the reaction mixture to remove DMF. The residue is cooled to room temperature and EtOAc (4 mL) and water (2 mL) are added. The resulting white solid is collected by filtration to afford the title compound (32 mg, 48%). LCMS (ESMS): m/z 325.61 ($M+H^+$).

Examples 175-180 are synthesized according to the procedure for Example 174, substituting either commercially available reagents or the appropriate intermediates described above.

Example 181

N-(5-ethyl-1,2-oxazol-3-yl)-1-oxo-2,3,4,5-tetrahydro-1H-[1,4]diazepino[1,2-a]indole-8-carboxamide

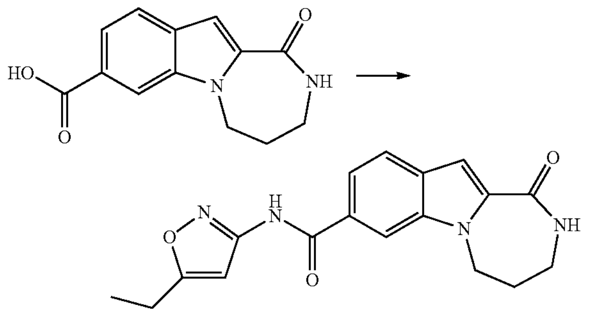

To a solution of 1-oxo-2,3,4,5-tetrahydro-1H-[1,4]diazepino[1,2-a]indole-8-carboxylic acid (Intermediate J, 75 mg, 0.31 mmol) in THF (2 mL) and DMF (0.5 mL) is added HATU (128 mg, 0.34 mmol). The mixture is stirred at room temperature for 1 h, after which polystyrene bound 2-tert-butylimino-1,3-dimethylperhydro-1,3,2-diazaphosphorine (419 mg, 0.92 mmol) is added. The mixture is stirred at room temperature for 10 min and 5-ethyl-3-aminoisoxazole (103 mg, 0.92 mmol) is added. The reaction is stirred at 60° C. for 16 h and is then cooled to room temperature. The mixture is filtered, washing with methanol and the filtrate is concentrated under reduced pressure. The residue is purified via preparative HPLC using a gradient elution from 10-90% acetonitrile/water with 0.1% TFA to obtain the title compound (5 mg, 5%). LCMS: 339.20 ($M+H^+$). (System V1)

Examples 182-206 are synthesized according to the procedure for Example 181, substituting either commercially available reagents or the appropriate intermediates described above.

Example 207

1-oxo-N-[3-(trifluoromethyl)-1,2-oxazol-5-yl]-2,3,4,5-tetrahydro-1H-[1,4]diazepino[1,2-a]indole-8-carboxamide

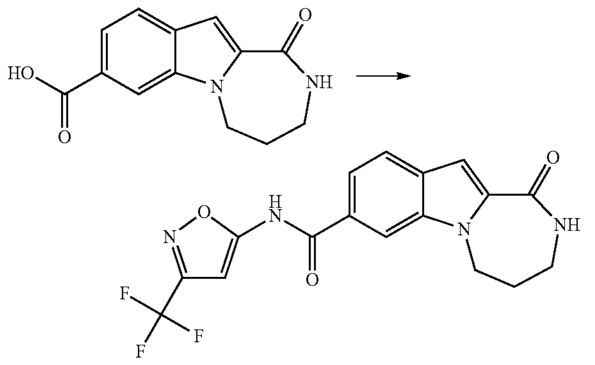

A mixture of HATU (0.086 g, 0.225 mmol) and 1-oxo-2,3,4,5-tetrahydro-1H-[1,4]diazepino[1,2-a]indole-8-carboxylic acid (Intermediate J, 0.050 g, 0.205 mmol) in dichlorethane (1 mL) in a microwave vial is heated in a microwave reactor at 60° C. for 60 minutes. Polystyrene bound 2-tert-butylimino-1,3-dimethylperhydro-1,3,2-diazaphosphorine (0.307 g, 0.615 mmol) and 3-trifluoromethyl-isoxazol-5-ylamine (0.094 g, 0.615 mmol) are added to the mixture and the vial is heated in a microwave at 120° C. for an additional 60 minutes. The resin is filtered off and washed several times with DMF. After the removal of solvent, the residue is purified by flash column chromatography using 5% methanol/dichlororomethane to afford title compound (0.012 g, 15.5%) as a white solid.

Examples 208-210 are synthesized according to the procedure for Example 207, substituting either commercially available reagents or the appropriate intermediates described above.

Example 211

1-oxo-N-(5-phenyl-1,2-oxazol-3-yl)-2,3,4,5-tetrahydro-1H-[1,4]diazepino[1,2-a]indole-8-carboxamide

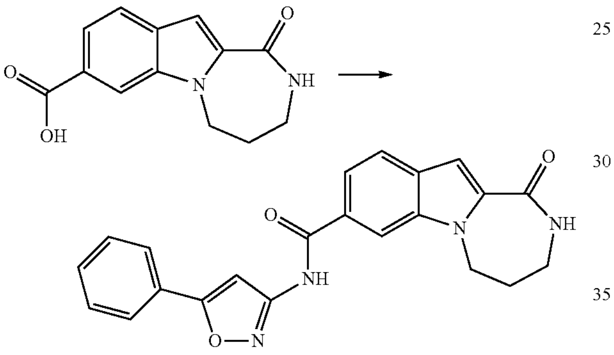

A 2-5 mL microwave reactor vial is charged with a solution of 1-oxo-2,3,4,5-tetrahydro-1H-[1,4]diazepino[1,2-a]indole-8-carboxylic acid (Intermediate J, 25 mg, 0.10 mmol) in NMP (2 mL). HATU (47 mg, 0.12 mmol) is added and the mixture is stirred at room temperature for 30 min. 5-phenyl-3-aminoisoxazole (66 mg, 0.41 mmol) and N-methylmorpholine (41 mg, 0.41 mmol) are added and the vial is sealed with a Teflon lined septa cap and is irradiated in a microwave reactor at 100° C. for 30 min then at 150° C. for 90 min. The mixture is purified via preparative HPLC using a gradient elution from 10-90% acetonitrile/water with 0.1% TFA to obtain the title compound (2 mg, 5%). LCMS: 387.20 ($M+H^+$). (System V1)

Example 212

N-(5-benzyl-1,2-oxazol-3-yl)-1-oxo-2,3,4,5-tetrahydro-1H-[1,4]diazepino[1,2-a]indole-8-carboxamide

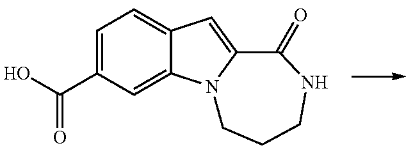

-continued

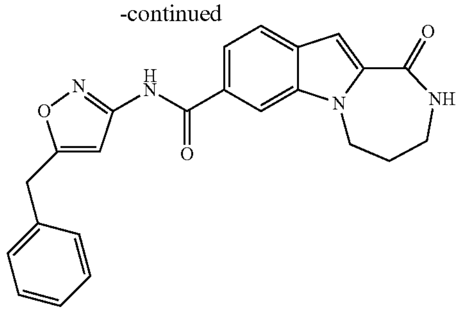

A 0.5-2 mL microwave reactor vial is charged with a mixture of 1-oxo-2,3,4,5-tetrahydro-1H-[1,4]diazepino[1,2-a]indole-8-carboxylic acid (Intermediate J, 100 mg, 0.41 mmol) and 5-benzyl-3-aminoisoxazole (107 mg, 0.61 mmol) in pyridine (500 μL) and the vial is sealed with a Teflon lined septa cap. The mixture is cooled to 0° C. and phosphorous oxychloride (40 μL, 0.43 mmol) is added. The mixture is allowed to warm to room temperature and is then irradiated in a microwave reactor at 150° C. for 60 min. The mixture is poured into water and the resulting solid is collected by filtration and is purified via preparative HPLC using a gradient elution from 10-75% acetonitrile/water with 0.1% TFA to obtain the title compound (87 mg, 53%). LCMS: 401.20 ($M+H^+$). (System V1)

Examples 213 and 214 are synthesized according to the procedure for Example 212, substituting either commercially available reagents or the appropriate intermediates described above.

Example 215

N-(2-carbamoylphenyl)-1-oxo-2,3,4,5-tetrahydro-1H-[1,4]diazepino[1,2-a]indole-8-carboxamide

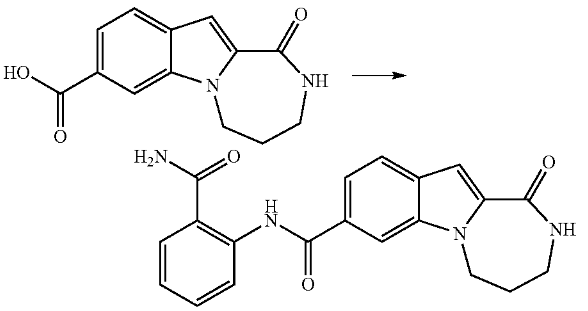

To a suspension of 1-oxo-2,3,4,5-tetrahydro-1H-[1,4]diazepino[1,2-a]indole-8-carboxylic acid (Intermediate J, 100 mg, 0.41 mmol) in $CH_2Cl_2$ (1.5 mL) is added 1-chloro-N,N,2-trimethylpropenylamine (0.20 mL, 1.43 mmol). The reaction mixture is stirred for 5 h. 2-Aminobenzamide (200 mg, 1.47 mmol) and pyridine (0.12 mL, 1.48 mmol) are added and the reaction mixture is stirred for another 16 h at room temperature. Water (55 mL) is added and the resulting white solid is collected by filtration and purified by flash column chromatography using methanol in $CH_2Cl_2$ to afford the title compound (40 mg, 27%). LCMS (ESMS): m/z 363.61 ($M+H^+$).

Examples 216-225 are synthesized according to the procedure for Example 215, substituting either commercially available reagents or the appropriate intermediates described above.

Example 226

N-[3-(1H-imidazol-4-yl)phenyl]-1-oxo-2,3,4,5-tetrahydro-1H-[1,4]diazepino[1,2-a]indole-8-carboxamide

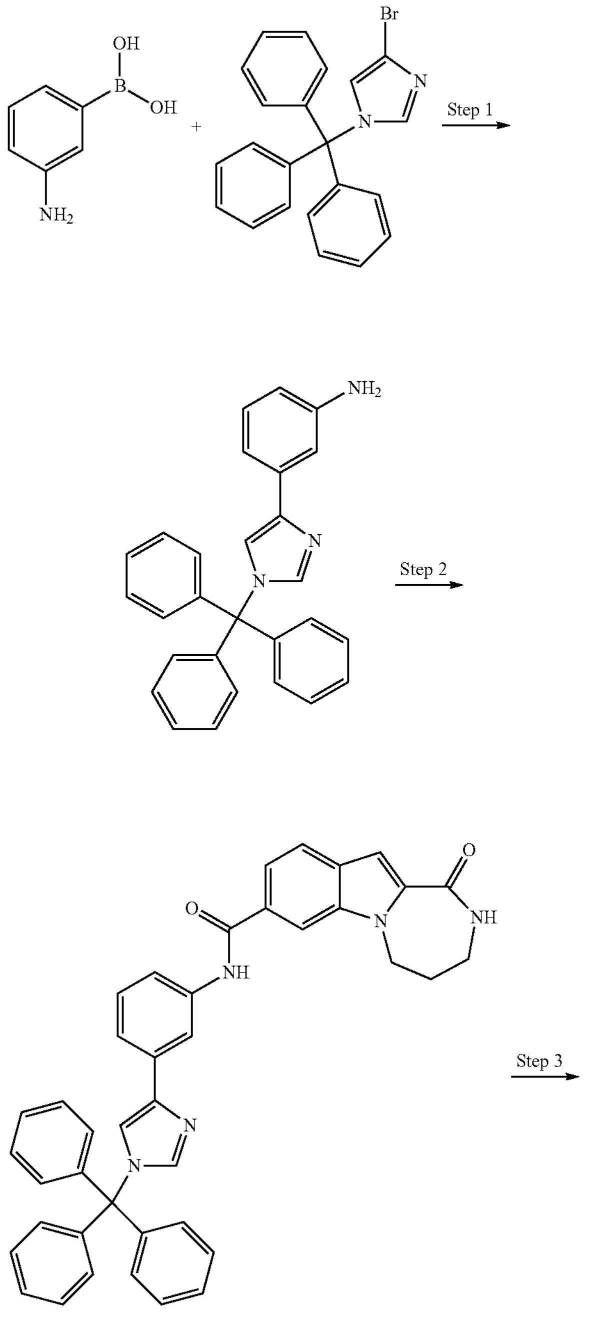

-continued

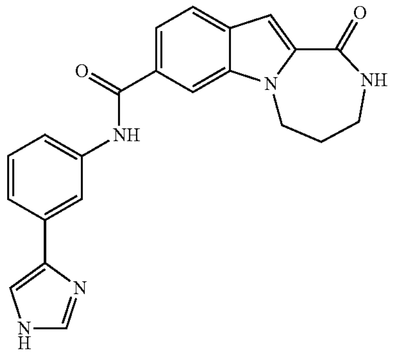

Step 1: Synthesis of 3-(1-trityl-1H-imidazol-4-yl)aniline (3-Aminophenyl)boronic acid (1.0 g, 7.3 mmol), 4-bromo-1-trityl-1H-imidazole (2.8 g, 7.3 mmol), tri-t-butylphosphonium tetrafluoroborate (424 mg, 1.5 mmol) and KF (1.4 g, 24.1 mmol) are added into dry THF (20 mL) and argon is bubbled through the mixture for 10 min. Tris-(dibenzylideneacetone)dipalladium(0) (669 mg, 0.7 mmol) is added and the reaction mixture is sealed and heated at 60° C. for 16 h. The solid is filtered and the filtrate is diluted with EtOAc (250 mL). The solution is washed with water (3×100 mL), brine (100 mL), dried ($Na_2SO_4$) and concentrated. The crude material is purified by flash column chromatography using methanol in $CH_2Cl_2$ to afford the title compound (1.1 g, 36%).

Step 2: Synthesis of 1-oxo-N-[3-(1-trityl-1H-imidazol-4-yl)phenyl]-2,3,4,5-tetrahydro-1H-[1,4]diazepino[1,2-a]indole-8-carboxamide To a solution of 1-oxo-2,3,4,5-tetrahydro-1H-[1,4]diazepino[1,2-a]indole-8-carboxylic acid (Intermediate J, 61 mg, 0.25 mmol) in DMF (1.5 mL) is added benzotriazol-1-yl-oxytripyrrolidinophosphonium hexafluorophosphate (194 mg, 0.37 mmol). The reaction mixture is stirred for 10 min and 3-(1-trityl-1H-imidazol-4-yl)aniline (100 mg, 0.25 mmol) and triethylamine (0.07 mL, 0.50 mmol) are added. The reaction mixture is stirred at room temperature for 16 h. Water (35 mL) is added and the resulting solid is collected by filtration and rinsed with water to afford the title crude compound which is used in the next step without purification.

Step 3: Synthesis of N-[3-(1H-imidazol-4-yl)phenyl]-1-oxo-2,3,4,5-tetrahydro-1H-[1,4]diazepino[1,2-a]indole-8-carboxamide To a solution of the crude 1-oxo-N-[3-(1-trityl-1H-imidazol-4-yl)phenyl]-2,3,4,5-tetrahydro-1H-[1,4]diazepino[1,2-a]indole-8-carboxamide from the preceding step in $CH_2Cl_2$ (1.5 mL) and methanol (1.5 mL) is added TFA (1.0 mL). The reaction is stirred for 16 h at room temperature. The solvents are evaporated and the crude material is purified by preparative HPLC using 10-80% acetonitrile/water with 0.1% TFA to afford the title compound (43 mg, 35% for 2 steps). LCMS (ESMS): m/z 386.20 (M+H$^+$).

Example 227

1-oxo-N-[3-(1H-pyrazol-3-yl)phenyl]-2,3,4,5-tetrahydro-1H-[1,4]diazepino[1,2-a]indole-8-carboxamide

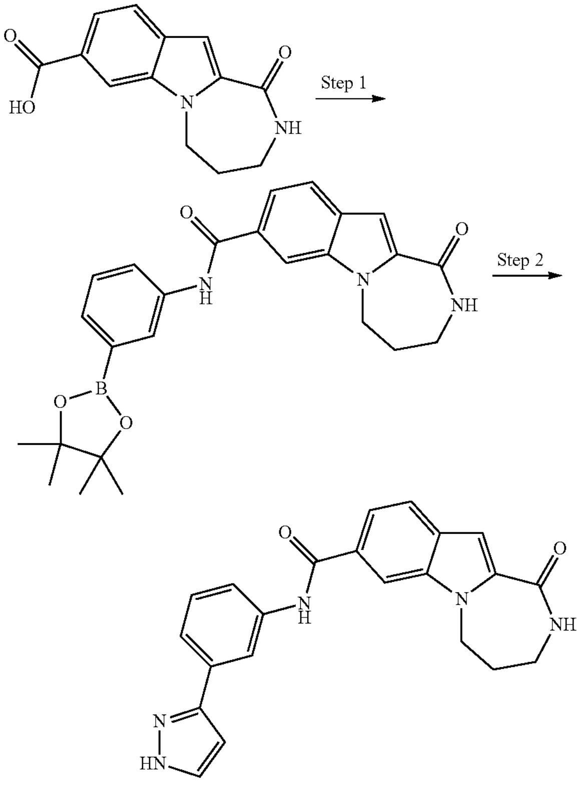

Step 1: Synthesis of 1-oxo-N-[3-(4,4,5,5-tetramethyl-1,3,2-dioxaborolan-2-yl)phenyl]-2,3,4,5-tetrahydro-1H-[1,4]diazepino[1,2-a]indole-8-carboxamide To a solution of 1-oxo-2,3,4,5-tetrahydro-1H-[1,4]diazepino[1,2-a]indole-8-carboxylic acid (Intermediate J, 2.3 g, 9.2 mmol) in DMF (30 mL) are added N,N,N',N'-tetramethyl-O-(7-azabenzotriazol-1-yl)uronium hexafluorophosphate (3.7 g, 9.7 mmol) and N-methylmorpholine (2.5 mL, 22.5 mmol). The reaction mixture is stirred for 1 h at room temperature and 3-(4,4,5,5-tetramethyl-1,3,2-dioxaborolan-2-yl)aniline (2.4 g, 11.1 mmol) is added. The reaction mixture is stirred for 16 h at room temperature and is poured into water (200 mL). The resulting solid is collected by filtration, rinsed with water and dried to afford the title compound (3.8 g, 92%).

Step 2: Synthesis of 1-oxo-N-[3-(1H-pyrazol-3-yl)phenyl]-2,3,4,5-tetrahydro-1H-[1,4]diazepino[1,2-a]indole-8-carboxamide To a solution of 1-oxo-N-[3-(4,4,5,5-tetramethyl-1,3,2-dioxaborolan-2-yl)phenyl]-2,3,4,5-tetrahydro-1H-[1,4]diazepino[1,2-a]indole-8-carboxamide in DME:$H_2O$:ethanol (7:3:2 v/v/v, 2.0 mL) is added $K_3PO_4$ (34.3 mg, 0.162 mmol) and Pd(dppf)$Cl_2$ $CH_2Cl_2$ adduct (11 mg, 0.0135 mmol). The solution is added to a microwave vial containing 3-bromo-1H-pyrazole (29.8 mg, 0.15 mmol). The resulting mixture is heated in a microwave reactor at 150° C. for 30 minutes. The mixture is filtered through Celite (100 mg) washed with ethyl acetate (3×1 mL) and concentrated in vacuo. The residue is purified by mass triggered HPLC to provide the title compound as a (31 mg, 39%).

Example 228 is synthesized according to the procedure for Example 227, substituting either commercially available reagents or the appropriate intermediates described above.

Example 229

N-[2-(methylcarbamoyl)phenyl]-1-oxo-2,3,4,5-tetrahydro-1H-[1,4]diazepino[1,2-a]indole-8-carboxamide

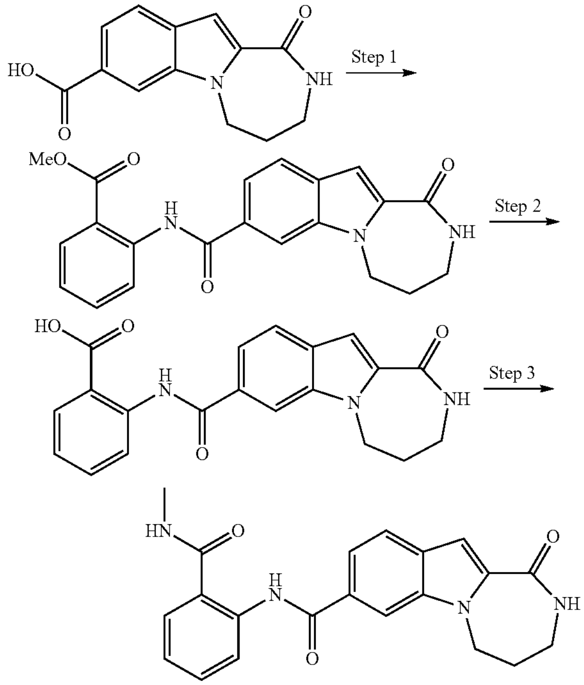

Step 1: Synthesis of methyl 2-{[(1-oxo-2,3,4,5-tetrahydro-1H-[1,4]diazepino[1,2-a]indol-8-yl)carbonyl]amino}benzoate To a suspension of 1-oxo-2,3,4,5-tetrahydro-1H-[1,4]diazepino[1,2-a]indole-8-carboxylic acid (Intermediate J, 500 mg, 2.0 mmol) in $CH_2Cl_2$ (10 mL) at room temperature is added 1-chloro-N,N,2-trimethylpropenylamine (0.98 mL, 7.2 mmol). After stirring for 3 h, methyl anthranilate (1.3 mL, 10.2 mmol) and pyridine (0.66 mL, 8.2 mmol) are added. The mixture is stirred for another 16 h at room temperature. Water (100 mL) is added and the mixture is extracted with EtOAc (3×100 mL). The organic layers are combined, dried and evaporated. Methanol (50 mL) is added to the oily residue, and a white solid is formed. The solid is filtered to afford the title compound (503 mg, 65%).

Step 2: Synthesis of 2-{[(1-oxo-2,3,4,5-tetrahydro-1H-[1,4]diazepino[1,2-a]indol-8-yl)carbonyl]amino}benzoic acid A suspension of methyl 2-{[(1-oxo-2,3,4,5-tetrahydro-1H-[1,4]diazepino[1,2-a]indol-8-yl)carbonyl]amino}benzoate (503 mg, 1.3 mmol) in methanol (7 mL) and 2M NaOH solution (2.0 mL, 4.0 mmol) is heated at 60° C. for 3 h. 1M HCl solution (10 mL) and water (80 mL) are added. The resulting solid is collected by filtration and dried to afford the title compound (438 mg, 90%).

Step 3: Synthesis of N-[2-(methylcarbamoyl)phenyl]-1-oxo-2,3,4,5-tetrahydro-1H-[1,4]diazepino[1,2-a]indole-8-carboxamide To a solution of 2-{[(1-oxo-2,3,4,5-tetrahydro-1H-[1,4]diazepino[1,2-a]indol-8-yl)carbonyl]amino}benzoic acid (100 mg, 0.28 mmol) in DMF (1.0 mL) are added 2M methylamine in THF (0.69 mL, 1.38 mmol), N-hydroxybenzotriazole (26 mg, 0.20 mmol), N,N-diisopropylethylamine (0.10 mL, 0.55 mmol) and 4-dimethylaminopyridine (6.7 mg, 0.06 mmol). After the reaction mixture is stirred for 10 min, 1-ethyl-3-(3-dimethylaminopropyl)carbodiimide (158 mg, 0.83 mmol) is added. The reaction mixture is then stirred for another 16 h at room temperature. The crude reaction mixture is purified by preparative HPLC using 10-85% acetonitrile/water with 0.1% TFA to afford the title compound (80 mg, 77%). LCMS (ESMS): m/z 377.20 ($M+H^+$).

Example 230 is synthesized according to the procedure for Example 229, substituting either commercially available reagents or the appropriate intermediates described above.

Example 231

N-[2-(tert-butylcarbamoyl)-1-methyl-1H-imidazol-4-yl]-4,4-dimethyl-1-oxo-1,2,3,4-tetrahydropyrazino[1,2-a]indole-7-carboxamide

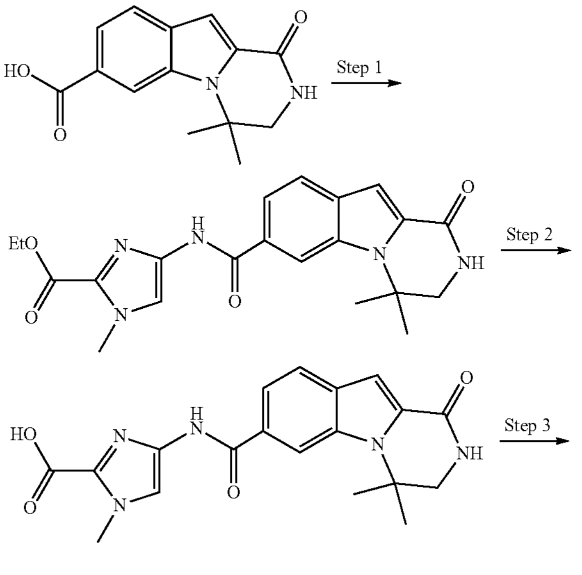

-continued

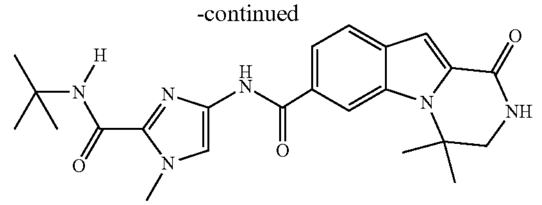

Step 1: Synthesis of ethyl 4-{[(4,4-dimethyl-1-oxo-1,2,3,4-tetrahydropyrazino[1,2-a]indol-7-yl)carbonyl]amino}-1-methyl-1H-imidazole-2-carboxylate To a solution of 4,4-dimethyl-1-oxo-1,2,3,4-tetrahydropyrazino[1,2-a]indole-7-carboxylic acid (336 mg, 1.3 mmol, Intermediate E) in DMF (1 mL) are added N-hydroxybenzotriazole (351 mg, 2.6 mmol) and 1-ethyl-3-(3-dimethylaminopropyl) carbodiimide (498 mg, 2.6 mmol). After stifling for 10 min, 4-amino-1-methyl-1H-imidazole-2-carboxylic acid ethyl ester (535 mg, 2.6 mmol), N,N-diisopropylethylamine (0.45 mL, 2.6 mmol) and 4-dimethylaminopyridine (32 mg, 0.26 mmol) are added. The reaction mixture is heated at 60° C. for 16 h. DMF is removed under a stream of $N_2$ at 40° C. and EtOAc (2 mL) and water (2 mL) are added. After stirring for 15 min, a white solid is formed and it is filtered and dried to afford the title compound (490 mg, 92%).

Step 2: Synthesis of 4-{[(4,4-dimethyl-1-oxo-1,2,3,4-tetrahydropyrazino[1,2-a]indol-7-yl)carbonyl]amino}-1-methyl-1H-imidazole-2-carboxylic acid A suspension of ethyl 4-{[(4,4-dimethyl-1-oxo-1,2,3,4-tetrahydropyrazino[1,2-a]indol-7-yl)carbonyl]amino}-1-methyl-1H-imidazole-2-carboxylate (540 mg, 1.3 mmol) in 3N NaOH solution (2.2 mL, 6.6 mmol) and methanol (5 mL) is heated at 60° C. for 2 h. The mixture is acidified with 2N HCl solution until the pH is about 2. The solution is allowed to cool with stifling. After 2 h the resulting solid is collected by filtration, washed with water and dried to afford the title compound (350 mg, 70%).

Step 3: Synthesis of N-[2-(tert-butylcarbamoyl)-1-methyl-1H-imidazol-4-yl]-4,4-dimethyl-1-oxo-1,2,3,4-tetrahydropyrazino[1,2-a]indole-7-carboxamide To a solution of 4-{[(4,4-dimethyl-1-oxo-1,2,3,4-tetrahydropyrazino[1,2-a]indol-7-yl)carbonyl]amino}-1-methyl-1H-imidazole-2-carboxylic acid (104 mg, 0.27 mmol) in DMF (2 mL) are added N-hydroxybenzotriazole (74 mg, 0.55 mmol) and 1-ethyl-3-(3-dimethylaminopropyl)carbodiimide (105 mg, 0.55 mmol). After stifling for 10 min at 50° C., tert-butylamine (0.06 mL, 0.55 mmol), N,N-diisopropylethylamine (0.10 mL, 0.55 mmol) and 4-dimethylaminopyridine (6.7 mg, 0.06 mmol) are added. The reaction mixture is stirred at room temperature for 8 h. The solvent is removed under $N_2$ stream to afford the crude compound which is purified by flash column chromatography to afford the title compound (61 mg, 51%). LCMS (ESMS): m/z 437.78 ($M+H^+$).

Examples 232-235 are synthesized according to the procedure for Example 231, substituting either commercially available reagents or the appropriate intermediates described above.

Example 236

N-{1-[3-(dimethylamino)propyl]-1H-benzimidazol-2-yl}-1-oxo-2,3-dihydro-1H-spiro[1,4-diazepino[1,2-a]indole-4,4'-piperidine]-8-carboxamide

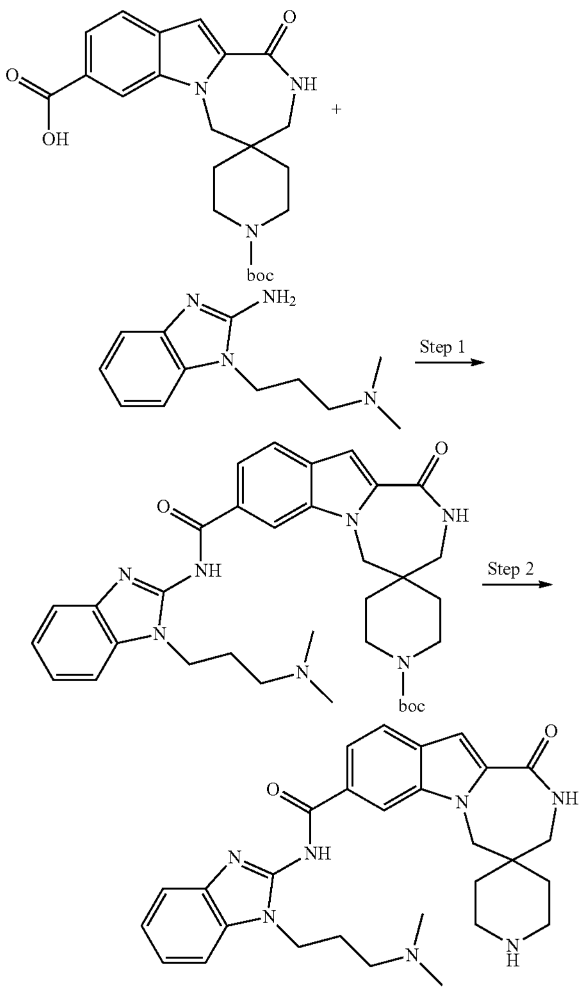

Step 1: Synthesis of tert-butyl 8-({1-[3-(dimethylamino)propyl]-1H-benzimidazol-2-yl}carbamoyl)-1-oxo-2,3-dihydro-1H,1'H-spiro[1,4-diazepino[1,2-a]indole-4,4'-piperidine]-1'-carboxylate To a solution of 1'-(tert-butoxycarbonyl)-1-oxo-2,3-dihydro-1H-spiro[1,4-diazepino[1,2-a]indole-4,4'-piperidine]-8-carboxylic acid (300 mg, 0.73 mmol) in DMF (5 mL) is added N,N,N'N'-tetramethyl-O-(benzotriazol-1-yl)uronium tetrafluoroborate (TBTU) (268 mg, 0.83 mmol). The reaction mixture is stirred for 10 min at room temperature. 1-[3-(dimethylamino)propyl]-1H-benzimidazol-2-amine (238 mg, 1.1 mmol) and triethylamine (0.30 mL, 2.2 mmol) are added. The reaction mixture is stirred for another 16 h at room temperature. Water (65 mL) is added and a light yellow solid is formed. The solid is filtered, rinsed with water and dried to afford the title compound (361 mg, 81%).

Step 2: Synthesis of N-{1-[3-(dimethylamino)propyl]-1H-benzimidazol-2-yl}-1-oxo-2,3-dihydro-1H-spiro[1,4-diazepino[1,2-a]indole-4,4'-piperidine]-8-carboxamide To a solution of tert-Butyl 8-({1-[3-(dimethylamino)propyl]-1H-benzimidazol-2-yl}carbamoyl)-1-oxo-2,3-dihydro-1H,1'H-spiro[1,4-diazepino[1,2-a]indole-4,4'-piperidine]-1'-carboxylate (302 mg, 0.49 mmol) in $CH_2Cl_2$ (7 mL) is added TFA (1 mL). The mixture is stirred for 16 h at room temperature. Methanol (25 mL) is added and the solvent is evaporated. The residue is purified by preparative HPLC using 10-75% acetonitrile/water with 0.1% TFA to afford the title compound as a bis-trifluoracetate salt (310 mg, 85%). LCMS (ESMS): m/z 514.81 ($M+H^+$).

Examples 237-239 are synthesized according to the procedure for Example 236, substituting either commercially available reagents or the appropriate intermediates described above.

Table 3 below, lists the mass spectral data and the retention times for Examples 1 to 239.

TABLE 3

| Example | m/z [M + H] | HPLC retention time (min) | Method |
|---|---|---|---|
| 1 | 354.63 | 1.51 | A1 |
| 2 | 325.17 | 2.03 | U2 |
| 3 | 383.59 | 6.88 | A2 |
| 4 | 354.07 | 0.58 | H1 |
| 5 | 371.2 | 1.14 | V1 |
| 6 | 345.08 | 0.73 | H1 |
| 7 | 405.2 | 1.07 | V1 |
| 8 | 410.2 | 1.32 | V1 |
| 9 | 349.20 | 1.01 | V1 |
| 10 | 335.67 | 0.97 | A1 |
| 11 | 324.53 | 5.63 | A2 |
| 12 | 418.42 | 5.23 | A2 |
| 13 | 352.53 | 4.97 | A2 |
| 14 | 386.55 | 5.51 | A2 |
| 15 | 309.95 | 0.41 | H1 |
| 16 | 338.20 | 0.96 | V1 |
| 17 | 324.20 | 0.90 | V1 |
| 18 | 417.59 | 5.32 | A2 |
| 19 | 403.29 | 0.73 | H1 |
| 20 | 375.23 | 0.58 | H1 |
| 21 | 338.61 | 4.58 | A2 |
| 22 | 324.20 | 0.88 | V1 |
| 23 | 323.39 | 1.70 | H1 |
| 24 | 364.20 | 1.01 | V1 |
| 25 | 352.60 | 4.77 | A2 |
| 26 | 380.56 | 5.66 | A2 |
| 27 | 394.61 | 5.72 | A2 |
| 28 | 428.60 | 6.87 | A2 |
| 29 | 414.57 | 6.60 | A2 |
| 30 | 414.56 | 6.54 | A2 |
| 31 | 470.36 | 0.81 | H1 |
| 32 | 400.48 | 5.04 | A2 |
| 33 | 406.56 | 6.77 | A2 |
| 34 | 414.64 | 6.64 | A2 |
| 35 | 380.16 | 5.35 | A2 |
| 36 | 395.61 | 4.95 | A2 |
| 37 | 423.63 | 4.94 | A2 |
| 38 | 368.61 | 5.66 | A2 |
| 39 | 374.20 | 1.13 | V1 |
| 40 | 402.20 | 1.37 | V1 |
| 41 | 385.20 | 1.14 | V1 |
| 42 | 402.20 | 1.23 | V1 |
| 43 | 428.20 | 1.29 | V1 |
| 44 | 458.97 | 0.93 | A1 |
| 45 | 466.20 | 1.17 | V1 |
| 46 | 493.63 | 1.19 | A1 |
| 47 | 394.20 | 1.21 | V1 |
| 48 | 408.70 | 1.41 | A1 |

TABLE 3-continued

| Example | m/z [M + H] | HPLC retention time (min) | Method |
|---|---|---|---|
| 49 | 408.20 | 1.25 | V1 |
| 50 | 507.20 | 0.98 | V1 |
| 51 | 378.20 | 1.25 | V1 |
| 52 | 408.20 | 1.26 | V1 |
| 53 | 422.20 | 1.32 | V1 |
| 54 | 479.20 | 0.94 | V1 |
| 55 | 360.20 | 1.03 | V1 |
| 56 | 374.20 | 1.07 | V1 |
| 57 | 360.20 | 1.05 | V1 |
| 58 | 374.67 | 1.17 | A1 |
| 59 | 388.20 | 1.20 | V1 |
| 60 | 402.20 | 1.27 | V1 |
| 61 | 374.20 | 1.17 | V1 |
| 62 | 388.20 | 1.21 | V1 |
| 63 | 388.76 | 1.33 | A1 |
| 64 | 374.20 | 1.15 | V1 |
| 65 | 416.20 | 1.39 | V1 |
| 66 | 432.20 | 0.89 | V1 |
| 67 | 416.67 | 5.71 | A2 |
| 68 | 402.73 | 1.56 | A1 |
| 69 | 402.73 | 1.55 | A1 |
| 70 | 430.62 | 7.24 | A2 |
| 71 | 416.95 | 1.52 | A1 |
| 72 | 402.20 | 1.32 | V1 |
| 73 | 416.67 | 1.61 | A1 |
| 74 | 402.66 | 1.56 | A1 |
| 75 | 428.20 | 1.41 | V1 |
| 76 | 436.20 | 1.40 | V1 |
| 77 | 457.20 | 1.00 | V1 |
| 78 | 485.20 | 1.17 | V1 |
| 79 | 402.56 | 5.73 | A2 |
| 80 | 402.60 | 6.84 | A2 |
| 81 | 388.20 | 1.26 | V1 |
| 82 | 402.2 | 1.24 | V1 |
| 83 | 388.20 | 1.03 | V1 |
| 84 | 473.76 | 1.18 | A1 |
| 85 | 432.20 | 1.03 | V1 |
| 86 | 460.20 | 1.12 | V1 |
| 87 | 442.20 | 1.27 | V1 |
| 88 | 471.70 | 1.13 | A1 |
| 89 | 465.20 | 0.98 | V1 |
| 90 | 459.78 | 4.46 | A2 |
| 91 | 459.64 | 5.47 | A2 |
| 92 | 473.68 | 5.57 | A2 |
| 93 | 459.93 | 1.11 | A1 |
| 94 | 459.95 | 1.11 | A1 |
| 95 | 515.44 | 0.58 | H1 |
| 96 | 445.20 | 1.05 | V1 |
| 97 | 485.20 | 0.96 | V1 |
| 98 | 459.2 | 0.90 | V1 |
| 99 | 473.40 | 0.99 | V1 |
| 100 | 445.20 | 1.18 | V1 |
| 101 | 459.20 | 0.97 | V1 |
| 102 | 459.20 | 1.04 | V1 |
| 103 | 431.20 | 1.07 | V1 |
| 104 | 473.20 | 0.86 | V1 |
| 105 | 389.67 | 5.17 | A2 |
| 106 | 341.08 | 0.41 | H1 |
| 107 | 400.20 | 1.22 | V1 |
| 108 | 310.20 | 0.50 | V1 |
| 109 | 324.35 | 1.00 | A1 |
| 110 | 384.56 | 6.68 | A2 |
| 111 | 367.20 | 1.13 | V1 |
| 112 | 361.20 | 1.14 | V1 |
| 113 | 414.60 | 5.30 | A2 |
| 114 | 401.59 | 3.51 | A2 |
| 115 | 436.67 | 1.44 | A1 |
| 116 | 351.21 | 1.05 | A1 |
| 117 | 418.54 | 6.75 | A2 |
| 118 | 520.33 | 0.81 | H1 |
| 119 | 381.58 | 4.92 | A2 |
| 120 | 443.28 | 4.65 | A2 |
| 121 | 481.74 | 1.17 | A1 |
| 122 | 428.76 | 1.43 | A1 |
| 123 | 347.66 | 1.12 | A1 |
| 124 | 471.78 | 1.26 | A1 |

TABLE 3-continued

| Example | m/z [M + H] | HPLC retention time (min) | Method |
|---|---|---|---|
| 125 | 426.73 | 1.42 | A1 |
| 126 | 339.66 | 1.33 | A1 |
| 127 | 351.65 | 1.39 | A1 |
| 128 | 325.62 | 1.32 | A1 |
| 129 | 445.77 | 1.19 | A1 |
| 130 | 400.70 | 1.36 | A1 |
| 131 | 445.77 | 1.18 | A1 |
| 132 | 325.61 | 1.30 | A1 |
| 133 | 400.70 | 1.38 | A1 |
| 134 | 414.71 | 1.14 | A1 |
| 135 | 414.70 | 1.43 | A1 |
| 136 | 428.65 | 5.08 | A2 |
| 137 | 428.67 | 5.02 | A2 |
| 138 | 440.73 | 1.48 | A1 |
| 139 | 459.64 | 4.38 | A2 |
| 140 | 414.63 | 4.93 | A2 |
| 141 | 459.64 | 4.40 | A2 |
| 142 | 414.63 | 4.94 | A2 |
| 143 | 414.70 | 1.41 | A1 |
| 144 | 414.72 | 1.41 | A1 |
| 145 | 362.70 | 1.63 | A1 |
| 146 | 362.70 | 1.57 | A1 |
| 147 | 350.66 | 1.42 | A1 |
| 148 | 350.66 | 1.39 | A1 |
| 149 | 350.67 | 1.35 | A1 |
| 150 | 349.59 | 4.38 | A2 |
| 151 | 349.59 | 4.22 | A2 |
| 152 | 357.66 | 1.11 | A1 |
| 153 | 361.71 | 1.17 | A1 |
| 154 | 321.62 | 1.13 | A1 |
| 155 | 321.62 | 1.01 | A1 |
| 156 | 321.62 | 0.97 | A1 |
| 157 | 353.45 | 1.39 | A1 |
| 158 | 349.72 | 1.09 | A1 |
| 159 | 339.20 | 1.10 | V1 |
| 160 | 381.20 | 1.33 | V1 |
| 161 | 350.84 | 1.47 | A1 |
| 162 | 417.75 | 1.36 | A1 |
| 163 | 352.20 | 1.06 | V1 |
| 164 | 338.20 | 1.03 | V1 |
| 165 | 416.20 | 1.39 | V1 |
| 166 | 402.60 | 1.48 | A1 |
| 167 | 361.63 | 1.36 | A1 |
| 168 | 339.58 | 4.86 | A2 |
| 169 | 353.58 | 4.87 | A2 |
| 170 | 365.71 | 1.42 | A1 |
| 171 | 339.58 | 4.84 | A2 |
| 172 | 339.58 | 4.80 | A2 |
| 173 | 339.68 | 1.34 | A1 |
| 174 | 325.23 | 1.24 | A1 |
| 175 | 367.32 | 0.85 | H1 |
| 176 | 367.28 | 0.86 | H1 |
| 177 | 359.40 | 1.45 | A1 |
| 178 | 320.64 | 1.37 | A1 |
| 179 | 335.68 | 1.05 | A1 |
| 180 | 335.68 | 1.04 | A1 |
| 181 | 339.20 | 1.09 | V1 |
| 182 | 339.20 | 1.10 | V1 |
| 183 | 351.20 | 1.10 | V1 |
| 184 | 405.11 | 0.87 | H1 |
| 185 | 345.14 | 0.77 | H1 |
| 186 | 391.89 | 0.78 | H1 |
| 187 | 362.13 | 0.74 | H1 |
| 188 | 387.02 | 0.55 | H1 |
| 189 | 389.27 | 0.61 | H1 |
| 190 | 371.28 | 2.27 | U2 |
| 191 | 366.29 | 0.67 | H1 |
| 192 | 386.14 | 0.75 | H1 |
| 193 | 325.17 | 2.15 | U2 |
| 194 | 359.08 | 0.65 | H1 |
| 195 | 367.24 | 2.85 | U2 |
| 196 | 353.21 | 0.78 | H1 |
| 197 | 365.18 | 0.78 | H1 |
| 198 | 351.21 | 0.72 | H1 |
| 199 | 401.10 | 0.92 | H1 |
| 200 | 401.14 | 0.93 | H1 |

TABLE 3-continued

| Example | m/z [M + H] | HPLC retention time (min) | Method |
|---|---|---|---|
| 201 | 401.2 | 1.26 | V1 |
| 202 | 353.17 | 0.77 | H1 |
| 203 | 377.10 | 0.68 | H1 |
| 204 | 351.10 | 0.58 | H1 |
| 205 | 391.10 | 0.72 | H1 |
| 206 | 351.10 | 0.47 | H1 |
| 207 | 379.19 | 0.85 | H1 |
| 208 | 383.27 | 0.61 | H1 |
| 209 | 393.28 | 0.95 | H1 |
| 210 | 388.66 | 1.19 | A1 |
| 211 | 387.20 | 1.21 | V1 |
| 212 | 401.20 | 1.23 | V1 |
| 213 | 353.20 | 1.16 | V1 |
| 214 | 387.07 | 2.81 | U2 |
| 215 | 363.61 | 1.27 | A1 |
| 216 | 354.59 | 1.46 | A1 |
| 217 | 345.63 | 1.32 | A1 |
| 218 | 386.62 | 5.14 | A2 |
| 219 | 324.68 | 4.55 | A2 |
| 220 | 310.56 | 5.45 | A2 |
| 221 | 377.20 | 1.06 | V1 |
| 222 | 377.20 | 1.15 | V1 |
| 223 | 322.71 | 1.14 | A1 |
| 224 | 352.74 | 1.30 | A1 |
| 225 | 339.68 | 1.33 | A1 |
| 226 | 386.20 | 0.86 | V1 |
| 227 | 386.20 | 0.80 | H1 |
| 228 | 416.20 | 1.19 | H1 |
| 229 | 377.20 | 1.07 | V1 |
| 230 | 434.20 | 0.81 | V1 |
| 231 | 437.78 | 1.40 | A1 |
| 232 | 435.20 | 1.11 | V1 |
| 233 | 449.20 | 1.23 | V1 |
| 234 | 449.20 | 1.13 | V1 |
| 235 | 454.72 | 1.53 | A1 |
| 236 | 514.81 | 0.95 | A1 |
| 237 | 394.69 | 1.07 | A1 |
| 238 | 469.77 | 1.21 | A1 |
| 239 | 589.71 | 1.29 | A1 |

Assessment of Biological Properties

The biological properties of the compounds of the invention are assessed using the assays described below.

Experimental Method A: Human RSK2 Assay

Compounds are assessed for their ability to inhibit the phosphorylation of a substrate peptide by RSK2.

Human RSK2 protein, purchased from Invitrogen, is used to measure kinase activity utilizing Kinase Glo Plus (Promega) a homogeneous assay technology, which uses a luciferin-luciferase based ATP detection reagent to quantify residual ATP. The assay is performed using 0.75 nM His-RSK2, 0.75 μM ATP and 1.0 μM S6 Kinase/RSK Substrate Peptide 1 (Upstate, catalog #12-124), in assay buffer consisting of 25 mM HEPES, pH 7.5, 10 mM $MgCl_2$, 5 mM $MnCl_2$, 50 mM KCl, 0.2% BSA, 0.01% CHAPS, 100 μM $Na_3VO_4$, 0.5 mM DTT, and 1% DMSO. Solutions of test compounds at various concentrations are prepared by 1:3 fold serial dilution of a 1 mM solution of compound in DMSO. The DMSO solutions are further diluted with assay buffer to a final concentration of DMSO of 5%.

The assay is performed in a 384 well, white, non-binding plate (Corning, catalogue #3574). Solutions of test compounds (10 μL) are transferred to a dry assay plate, followed by addition of 20 μL kinase and 20 μL ATP+Substrate Peptide 1 described above. The kinase reaction mixture is incubated for 90 minutes at 28° C. followed by addition of 30 μL of ATP detection reagent for 15 minutes at room temperature. The relative light unit (RLU) signal is measured on a LJL Analyst (Molecular Devices) in luminescence mode using 384 aperture. The RLU signals were converted to percent of control (POC) values using the formula:

$$POC=100*(BCTRL-Signal)/(BCTRL-PCTRL),$$

where Signal is the test well RLU signal, BCTRL is the average of background (negative control), which consists of ATP+peptide and compound buffer, well signals on the plate, and PCTRL is the average of positive control, which consists of kinase, ATP+peptide, and compound buffer, well signals on the plate. For concentration-responsive compounds, POC as a function of test compound concentration are fitted to a 4-parameter logistic equation of the form:

$$Y=A+(B-A)/[1+(x/C)^D],$$

where A, B, C, and D are fitted parameters (parameter B is fixed at zero POC), and x and y are the independent and dependent variables, respectively. The $IC_{50}$ (50% inhibitory concentration) is determined as the inflection point parameter, C.

Experimental Method B: Human RSK2 Trans-Reporter Assay

Compounds are assessed for their ability to inhibit the phosphorylation of the transcription factor CREB (cAMP Response Element Binding) by RSK2 in cells.

A cell monolayer of exponentially growing HLR-CREB cells (PathDetect® HeLa Luciferase Reporter CREB cells, Stratagene) is prepared by the following method. In a 100 mm culture dish, $7.5\times10^5$ HLR-CREB cells are added to 10 mL culture medium consisting of RPMI-1640, 10% heat inactivated FCS, 2 mM glutamine, and 50 μg/mL gentamycin. The cells are allowed to adhere overnight, at which point 6 mL of medium is removed.

The cell monolayer is transfected using Effectene (Quiagen) with RSK2 by the following method. A mixture of DNA, pCMV6-XL-RSK2 (1.0 μg) and pcDNA 3.1 (1.0 μg), is added to 300 μL DNA-condensation buffer. The complexes are formed by addition of 16 μL enhancer, and the mixture is incubated for 5 minutes at room temperature. Then, 60 μL Effectene is added, and the mixture is incubated for an additional 10 minutes at room temperature. The final volume is adjusted to 2.0 mL with complete media, and added to the cell monolayer.

Five hours after transfection, the cells are plated into white 96 well culture plates (Greiner Bio-One 655083). Compounds are added at various concentrations to the cells 20-24 hours after transfection, and are stimulated with 20 nM Phorbol 12-myristate 13-acetate (PMA). Determination of the luciferase expression was 48 hours after transfection. The luciferase activity was determined using the protocol provided by Steady-Glo (Promega).

The results are represented as the percent luciferase activity relative to the control measured in the absence of inhibitors (POC). The data representing POC as a function of test compound concentration were fitted to a 4-parameter logistic equation of the form: Y=A+(B−A)/[1+(x/C) D], where A, B, C, and D are fitted parameters, and x and y are the independent and dependent variables, respectively. The $IC_{50}$ (50% inhibitory concentration) was determined as the inflection point parameter, C. Each data point represents an average of triplicate observations.

Concurrently, compound cytotoxicity was assessed by reduction of AlamarBlue (Invitrogen). Five hours after transfection, the cells are plated into clear 96 well culture plates (Costar 3595) and cultured with compounds as described above for luciferase expression. AlamarBlue was added to each well 48 hours after transfection and returned to incubator for an additional 3-4 hours at 37° C. Fluorescent units were determined using 540 nm for excitation and 590 nm for emission.

The AlamarBlue results are represented as the percent fluorescent units relative to the control measured in the absence of inhibitors (POC). The data representing POC as a function of test compound concentration were fitted to a 4-parameter logistic equation of the form: Y=A+(B−A)/[1+(x/C) D], where A, B, C, and D are fitted parameters, and x and y are the independent and dependent variables, respectively. Each data point represents an average of triplicate observations.

The RSK2 ($IC_{50}$) activity of Examples 1 to 239 are shown in Table 4 below.

TABLE 4

| Example | RSK2 $IC_{50}$ (nM) |
|---|---|
| 1 | 270 |
| 2 | 30 |
| 3 | 240 |
| 4 | 190 |
| 5 | 70 |
| 6 | 140 |
| 7 | 60 |
| 8 | 900 |
| 9 | 4600 |
| 10 | 41 |
| 11 | 540 |
| 12 | 220 |
| 13 | 1600 |
| 14 | 108 |
| 15 | 43 |
| 16 | 2500 |
| 17 | 145 |
| 18 | 8.1 |
| 19 | 53 |
| 20 | 87 |
| 21 | 4.3 |
| 22 | 5.1 |
| 23 | 11 |
| 24 | 320 |
| 25 | 14 |
| 26 | 27 |
| 27 | 46 |
| 28 | 1.9 |
| 29 | 1.9 |
| 30 | 10 |
| 31 | 900 |
| 32 | 4 |
| 33 | 7.4 |
| 34 | 7.9 |
| 35 | 11 |
| 36 | 84 |
| 37 | 84 |
| 38 | 19 |
| 39 | 3 |
| 40 | 4.8 |
| 41 | 4.9 |
| 42 | 6.2 |
| 43 | 24 |
| 44 | 2.6 |
| 45 | 3.6 |
| 46 | 8.7 |
| 47 | 8 |
| 48 | 2.5 |
| 49 | 26 |
| 50 | 34 |
| 51 | 5.2 |
| 52 | 170 |
| 53 | 12 |
| 54 | 20 |
| 55 | 4.4 |
| 56 | 0.89 |
| 57 | 0.59 |
| 58 | 0.77 |
| 59 | 0.62 |

TABLE 4-continued

| Example | RSK2 $IC_{50}$ (nM) |
|---|---|
| 60 | 20 |
| 61 | 2.2 |
| 62 | 8.2 |
| 63 | 1.6 |
| 64 | 9 |
| 65 | 19 |
| 66 | 610 |
| 67 | 3.4 |
| 68 | 1.9 |
| 69 | 21 |
| 70 | 1.8 |
| 71 | 1.4 |
| 72 | 20 |
| 73 | 2 |
| 74 | 7.3 |
| 75 | 25 |
| 76 | 61 |
| 77 | 14 |
| 78 | 58 |
| 79 | 0.64 |
| 80 | 5 |
| 81 | 1.1 |
| 82 | 0.25 |
| 83 | 0.63 |
| 84 | 30 |
| 85 | 5.4 |
| 86 | 5.9 |
| 87 | 4.8 |
| 88 | 21 |
| 89 | 22 |
| 90 | 2.1 |
| 91 | 8.5 |
| 92 | 2 |
| 93 | 1.1 |
| 94 | 14 |
| 95 | 16 |
| 96 | 21 |
| 97 | 11 |
| 98 | 0.38 |
| 99 | 27 |
| 100 | 1.3 |
| 101 | 13 |
| 102 | 1.3 |
| 103 | 23 |
| 104 | 54 |
| 105 | 4.4 |
| 106 | 300 |
| 107 | 500 |
| 108 | 25.5 |
| 109 | 2200 |
| 110 | 96 |
| 111 | 1800 |
| 112 | 370 |
| 113 | 17 |
| 114 | 1.9 |
| 115 | 32 |
| 116 | 110 |
| 117 | 98 |
| 118 | 18 |
| 119 | 120 |
| 120 | 3.8 |
| 121 | 23 |
| 122 | 110 |
| 123 | 430 |
| 124 | 9.25 |
| 125 | 11 |
| 126 | 36 |
| 127 | 145 |
| 128 | 6.6 |
| 129 | 0.7 |
| 130 | 0.6 |
| 131 | 15 |
| 132 | 495 |
| 133 | 17.5 |
| 134 | 1.8 |
| 135 | 7.6 |
| 136 | 9.3 |

TABLE 4-continued

| Example | RSK2 $IC_{50}$ (nM) |
|---|---|
| 137 | 43.5 |
| 138 | 26.5 |
| 139 | 0.18 |
| 140 | 0.42 |
| 141 | 13.7 |
| 142 | 65.5 |
| 143 | 0.71 |
| 144 | 80 |
| 145 | 140 |
| 146 | 89 |
| 147 | 400 |
| 148 | 190 |
| 149 | 110 |
| 150 | 240 |
| 151 | 1100 |
| 152 | 1700 |
| 153 | 3300 |
| 154 | 220 |
| 155 | 2300 |
| 156 | 39 |
| 157 | 1800 |
| 158 | 39 |
| 159 | 12 |
| 160 | 32 |
| 161 | 21 |
| 162 | 19 |
| 163 | 335 |
| 164 | 10 |
| 165 | 1.8 |
| 166 | 0.60 |
| 167 | 670 |
| 168 | 160 |
| 169 | 570 |
| 170 | 1300 |
| 171 | 4 |
| 172 | 1100 |
| 173 | 1200 |
| 174 | 34 |
| 175 | 150 |
| 176 | 25 |
| 177 | 8 |
| 178 | 290 |
| 179 | 45 |
| 180 | 895 |
| 181 | 34.5 |
| 182 | 150 |
| 183 | 26 |
| 184 | 155 |
| 185 | 106 |
| 186 | 270 |
| 187 | 160 |
| 188 | 7700 |
| 189 | 1300 |
| 190 | 34 |
| 191 | 48 |
| 192 | 18 |
| 193 | 19 |
| 194 | 3300 |
| 195 | 44 |
| 196 | 26 |
| 197 | 27 |
| 198 | 18 |
| 199 | 115 |
| 200 | 160 |
| 201 | 15 |
| 202 | 16 |
| 203 | 180 |
| 204 | 17 |
| 205 | 10 |
| 206 | 96 |
| 207 | 85 |
| 208 | 96 |
| 209 | 39 |
| 210 | 30 |
| 211 | 290 |
| 212 | 30 |
| 213 | 66 |

TABLE 4-continued

| Example | RSK2 $IC_{50}$ (nM) |
|---|---|
| 214 | 87 |
| 215 | 21 |
| 216 | 6000 |
| 217 | 7000 |
| 218 | 40 |
| 219 | 68 |
| 220 | 93 |
| 221 | 8.2 |
| 222 | 11 |
| 223 | 76 |
| 224 | 9.1 |
| 225 | 12 |
| 226 | 52 |
| 227 | 41 |
| 228 | 4100 |
| 229 | 154 |
| 230 | 125 |
| 231 | 6 |
| 232 | 9 |
| 233 | 3.7 |
| 234 | 2.1 |
| 235 | 10.9 |
| 236 | 540 |
| 237 | 6300 |
| 238 | 350 |
| 239 | 51 |

Method of Use

The compounds of the invention are effective inhibitors of RSK2. Therefore, in one embodiment of the invention, there is provided methods of treating RSK2 regulated disorders using compounds of the invention. In another embodiment, there is provided methods of treating cardiovascular, inflammatory, allergic, pulmonary and fibrotic diseases, renal diseases and cancer using compounds of the invention.

The inhibition or modulation of RSK2 activity is an attractive means for preventing and treating a variety of diseases mediated by RSKs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection; and Cancer including solid tumors, leukemias and lymphomas.

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound selected from the group consisting of:

N-(2-methoxypyridin-4-yl)-1-oxo-2,3,4,5-tetrahydro-1H-[1,4]diazepino[1,2-a]indole-8-carboxamide;

N-(1-ethyl-1H-benzimidazol-2-yl)-4,4-dimethyl-1-oxo-1,2,3,4-tetrahydropyrazino[1,2-a]indole-7-carboxamide;

N-(1-ethyl-1H-benzimidazol-2-yl)-cis-3,4-dimethyl-1-oxo-1,2,3,4-tetrahydropyrazino[1,2-a]indole-7-carboxamide;

(4R)—N-{1-[3-(dimethylamino)propyl]-1H-benzimidazol-2-yl}-4-methyl-1-oxo-1,2,3,4-tetrahydropyrazino[1,2-a]indole-7-carboxamide;

N-(1-ethyl-1H-benzimidazol-2-yl)-5-methyl-1-oxo-2,3,4,5-tetrahydro-1H-[1,4]diazepino[1,2-a]indole-8-carboxamide;

5-methyl-1-oxo-N-[1-(propan-2-yl)-1H-benzimidazol-2-yl]-2,3,4,5-tetrahydro-1H-[1,4]diazepino[1,2-a]indole-8-carboxamide;

(4R)—N-(1-benzyl-1H-pyrazol-4-yl)-4-methyl-1-oxo-1,2,3,4-tetrahydropyrazino[1,2-a]indole-7-carboxamide;

N-(1H-benzimidazol-2-yl)-4,4-dimethyl-1-oxo-1,2,3,4-tetrahydropyrazino[1,2-a]indole-7-carboxamide;

(3S,4R)—N-(1-benzyl-1H-pyrazol-4-yl)-3,4-dimethyl-1-oxo-1,2,3,4-tetrahydropyrazino[1,2-a]indole-7-carboxamide;

N-(1H-benzimidazol-2-yl)-4-methyl-1-oxo-1,2,3,4-tetrahydropyrazino[1,2-a]indole-7-carboxamide;

4,4-dimethyl-N-(1-methyl-1H-benzimidazol-2-yl)-1-oxo-1,2,3,4-tetrahydropyrazino[1,2-a]indole-7-carboxamide;

N-{1-[3-(dimethylamino)propyl]-1H-benzimidazol-2-yl}-4,4-dimethyl-1-oxo-1,2,3,4-tetrahydropyrazino[1,2-a]indole-7-carboxamide;

4-methyl-N-(1-methyl-1H-benzimidazol-2-yl)-1-oxo-1,2,3,4-tetrahydropyrazino[1,2-a]indole-7-carboxamide;

(5R)-5-methyl-1-oxo-N-[1-(propan-2-yl)-1H-benzimidazol-2-yl]-2,3,4,5-tetrahydro-1H-[1,4]diazepino[1,2-a]indole-8-carboxamide;

N-(1-ethyl-1H-benzimidazol-2-yl)-4-methyl-1-oxo-1,2,3,4-tetrahydropyrazino[1,2-a]indole-7-carboxamide;

N-(1H-benzimidazol-2-yl)-5-methyl-1-oxo-2,3,4,5-tetrahydro-1H-[1,4]diazepino[1,2-a]indole-8-carboxamide;

(5R)—N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide;

N-{1-[3-(dimethylamino)propyl]-1H-benzimidazol-2-yl}-1'-oxo-2',3'-dihydro-1'H-spiro[cyclopropane-1,4'-[1,4]diazepino[1,2-a]indole]-8'-carboxamide;

(5R)—N-(1-benzyl-1H-pyrazol-4-yl)-5-methyl-1-oxo-2,3,4,5-tetrahydro-1H-[1,4]diazepino[1,2-a]indole-8-carboxamide;

N-(1-benzyl-1H-pyrazol-4-yl)-cis-3,4-dimethyl-1-oxo-1,2,3,4-tetrahydropyrazino[1,2-a]indole-7-carboxamide;

N-{1-[3-(dimethylamino)propyl]-1H-benzimidazol-2-yl}-cis-3,4-dimethyl-1-oxo-1,2,3,4-tetrahydropyrazino[1,2-a]indole-7-carboxamide;

(3S,4R)—N-{1-[3-(dimethylamino)propyl]-1H-benzimidazol-2-yl}-3,4-dimethyl-1-oxo-1,2,3,4-tetrahydropyrazino[1,2-a]indole-7-carboxamide;

N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide;

N-(1-ethyl-1H-benzimidazol-2-yl)-1-oxo-2,3,4,5-tetrahydro-1H-[1,4]diazepino[1,2-a]indole-8-carboxamide;

N-(5-chloro-1H-benzimidazol-2-yl)-5-methyl-1-oxo-2,3,4,5-tetrahydro-1H-[1,4]diazepino[1,2-a]indole-8-carboxamide;

N-(1-ethyl-5-methyl-1H-benzimidazol-2-yl)-1-oxo-2,3,4,5-tetrahydro-1H-[1,4]diazepino[1,2-a]indole-8-carboxamide;

cis-3,4-dimethyl-1-oxo-N-[1-(propan-2-yl)-1H-benzimidazol-2-yl]-1,2,3,4-tetrahydropyrazino[1,2-a]indole-7-carboxamide;

N-(1-benzyl-1H-pyrazol-4-yl)-4,4-difluoro-1-oxo-2,3,4,5-tetrahydro-1H-[1,4]diazepino[1,2-a]indole-8-carboxamide;

4,4-dimethyl-1-oxo-N-[1-(propan-2-yl)-1H-benzimidazol-2-yl]-1,2,3,4-tetrahydropyrazino[1,2-a]indole-7-carboxamide; or a pharmaceutically acceptable salt thereof.

2. A compound selected from the group consisting of:

5-methyl-N-(1-methyl-1H-benzimidazol-2-yl)-1-oxo-2,3,4,5-tetrahydro-1H-[1,4]diazepino[1,2-a]indole-8-carboxamide; N-(1-benzyl-1H-pyrazol-4-yl)-4,4-dimethyl-1-oxo-1,2,3,4-tetrahydropyrazino[1,2-a]indole-7-carboxamide;

N-[2-(cyclopentylcarbamoyl)-1-methyl-1H-imidazol-4-yl]-5-methyl-1-oxo-2,3,4,5-tetrahydro-1H-[1,4]diazepino[1,2-a]indole-8-carboxamide;

N-(1H-indol-2-yl)-4-methyl-1-oxo-1,2,3,4-tetrahydropyrazino[1,2-a]indole-7-carboxamide;

N-(5-methyl-1H-benzimidazol-2-yl)-1-oxo-2,3,4,5-tetrahydro-1H-[1,4]diazepino[1,2-a]indole-8-carboxamide;

1-oxo-N-[1-(2,2,2-trifluoroethyl)-1H-benzimidazol-2-yl]-2,3,4,5-tetrahydro-1H-[1,4]diazepino[1,2-a]indole-8-carboxamide;

(4S)-4-methyl-1-oxo-N-[1-(propan-2-yl)-1H-benzimidazol-2-yl]-1,2,3,4-tetrahydropyrazino[1,2-a]indole-7-carboxamide;

N-{1-[3-(dimethylamino)propyl]-1H-benzimidazol-2-yl}-4-methyl-1-oxo-1,2,3,4-tetrahydropyrazino[1,2-a]indole-7-carboxamide;

5-methyl-N-(1-methyl-1H-benzimidazol-2-yl)-1-oxo-2,3,4,5-tetrahydro-1H-[1,4]diazepino[1,2-a]indole-8-carboxamide;

N-[2-(cyclopentylcarbamoyl)-1-methyl-1H-imidazol-4-yl]-4,4-dimethyl-1-oxo-1,2,3,4-tetrahydropyrazino[1,2-a]indole-7-carboxamide;

N-{1-[3-(dimethylamino)benzyl]-1H-pyrazol-4-yl}-1-oxo-2,3,4,5-tetrahydro-1H-[1,4]diazepino[1,2-a]indole-8-carboxamide;

cis-4,5-dimethyl-1-oxo-N-[1-(propan-2-yl)-1H-benzimidazol-2-yl]-2,3,4,5-tetrahydro-1H-[1,4]diazepino[1,2-a]indole-8-carboxamide;

N-(5-chloro-1H-benzimidazol-2-yl)-1-oxo-2,3,4,5-tetrahydro-1H-[1,4]diazepino[1,2-a]indole-8-carboxamide;

N-[2-(tert-butylcarbamoyl)-1-methyl-1H-imidazol-4-yl]-4,4-dimethyl-1-oxo-1,2,3,4-tetrahydropyrazino[1,2-a]indole-7-carboxamide;

N-(6-methoxypyrimidin-4-yl)-1-oxo-2,3,4,5-tetrahydro-1H-[1,4]diazepino[1,2-a]indole-8-carboxamide;

N-(1-ethyl-1H-benzimidazol-2-yl)-trans-3,4-dimethyl-1-oxo-1,2,3,4-tetrahydropyrazino[1,2-a]indole-7-carboxamide;

(3S,4R)-3,4-dimethyl-N-(5-methyl-1,2-oxazol-3-yl)-1-oxo-1,2,3,4-tetrahydropyrazino[1,2-a]indole-7-carboxamide;

4-methyl-1-oxo-N-[1-(propan-2-yl)-1H-benzimidazol-2-yl]-1,2,3,4-tetrahydropyrazino[1,2-a]indole-7-carboxamide;

N-(1-benzyl-1H-pyrazol-4-yl)-cis-4,5-dimethyl-1-oxo-2,3,4,5-tetrahydro-1H-[1,4]diazepino[1,2-a]indole-8-carboxamide;

N-(2-carbamoylphenyl)-4,4-dimethyl-1-oxo-1,2,3,4-tetrahydropyrazino[1,2-a]indole-7-carboxamide;

N-[1-(2-hydroxy-2-methylpropyl)-1H-benzimidazol-2-yl]-4,4-dimethyl-1-oxo-2,3,4,5-tetrahydro-1H-[1,4]diazepino[1,2-a]indole-8-carboxamide;

N-(3-ethyl-3H-imidazo[4,5-b]pyridin-2-yl)-1-oxo-2,3,4,5-tetrahydro-1H-[1,4]diazepino[1,2-a]indole-8-carboxamide;

N-(1-benzyl-1H-pyrazol-4-yl)-1'-oxo-2',3'-dihydro-1'H-spiro[cyclopropane-1,4'-[1,4]diazepino[1,2-a]indole]-8'-carboxamide;

1-oxo-N-[5-(propan-2-yl)-1H-benzimidazol-2-yl]-2,3,4,5-tetrahydro-1H-[1,4]diazepino[1,2-a]indole-8-carboxamide;

cis-3,4-dimethyl-1-oxo-N-[1-(propan-2-yl)-1H-pyrazolo[3,4-b]pyridin-5-yl]-1,2,3,4-tetrahydropyrazino[1,2-a]indole-7-carboxamide;

4,4-dimethyl-1-oxo-N-(3-phenyl-1,2-oxazol-5-yl)-1,2,3,4-tetrahydropyrazino[1,2-a]indole-7-carboxamide;

N-{1-[3-(dimethylamino)propyl]-1H-benzimidazol-2-yl}-cis-4,5-dimethyl-1-oxo-2,3,4,5-tetrahydro-1H-[1,4]diazepino[1,2-a]indole-8-carboxamide;

N-(6-chloro-1-ethyl-1H-benzimidazol-2-yl)-1-oxo-2,3,4,5-tetrahydro-1H-[1,4]diazepino[1,2-a]indole-8-carboxamide;

1-oxo-N-[1-(pyridin-4-ylmethyl)-1H-pyrazol-4-yl]-2,3,4,5-tetrahydro-1H-[1,4]diazepino[1,2-a]indole-8-carboxamide;

N-(1-benzyl-1H-pyrazol-4-yl)-1-oxo-2,3,4,5-tetrahydro-1H-[1,4]diazepino[1,2-a]indole-8-carboxamide;

(5 S)—N-{1-[3-(dimethylamino)propyl]-1H-benzimidazol-2-yl}-5-methyl-1-oxo-2,3,4,5-tetrahydro-1H-[1,4]diazepino[1,2-a]indole-8-carboxamide; or a pharmaceutically acceptable salt thereof.

3. A pharmaceutical composition comprising one or more compounds of claim 1, or the pharmaceutically acceptable salts thereof, optionally combined with one or more excipients and/or carriers.

* * * * *